(12) United States Patent
Schultz

(10) Patent No.: US 8,271,128 B1
(45) Date of Patent: Sep. 18, 2012

(54) PHARMACY WORKFLOW MANAGEMENT SYSTEM INCLUDING PLURAL COUNTERS

(75) Inventor: David A. Schultz, Palatine, IL (US)

(73) Assignee: Kirby Lester, LLC, Lake Forest, IL (US)

( * ) Notice: Subject to any disclaimer, the term of this patent is extended or adjusted under 35 U.S.C. 154(b) by 428 days.

(21) Appl. No.: 12/350,684

(22) Filed: Jan. 8, 2009

Related U.S. Application Data

(63) Continuation-in-part of application No. 12/182,669, filed on Jul. 30, 2008.

(51) Int. Cl.
*G06F 17/00* (2006.01)

(52) U.S. Cl. ......... 700/236; 700/240; 700/242; 700/244

(58) Field of Classification Search ............ 700/240, 700/242, 244
See application file for complete search history.

(56) References Cited

U.S. PATENT DOCUMENTS

| | | |
|---|---|---|
| 3,789,194 A | 1/1974 | Kirby |
| 4,847,764 A | 7/1989 | Halvorson |
| 4,901,841 A | 2/1990 | Haggerty et al. |
| 4,903,861 A | 2/1990 | Yuyama |
| 5,027,938 A | 7/1991 | Haggarty et al. |
| D337,539 S | 7/1993 | Leamon |
| 5,317,645 A | 5/1994 | Perozek et al. |
| 5,337,919 A | 8/1994 | Spaulding et al. |
| 5,473,703 A | 12/1995 | Smith |
| 5,597,995 A | 1/1997 | Williams et al. |
| 5,666,492 A | 9/1997 | Rhodes et al. |
| 5,713,485 A | 2/1998 | Liff et al. |
| 5,713,487 A | 2/1998 | Coughlin |
| 5,737,539 A | 4/1998 | Edelson et al. |
| 5,758,095 A | 5/1998 | Albaum et al. |
| 5,762,235 A | 6/1998 | Coughlin |
| 5,768,327 A | 6/1998 | Pinto et al. |
| 5,797,515 A | 8/1998 | Liff et al. |
| 5,845,255 A | 12/1998 | Mayaud |
| 5,883,370 A | 3/1999 | Walker et al. |
| 5,907,493 A | 5/1999 | Boyer et al. |
| 5,993,046 A | 11/1999 | McGrady et al. |
| 6,021,392 A | 2/2000 | Lester et al. |
| 6,036,812 A | 3/2000 | Williams et al. |
| 6,068,156 A | 5/2000 | Liff et al. |
| 6,112,182 A | 8/2000 | Akers et al. |
| 6,152,364 A | 11/2000 | Schoonen et al. |
| 6,155,485 A | 12/2000 | Coughlin et al. |
| 6,181,979 B1 | 1/2001 | Murakami |
| 6,202,923 B1 | 3/2001 | Boyer et al. |

(Continued)

OTHER PUBLICATIONS

U.S. Appl. No. 12/182,669, Schultz.

(Continued)

*Primary Examiner* — Timothy Waggoner
(74) *Attorney, Agent, or Firm* — Jansson Shupe & Munger Ltd.

(57) ABSTRACT

A pharmacy workflow management system including plural counters and a pharmacy workflow management method. In embodiments, the system includes a housing, a first automatic object counter and a cassette dispenser which feeds objects from a cassette mounted thereto to the first object counter. A second object counter counts objects fed from a cassette mounted to the cassette dispenser. A data processing platform within the housing is programmed with instructions that enable the system to compare the counts from the first and second object counters. The data processing platform also provides for management of pharmacy workflow by providing improved control of prescription fulfillment.

25 Claims, 83 Drawing Sheets

U.S. PATENT DOCUMENTS

| | | | |
|---|---|---|---|
| 6,219,587 B1 | 4/2001 | Ahlin et al. | |
| 6,256,967 B1 | 7/2001 | Hebron et al. | |
| 6,318,630 B1 | 11/2001 | Coughlin et al. | |
| 6,330,491 B1 | 12/2001 | Lion | |
| 6,352,200 B1 | 3/2002 | Schoonen et al. | |
| 6,370,215 B1 * | 4/2002 | Pinto et al. | 377/6 |
| 6,421,584 B1 | 7/2002 | Norberg et al. | |
| 6,438,451 B1 | 8/2002 | Lion | |
| RE37,829 E | 9/2002 | Charhut et al. | |
| 6,449,927 B2 | 9/2002 | Hebron et al. | |
| 6,471,090 B1 * | 10/2002 | Inamura et al. | 221/124 |
| 6,497,339 B1 | 12/2002 | Geltser et al. | |
| 6,529,801 B1 | 3/2003 | Rosenblum | |
| 6,554,157 B2 | 4/2003 | Geltser et al. | |
| 6,578,733 B2 | 6/2003 | Geltser et al. | |
| 6,631,826 B2 * | 10/2003 | Pollard et al. | 221/156 |
| 6,659,304 B2 * | 12/2003 | Geltser et al. | 221/7 |
| 6,684,914 B2 | 2/2004 | Gershman et al. | |
| 6,702,146 B2 | 3/2004 | Varis | |
| 6,742,671 B2 | 6/2004 | Hebron et al. | |
| 6,775,589 B2 | 8/2004 | Williams et al. | |
| 6,836,527 B1 | 12/2004 | Wooldridge et al. | |
| 6,899,144 B1 | 5/2005 | Geltser et al. | |
| 6,899,148 B1 | 5/2005 | Geltser et al. | |
| 7,006,893 B2 | 2/2006 | Hart et al. | |
| 7,073,544 B2 | 7/2006 | Geltser et al. | |
| 7,124,791 B2 | 10/2006 | Geltser et al. | |
| 7,139,639 B2 * | 11/2006 | Broussard et al. | 700/240 |
| 7,219,703 B2 | 5/2007 | Geltser et al. | |
| 7,316,328 B2 | 1/2008 | Yuyama et al. | |
| 7,344,049 B2 | 3/2008 | Daniels et al. | |
| 7,349,858 B1 | 3/2008 | McGrady et al. | |
| 7,383,862 B2 | 6/2008 | Geltser et al. | |
| 7,395,841 B2 | 7/2008 | Geltser et al. | |
| 7,395,946 B2 | 7/2008 | Yuyama et al. | |
| 7,434,704 B2 | 10/2008 | Yuyama et al. | |
| 7,631,670 B2 | 12/2009 | Geltser et al. | |
| 7,747,345 B2 * | 6/2010 | Ohmura et al. | 700/231 |
| 7,789,267 B2 * | 9/2010 | Hutchinson et al. | 221/211 |
| 7,930,064 B2 * | 4/2011 | Popovich et al. | 700/244 |
| 2001/0002448 A1 | 5/2001 | Wilson et al. | |
| 2001/0025208 A1 | 9/2001 | Bartur | |
| 2003/0057230 A1 | 3/2003 | Stevens et al. | |
| 2003/0149599 A1 | 8/2003 | Goodall et al. | |
| 2003/0225595 A1 | 12/2003 | Helmus et al. | |
| 2004/0088187 A1 * | 5/2004 | Chudy et al. | 705/2 |
| 2004/0107022 A1 | 6/2004 | Gomez | |
| 2005/0125097 A1 | 6/2005 | Chudy et al. | |
| 2006/0253346 A1 | 11/2006 | Gomez | |
| 2007/0158357 A1 | 7/2007 | Yuyama et al. | |
| 2007/0173971 A1 | 7/2007 | Richardson et al. | |
| 2008/0011764 A1 | 1/2008 | Geltser et al. | |
| 2008/0029530 A1 | 2/2008 | Yuyama et al. | |

OTHER PUBLICATIONS

KL15i Automatic Tablet Counter brochure, Kirby Lester, Inc., Stamford, CT. Date: 1998.

KL15e Automatic Tablet Counter brochure, Kirby Lester, Inc., Stamford, CT. Date: 1996.

KL15df Automatic Tablet Counter brochure, Kirby Lester, Inc., Stamford, CT. Date: 1996.

KL16ipc Automatic Tablet Counter brochure, Kirby Lester, Inc., Stamford, CT. Date: 2002.

KL16 Operating Instructions, Kirby Lester LLC, Stamford, CT. Date: 2006.

KL16df Automatic Tablet Counter brochure, Kirby Lester, Inc., Stamford, CT. Date: 2003.

BSI Batchmaster product information, <www.tosspackaging.com>, Batch Systems, Inc., Prince Frederick, MD. Date: 2008.

Bosspack RTC 200 product brochure, Romaco US, Morris Plains, NJ. Date: 2008.

Yuyama EV-120 product brochure, Yuyama USA, Inc., Elk Grove Village, IL. Undated.

Yuyama EV-220 product brochure, Yuyama USA, Inc., Elk Grove Village, IL. Undated.

Yuyama Cassettes product information, <www.yuyamarx.com>, Yuyama USA, Inc., Elk Grove Village, IL. Date: 2008.

Yuyama Vial Filling Technology product information, <www.yuyamarx.com>, Yuyama USA, Inc., Elk Grove Village, IL. Date: 2008.

Yuyama Adding New Medications product information, <www.yuyamarx.com>, Yuyama USA, Inc., Elk Grove Village, IL. Date: 2008.

Office Action mailed Dec. 14, 2011, U.S. Appl. No. 12/182,669.

* cited by examiner

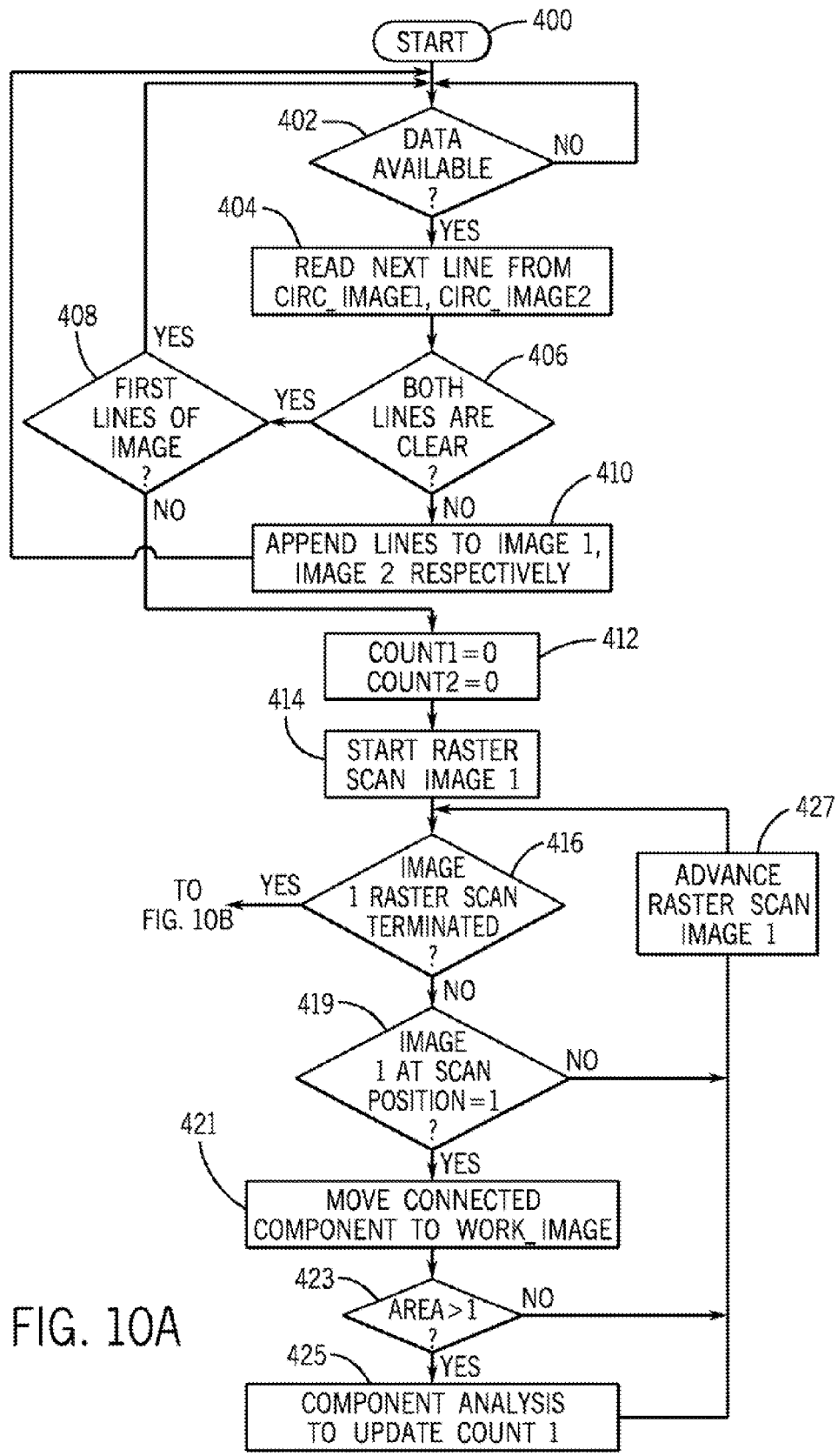

FIG. 37A

| PATIENT NAME | RX NUMBER | DRUGID | DRUGNAME | QUANTITY | FILLED | VERIFIED |
|---|---|---|---|---|---|---|
| PABLO MARTINI | 015644 | 00002322830 | STRATTERA 25MG CAPSULE | 20 | 2008-07-01 14:38:03 | 2008-07-01 14:43:15 |

FIG. 37B

| PATIENT NAME | RX NUMBER | DRUGID | DRUGNAME | QUANTITY | FILLED | VERIFIED |
|---|---|---|---|---|---|---|
| PABLO MARTINI | 015644 | 00002322830 | STRATTERA 25MG CAPSULE | 20 | 2008-07-01 14:08:18 | 2008-07-01 14:17:12 |
| PABLO MARTINI | 015645 | 00028054201 | AMBIEN 10 Mg TABLET | 30 | 2008-07-01 14:13:09 | 2008-07-01 14:19:06 |
| PABLO MARTINI | 015646 | 00024039202 | DRISDOL 50,000 UNITS CAPSULE | 36 | 2008-07-01 14:15:42 | 2008-07-01 14:20:51 |

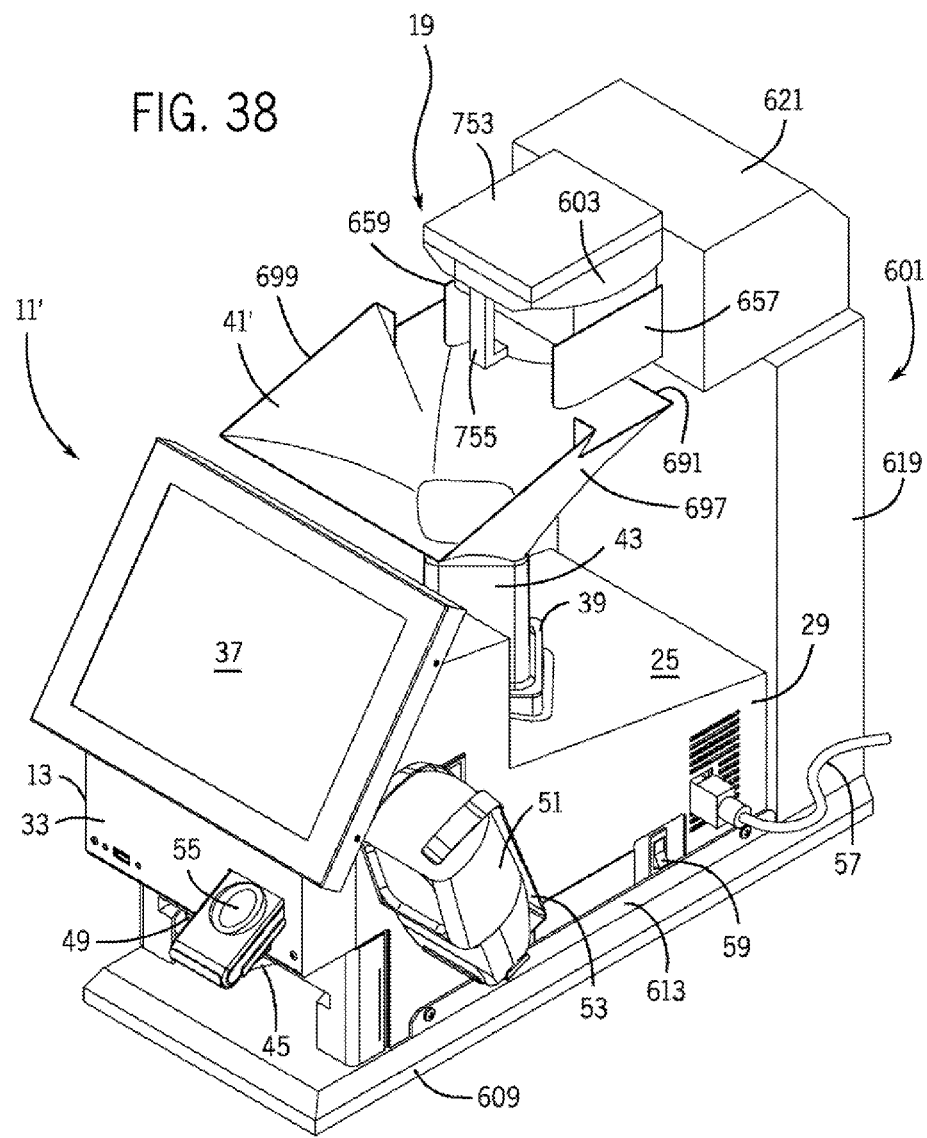

PHARMACY WORKFLOW MANAGEMENT SYSTEM INCLUDING PLURAL COUNTERS

RELATED APPLICATION

This application is a continuation-in-part of U.S. patent application Ser. No. 12/182,669 filed Jul. 30, 2008, the contents of which are fully incorporated herein by reference.

FIELD

The field relates generally to pharmacy workflow management and, more particularly, to prescription management including counting of tablet-form medication.

BACKGROUND

In retail, hospital, long-term-care and mail order medication dispensing, a large number of different prescription orders made up of one or more prescriptions for single-dose medications, such as tablets, must be fulfilled. "Fulfillment" as used herein refers to the process of handling and executing customer orders. For pharmacies, the customer is most typically a patient, that is someone for whom the medication is intended. However, pharmacy customers are not limited to patients and may include persons who seek fulfillment of orders for non-prescription tablets such as nutriceuticals, vitamins and supplements. The term "tablets" as used herein should be understood as being generic to pills, tablets, capsules, caplets, gel-filled capsules (gel-caps), liquid-filled capsules, particle-filled capsules and any other solid-dose medication type including prescription and non-prescription medications and products. Tablets, as used herein, are a type of discrete object capable of being counted automatically.

For prescriptions requiring small quantities of a medication, the prescription is often filled by hand; that is, a bulk storage container containing the prescription medication is removed from a shelf and opened. A quantity of the medication is poured into a tray and the medication tablets are counted by a pharmacist and then dispensed into a patient prescription container, such as a bottle or vial. The remainder of the medication in the tray is returned to the bulk container, the bulk container is closed and then replaced on a pharmacy storage shelf.

Larger quantity prescriptions are often filled with the aid of a counting apparatus intended to more rapidly count different quantities of different tablets. For example, a prescription for ninety (90) tablets of 10 mg Claritin® may need to be filled after a prescription for sixty (60) tablets of 400 mg Motrin®. Counting apparatus can be used to expedite the process of filling prescriptions calling for larger quantities of tablets that would be time-consuming and laborious to count manually.

One type of counting apparatus effective for rapid counting of different quantities of different tablets is known as a pour-through counter. With a pour-through tablet counter, the pharmacist pours tablets from a bulk container directly into a funnel. The tablets are counted when they drop past a tablet-counting sensor. The tablets fall past the tablet-counting sensor and into a removable tray, or are directed into a container for the patient prescription order. The pharmacist pours the tablets until a digital readout of the counter apparatus displays the required number of tablets, and then stops. As such, there is usually no excess. However, should an extra tablet or so fall into the funnel, the readout clearly indicates the extra number, and the excess can easily be removed by the pharmacist and returned to the bulk storage container.

Pour-through tablet counters are quite effective at providing an accurate count of the tablets required by a prescription. However, a drawback of such tablet counters is that the counters do not manage a broader range of pharmacy workflow tasks.

As an alternative to manual pouring of tablets into the tablet counter, an automatic-type tablet feeder may be provided to feed tablets to the counter. Examples of automatic-type feeders are cassette-type or vibratory-bowl-type feeders described in U.S. Pat. Nos. 6,497,339 and 6,659,304 or a mechanical feeder such as the rotating assembly described in U.S. Pat. No. 7,219,703.

A cassette is a container that holds bulk-form tablets and objects. Each cassette is pre-loaded, or filled, by pharmacy personnel with a bulk quantity of a tablet-form medication or other product. Tablets are fed from the cassette.

There are many potential advantages to the use of cassettes by a pharmacy. For example, cassettes are efficient and reduce the time required to fulfill a prescription. Cassettes can hold a large amount of tablets, thereby reducing the need to retrieve and return to storage a container holding the medication and the need to manually pour tablets from the manufacturer's container. Cassette usage permits the pharmacist to perform other value-added tasks while tablets are automatically fed from the cassette. Cassettes for more frequently-used tablets can be stored at a convenient location proximate the tablet counter. Cassettes can be used to dispense tablets at a rapid rate, thereby reducing the time required to fulfill a prescription.

Certain cassette types are calibrated or designed for a specific size and shape tablet. U.S. Pat. No. 7,395,946 describes tablet cassettes which may be calibrated. Calibration involves adjustment of the cassette so that the cassette will dispense tablets in a singulated manner, that is one tablet after the other. Calibration can involve adjustment of the size of the cassette opening through which the tablet exits the cassette, for example, by providing a smaller opening for small-size tablets or a larger opening for large-size tablets. As an alternative to calibration, the cassette may be manufactured with a single-size opening for a particular tablet size or shape.

Problems can arise if the cassette is not calibrated properly or if the cassette is incorrectly sized for the type of tablet to be dispensed from the cassette. More specifically, use of an incorrectly calibrated or sized cassette can result in plural tablets being fed simultaneously from the cassette. The tablets are fed from the cassette and pass a sensor. Detection of the tablets by the sensor is used to make a tablet count.

The process of counting from the cassette is not completely accurate. If tablets fed from the cassette pass the sensor simultaneously, a single count may be registered even though plural tablets are dispensed. Missed tablet counts result in prescription order fulfillment errors and can amount to "giving away" costly tablet-form medication. Many dispensing cycles may be performed before the error is detected by pharmacy personnel. Small tablets or tablet fragments may not be detected by the sensor. Tablet fragments may be detected as a complete tablet, thereby failing to completely fulfill the prescription.

Because pharmacy-personnel time is valuable, obtaining an accurate count in the least amount of time is advantageous. Vibratory-type dispensers which feed tablets from a cassette as described in U.S. Pat. Nos. 6,497,339 and 6,659,304 are potentially excellent for their intended purpose, but tend to require a relatively greater amount of time to automatically dispense the required tablets or other discrete objects. This is because the vibratory action required to singulate the discrete objects from the vibrating cassette tends to be somewhat slow. Moreover, tablet counting for vibratory systems is performed only by the discrete object counter. Additional time is required for the tablets to exit the cassette, fall past the object counter to make a count and for the appropriate feedback to be provided to the vibration system which controls feeding to the objects to the discrete object counter.

The time required to count a specified quantity of tablets from a vibratory dispenser system can be excessive. For example, a pharmacy may be required to perform repetitive counting and packaging operations for unit-of-use containers. Unit-of-use containers are frequently used to hold pre-packaged 30, 60 or 90-day tablet quantities. The pre-packaged unit-of-use containers may be stocked at a pharmacy "speed-shelf" permitting rapid retrieval by pharmacy personnel. As can be appreciated, rapid, accurate counting is desirable to minimize the time required for performance of these repetitive counting operations.

Workflow in a retail, hospital or mail order pharmacy is typically managed by a computer-driven system known generally as a pharmacy management system, or PMS. For each prescription order, information required to fulfill each prescription of the prescription order is input to the PMS, typically by a pharmacy technician. The PMS processes each prescription of the prescription order to determine that the pharmacy can fulfill the prescription order.

For prescriptions requiring manual tablet counting, the PMS generates prescription order paperwork known generally by the term "label." The paperwork includes all information necessary for fulfillment of the prescription and typically includes an adhesive-backed label for application to each container for each prescription within the prescription order. The paperwork is typically printed by an automatic printer located within the pharmacy. Each prescription of a prescription order is simply filled in the order in which the paperwork is generated by the PMS. The pharmacist or pharmacy technician follows the information on the paperwork and can use the tablet counter to count out the desired quantity of tablets as previously described. The fulfilled prescription order is provided to the patient in one or more containers once all medications required by the prescription order have been verified and payment has been made or arranged.

A drawback of such a system is that the pharmacist operating the tablet counter does not have the ability to manage pharmacy workflow. The pharmacist simply fulfills the prescription orders in the order in which they are provided by the PMS. There may be a large number of prescription orders awaiting fulfillment at any given time. By way of example only, in certain circumstances it may be desirable to fulfill patient prescription orders out of turn. One such circumstance could involve a need to fulfill a prescription order for a patient who is waiting to pick up medications before an earlier processed prescription order for a patient who will not pick up the prescription order until the following day.

By way of further example, a patient might have a question of the pharmacist operating the tablet counter. The pharmacist may be unable to respond to the question because the printed label paperwork might not yet be available from the PMS.

Presently, the pharmacist would be required to access the PMS to perform any modification of the pharmacy workflow or obtain detailed information about the patient's prescription order with which to answer the patient's questions. Utilization of the PMS for these or other purposes may be inconvenient or require more time to complete than if the workflow management process could simply be controlled by means of the tablet counter.

It would be an advance in the art to provide an improved pharmacy workflow management system which would facilitate tablet counting, would enable improved control of pharmacy workflow, and which would contribute to an improvement in the overall quality of patient care. And, it would be an advance in the art to provide an improved tablet counter which could be used with the pharmacy workflow management system or as a stand-alone apparatus and which would enable use of the tablet counter with medication-specific cassettes, also improving the quality of patient care.

SUMMARY

A pharmacy workflow management system including plural automatic object counters and a method for pharmacy workflow management are shown and described. The preferred system provides the user with the capability of fulfilling prescriptions by feeding objects from a cassette or by manual pouring of tablets into the system. The system is preferably used to feed and count tablet-form objects of the types described herein, although other types of countable objects may be counted with the system. The plural counters facilitate improved object feeding and counting.

In a preferred embodiment, the system comprises a first automatic object counter and a cassette dispenser. The first object counter is preferably within a housing. The cassette dispenser includes a cassette mount which positions a cassette mounted thereon to feed discrete objects to the first object counter. The cassette dispenser further includes a drive system which powers a mounted cassette to feed objects from the mounted cassette. The system further comprises a second automatic object counter which counts objects fed from the mounted cassette. A data processing platform compares counts of the first and second object counters.

Preferably, the data processing platform compares the counts to determine whether the counts differ by more than a predetermined amount. Preferably, the data processing platform generates a signal if the counts differ by more than the predetermined amount. The counts could differ, for example, if a jam condition were to exist preventing flow of tablets to the first tablet counter. It is also preferred that the drive system stops responsive to the signal. A visual message may appear on a video display to notify a user that the counts differ. Preferably, the data processing platform compares the counts during counting. The data processing platform may further compare the counts to determine whether the counts match a required count, such as the count required to fulfill a prescription. Such a comparison would be useful to confirm that all tablets required by the prescription were fed from the cassette.

Preferably, the first object counter count is displayed on the video display.

In an embodiment, the first object counter counts objects both fed from a mounted cassette and poured manually. To facilitate system operation, a funnel and a chute connected thereto are preferably provided. The funnel and chute direct objects to the first object counter for counting. The funnel preferably has an inlet sized to receive objects both fed from the mounted cassette and poured manually.

In a further embodiment, the second object counter comprises a cassette dispenser detector which detects an object fed from the mounted cassette and a cassette dispenser controller which increments a count responsive to each detected object. The detector preferably generates a signal responsive to each detection. The detector signal is received by the cassette dispenser controller to increment the count. The count is used by the data processing platform, for example, for purposes of the count comparison.

In an embodiment, the data processing platform is programmed with instructions which, when executed, perform a method of pharmacy workflow management. In an embodiment, the system can receive a plurality of prescriptions and store the received prescriptions. The system enables user-selection of a prescription. A stored prescription is retrieved followed by counting with the first and second automatic tablet counters of a quantity of tablets required by the retrieved prescription. Thereafter, a record may be created that the quantity of the tablet-form medication required by the retrieved prescription has been counted.

Retrieving one of the stored patient prescription orders for fulfillment preferably is triggered by touching the display proximate a displayed prescription or by reading a code on a label for the selected prescription. It is preferred that all prescriptions stored for a patient are displayed on the display collated for the patient. Thus, any number of pending prescriptions for the patient are preferably grouped together making it easier for a user of the system to fulfill all pending prescriptions for the patient. If cassette dispensing is selected by the user, the counts can then be compared by the first and second automatic tablet counters for the displayed prescription.

In embodiments, the method performed by the instructions, when executed, further comprises verifying that a cassette contains the required medication or that a container for the medication matches the medication required by the retrieved prescription. For cassettes, the verifying executed by the instructions preferably includes verifying that the cassette contains the required medication. One medication is associated with each cassette and each cassette is associated with a unique cassette identification code by means of a database stored in the non-volatile memory of the data processing platform. An identification code of the mounted cassette is read by a reader of the cassette dispenser. A match between the expected and actual cassette identification codes confirms that the correct cassette has been selected by the user. Once verified, the instructions initiate operation of the drive system which powers a mounted cassette to feed objects therefrom for counting by the first and second object counters. In the embodiment, the data processing platform compares the counts.

For containers, the verifying executed by the instructions preferably includes associating an expected container identification code with the prescription. This may be accomplished by means of a database stored in the non-volatile memory of the data processing platform. The expected identification code may be a UPC barcode on the container which may be associated with the prescription number for the patient prescription through the database. In other embodiments, the expected container identification code may be associated or with the National Drug Code (NDC) included on paperwork for the patient prescription in the database. The identification code on the container, typically a barcode, is read by a code reader such as a barcode scanner. The system then compares the expected and actual identification codes for a match. If there is a match, then the medication from the container can be poured into the system and counted to fulfill the prescription. Each prescription for the patient may be selected, retrieved and fulfilled one after the other until all collated prescriptions for the patient have been fulfilled.

The system may be configured to perform a further verification process which occurs after counting but before the prescription is given to the patient. Such verification performed by the executed instructions comprises retrieving a prescription for verification, comparing the prescription with the counted tablets and confirming that the prescription and counted tablets match.

The system may be interfaced with a pharmacy management system or may operate as a stand-alone product. The system may be enabled to perform different modes of counting depending on the level of verification desired by the user.

BRIEF DESCRIPTION OF THE DRAWINGS

Exemplary pharmacy workflow management systems and methods of pharmacy workflow management may be understood by reference to the following description taken in conjunction with the accompanying drawings, in which like reference numbers identify like elements throughout the different views. The drawings are not necessarily to scale, emphasis instead being placed upon illustrating the principles of the invention. In the accompanying drawings:

FIGS. 10A, 10B and 10C (FIG. 10C consists of FIGS. 10C-1 and 10C-2) are flow diagrams describing image analysis to determine a count;

FIG. 37A is a schematic illustration of a fulfilled patient prescription record for a system of FIG. 1 or 38 which is not interfaced with a Pharmacy Management System;

FIG. 37B is a schematic illustration of a fulfilled patient prescription record for a system of FIG. 1 or 38 which is interfaced with a Pharmacy Management System, including three fulfilled prescriptions collated by patient;

FIG. 38 is a perspective view of a further exemplary pharmacy workflow management system including an integrated automatic tablet counter with a cassette dispenser;

Figure 1:
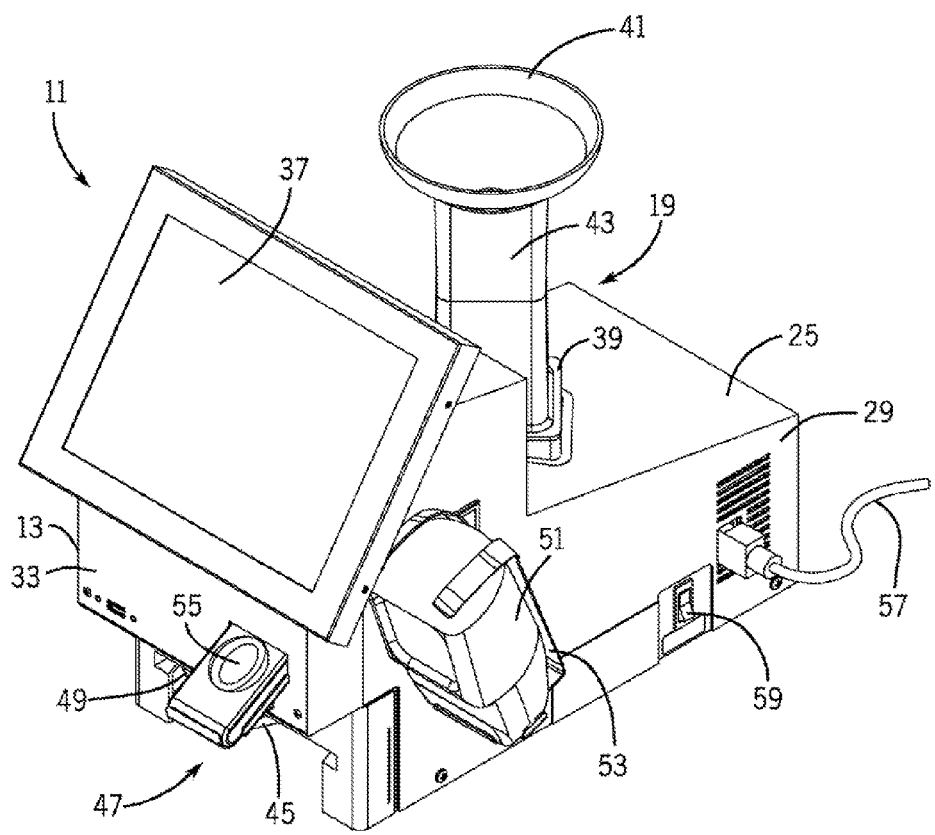
FIG. 1 is a perspective view of an exemplary pharmacy workflow management system including an integrated automatic tablet counter according to the invention.

While the systems, apparatus and methods are susceptible to various modifications and alternative forms, specific embodiments thereof have been shown by way of example in the drawings and are herein described in detail. It should be understood, however, that the description herein of specific embodiments and methods is not intended to limit the invention to the particular forms disclosed, but on the contrary, the intention is to cover all modifications, equivalents, and alternatives falling within the spirit and scope of the invention as defined by the appended claims.

DETAILED DESCRIPTION

Workflow Management System 11

Referring first to FIGS. 1-6, an exemplary pharmacy workflow management system 11 including an integrated automatic tablet counter in accordance with the present invention includes a housing 13 that houses an automatic tablet counter 15 and a data processing platform 17. System 11 is described in U.S. patent application Ser. No. 12/182,669 filed Jul. 30, 2008, the contents of which are fully incorporated herein by reference. Data processing platform 17 (e.g., one or more printed circuit boards that include a microprocessor, memory and interface circuitry mounted thereon) interfaces to tablet counter 15 and possibly to a tablet feeder 19 to control the operations of system 11 during the pharmacy workflow management operations carried out by system 11. These operations include control of pharmacy workflow involving fulfillment of prescriptions which require tablet counting and, in embodiments, may also include control of pharmacy workflow involving fulfillment of prescriptions for other medication types such as unit-of-use medications, pre-packaged medications and things (e.g., ointments, syringes, inhalers, etc.).

Figure 6:
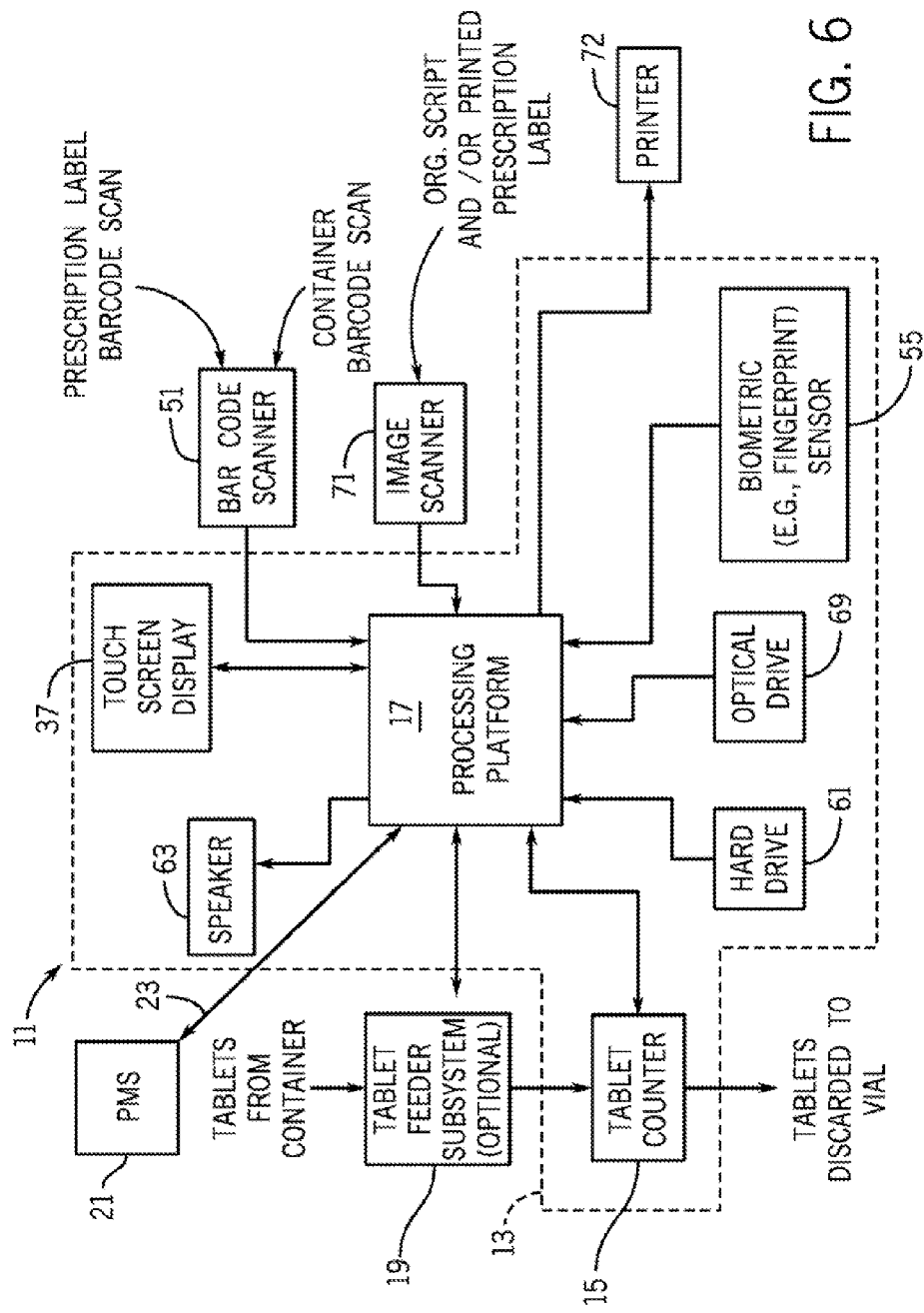
FIG. 6 is a schematic block diagram showing an exemplary data processing platform for use with the exemplary system of FIG. 1, together with other components.

Data processing platform 17 may interface with a Pharmacy Management System (PMS) 21 through a communication link represented by line 23 in FIG. 6 providing a means for bi-directional data transmission between PMS 21 and system 11. An interface between system 11 and PMS 21 may be provided by means other than link 23, such as by batch delivery of prescription orders from PMS 21 to system 11 via a portable non-volatile memory device (not shown). Prescription order data downloaded onto the memory device could then be transferred to system 11 by pharmacy personnel.

System 11 can also function as a stand-alone system which is not interfaced with PMS 21. Workflow management performed by system 11 is described herein for embodiments of system 11 which are interfaced with PMS 21 and for embodiments of system 11 which are not interfaced with PMS 21.

PMS 21 is representative of any system which manages prescription orders. As already noted, a prescription order is an order for one or more prescriptions. Pharmacy Management Systems of various types are routinely utilized by pharmacies serving retail, hospital, long-term care, mail order and other markets to manage workflow. Prescriptions to be fulfilled are output from PMS 21 to system 11 and records of fulfilled prescriptions are output from system 11 to PMS 21 providing pharmacy workflow management.

PMS 21 may be a computer or combination of computers running any suitable workflow management program or programs. PMS 21 may be accessed from one or more pharmacy workstations. PMS 21 may be located at a single site or at a plurality of sites. Communication link 23 may be any suitable connection enabling one-way or two-way data transmission between system 11 and PMS 21 and may include a cable connection, a wireless connection, or an Internet connection. Communication link 23, if provided, enables real-time data transmission between system 11 and PMS 21. Batch delivery of data as previously described, or any other suitable means of data transmission, may be used in conjunction with, or substituted for, link 23.

The operations of PMS 21 will typically be customized for the workflow requirements of a particular pharmacy. As already noted, a prescription order comprising one or more prescriptions is entered into PMS 21 by a pharmacy technician or pharmacist at an input workstation. The prescription order may be delivered to the pharmacy in any suitable manner, including by physically providing a paper prescription order to the technician or by electronic data transmission.

The pharmacy technician or pharmacist enters all information relevant to fulfillment of the prescription order into PMS 21 using an input device such as a keyboard, mouse and/or touch-screen video display. Information entered into PMS 21 will typically include patient name, medication type and quantity, National Drug Code (NDC) for the prescribed medication, physician name, refill information, medication interaction information and insurance information or other information related to payment.

After data entry, the prescription order is processed by PMS 21. Processing by PMS 21 includes any steps deemed necessary by the pharmacy to make a determination that a prescription of the order should be fulfilled. Processing can include determination of whether the prescribed medication is available in the pharmacy, determination of whether a generic medication can be substituted for a branded medication, determination of whether the prescribed medication presents any risk of adverse medication interactions with medications currently taken by the patient and a drug utilization review (DUR) which includes confirmation that a third-party payor will pay for some or all of the prescription being fulfilled.

A prescription is deemed validated once it has been determined by means of PMS 21 that the prescription should be fulfilled. A prescription order is deemed validated when all prescriptions of the order have been validated. Validated prescription orders are transmitted electronically from PMS 21 via link 23, or by batch, to data processing platform 17 of system 11 for managed prescription order fulfillment as described in detail below. Following prescription order fulfillment by a pharmacy technician and/or registered pharmacist utilizing system 11, a record of each completed prescription order may be sent by system 11 back to PMS 21 providing confirmation of prescription order fulfillment.

For non-interfaced embodiments of system 11, PMS 21 provides instructions and information for fulfillment of separate prescriptions. This information may be in the form of prescription order paperwork 147 which includes all information required to fulfill a validated prescription as described herein.

Referring further to FIGS. 1-6, housing 13 includes top 25 and bottom walls 27, sidewalls 29, 31 and front 33 and rear walls 35. A display 37 is mounted to housing 13 front wall 33 and interfaces with data processing platform 17. Display 37 outputs information to a user of system 11, such as a pharmacy technician or pharmacist. Display 37 preferably provides status messages to the user, including information relevant to the management of pharmacy workflow, the number of tablets counted by tablet counter 15, and prescription status. Examples of screen displays are discussed in connection with FIGS. 15-36. In the examples, display 37 is a flat panel liquid crystal display (LCD). It is preferred that display 37 is a touch-screen-type display thereby enabling display 37 to also serve as an input device for transmission of information from the user to data processing platform 17. Data is transmitted from display 37 to data processing platform 17 when a user touches display 37 proximate information or an image shown on display 37. A touch-screen-type display may display an image of a QWERTY-type or ABC-type keypad (e.g., QWERTY keypad 65, FIG. 70) which enables a user to input information to data processing platform 17 by touching keys of the keypad. Such a keypad would be useful for inputting information to data processing platform 17, for instance user login information, prescription number information or NDC information. Other types of displays, such as a cathode ray tube (CRT) or digital numeric display, may be used. Tablet feeder 19 is removably seated in a mount 39 on housing top wall 25.

Figure 12A:
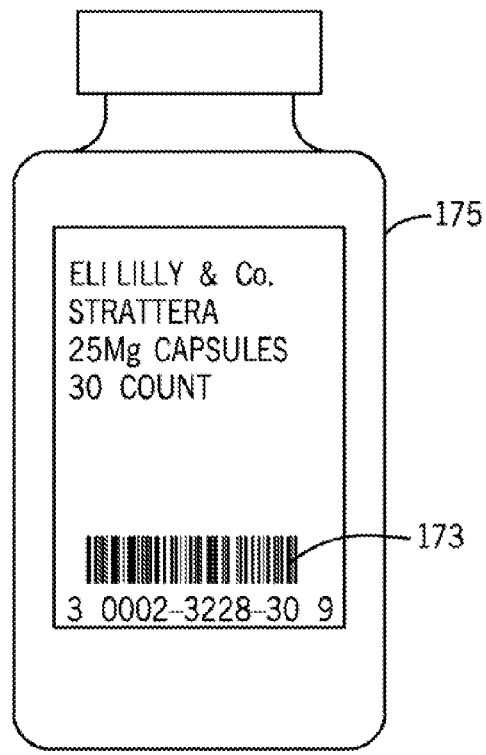
FIG. 12A is an exemplary medication container holding tablet-form medication.

Feeder 19 is provided to direct tablets toward tablet counter 15. In the example, tablet feeder 19 is of a pour-through type with an upper funnel 41 and a vertically-oriented chute 43. Tablet-form medications are poured by a user from a bulk storage container 175 (FIG. 12A) into funnel 41 and fall by means of gravity through chute 43, past tablet counter 15 into a tray 45 removably positioned in tray bay 47 provided in housing front wall 33. Tray 45 may be removed from housing 13 bay 47 by grasping and pulling tray handle 49, thereby permitting medication in tray 45 to be conveniently poured into a container (not shown) such as a vial or bottle which is subsequently provided to the patient.

While a pour-through type feeder 19 is shown, feeder 19 may be of other suitable types capable of delivering tablet-form medication to tablet counter 15. For example, tablet feeder 19 may be an automatic-type feeder such as the vibratory bowl feeder described in U.S. Pat. No. 6,497,339, a mechanical feeder such as the rotating assembly described in U.S. Pat. No. 7,219,703, or a cassette system such as described in U.S. Pat. No. 6,659,304, all of which are commonly assigned to the assignee of the present invention and hereby incorporated by reference in their entireties. Automatic-type tablet feeders 19 preferably feed tablets in a singulated manner to tablet counter 15.

By way of further example, feeder 19 may include cassette dispenser 601 and plural counters as described below in connection with system 11'.

In place of tray 45, system 11 may include a storage compartment or possibly a cell-based architecture (such as the cell-based architecture as described in U.S. Pat. No. 7,124,791 and U.S. Pat. No. 7,395,841 both commonly assigned to the assignee of the present invention and herein incorporated by reference in their entireties) that accumulates the tablets counted by tablet counter 15 prior to discharge from system 11.

Automatic tablet counter 15 within housing 13 is preferably an optical system which uses an optical sensor array to count tablets on a piece-count basis, such as that disclosed in U.S. Pat. No. 5,768,327, which is commonly assigned to the assignee of the present invention and is hereby incorporated by reference in its entirety.

Figure 3:
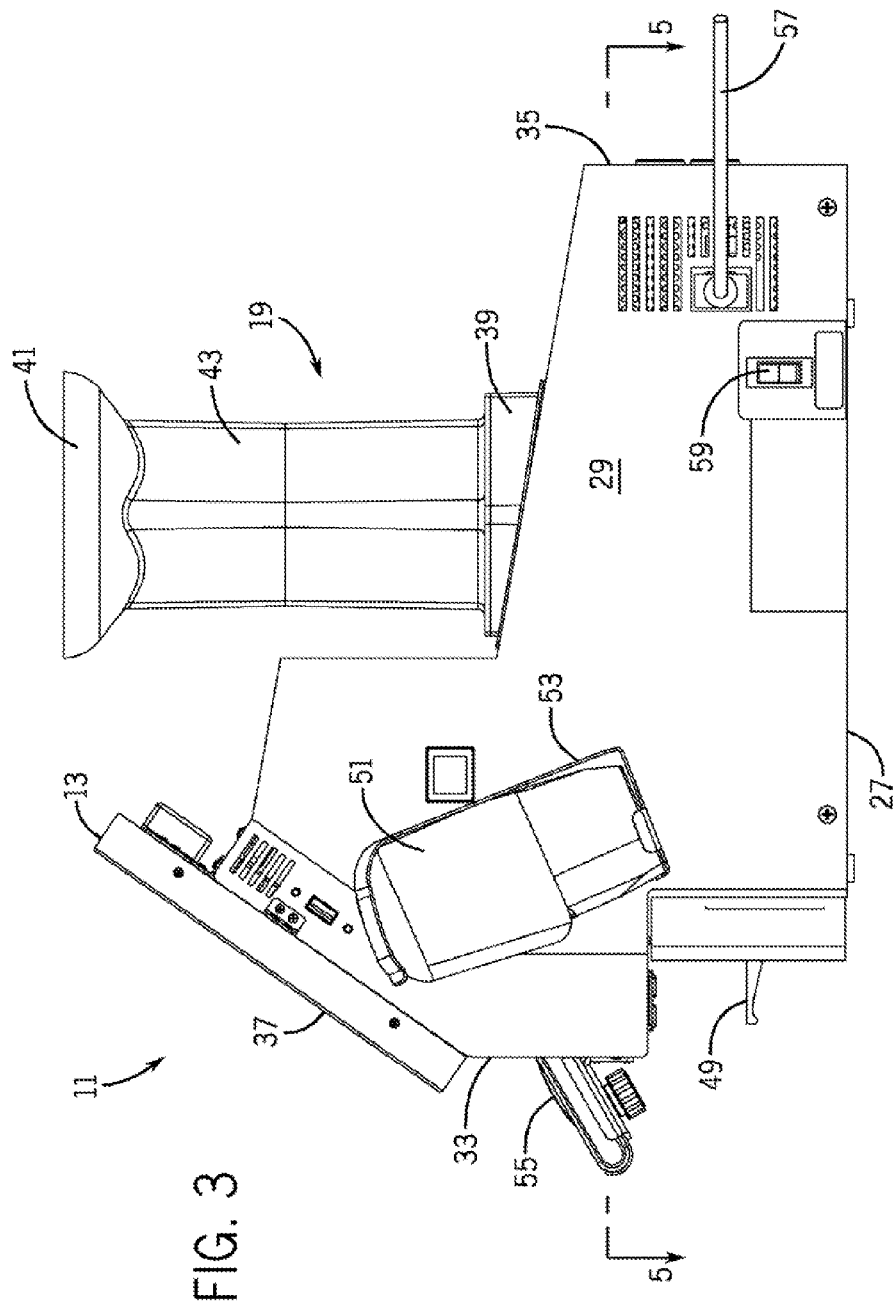
FIG. 3 is a side elevation view of the exemplary system of FIG. 1.
Figure 5:
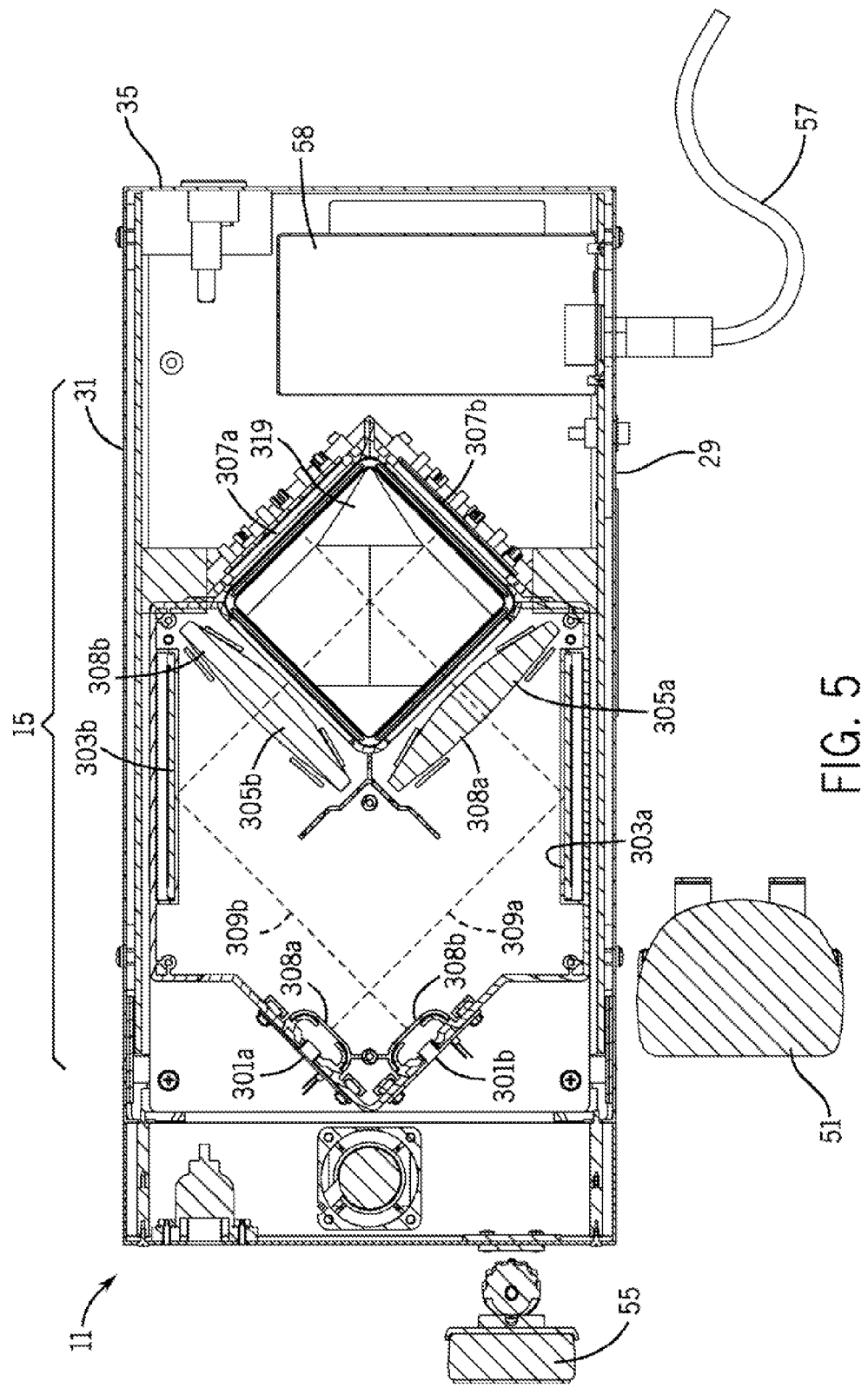
FIG. 5 is a section view taken along section 5-5 of FIG. 3 showing tablet counter and other internal components.

Components of exemplary tablet counter 15 of system 11 are illustrated in FIG. 5 which is a section view taken along section 5-5 of FIG. 3. Tablet counter 15 primarily consists of optical sensors, infrared (IR) sources, and the accompanying electronics and software to perform the counting function as required for tablet counter 15. These elements include IR emitters 301a, 301b, mirrors 303a, 303b, collimating lenses 305a, 305b, and IR sensor linear arrays 307a, 307b. Dotted paths 309a, 309b indicate the nominal optical path for the IR energy emitted from IR emitters 301a, 301b. Each of the optical elements are in pairs with linear sensor arrays 307a, 307b mounted perpendicular one to the other and the IR emitters 301a, 301b, mirrors 303a, 303b, and lenses 305a, 305b arranged such that IR radiation is collimated into two sets of parallel beams, each set striking one of the sensor arrays 307a, 307b such that an optical grid of orthogonal beams is formed within the region bounded generally by lenses 305a, 305b and sensor arrays 307a, 307b.

In this embodiment of tablet counter 15, each sensor array 307a, 307b has forty-eight sensor elements (spaced about 0.05 inches on center) within linear arrays 307a, 307b, such that the grid can be thought of as a 48×48 optical grid. Each IR emitter 301a, 301b and its corresponding mirror 303a, 303b and collimating lenses 305a, 305b form collimated IR sources 308a, 308b each of which illuminates its corresponding sensor array 307a, 307b with a collimated beam emanating from each lens 305a, 305b.

Figure 4:
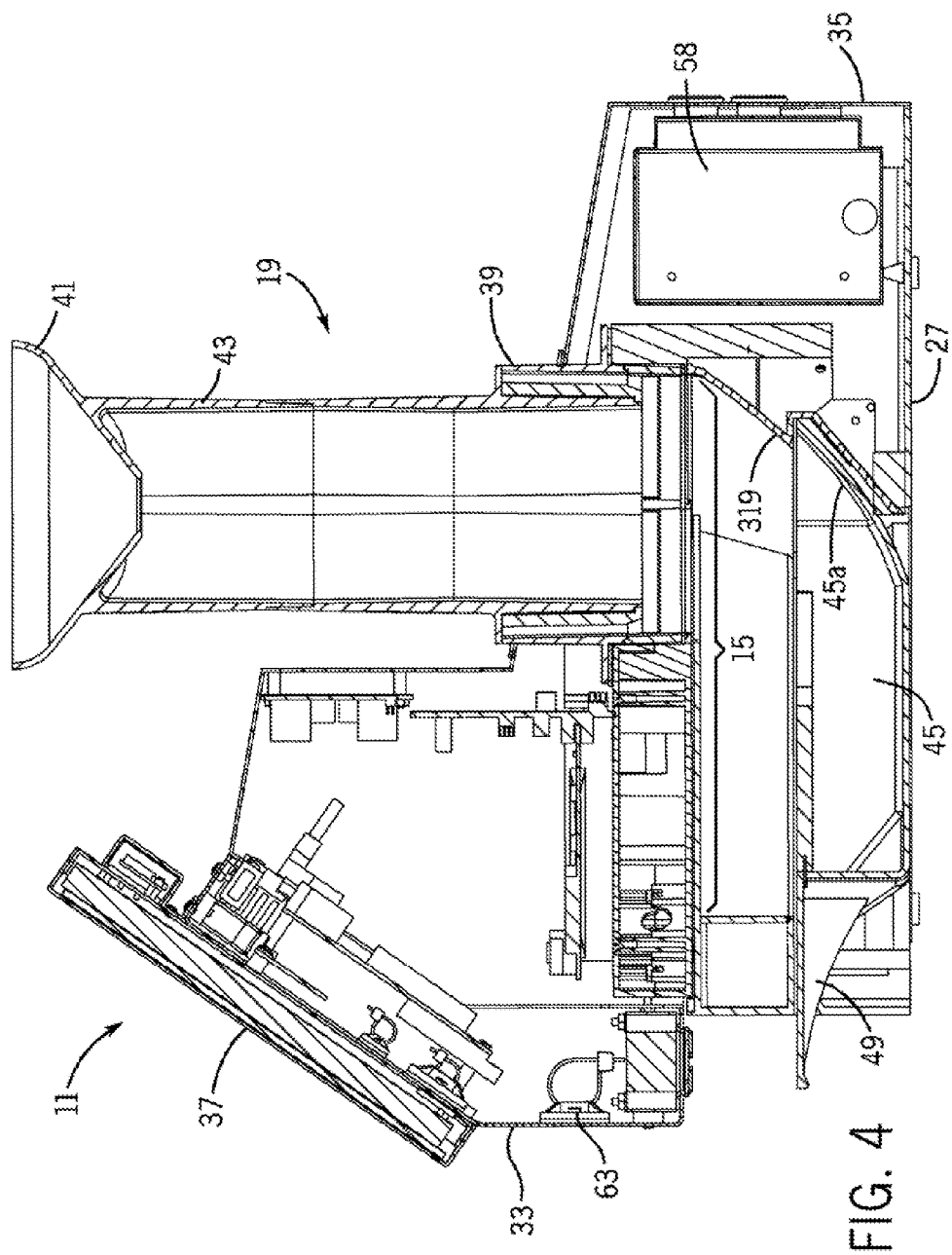
FIG. 4 is a side section view taken along section 4-4 of FIG. 2 showing tablet counter and other internal components.

FIG. 4 is a section view showing components of a preferred tablet feeder 19. In order to aid in the vertical separation of free-falling tablets to be counted, the vertical distance from the top of feeder 19, through funnel 41 and chute 43 to the sensor arrays 307a, 307b is chosen to be at least six inches, and preferably approximately eight inches. Likewise, in order to aid in the horizontal separation of tablets falling through chute 43, the smallest inside horizontal dimension of chute 43 is chosen to be at least 2.5 times the largest dimension of the tablets being counted. Thus, in system 11 as shown, the horizontal dimensions of chute 43 are approximately 2.5 inches by 2.5 inches, because the largest tablet expected to be counted is approximately 0.9 inches in its largest dimension.

Figure 7:
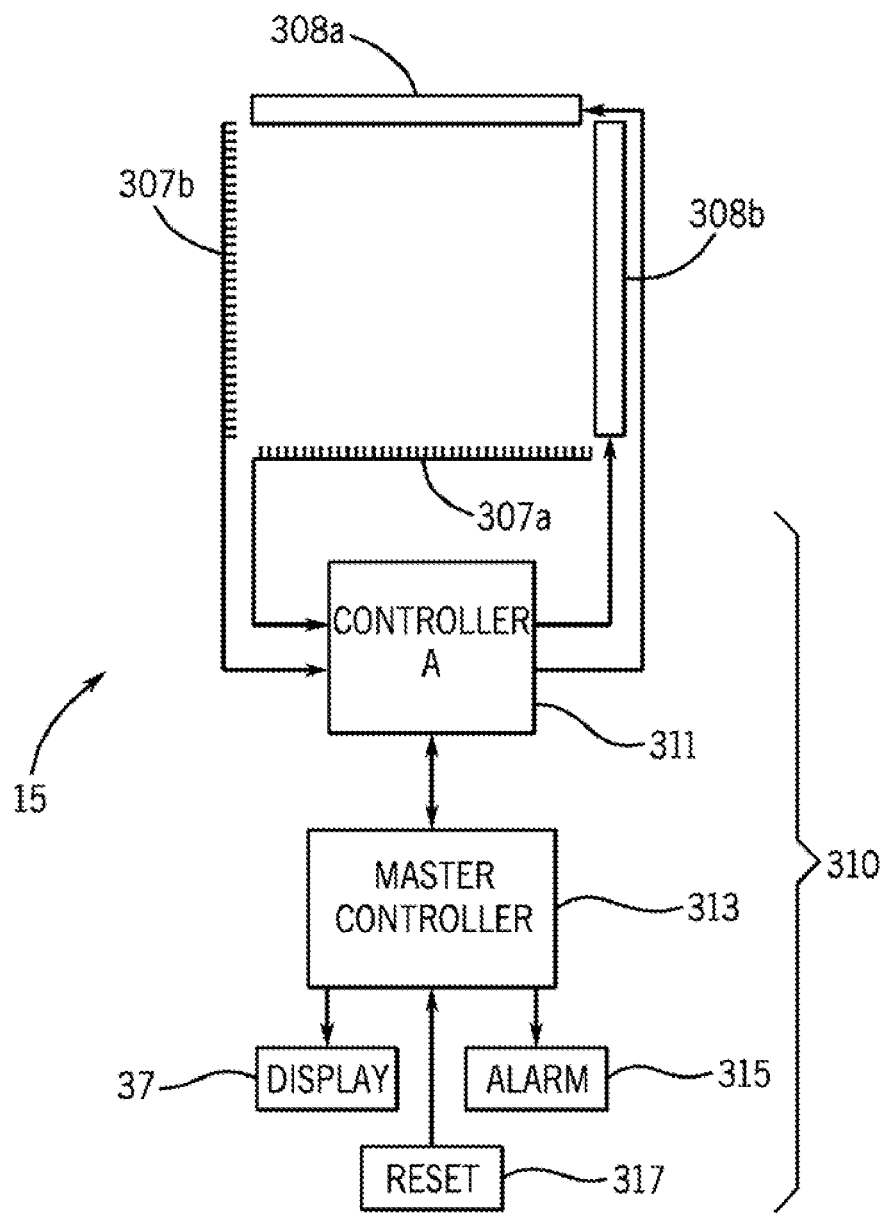
FIG. 7 is a block diagram of the circuit used for processing the outputs of the sensor arrays of FIG. 5.

Collimated IR sources 308a, 308b are also shown schematically in FIG. 7, as are sensor arrays 307a, 307b. Tablet counter 15 also includes circuitry 310 which is embedded within the circuitry of data processing platform 17 (FIG. 6). Other elements which cooperate to accomplish the functions of tablet counter 15 include display 37, microprocessor-based controllers 311 and 313, an overspeed warning indicator alarm 315 (which generates a message on display 37), and a resetting device 317, all of which are discussed in more detail hereinafter. At least some of circuitry 310 may be incorporated on a printed circuit (PC) board on which one of sensor arrays 307a or 307b is mounted.

System 11 includes a deflector 319 which is provided below sensor arrays 307a, 307b for deflecting tablets into the removable tray 45. Tray 45 preferably includes a curved inner-surface portion 45a which cooperates with and continues from deflector 319. Deflector 319 and curved surface portion 45a of tray 45 together present a surface which prevents tablets falling into tray 45 from bouncing up into feed device 19 and being recounted. It will be appreciated that deflector 319 is housed in system 11 housing 13.

When system 11 is assembled as shown in FIGS. 1-6, tablets which are placed in funnel 41 fall into tablet feeder 19 and cast shadows on sensor arrays 307a, 307b of tablet counter 15 as they fall past arrays 307a, 307b. As is discussed below, the shadows are used in determining a count. After passing sensor arrays 307a, 307b, the tablets hit the deflector 319 which directionally deflects the tablets so that they do not bounce back up into chute 43.

Referring to FIG. 5, sensor arrays 307a, 307b are arranged at approximately 45 degrees relative to sidewalls 29, 31 of housing 13. According to this preferred embodiment, mirrors 303a, 303b are each arranged so that the path of light 309a, 309b from each IR emitter 301a, 301b to a respective lens 305a, 305b is deflected approximately 90 degrees. This arrangement permits housing 13 to be more compact because the focal length of lenses 305a, 305b is traversed in two orthogonal segments, and IR emitters 301a, 301b therefore need not be placed so far away from lenses 305a, 305b.

Turning now to FIG. 7, the outputs of sensor arrays 307a, 307b are coupled to a microprocessor-based controller 311 which is also coupled to collimated IR sources 308a, 308b. Controller 311 is preferably bidirectionally coupled to microprocessor-based master controller 313 which provides output to display 37 and operates speaker 63 (FIG. 6) to generate audible alarm 315. An overspeed indication may also be visually presented on display 37. Master controller 313 is also preferably provided with resetting device 317 such as a "reset" button or switch. Resetting device 317, for example, may be a switch activated by the position of tray 45 being fully inserted into tray bay 47 such that when tray 45 is re-inserted into tray bay 47, a "reset" signal is generated. Such a switch is not shown in FIGS. 1-5. Resetting device 317 may also be any suitable manual input device.

In the example, controller 311 strobes IR emitters 301a, 301b at a relatively high rate and preferably alternatingly so that only one IR emitter 301a or 301b is activated at any instant. According to a preferred embodiment, the IR emitters 301a, 301b are strobed at approximately 1200-1600 Hz with a duty cycle of approximately 5%. As tablets pass between each sensor array 307a, 307b and its respective collimated IR source 308a, 308b, shadows will be cast on one or more of the forty-eight sensors in each array 307a, 307b. The output of each array 307a, 307b is processed as a forty-eight bit binary number wherein sensors of arrays 307a, 307b which receive light are indicated with a binary zero and sensors of arrays 307a, 307b which are blocked from receiving light are indicated with a binary 1. Thus, when no tablet is blocking the path of light to the sensor arrays 307a, 307b, the outputs of the sensor arrays 307a, 307b will be: 000000000000000000000000000000000000000000000000. If a single tablet passes between a collimated IR light source 308a or 308b and sensor array 307a or 307b, the output of array 307a or 307b, for example, might be: 000000000000111111110000000000000000000000000000.

If two tablets pass side-by-side between a collimated IR light source 308a or 308b and sensor array 307a or 307b, the output of array 307a or 307b, for example, might be: 000000000000111111110000000000000111111110000000.

Figure 8:
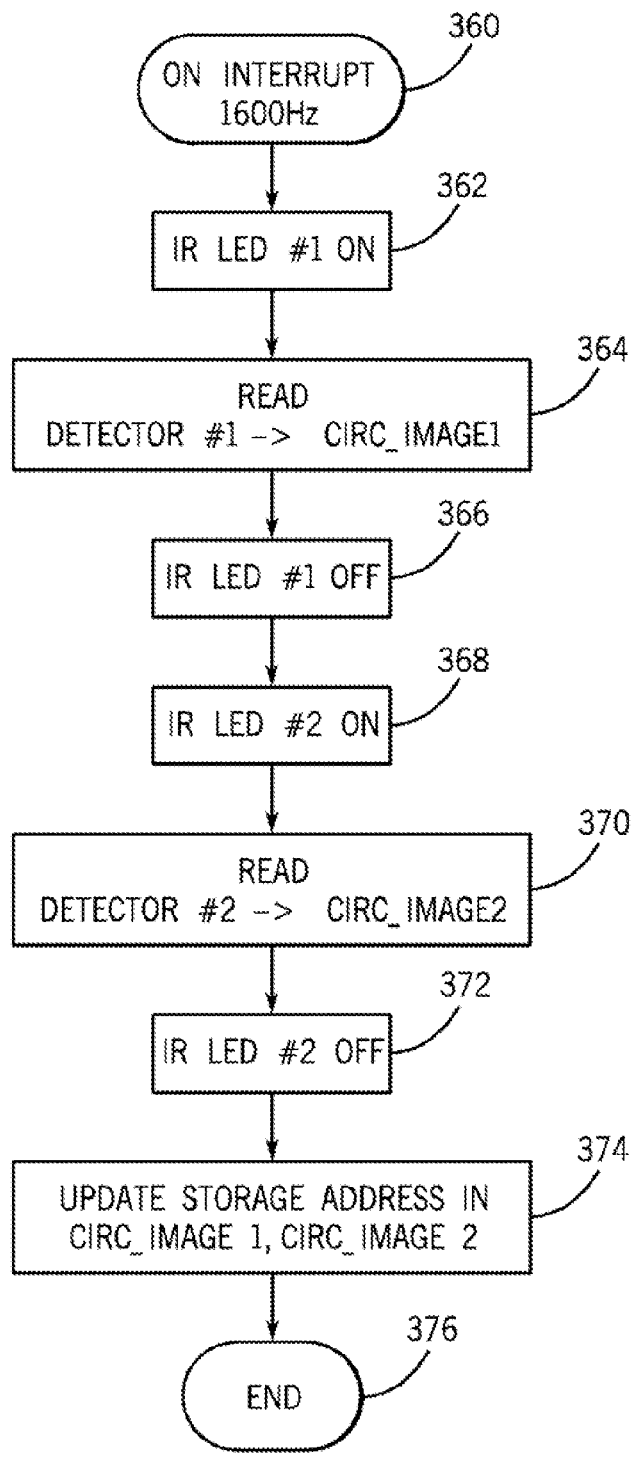
FIG. 8 is a flow diagram describing image acquisition by the controller of FIG. 7.

Controller 311 is preferably programmed to perform various functional steps which are seen in the flow diagram of FIG. 8 wherein the operation of controller 311 is described. Upon receiving an interrupt at 360, controller 311 activates the first collimated IR light source 308a, at 362. Controller 311 reads the output of the corresponding first sensor array 307a at 364 and places the output in a buffer "circ_image1." The first collimated IR light source 308a is de-activated at 366, and the second collimated IR light source 308b is activated at 368. Controller 311 reads the output of the second sensor array 307b at 370 and places this output in a buffer "circ_image2." The second collimated IR light source 308b is deactivated at 372.

Controller 311 then updates the addresses of the buffers at 374, and the subroutine ends at 376 until the next interrupt is received at 360. Those skilled in the art will appreciate that the contents of each buffer will be "n" forty-eight bit binary numbers which, when arranged as a 48×n matrix, reveal a two-dimensional projection of an image of the tablets scanned. For example, such an image (n=12) may appear as shown below:
000000000000111111110000000000000111111110000000
000000000000111111110000000000000111111110000000
000000000000111111110000000000000111111110000000
000000000000111111110000000000000111111110000000
000000000000111111110000000000000111111110000000
000000000000111111110000000000000111111110000000
000000000000111111110000000000000111111110000000
000000000000111111110000000000000111111110000000
000000000000111111110000000000000111110000000000
000000000000111000000000000000000000000000000000
which would represent two tablets passing in between a collimated IR light source 308a or 308b and its corresponding sensor array 307a or 307b. Other possible representations of the image are shown and described in the co-owned U.S. Pat.

No. 5,317,645. Each image (or frame) may be analyzed according to the methods disclosed in U.S. Pat. No. 5,317,645. As described below with reference to FIGS. 10A and 10B, each image is also preferably analyzed to determine whether the image represents a fragment of a tablet.

Co-owned U.S. Pat. No. 5,317,645 is hereby incorporated by reference in its entirety. This patent discloses a method and apparatus for counting discrete objects and addresses the issue of counting two or more clustered or bunched objects which a simple optical sensor would count as one object.

Figure 9:
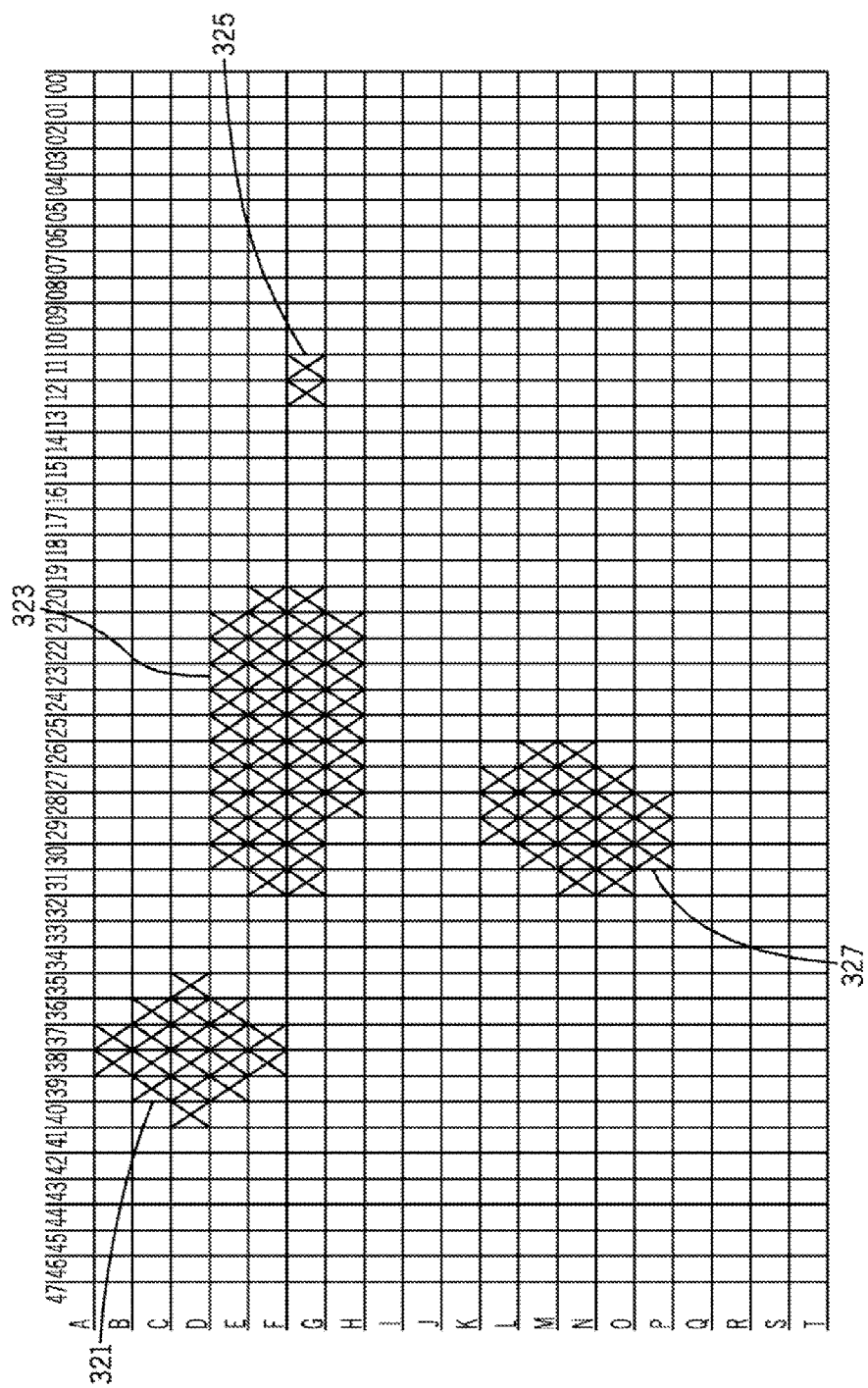
FIG. 9 is a diagram illustrating the images captured by the sensor arrays for image analysis.
Figure 10B:
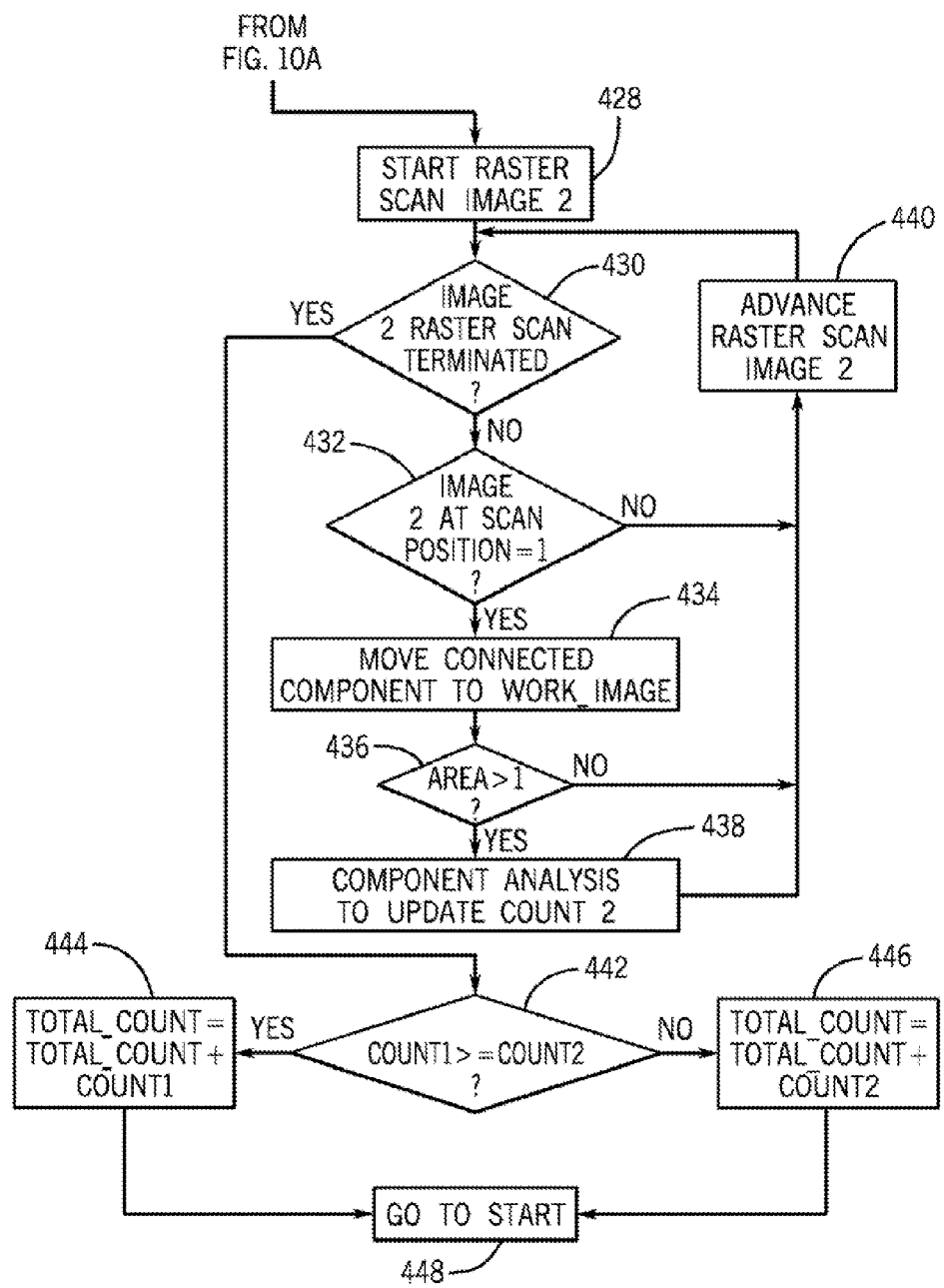

Turning now to FIGS. 9, 10A and 10B, the contents of the buffers circ_image1 and circ_image2 are read line-by-line to determine the start and the end of an image. An image includes at least one dark pixel (non-zero bit in an array) and typically includes many dark pixels which represent one or several tablets. The image represented in each buffer is then separately and conservatively analyzed to determine a count, and the higher count is accepted as the accurate count. For example, FIG. 9 shows a schematic rendering of the contents of the buffer circ_image1 as a 48×20 grid wherein empty boxes in the grid represent digital "zeros" and boxes marked with an "X" represent digital "ones." The image shown in FIG. 9 represents possibly four tablets 321, 323, 325 and 327. As will be explained below, tablet 325 is a tablet fragment and will not be counted as a tablet. Tablets 321 and 327 represent end views and tablet 323 represents a side view.

Figures 1, 10C:
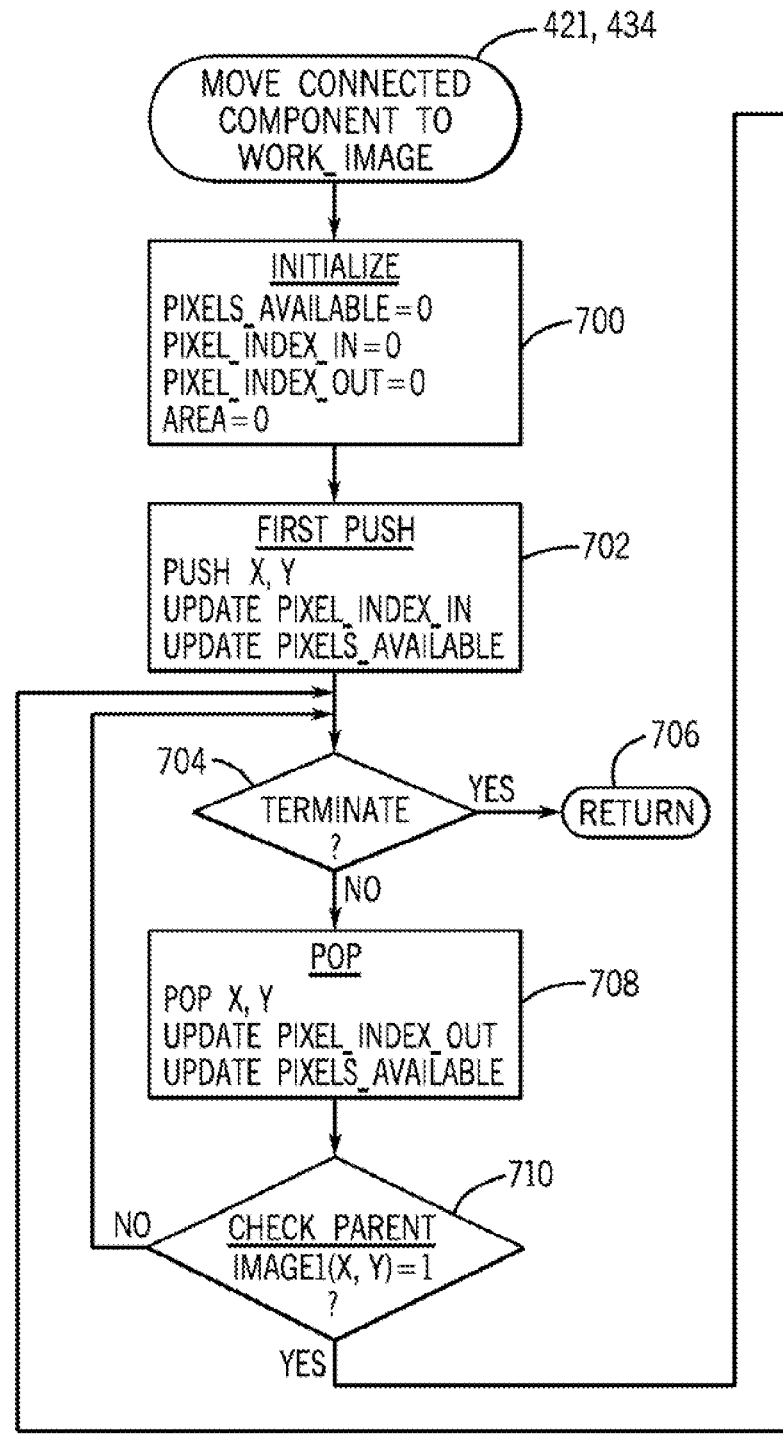
Figures 2, 10C:
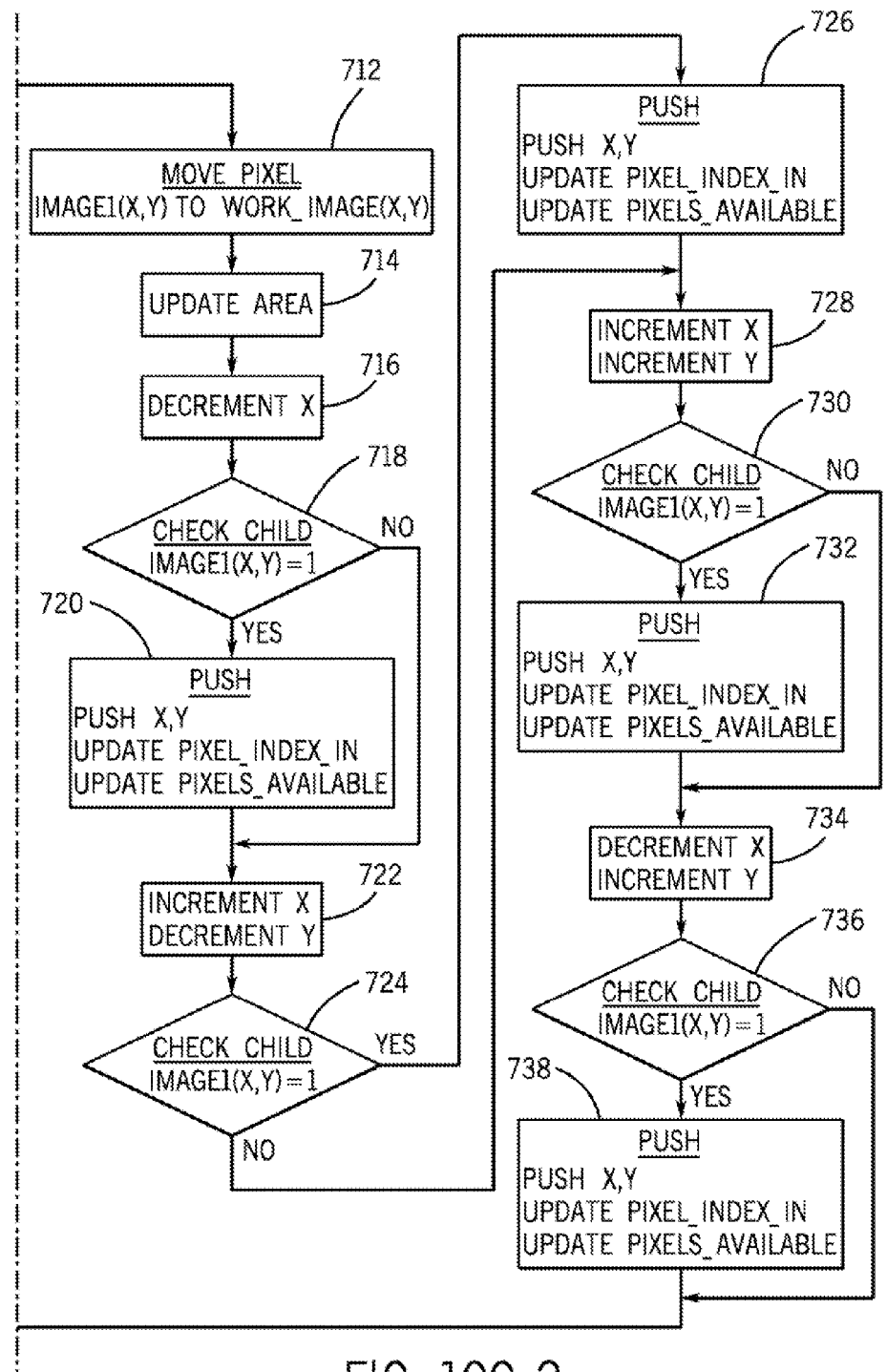

The image buffers circ_image1 and circ_image2 are analyzed according to the methods illustrated in FIGS. 10A, 10B and 10C. As shown in FIGS. 10A, 10B and 10C, starting at 400, controller 311 repeatedly reads the buffers at 402 to determine if any new data is available in the buffers circ_image1 and circ_image2. When data becomes available, the first line of data is read from each buffer at 404. The lines of data are analyzed at 406 to determine whether both lines are clear, i.e. all zeros. For example, line "A" in FIG. 9 would be represented in the buffer as all zeros. If the lines from both buffers are clear, it is determined at 408 whether these lines represent the end of an image or the fact that no image has been encountered yet. For example, line "A" in FIG. 9 represents the fact that no image has been encountered yet, and line "I" in FIG. 9 represents the end of an image. If the line read represents no image encountered yet, controller 311 returns to 402 and prepares to read the next line from each buffer circ_image1 and circ_image2 at 404. If at least one line read is not clear, as determined at 406, both lines are appended to "image1" and "image2" (additional buffers, not shown) at 410. Controller 311 continues to repeat this process until it again finds that both lines from the buffers circ_image1 and circ_image2 are clear at 406. For example, lines "B" through "H" in FIG. 9 would be appended to the buffer "image1." Line "I" in FIG. 9 indicates the end of the images which is determined at 408 in FIG. 10A. Prior to analyzing image1 and image2, controller 311 sets count1 and count2 to zero at 412. Both image1 and image2 are "raster scanned." That is, each bit of each line of the buffers image1 and image2 is read. As described above, the contents of the buffer image1 at this point in the analysis is represented in FIG. 9 as lines "B" through "H."

Generally, the scanning of image1 is commenced at 414. Scanning continues until terminated at 416. At 419, it is determined whether the bit (pixel) at the scan position is a digital one or a digital zero. For example, referring again to FIG. 9, raster scanning would begin at the position B00 and move across to position B47, continue from C00, etc. After scanning each position, if the position does not contain a digital one, the raster scan position is advanced at 427, and this is repeated until the scan is terminated at 416 or the raster scan position is determined at 418 to be a 1. The first time the raster scan detects a digital one, e.g., at B37 in FIG. 9, a subroutine "MOVE CONNECTED COMPONENT TO WORK_IMAGE" is performed at 421 (and described in detail below with reference to FIG. 10C). The main task of this routine is to copy the entire cluster of digital "ones" connected to the detected "one" into a new array named "work_image." A further task of this routine is to count the number of "ones" in the given cluster. Each cluster is referred to as a "connected component."

At 423 in FIG. 10A, it is determined whether the connected component represents one or more tablets or whether it is simply noise. If the area of the connected component is 1, it is considered to represent noise and the raster scan is advanced to the next pixel at 427. If the area is greater than 1, the connected component is preferably conservatively analyzed at 425 to determine how many tablets it represents and to update the count1 for image1 accordingly. The analysis at 425 is preferably performed according to co-owned U.S. Pat. No. 5,317,645 and also includes a comparison of the area of the connected component with a known average area to determine if the connected component represents a fragment. The raster scan is again advanced at 427 and the process continues until all the lines of image1 have been scanned. This is determined at 416 whereupon the scanning of image2 commences at 428.

The raster scanning of image2 (FIG. 10B) proceeds in substantially the same manner as the raster scanning of image1 until terminated at 430. At 432, it is determined whether the pixel scanned is a one or a zero. If it is a zero, the raster scan is advanced at 440, and this is repeated until scan is terminated at 430 or the pixel scanned is determined at 432 to be a one. The first time a non-zero pixel is encountered in the raster scan, the subroutine "MOVE CONNECTED COMPONENT TO WORK_IMAGE" is called at 434. The subroutine, mentioned above and described in detail below, determines whether the pixel is an orphan having an area of only one or part of a cluster having an area greater than one. If the area is not greater than one as determined at 436, the raster scan is advanced to the next pixel at 440. If the area of the work_image is greater than one as determined at 436, the area is preferably conservatively analyzed at 438 and count2 is updated for image2 accordingly. The raster scan is again advanced at 440, and the process continues until all the lines of image2 have been scanned. This is determined at 430 whereupon count1 and count2 are compared at 442. If count1>count2, the total_count is incremented by count1 at 444. If count2>count1, the total_count is incremented by count2 at 446. At 448, the controller returns to the start 400 (FIG. 10A) to analyze another two images. It will be recognized that each image is counted individually in order to provide a total count. Preferably, though not shown in FIGS. 10A-10C, controller 311 will maintain counts for the number of images which were analyzed as containing one tablet, the number of images which were analyzed as containing two tablets, the number of images which were analyzed as containing three tablets, etc.

FIG. 10C illustrates the operation of the subroutine "MOVE CONNECTED COMPONENT TO WORK_IMAGE" referred to above with reference to FIG. 10A at 421. It will be understood that the subroutine "MOVE CONNECTED COMPONENT TO WORK_IMAGE" referred to above with reference to FIG. 10B at 434, operates in the same manner but with reference to image2 rather than image1. In general, when a non-zero pixel is encountered in the scan of image1, the subroutine will look at four surrounding pixels to determine whether any of them are also non-zero pixels. The surrounding pixels are referred to as child pixels, and the surrounded pixel is referred to as a parent pixel. In addition, each non-zero child pixel will be treated as a parent, and its children will be examined. So long as new children are found, the process will continue until the area of an entire "connected component" is counted. In order to keep track of which pixels have been examined and which have not, the routine uses a stack which records the x-y coordinates of parent pixels which need to be examined. The stack is a FIFO (first in, first out) stack from which data is popped in the same order in which it has been pushed. As mentioned above, the connected component is thus incrementally copied into the two-dimensional array called "work_image."

Figure 2:
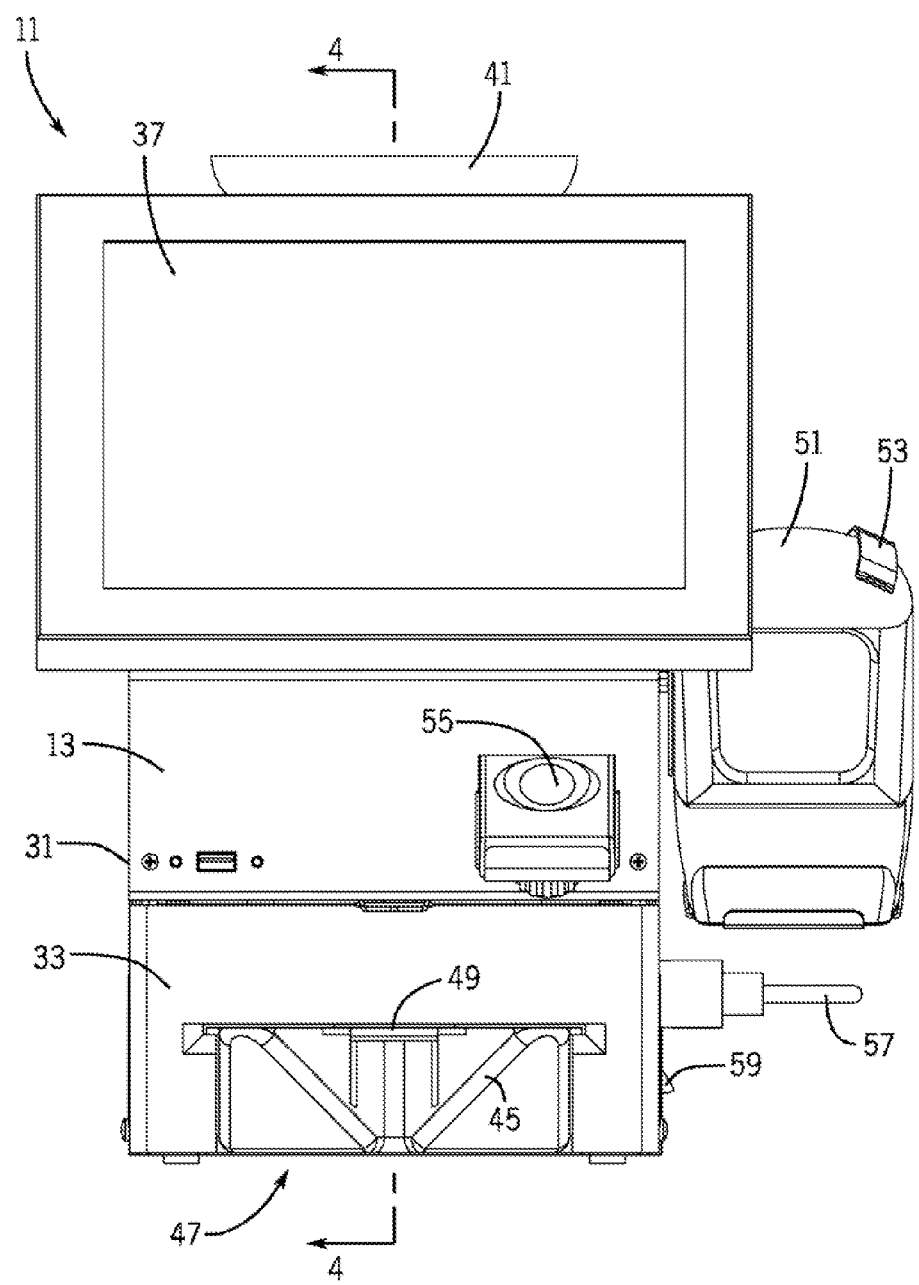
FIG. 2 is a front elevation view of the exemplary system of FIG. 1.

Turning now to FIGS. 10C-1 and 10C-2, the routines 421, 434 begin with initializing variables at 700. Pixels_available counts the number of parent pixels that are queued in the stack to be examined, and it is initialized to zero. Pixel_index_in is the index by which new pixel x-y data is pushed into the stack, and it is initialized to zero, the first location in the stack. Pixel_index_out is the index by which pixel x-y data is popped from the stack, and it is initialized to zero. The variable "area" is the total number of pixels in the connected component, and it is initialized to zero. At 702, the pixel encountered at 419, 432 (FIGS. 10A, 10B) is pushed into the stack, the variable pixel_index_in is updated, and the variable pixels_available is incremented by one. If it is determined at 704 that pixels_available=0, the process is complete and returns at 706 to 423, 436 (FIGS. 10A, 10B). Otherwise, the process continues at 708 to pop the next pixel from the queue, the variable pixel_index_out is updated, and the variable pixels_available is decremented by one. The popped pixel is examined at 710. If the popped pixel is zero, it means that the pixel was cleared in a previous iteration of the routine at 712 and cannot become a parent to new children. In this case, the routine returns to 704 to pop another pixel if there is one available. If the popped pixel is determined at 710 to be a one, it is copied at 712 to work_image and deleted from image1, i.e., the location variable image1 (x,y) is set to zero and the location variable work_image (x,y) is set to one. The area of the work_image is incremented by one at 714, and the x-coordinate of the parent pixel is decremented at 716 so that the child pixel to its right can be examined at 718. If the child pixel has the value 1, it is pushed into the stack at 720 and variables are updated as described above with reference to 702. In this way, the child pixel will be examined later as a parent pixel when the routine eventually returns to 408. If the child pixel has the value 0 as determined at 718, the routine continues to step 722 without pushing the pixel into the stack. At 722, the x-coordinate is incremented and the y-coordinate is decremented so that the next child pixel examined is located directly above the parent pixel. Steps 724 and 726 are substantially the same as steps 718 and 720. Both the x and y coordinates are incremented at 728 so that the next child pixel examined is located to the left of the parent pixel. Steps 730 and 732 are substantially the same as steps 718 and 720. At 734, the x-coordinate is decremented and the y-coordinate is incremented so that the next child pixel examined is located directly below the parent pixel. Steps 736 and 738 are substantially the same as steps 718 and 720. Now that the four children of the parent pixel have been examined and all of the non-zero children have been pushed into the stack, the routine returns to 704 to examine each of the non-zero child pixels as parents.

Figure 11A:
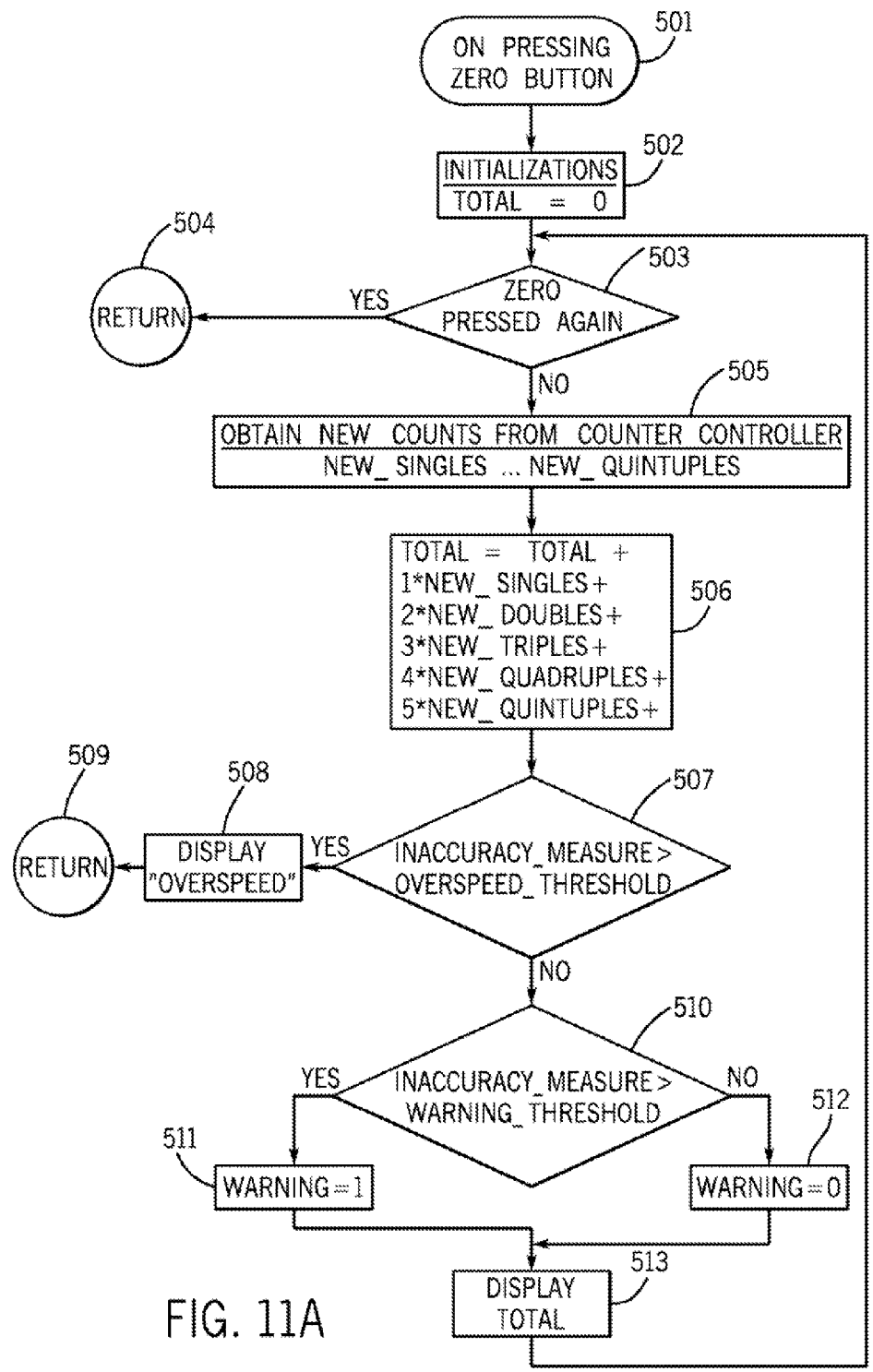
FIGS. 11A and 11B are flow diagrams illustrating processing of the counts determined from image analysis.
Figure 11B:
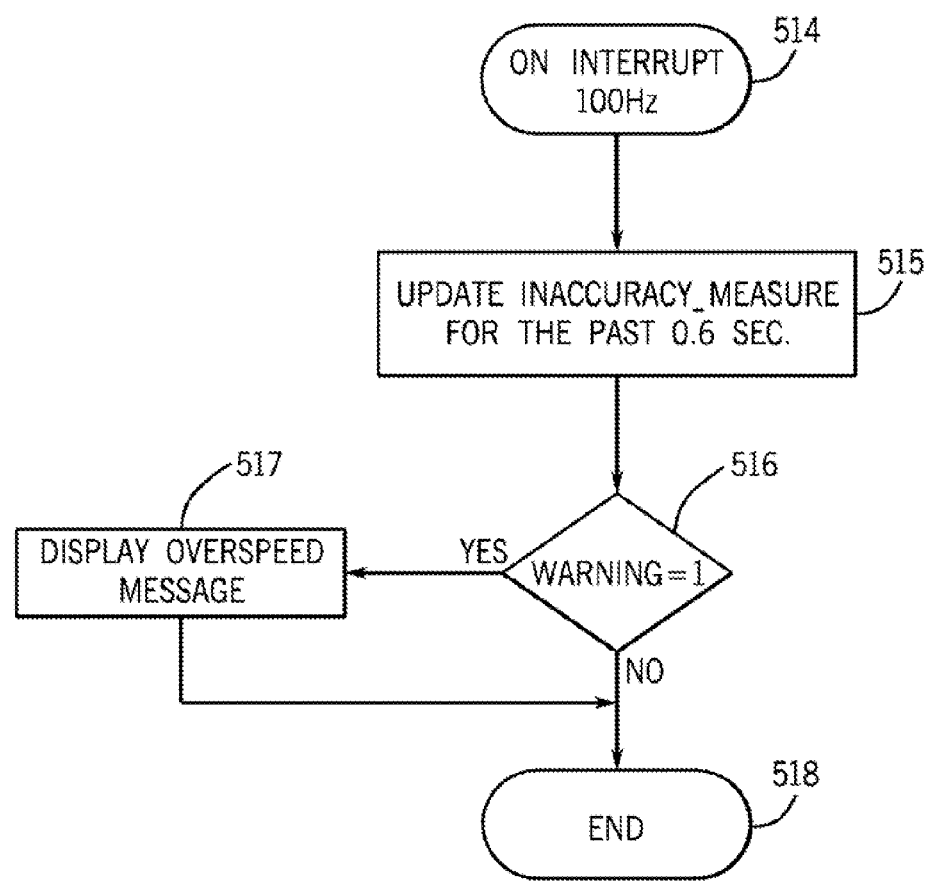

FIGS. 11A and 11B show flow charts for the programming of master controller 313. Referring now to FIGS. 11A and 11B, the main routine is initialized when a user activates resetting device 317 at 501. The total count is set to zero at 502. (Thus, resetting device 317 is referred to as a ZERO button in FIG. 11A.) If resetting device 317 is activated again during iterations of the routine, it is detected at 503 and returns at 504 to 501. Barring a halt by activation of resetting device 317, the routine obtains count information at 505 from controller 311. According to a preferred method, controller 311 provides master controller 313 with up to five different counts, each count relating to a number of images of a number of tablets. For example, as shown in FIG. 11A, the counts received from controller 311 are designated new_singles, new_doubles, new_triples, new_quadruples and new_quintuples. The new_singles count refers to the number of images determined by controller 311 to represent single tablets. The new_doubles count refers to the number of images determined by controller 311 to represent two tablets, etc. The total number of tablets is computed at 506 by multiplying each of the counts by the appropriate number, summing the products and adding to a previous total. After computing the total count, the routine determines at 507 whether an overspeed condition is present by comparing a periodically updated "inaccuracy_measure" to a constant "overspeed_threshold." If an overspeed condition is determined at 507, overspeed indicator 315 (alarm) is triggered at 508, and the routine returns at 509 to 501. If it is determined at 507 that no overspeed condition exists, it is determined at 510 whether a preset warning_threshold has been exceeded. If the warning_threshold has been exceeded, a warning flag is set at 511 to "1." If not, the warning flag is set at 512 to "0." Display 37 Count field 95, 1095 (e.g., FIGS. 24, 25) is then updated at 513, and the routine returns to 503 to obtain more new counts or be halted by resetting device 317.

The routine shown in FIG. 11A is interrupted at intervals of 10 ms to obtain an updated inaccuracy_measure which is used to determine an overspeed condition and set a warning flag as described above. The inaccuracy_measure is an indication of how quickly tablets are falling past sensor arrays 307a, 307b. If tablets are poured into system 11 and pass tablet counter 15 at too high a rate, an accurate count cannot be assured. In this preferred embodiment, the inaccuracy_measure is a weighted sum of the clustered tablets counted during the last 0.6 seconds. According to the preferred embodiment, the inaccuracy_measure is the sum of new_singles__06+4*new_doubles__06+9*(new_triples__06+new_quadruples__06+new_quintuples__06), where new_singles__06 is the number of new_singles received in the past 0.6 seconds, new_doubles__06 is the number of new_doubles received in the past 0.6 seconds, etc. The inaccuracy_measure is therefore a function of the actual rate at which tablets are poured as well as a function of the tendency of the tablets to cluster.

FIG. 11B shows a flow chart of the routine for updating the variable inaccuracy_measure. On a 100 Hz interrupt at 514, inaccuracy_measure is updated at 515. At 516, the previously set warning flag is checked and if the flag is set to "1", a warning message is triggered at 517 resulting in display of an overspeed message on display 37. The overspeed message may, for example, be a pop-up message on display 37 or a message such as "Pour is Too Fast! Count Failed." may be displayed in Main Instructions field 91, 1091 (e.g., shown on screen displays of FIGS. 24, 25). The overspeed message presented on display 37 prompts the user to re-pour the medication into feeder 19 in order to ensure an accurate count. The routine ends at 518. It will be appreciated that, although not required, the overspeed_threshold and the warning threshold values can be set according to the accuracy requirements of the user.

Figure 12B:
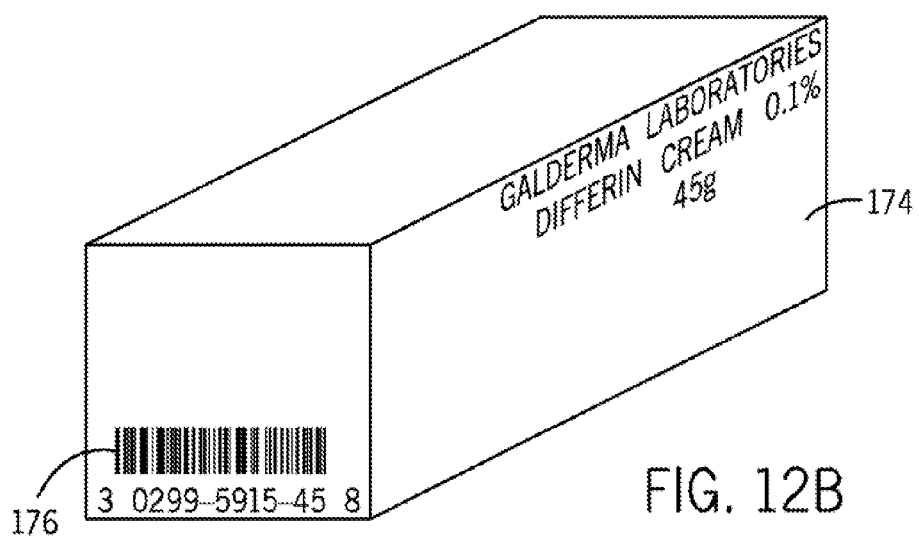
FIG. 12B is an exemplary box containing a tube of an ointment-type medication.

Referring once again to FIGS. 1-7, there are shown other external and internal components of system 11. A barcode scanner 51 is secured to housing 13 sidewall 31 by support 53. Barcode scanner 51 is a type of input device which enables a user to input information embedded in a barcode to data processing platform 17. While barcode scanner 51 is shown in the example, other types of code readers, such as a radio frequency identification tag (RFID) reader (not shown) may be utilized separately or in combination with barcode scanner 51. An RFID reader would be useful, for example, to read an RFID tag associated with a medication container (e.g., containers 174, 175 in FIGS. 12A, 12B).

A biometric sensor 55 is mounted to housing 13 front wall 33. Biometric sensor 55 may be realized by a fingerprint sensor as illustrated, a voice print analyzer, or other suitable means. In the example, data processing platform 17 interfaces with both barcode scanner 51 and biometric sensor 55.

Power cord 57 supplies electrical power to power supply 58 of system 11. A rocker-type ON/OFF switch 59 is provided along housing 13 sidewall 31 to control the electrical power delivered to power supply 58.

Figure 14A:
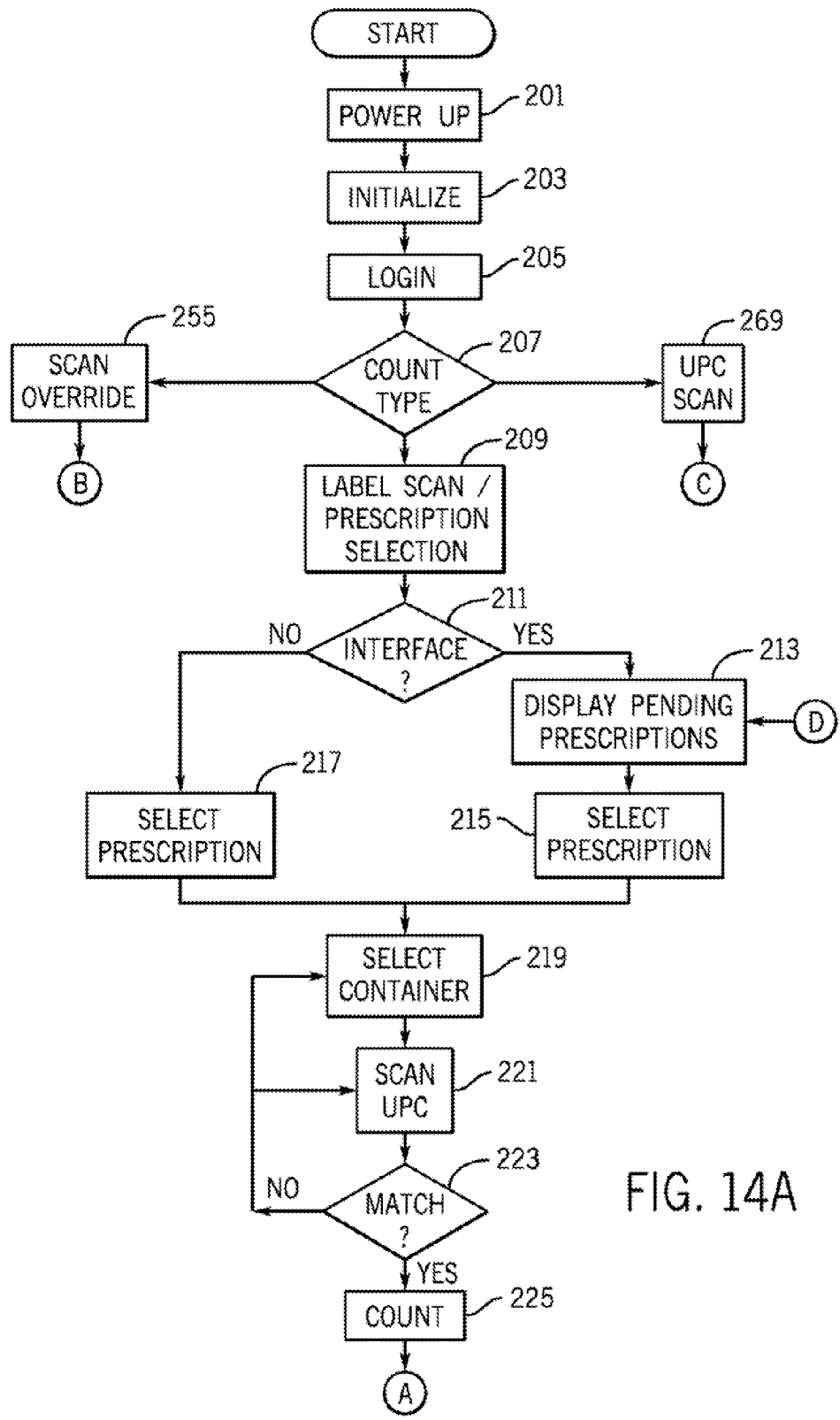
FIGS. 14A-14C are flow diagrams showing exemplary steps of a pharmacy workflow management process capable of being performed by the system of FIG. 1.
Figure 14B:
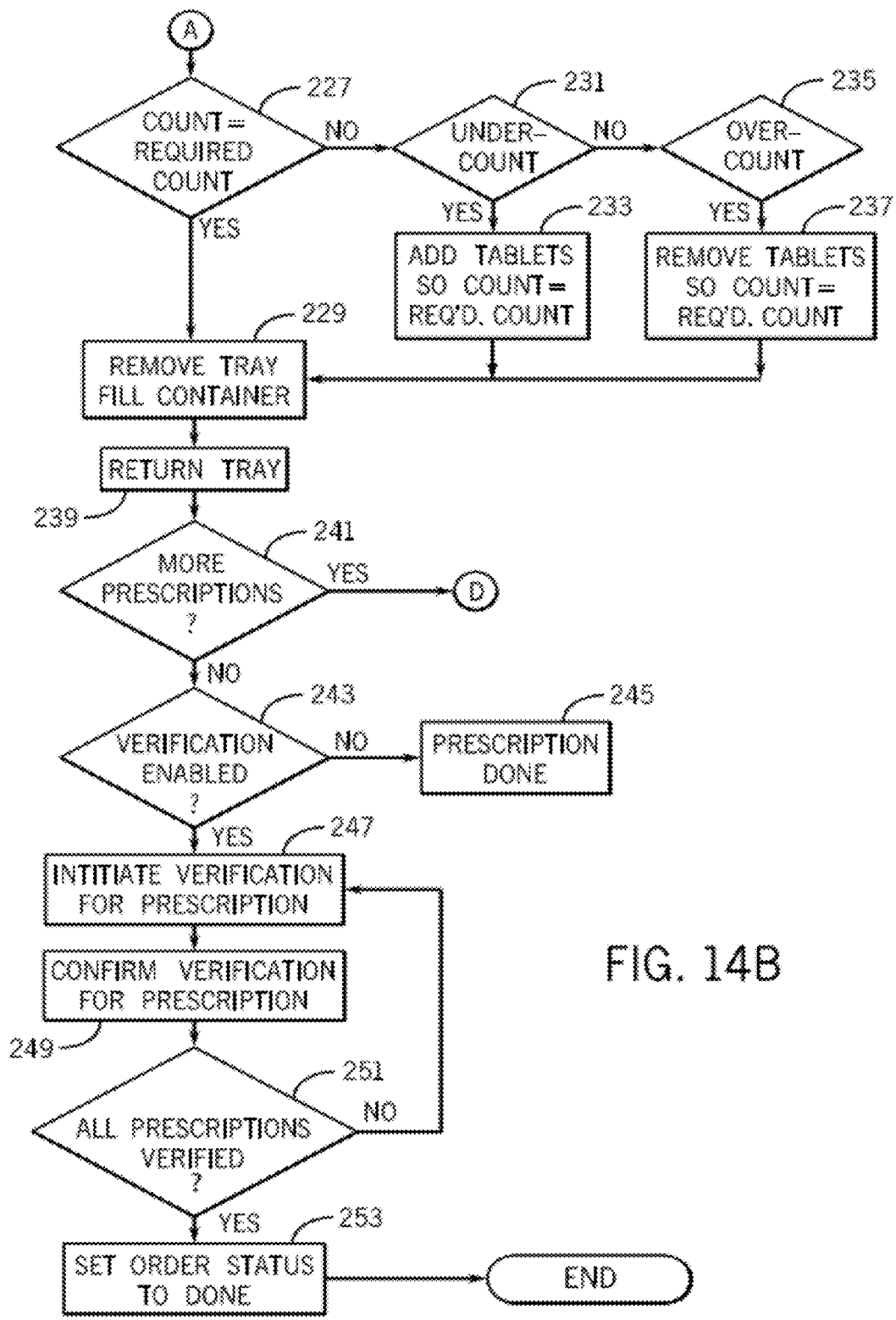
Figure 14C:
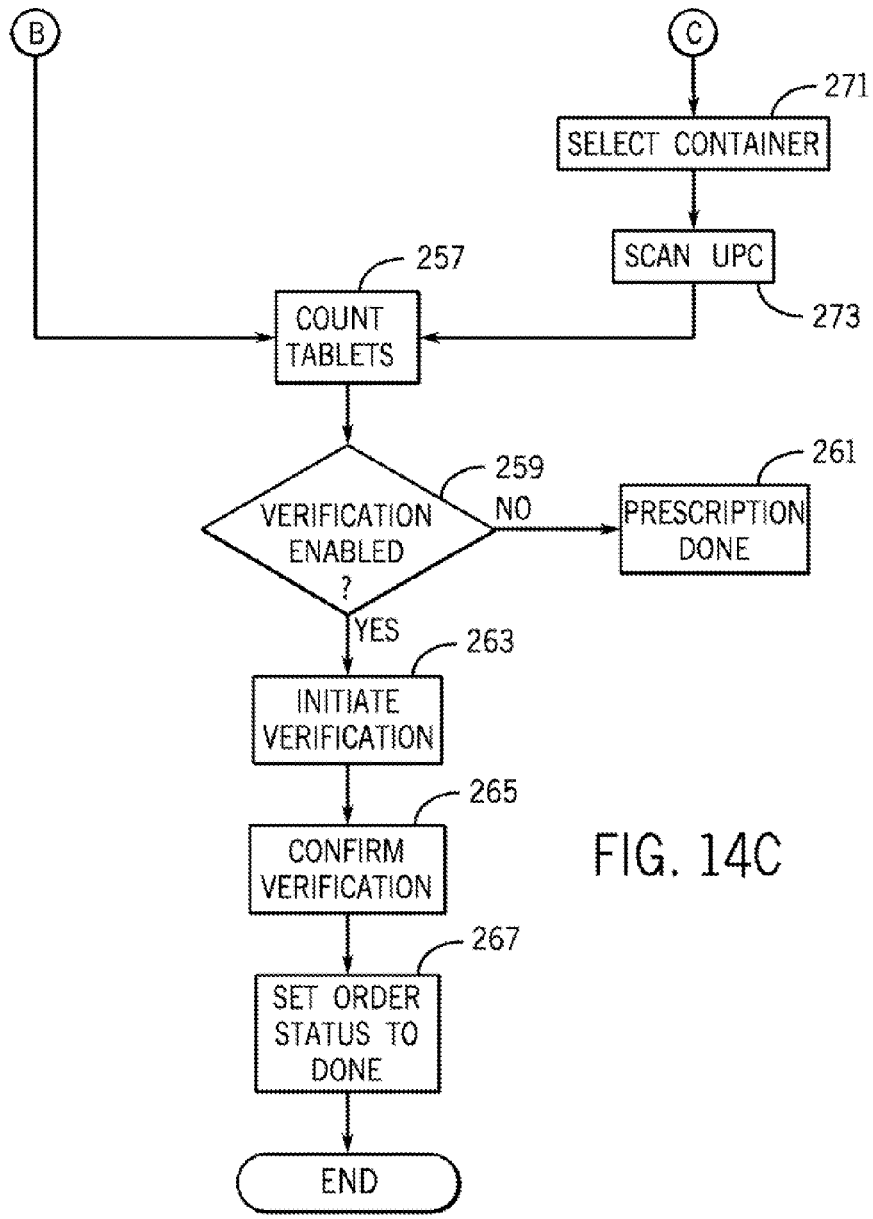

Referring now to FIG. 6, data processing platform 17 interfaces to a number of components that are housed within system housing 13, including non-volatile data storage 61 (which may be realized by a hard drive, flash memory or other suitable non-volatile memory means), an audio speaker 63 and display 37. Data processing platform 17 (which is preferably realized by a printed circuit board having a microprocessor, memory and supporting interface circuitry) executes operating system and application logic that is persistently stored in the non-volatile data storage 61 and loaded onto the data processing platform 17 for execution thereon. Such execution provides for automatic control over system 11 in accordance with the operations described herein (FIGS. 14A, 14B and 14C).

Optionally, a keyboard and mouse (not shown) represent further types of input devices which could be utilized with system 11 permitting a user to input information to data processing platform 17. Optional keyboard and mouse would provide the user with the ability to enter relevant information about a prescription. Such information is more preferably input by the user through touch-screen-type display 37 and/or barcode scanner 51 as previously described. In other systems, information may be provided from another data processing system that is coupled to system 11 over a communication link therebetween.

Data processing platform 17 also preferably interfaces to an optical drive 69 (which may be realized by a CDROM drive, DVD-ROM drive or other suitable device) and an image scanner 71. Optical drive 69 can be mechanically supported in an independent housing and interfaced to data processing platform 17 through suitable connection means. Barcode scanner 51 and image scanner 71 are preferably mechanically supported in independent housings and interfaced to data processing platform 17 through suitable connections (such as a wired or wireless data link therebetween). Alternatively, barcode scanner 51 and/or image scanner 71 can be housed within housing 13. In addition, system 11 may include a printer 72 that prints a prescription label 143 and prescription order paperwork 147 for each prescription of a prescription order. System 11 may also include a connection such as a USB port or other similar connection to enable batch prescription data to be transferred to/from system 11.

Non-volatile data storage 61 stores an image database that maintains image files for a large number of commercially-available medications indexed by NDC number (hereinafter referred to as the "medication image database"). Each image file is an electronic image of a particular medication as identified by its corresponding NDC number. Exemplary image files from medication image database are illustrated in Medication Image field 77, Image field 138 and Collated Order field 89 of the interfaced system 11 screen displays (e.g., FIGS. 17, 18, 20, 22, 24, 26, 28, 30, 31, 34-35) and Medication Image field 1077 of the non-interfaced system 11 screen displays (e.g., FIGS. 19, 21, 23, 25, 27, 32-33). The medication image database is updated periodically by loading updated files stored on an optical disk into the system via optical drive 69 or via updates from PMS 21 via link 23. Alternatively, the medication image database may be updated from a remote computer system coupled thereto over a network link (e.g., over a LAN or WAN/Internet), for example, from a database provider such as First DataBank® of San Bruno, California or Medi-Span® of Indianapolis, Ind.

Non-volatile data storage 61 may also store a database of records indexed by prescription numbers (hereinafter referred to as the "prescription record database"). A prescription number is a unique number assigned by the pharmacy to each prescription. Exemplary prescription numbers can be seen in Prescription Number field 135 of New Order screen 119 of FIG. 17. The unique prescription number is used to track all information related to fulfillment of the prescription. The prescription record database may be local on storage 61 for systems which are interfaced with PMS 21 and for stand-alone systems 11 which are not interfaced with PMS 21. Alternatively, the prescription record database could be maintained by PMS 21 and accessed by system 11 via link 23.

As described below, the prescription record database for an interfaced system 11 may include a record of each prescription awaiting fulfillment, examples of which (prescriptions 127, 129, 131) are seen on New Order screen 119 of FIG. 17. The information could include patient name, prescription number, medication type, strength and form, and required medication quantity. Other information in prescription record database for each prescription may include the status of each such prescription (e.g., fully or partially fulfilled, held because medication is not available, held because of a prescription data error, etc.).

The prescription record database for a non-interfaced system 11 may include a record of each prescription for which fulfillment has been initiated as well as the status of each such prescription (e.g., fully or partially fulfilled, held because medication not available, held because of an error, etc.). The record could include the NDC, the prescription number, the medication type, strength and form, and the required medication quantity.

The prescription records for each prescription number in the prescription record database may also include an image file of the original script of the prescription (as written by the doctor) and an image file of the printed prescription label for the prescription number. These image files are output to system 11 prescription record database from PMS 21 or may be loaded into the prescription record database by means of image scanner 71.

The prescription record database for each prescription number is updated following prescription fulfillment with a record such as record 70a (FIG. 37A) for a single prescription or record 70b (FIG. 37B) for all prescriptions collated by patient including all desired information relating to the fulfillment transaction. Record 70a or 70b of prescription fulfillment may be accessed from non-volatile data storage 61 for a user-determined amount of time.

For interfaced systems 11, a prescription record database maintained by PMS 21 may also be updated following prescription fulfillment with a record including all desired information relating to the fulfillment transaction. Such record is maintained for archival purposes.

Pharmacy workflow in conjunction with operation of system 11 will now be described with reference to the flow diagram of FIGS. 14A, 1413 and 14C and exemplary screen displays of FIGS. 15-36. The pharmacy workflow management executed by system 11 as shown in the examples of FIGS. 14A-14C and the screen displays of FIGS. 15-36 is enabled by a program of instructions residing in non-volatile data storage 61 of data processing platform 17. When executed, the instructions enable system 11 to perform the pharmacy workflow management described herein. For interfaced systems 11, the instructions enable system 11 to receive prescriptions from PMS 21. The prescriptions may be stored in prescription record database on non-volatile storage 61. The instructions further enable a user to select one of the stored prescriptions for fulfillment and for the selected prescription to be retrieved. The instructions enable required medication to be counted and can create a record (e.g., record 70a or 70b) that the quantity of the medication required by the retrieved prescription has been counted. For non-interfaced systems 11, the instructions enable counting and verification of prescriptions as described herein.

It will be apparent that system 11 provides the user (e.g., a registered pharmacist, a pharmacy technician or other authorized person) with a powerful tool which enables control of pharmacy workflow directly from system 11. System 11 enables counting of any tablet-form product including medications, nutriceuticals, and supplements. System 11 can also manage workflow involving containers not requiring tablet counting, such as a medication-containing box 174 as will be described.

The operations begin at block 201 when the user places an on/off switch 59 in the "on" position if system 11 is not already operating. In block 203, data processing platform 17 is initialized, and system 11 is placed in a ready state.

During initialization, a check is performed to determine whether system 11 is interfaced with PMS 21. If an interface with PMS 21 does not exist, system 11 is operable as a stand-alone system. Prescription order fulfillment processing steps are described herein for both interfaced and non-interfaced systems 11. If an interface is present, all prescription orders which have been validated by PMS 21 are sent to system 11 via communication link 23 and are stored in prescription record database in files organized by prescription number in non-volatile data storage 61 awaiting fulfillment. Alternatively, validated prescription orders may be delivered to system 11 via batch data delivery as previously described.

In block 205, a user is authenticated and logs into system 11. In the example, user authentication and login can occur in several ways. For example, a user can enter a user ID (name and password in the example) into system 11 by means of a QWERTY-type keypad (e.g., keypad 65, FIG. 70) displayed on touch-screen-type display 37, by means of an optional keyboard (not shown), or by means of biometric sensor 55. The user ID is received by data processing platform 17.

In the example, biometric sensor 55 is a fingerprint sensor. Everyone is known to have unique, immutable fingerprints. A wide number of fingerprint sensors are commercially available including, for example, the VPASS fingerprint sensor distributed by Bioscrypt Inc. of Mississauga, Ontario, Canada. If the presented fingerprint matches a stored fingerprint, biometric sensor 55 communicates the user ID associated with the stored fingerprint to processing platform 17. If the presented fingerprint fails to match a stored fingerprint, biometric sensor 55 communicates an error message to processing platform 17.

If the user ID keyed in by the user or output from biometric sensor 55 to processing platform 17 is valid, processing platform 17 identifies the user and permits user login, enabling continued processing (blocks 207 and on). If the user ID is incorrect or if an error message is transmitted from biometric sensor 55, then data processing platform 17 denies user access, and the continued operations of blocks 207 and after are not performed. In this manner, only authenticated users can use system 11 for its intended purpose. Similar authentication operations may be performed for other biometric sensor types. Alternatively, user authentication can be accomplished by other known means, such as a smart card reader or an RFID reader.

Figure 15:
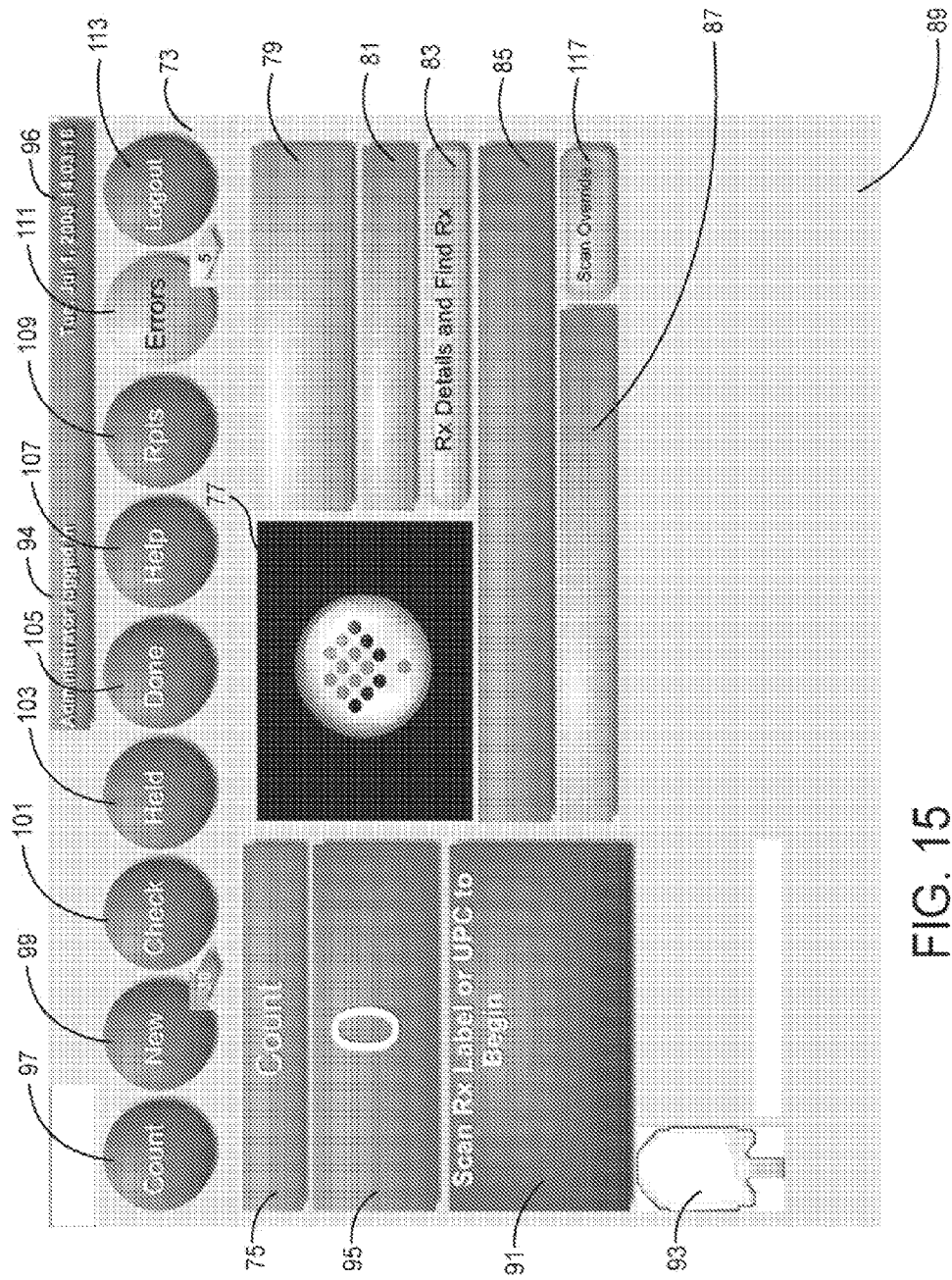
FIGS. 15-36 are exemplary images of various user interfaces for the software of the system of FIG. 1 separately shown for (a) the system when interfaced with a Pharmacy Management System and (b) for the system when not interfaced with a Pharmacy Management System with certain interfaces being applicable to the system of FIG. 38.
Figure 16:
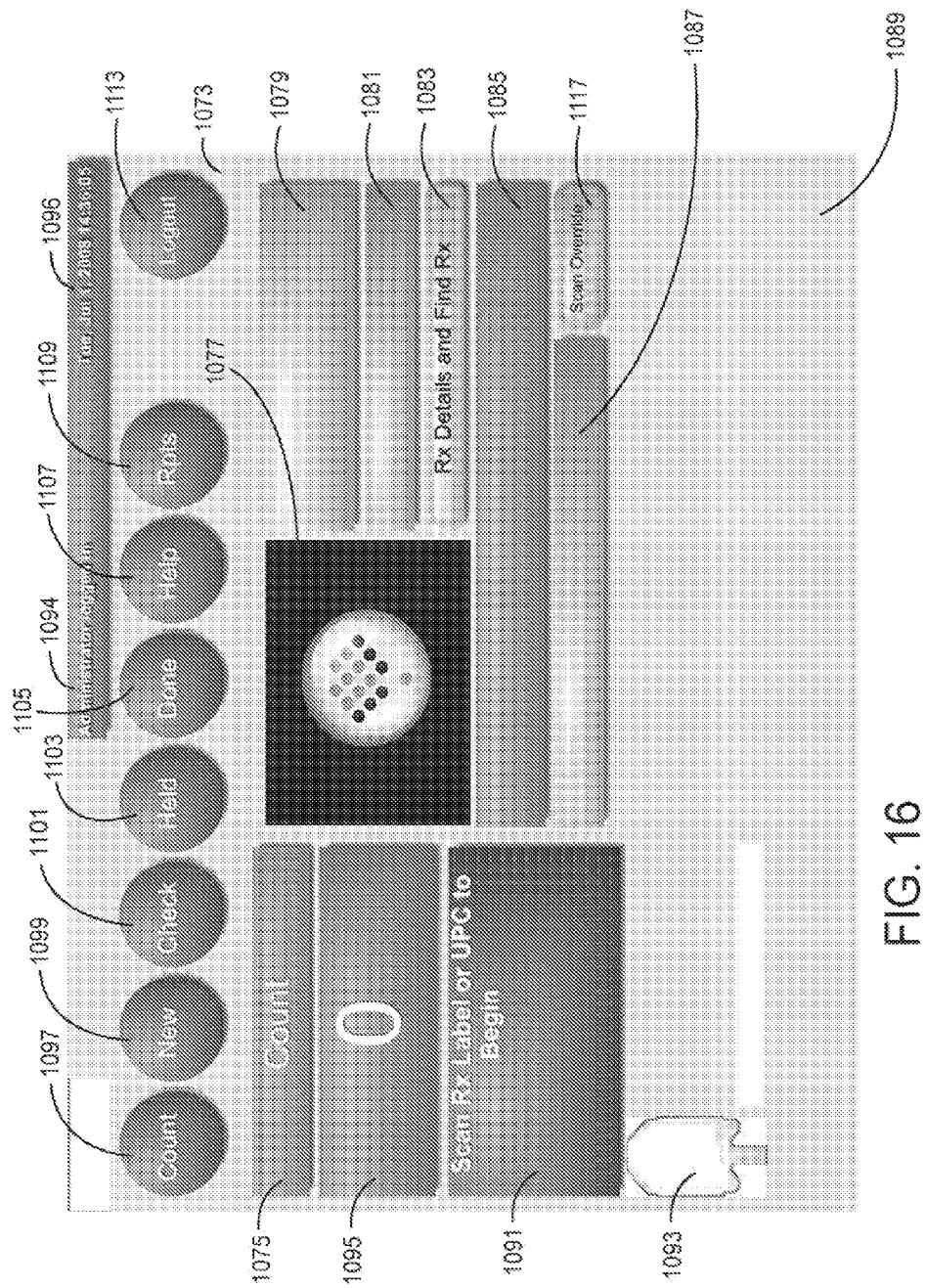

Following successful login at block 205, a Start screen 73 or 1073 is shown on touch-screen-type display 37 as illustrated in FIGS. 15 and 16. Start screen 73 is shown if system 11 is interfaced to PMS 21 and Start screen 1073 is shown if system 11 is not interfaced to PMS 21. In the example, each Start screen 73, 1073 includes controls in the form of graphical user interfaces (GUIs) which permit the user to select from several processing options. Information-displaying fields are also provided. The controls and fields shown on Start screens 73, 1073 and on the further displays of FIGS. 17-36 are non-limiting examples provided for purposes of illustration only. It should further be recognized that the screen displays shown in FIGS. 15-36, and the sequence of the screen displays, are illustrative and are not intended to be limiting.

In the example, each Start screen 73, 1073 provides information indicating that three counting modes are available. The counting modes are: (1) a customer label scan/prescription selection counting mode (blocks 209-253), (2) a scan override counting mode (blocks 255-267) and (3) a Universal Product Code ("UPC") barcode scan counting mode (blocks 269, 271, 273 and 257-267). Each counting mode can be performed by either interfaced or non-interfaced systems 11 except that non-interfaced systems do not receive validated prescriptions orders directly from PMS 21 via link 23 or batch delivery. Each counting mode is described below.

Referring to FIG. 15, Start screen 73 of interfaced system 11 shows exemplary fields and controls. The fields and controls which are active on a particular screen correspond to the particular action then in process. Fields include: an Activity field 75, a Medication Image field 77, a Prescription Status Indicator field 79, a Customer/Patient field 81, a Prescription Number field 83, a Medication Description field 85, a Medication NDC field 87, a Collated Prescription Status field 89, a Main Instructions field 91, a Tray Status field 93 and a Count Status field 95. Fields for the User Name 94 and Date and Time of Day 96 are also provided. In the example, the user name is shown as "Administrator" indicating that the logged-in user is also system Administrator. System 11 may be configured to display the user's given and surnames in field 94, if desired.

Activity field 75 shows the current system 11 operation. Medication Image field 77 shows a graphic image of the color, shape, markings and form of the medication required by the prescription being fulfilled. Each image is retrieved from the medication image database based on the NDC number of the medication required by each prescription. Prescription Status Indicator field 79 indicates the status of the prescription in the workflow. Customer/Patient field 81, Prescription Number field 83, Medication Description field 85 and NDC field 87, respectively, provide information about the patient name, prescription number, medication description and medication NDC for the selected prescription. Collated Prescription Status field 89 shows the status of all prescriptions grouped together for the patient and may include an image of each medication required by the prescription.

Main Instructions field 91 prompts the user to take an action. As shown on Start screen 73 of FIG. 15, Main Instructions field 91 includes a prompt to scan a prescription label or a UPC barcode on a medication package to initiate one of the first two counting modes. Tray Status field 93 indicates whether a tray 45 is detected in bay 47. Tray 45 is shown as detected in Start screen 73 because no "x" symbol is imposed over the tray icon. Vial size field 92, 1092 indicates a recommended vial size suitable to hold the counted tablets. The recommended vial size may be based on the size of the tablets and count. Finally, Count Status field 95 indicates the quantity of tablets counted by tablet counter 15. Start screen 73 displays a 0 in Count Status field 95 indicating that no count has yet occurred.

Referring further to FIG. 15, controls include: a Count push button 97, a New push button 99, a Check push button 101, a Held push button 103, a Done push button 105, a Help push button 107, a Rpts (reports) push button 109, an Errors push button 111 and a Logout push button 113. Additional control push buttons include a Cancel Fill push button 115 and a Scan Override push button 117.

Selection of Count push button 97 clears the current screen for a new count while selection of New push button 99 causes system 11 to display any existing prescription orders in non-volatile data storage 61 that await selection for fulfillment (block 213).

Selection of Check push button 101 causes system 11 to display any prescription orders that have been counted using system 11, but which await final checking and verification by a registered pharmacist (blocks 247-251).

Selection of Held push button 103 shows any prescriptions that have been placed on hold and have not been fulfilled. Prescriptions may be placed on hold, for example, if medication is not available to fulfill the prescription.

Selection of Done push button 105 causes system 11 to display any existing prescription orders that have been fulfilled using system 11. If an interface with PMS 21 is provided, prescriptions are preferably collated by patient for ease of review by the user.

Selection of Help push button 107 provides access to support, system setup and configuration details, user and medication database maintenance as well as technical resources.

Selection of Rpts (reports) push button 109 takes the user to a list of available reports which can be sorted by category and viewed on display 37 or printed with printer 72. For example, the reports include a record (e.g., record 70a or 70b of FIGS. 37A, 37B) of each prescription fulfilled by system 11.

Errors push button 111 appears only if system 11 has determined that data received from PMS 21 cannot be processed. Selection of Errors push button 111 displays prescriptions flagged with the error so that the user can determine the source of the error and make appropriate corrections so that the prescription can be fulfilled using system 11.

Selection of Logout push button 113 permits the user to log off system 11.

Selection of the Cancel Fill push button 115 permits a user to interrupt any process at any time. The Cancel Fill push button 115 can be selected once a prescription is selected for processing, or counting has begun, or at any time the Cancel Fill button is visible. Interrupting a process may be useful if the user wishes to start over or stop use of system 11 to perform a task unrelated to system 11.

Scan Override push button 117 permits a user to proceed directly to tablet counting without any preliminary processing steps (blocks 255-267). For example, Scan Override 117 can be selected when only a tablet count is required as part of managing inventory by counting tablets in inventory.

Referring next to FIG. 16, Start screen 1073 of non-interfaced system 11 also includes information-providing fields and user-selectable control push buttons. These fields and controls provide the information and control as described in connection with the like fields and push buttons described in connection with Start screen 73. Fields include: an Activity field 1075, a Medication Image field 1077, a Prescription Status Indicator field 1079, a Customer/Patient field 1081, a Prescription Number field 1083, a Medication Description field 1085, a Medication NDC field 1087, a Main Instructions field 1091, a Tray Status field 1093 and a Count Status field 1095. Fields for the User Name 1094 and Date and Time of Day 1096 are provided. No Collated Prescription field 89 is required because the non-interfaced system 11 does not access PMS 21 to receive and manage collated prescriptions.

Control push buttons on Start screen 1073 include: a Count push button 1097, a New push button 1099, a Check push button 1101, a Held push button, a Done push button 1105, a Help push button 1107, a Rpts (reports) push button 1109 and a Logout push button 1113. Additional control push buttons include a Cancel Fill push button 1115 and a Scan Override push button 1117. These controls function as described in connection with screen 73. A Hold 1116 and a Cancel Rx 1118 push button (FIG. 32) may be provided to place the prescription into a hold status for fulfillment at a future time or to terminate the prescription. If desired, a single prescription or even an entire prescription order can be cancelled by pushing Cancel Rx button 1118. This status will complete the processing for the prescription (e.g., prescription 127) and require nothing further. Hold and Cancel Rx push buttons may also be provided on displays for interfaced systems 11.

Referring again to the flow diagram of FIG. 14A, at decision point 207, the user determines the type of counting mode. The process proceeds to entry block 209 if the user selects the customer label scan/prescription selection counting mode, to entry block 269 if the user selects the medication container UPC barcode scan counting mode, or to entry block 255 if the user selects the scan override counting mode.

Referring to FIGS. 14A and 14B, exemplary steps of the customer label scan/prescription selection counting mode are now described with respect to blocks/decision points 209-253. If an interface between system 11 and PMS 21 exists (decision point 211) the process moves to block 213. Entry of block 213 (by pressing New button 99) results in display of prescriptions which await fulfillment on New Order screen 119 illustrated in FIG. 17. The prescriptions received from PMS 21 are retrieved from the prescription record database residing in non-volatile data storage 61.

New Order screen 119 contains fields which provide information for the user regarding each prescription and the prescription order. Fields include: a Patient Name field 121, a Pharmacy-Assigned Patient Identification Code field 123 and a Delivery-Status field 125 indicative of whether the patient is waiting for the prescription or will pick up the prescription later.

New Order screen 119 also shows one or more prescriptions for each patient. The prescriptions are preferably collated by patient as illustrated in FIG. 17. Grouping together of pending prescriptions by patient makes it easier for the pharmacist or pharmacy technician to fulfill all prescriptions of all prescription orders pending for each patient. As illustrated in FIG. 17, three prescriptions 127, 129, 131 are shown for fictitious patient Pablo Martini. Each prescription 127-131 shown includes fields for the patient's name 133, pharmacy-assigned prescription number 135, medication name, strength and form information 137, medication quantity 139, medication image 138 and status as a new or previously-fulfilled prescription 140. Collectively, prescriptions 127-131 may represent a single prescription order if placed for fulfillment together or may represent separate prescription orders if placed separately. Touching one of the up/down arrows 141 permits the user to scroll up or down to view pending prescriptions for patients Zage and Gelty and others.

New Order screen 119 may also include some or all of the control push buttons 97-113 described above in connection with Start screen 73. New Order screen 119 may also include User Name and Date/Time fields 94, 96 or other information fields.

In block 213 of FIG. 14A, a user may display New Order screen 119 and retrieve a prescription for fulfillment in subsequent block 215. The user may select New push button 99 on any screen on which New push button 99 is displayed. This will call up the New Order screen 119 of FIG. 17. The user may then touch one of the prescriptions to select a prescription for fulfillment at block 215 and trigger retrieval of the selected prescription from non-volatile storage 61.

Figure 17:
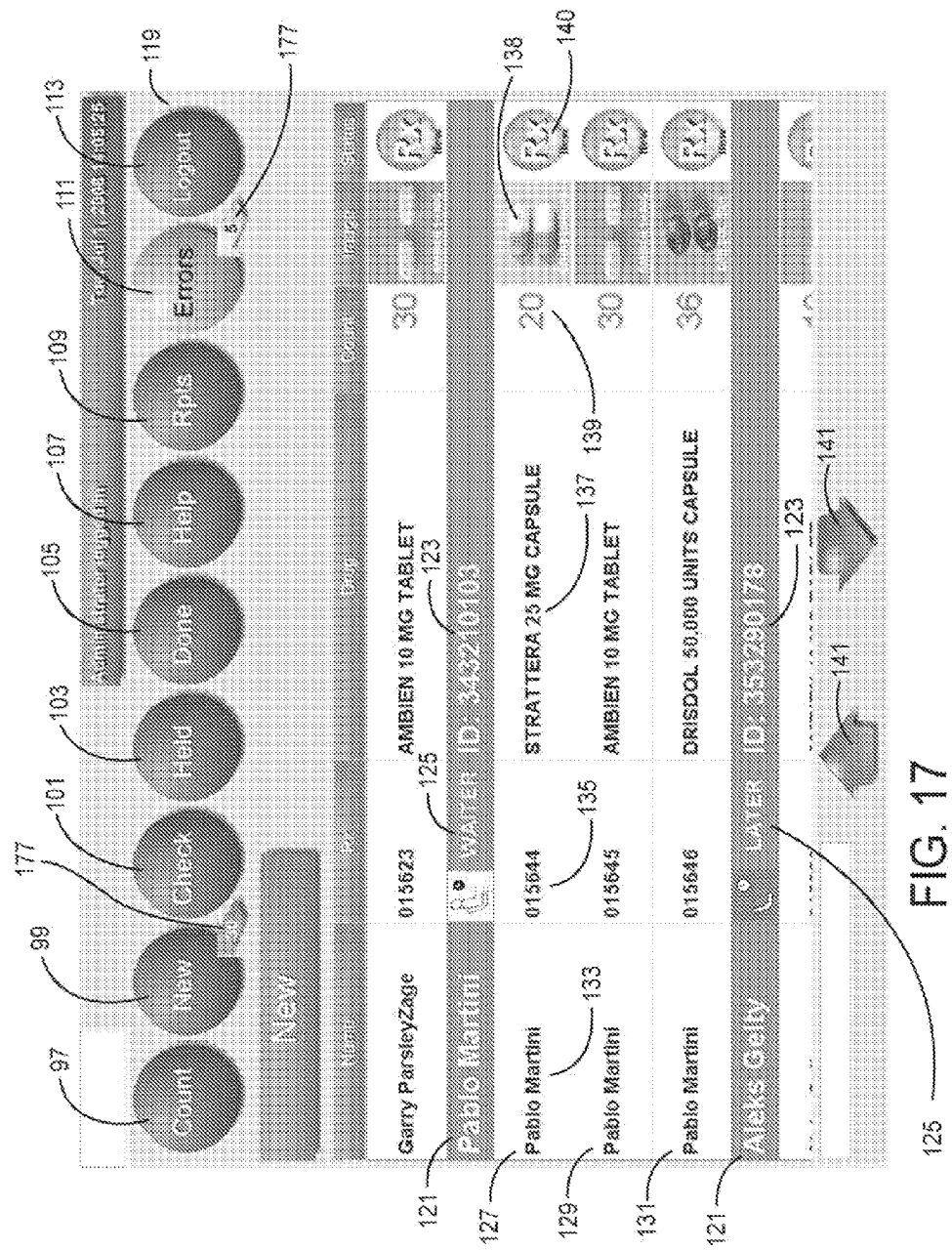
Figure 18:
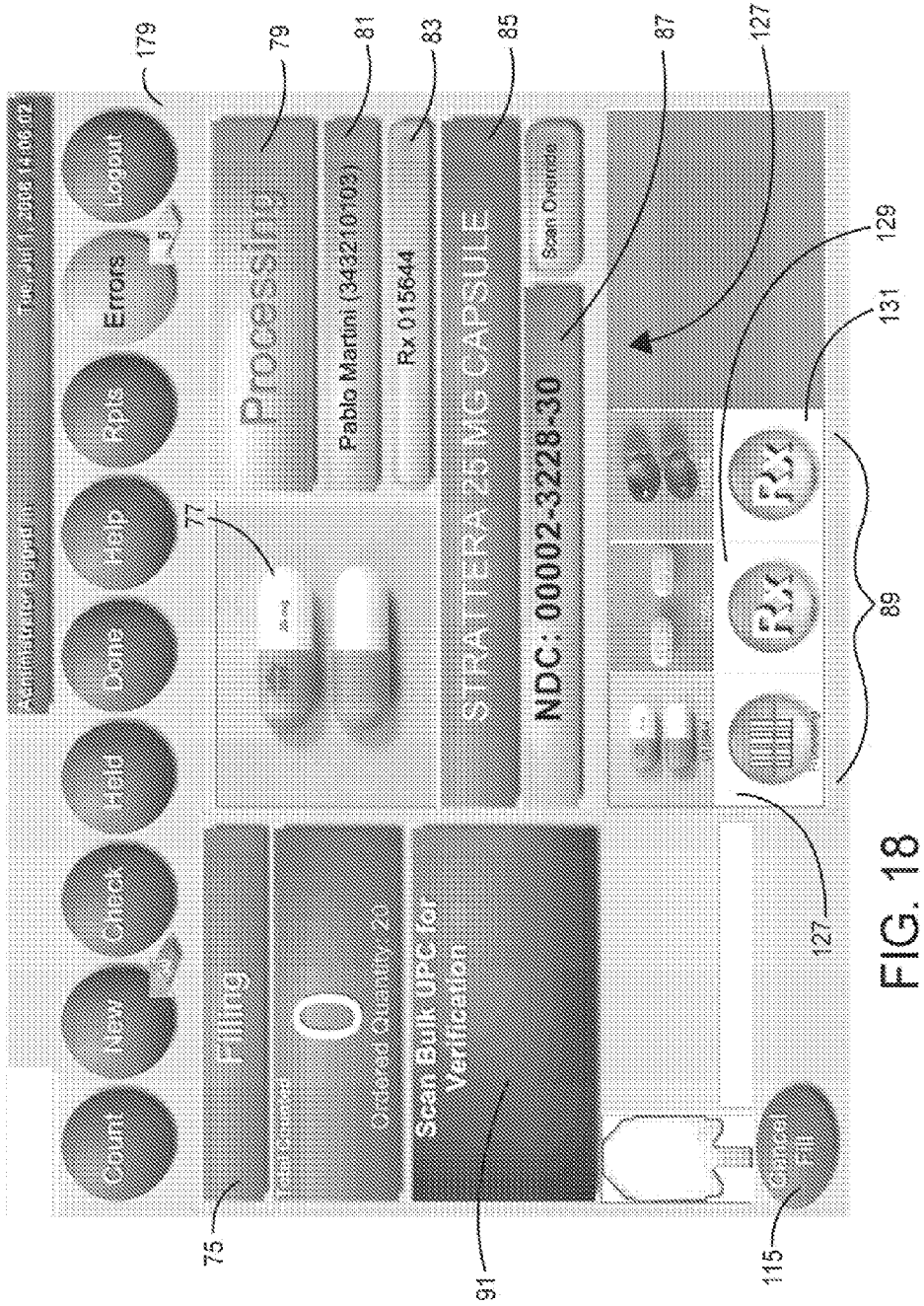

Referring further to New Order screen 119 of FIG. 17, an arrow 177 may appear on any screen pointing to one of the control push buttons 97-113. A number in such arrow 177 is indicative of the number of prescriptions residing in each control category. For example, arrow 177 pointing to New push button 99 indicates that there are 30 new prescriptions awaiting fulfillment, and arrow 177 pointing to Errors push button 111 indicates that there are five prescriptions with errors that require attention. The number in each arrow 177 is incremented or decremented as new prescriptions are added or removed from each control push button category.

Therefore, New Order screen 119 of interfaced system 11 provides the user with a centralized point of control including user access to all information required to fulfill any pending validated prescription order. The user may scroll up or down using arrows 141 to access any of the pending validated prescription orders. Access to the entirety of the pending validated prescription orders through system 11 provides the user with an improved level of control over pharmacy workflow because, for example, the user may fulfill any prescription in any sequence that is most efficient and is no longer required to wait for physical delivery of prescription order paperwork (e.g., paperwork 147) from pharmacy PMS 21. For instance, the user can advance the order for fictitious patient Martini past an order for fictitious patient Gelty because patient Martini is indicated to be waiting for his order as indicated in field 125, whereas patient Gelty will pick up his order at a later time as indicated in field 125 next to his order on New Order screen 119.

Referring again to FIG. 14A, in block 215, for interfaced system 11a single prescription is selected and retrieved for fulfillment. As noted, a single prescription may be selected simply by touching touch-screen-type display 37 proximate the prescription (e.g., one of prescriptions 127-131). Selection in block 215 triggers retrieval of the selected prescription from non-volatile storage 61.

As an alternative to prescription selection using New Order screen 119, at block 215 a user may select a prescription for fulfillment by scanning a prescription label 143 barcode 145 with scanner 51. Prescription selection by label scanning triggers retrieval of the selected prescription from non-volatile storage 61. In this case of prescription selection by label scanning, New Order screen 119 is bypassed and the process proceeds directly to collate all other pending prescriptions for the patient and to start processing of the prescription corresponding to the scanned label as described in connection with FIG. 18.

Figure 13:
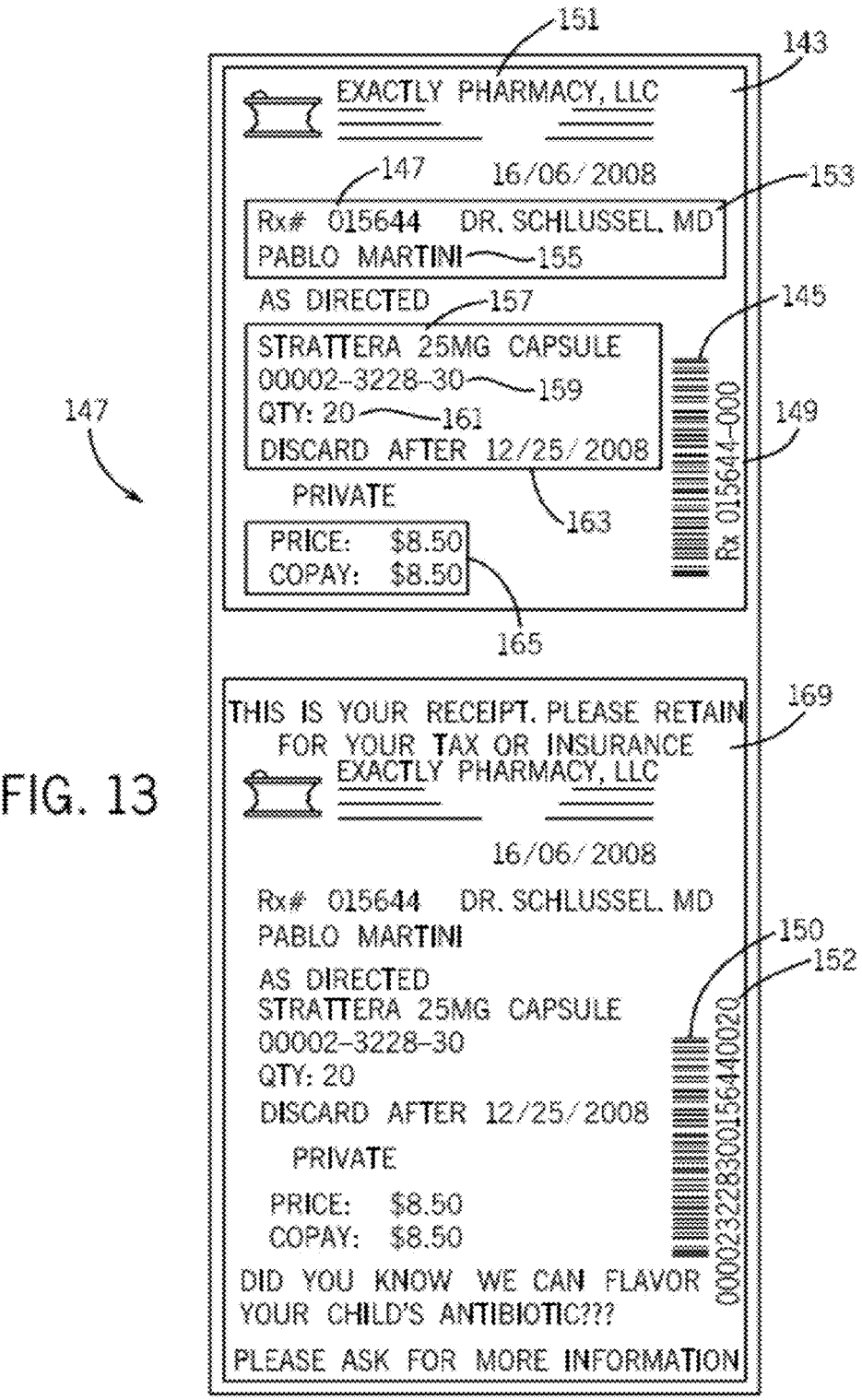
FIG. 13 is exemplary pharmacy-generated paperwork for a prescription order, including an adhesive-backed label.

Referring to FIG. 13, there is shown exemplary prescription order paperwork 147 including an exemplary prescription label 143 with machine-readable indicia in the form of barcode 145 which may be scanned to select the prescription for fulfillment and trigger retrieval of the selected prescription from non-volatile storage 61. Label 143 is generated by PMS 21 as prescription order paper work 147 for each prescription for each patient. Prescription label 143 of prescription order paperwork 147 is adhesive-backed and is peeled off of paperwork 147 and applied to the patient prescription container (not shown) for the patient's prescription.

If system 11 is interfaced to PMS 21, then barcode 145 need only include a prescription number 149 which matches the prescription number (e.g., prescription number 015644 in Field 135) in the prescription record database in data storage 61. The record of the prescription in the prescription record database will include the data expected to be embedded in the UPC barcode 173 of the medication container 175 (FIG. 12A) for the medication called for in each prescription being filled. Scanning of barcode 145 will retrieve the corresponding prescription from prescription records database in storage 61 and will further result in retrieval of all other prescriptions collated for that patient so that all pending prescriptions for the patient are collated. The process for the interfaced system 11 moves directly to processing of the prescription of the scanned label in FIG. 18 as described below.

Other information provided on prescription paperwork 147 includes: pharmacy identification information 151, prescribing physician name 153, patient name 155, medication name 157, NDC 159, medication quantity 161, prescription expiration date 163, and prescription price 165. Paperwork 147 may also include a receipt 169 with information corresponding to that of prescription label 143.

At block 217, label scanning can also be used to select a prescription for non-interfaced systems 11. Selection in this context refers to selecting a prescription by selecting and scanning prescription paperwork 147 to initiate fulfillment of the corresponding prescription. More specifically, receipt 169 includes a barcode 150 which may be used for label scan prescription selection for non-interfaced system 11. Embedded in barcode 150 are three fields of information 152 shown next to barcode 150 including the 11-digit NDC used by the pharmacy (00002-3228-30), the pharmacy-assigned prescription number (015644) and the quantity of tablets required by the patient's prescription (0020). For non-interfaced systems 11, the NDC number in barcode 150 can be used with a commercially-available database provided in non-volatile storage 61 to look up UPC 173 of container 175 for subsequent scan verification and can be used to retrieve a reference image of the medication from non-volatile storage 61 in Medication Image field 1077 as described herein. Each NDC identifies the medication source, medication type and strength and package type and medication quantity. The database will include the specific UPC code 173 or other code on the container 175 for the medication identified by the NDC. If barcode 150 on paperwork 147 is scanned, then non-interfaced system 11 immediately begins to process that prescription (e.g., prescription 127) resulting in selection of the prescription at block 217 and retrieval of the UPC 173 and reference image information from non-volatile storage 61.

Fulfillment of prescription 127 requiring 20 capsules of 25 mg Eli Lily & Co. Strattera medication for fictitious patient Pablo Martini is described below for both interfaced and non-interfaced systems 11. Fulfillment of prescriptions 129, 131 for patient Martini would occur in the same manner.

If system 11 is interfaced, then block 215 of FIG. 14A is entered. The user selects a prescription by touching a prescription shown on New Order Screen 119 or by scanning a barcode 145 on the prescription label 143 as previously described. Upon selection, the screen shown on display 37 of interfaced system 11 changes to the Prescription Filling Screen 179 of FIG. 18, and all relevant information pertaining to fulfillment of prescription 127 is presented to the user. Activity field 75 is set to "Filling" and Prescription Status Indicator field 79 is set to "Processing" to indicate that fulfillment of the prescription is in process. Patient name field 81 is set to show the patient name and the prescription number of the prescription being fulfilled is shown in field 83. The prescribed medication image, medication name, strength and form and NDC number are set in respective fields 77, 85, 87. All three prescriptions 127, 129, 131 are collated together in Collated Order field 89 with prescription 127 indicated as being in a "Processing" mode. Main Instructions field 91 prompts the user to scan the UPC barcode on a medication container for the required medication.

If system 11 is a stand-alone system with no interface to PMS 21, then block 217 of FIG. 14A is entered. In order to fulfill prescription 127 (and other prescriptions), the user scans prescription paperwork 147 barcode 150 (FIG. 13) with scanner 51. Barcode 150 may include fields for the NDC of the prescribed medication, the prescription number and required quantity of medication for the prescription as previously described. A record of the prescription (e.g., prescription 127) is established for each prescription number in the prescription record database of storage 61. The NDC, prescription number and medication quantity is stored in the record. A relational database stored in non-volatile data storage 61 is accessed to associate the UPC barcode 173 of medication container 175 (FIG. 12A) with the NDC number for the required medication.

Figure 19:
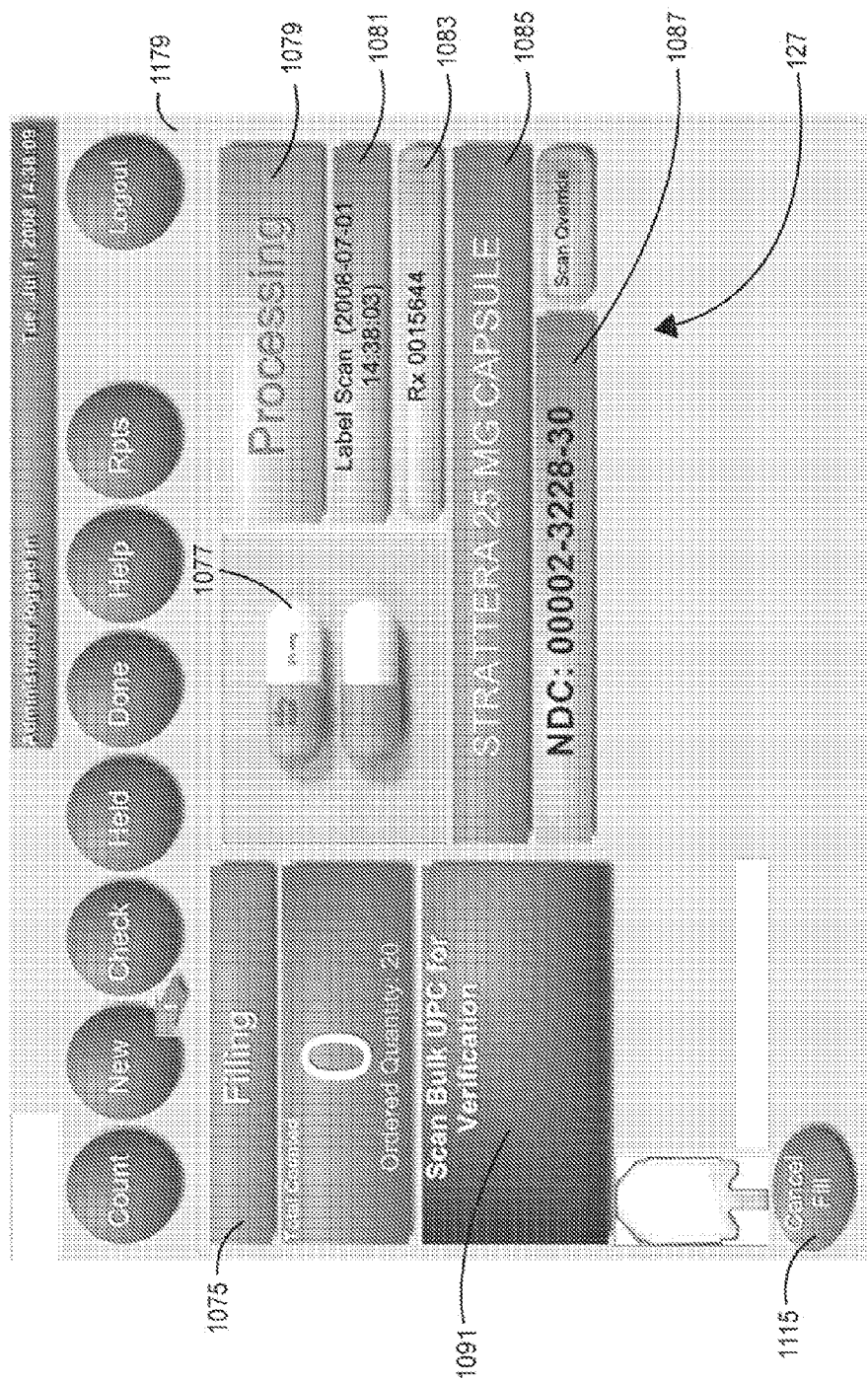

Referring now to FIGS. 14A and 19, selection of prescription 127 at block 217 for the non-interfaced system 11 by scanning barcode 150 causes Start screen 1073 to be replaced with Prescription Filling screen 1179. As with screen 179 of interfaced system 11 (FIG. 18), Activity field 1075 is set to "Filling" and Prescription Status Indicator field 1079 is set to "Processing" to indicate that fulfillment of the prescription is in process. Because the patient name is not known from scanning barcode 150, patient name field 1081 is set to show the date and time of day while the prescription number of the prescription being fulfilled is shown in field 1083. The medication image, medication name, strength and form and NDC number for the Strattera medication required by prescription 127 are again set in respective fields 1077, 1085, 1087. This information is retrieved from a relational database corresponding to the NDC number in barcode 150 from non-volatile data storage 61. Also retrieved from the relational database is UPC barcode 173 expected to be on container 175. The expected UPC barcode is related directly to the NDC number embedded in barcode 150. Single prescription 127 being filled is shown with prescription 127 indicated as being in a processing mode in field 1079. Main Instructions field 1091 prompts the user to scan the machine-readable UPC barcode indicia 173 on container 175 for the required medication.

Block 219 of FIG. 14A is entered next for both interfaced and non-interfaced systems 11. In block 219, the user selects a medication container (e.g., container 175) containing tablet-form medication required by the prescription (e.g., prescription 127).

In block 221, the user scans UPC barcode 173 on container 175 with barcode scanner 51.

At decision point 223, actual UPC 173 on container 175 is compared by the program of instructions operating on data processing platform 17 with the expected UPC for the medication from the prescription record database in non-volatile data storage 61.

Figure 20:
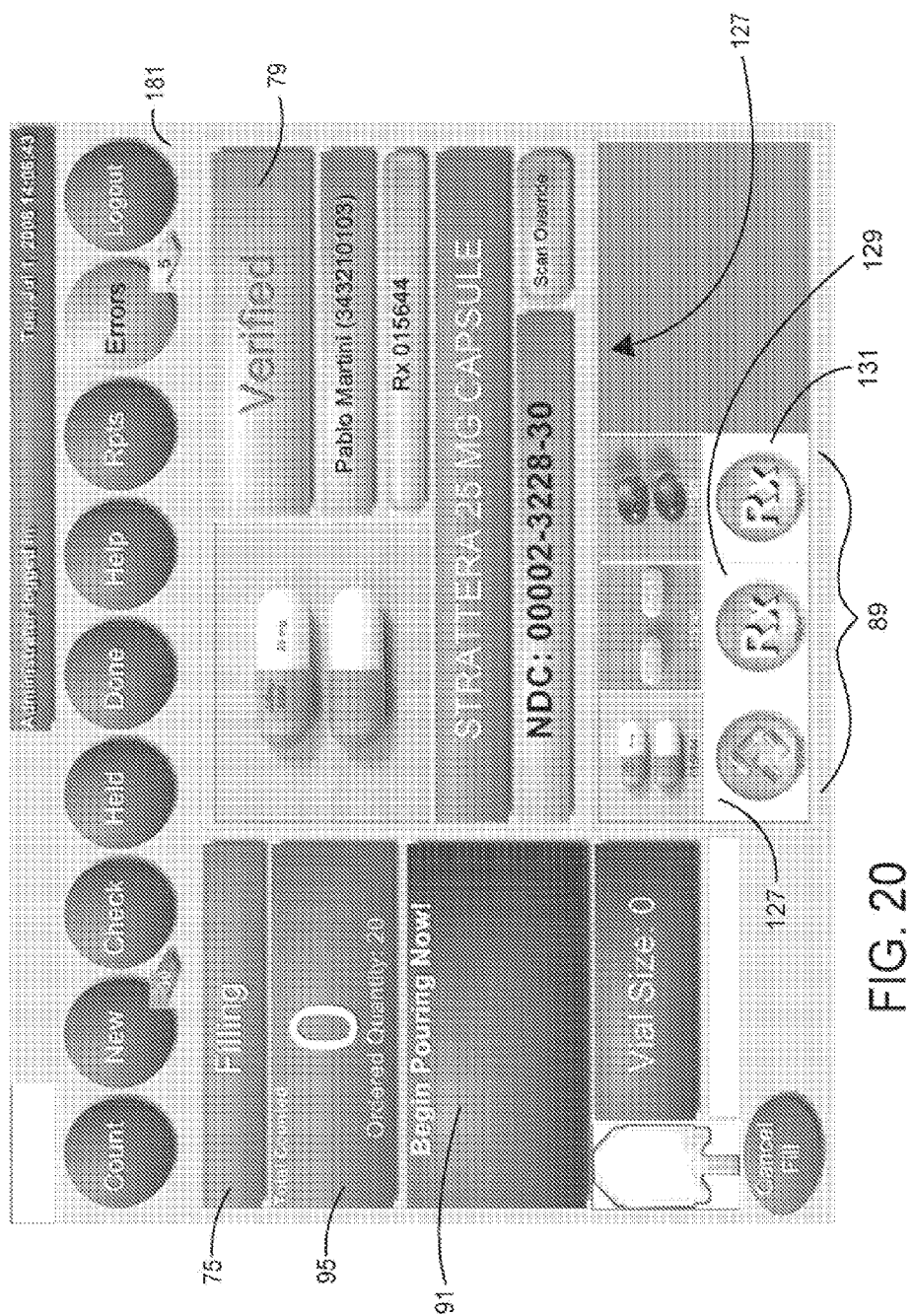
Figure 21:
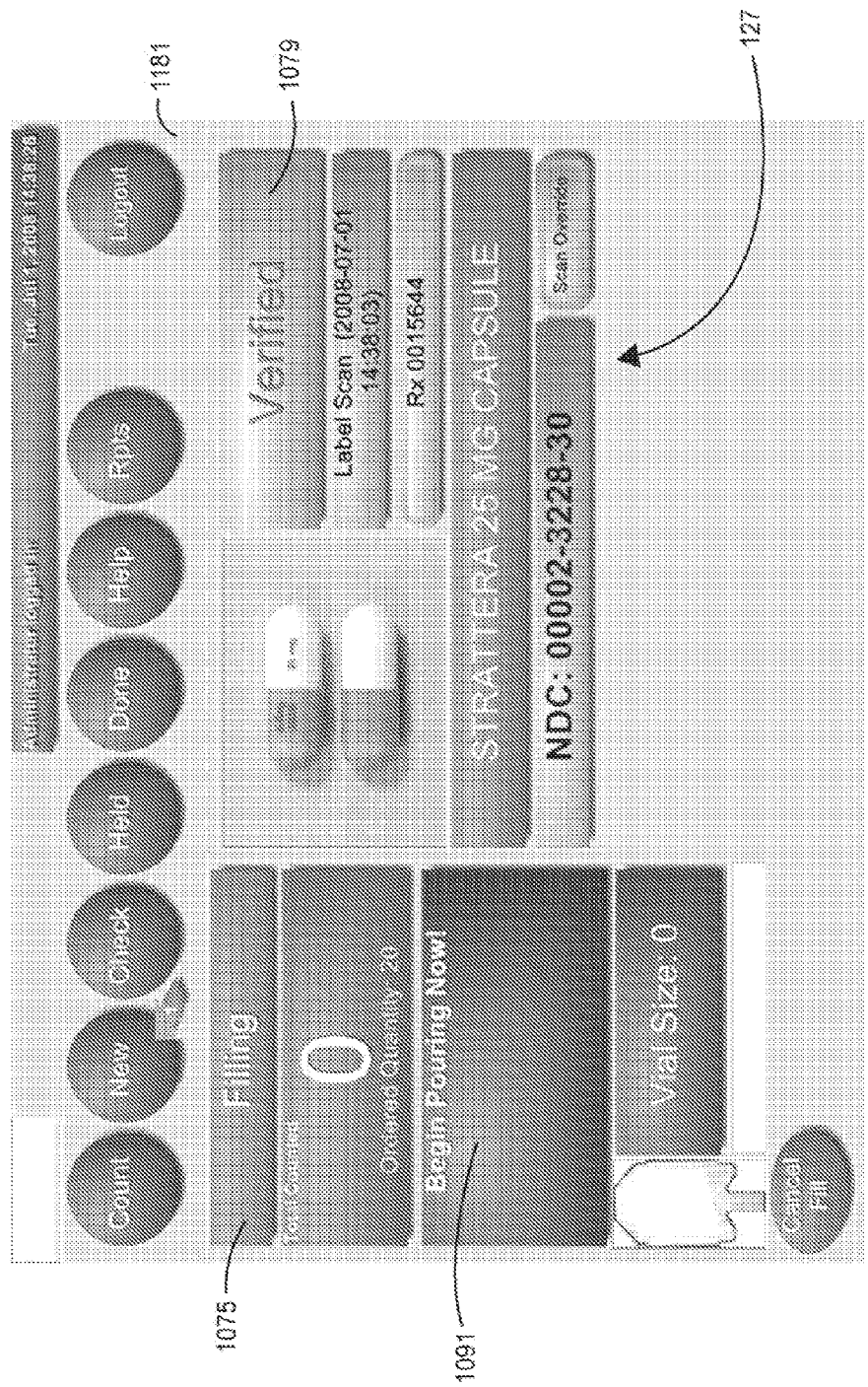

Referring to FIGS. 14A, 20 and 21, if the comparison at point 223 results in a match between the actual UPC 173 and expected UPC, counting of tablets is enabled and Begin-Pouring screen 181 of FIG. 20 is shown on display 37 for an interfaced system 11 or the Begin-Pouring screen 1181 of FIG. 21 is shown on display 37 at block 223 for non-interfaced system 11.

Figure 22:
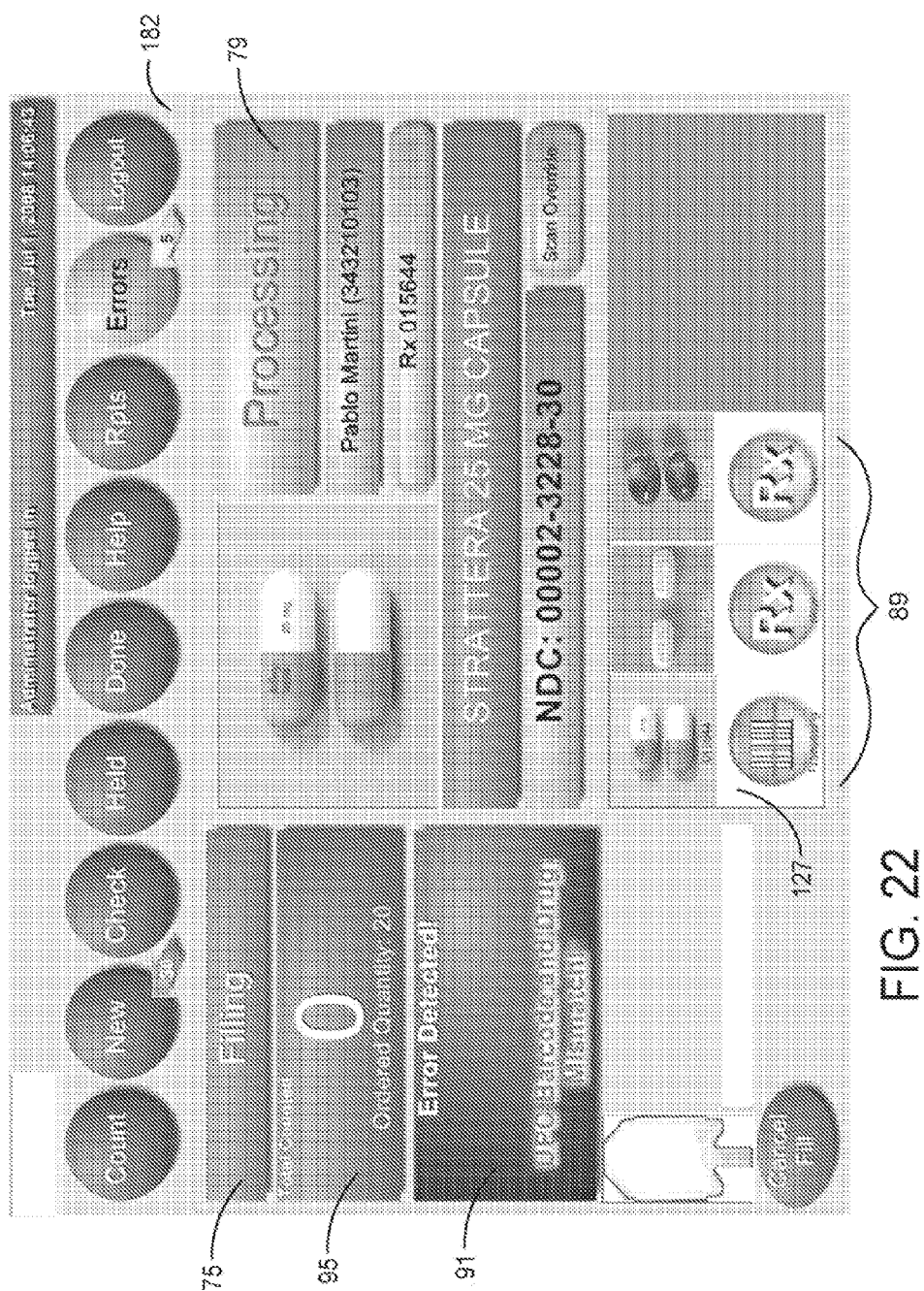

For the interfaced system 11, if there is no match then Error screen 182 of FIG. 22 is presented to the user. In addition, speaker 63 may generate an audible signal indicating that the comparison did not result in a match. Instructions in Main Instructions field 91 indicate that an error has been detected to prompt the user at block 223 to re-scan UPC 173 (repeat block 221) or to select a different container 175 (repeat block 219). Prescription Status Indicator field 79 remains set to "Processing" and the word "Processing" also appears in Collated Order field 89 for prescription 127 because no match has occurred at point 223.

Figure 23:
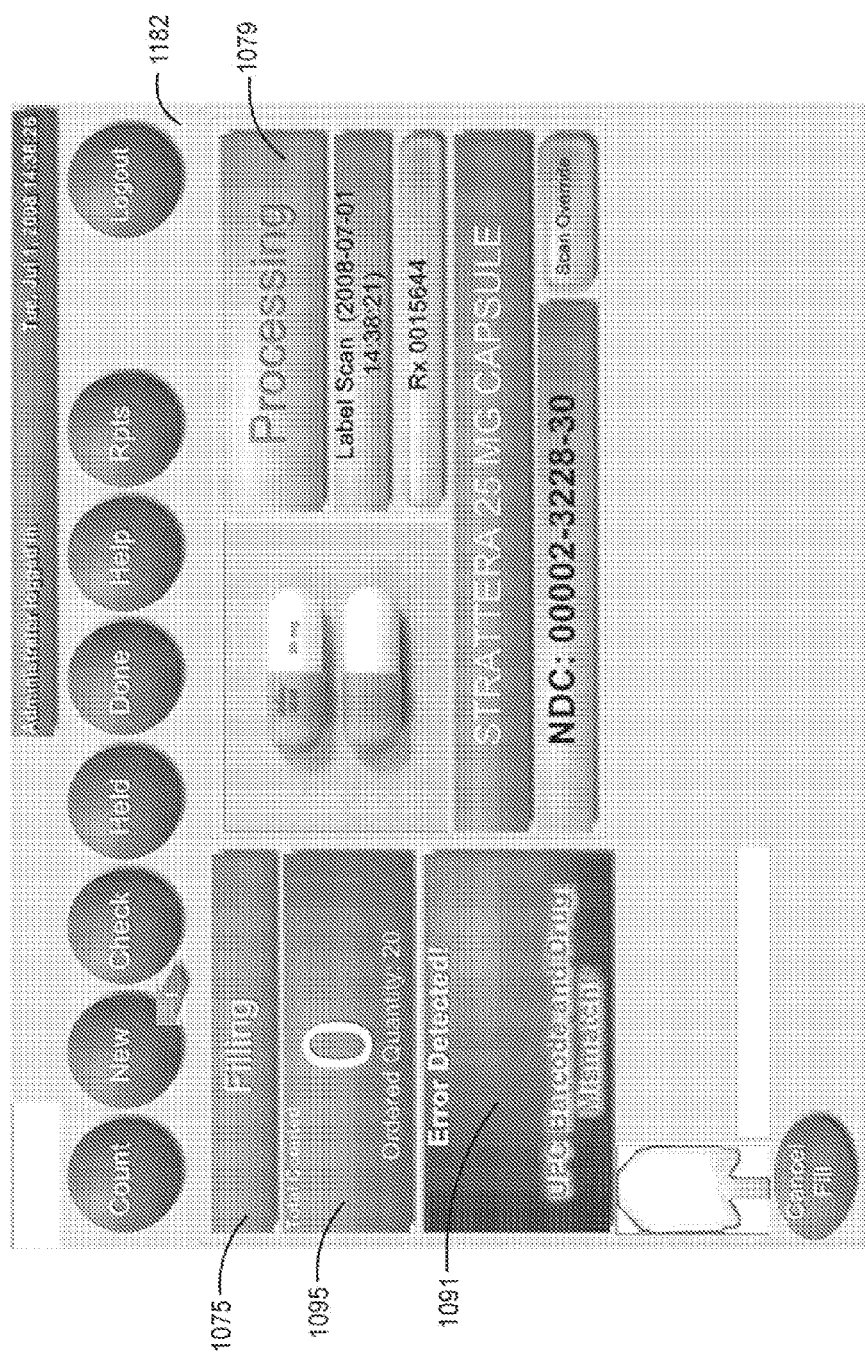

For the non-interfaced system 11, if there is no match then Error screen 1182 of FIG. 23 is presented to the user. An audible error signal can be generated by speaker 63. Instructions in Main Instructions field 1091 indicate that an error has been detected to prompt the user at block 223 to re-scan UPC 173 (repeat block 221) or to select a different container 175 (repeat block 219).

Other error types can occur during the fulfillment process and information can be displayed to alert the user to such errors. Examples of errors can include, for example, that the medication is not in the prescription record database in storage 61, that data was erroneously entered for the prescription (for example erroneously indicating that zero tablets are required), that the UPC was not found in the relational database in storage 61, or that the lengths of barcodes 145 and 173 do not match. These and other error conditions can trigger system 11 to display instructions in Main Instructions field 91 or 1091, prompting the user to take appropriate corrective action.

Referring to FIGS. 14A, 20 and 21, block 225 is entered to start a tablet count if there is a match in block 223. As illustrated in FIG. 20 (interfaced system 11) and FIG. 21 (non-interfaced system 11), Main Instructions fields 91, 1091 of the Begin-Pouring screens prompt the user to begin pouring the tablets from a container (e.g., container 175) into feeder device 19 in response to the match in block 223. Prescription Status Indicator fields 79, 1079 are set to "Verified" indicating to the user that UPC 173 of container 175 matches the medication required by the prescription. Collated Order field 89 is also set to "Verified" for prescription 127 also indicative of the match. (Collated Order field 89 is set to "New" for prescriptions 129 and 131 because fulfillment of these prescriptions has not yet commenced.) Count Status field 95, 1095 are set to 0, and the tablet quantity required by the prescription (e.g., prescription 127) is displayed.

In the example of FIGS. 1-6, the user pours tablet-form medication from container 175 into funnel 41. Tablet counter 15 automatically counts each tablet as it falls from funnel 41 past collimated IR sources 308a, 308b and sensors 307a, 307b and into tray 45. The system software previously described performs the count, and Count Status fields 95, 1095 are instantaneously updated as each tablet is counted.

Figure 24:
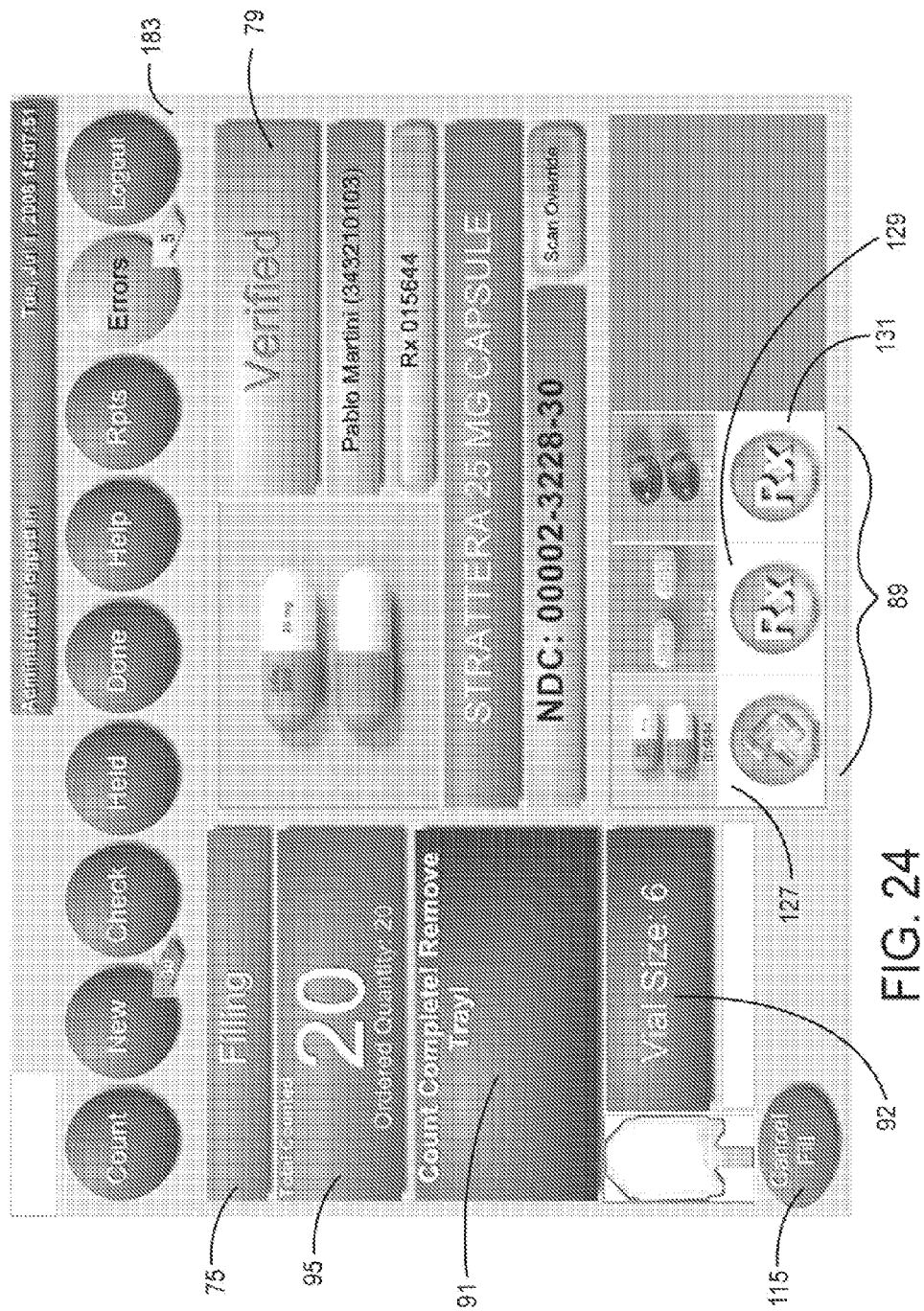
Figure 25:
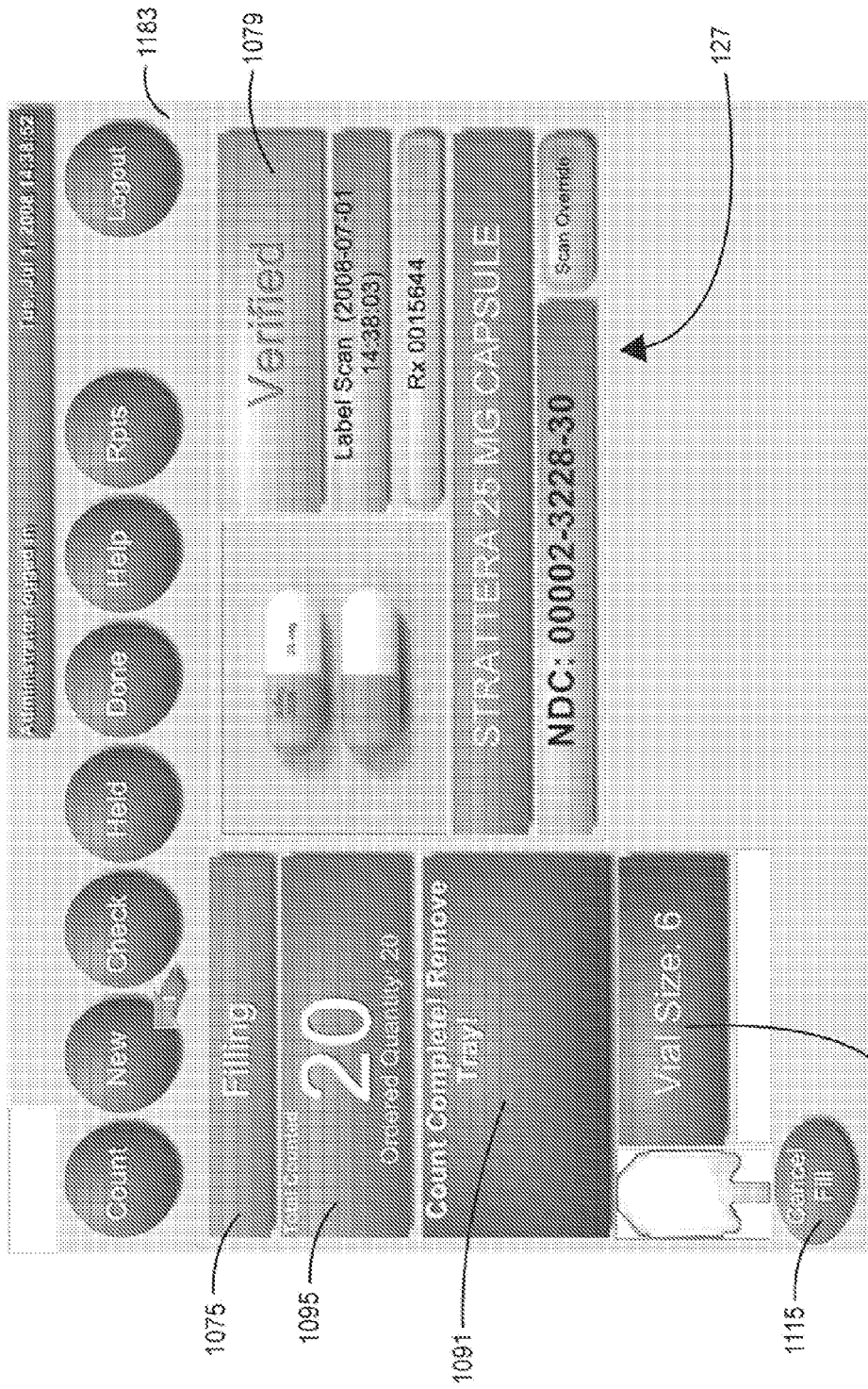

Referring next to FIGS. 14B, 24 and 25, at decision point 227 the actual tablet count is compared to the required tablet count for the prescription. If the actual tablet count equals the required tablet count, then Count-Complete screen 183 of FIG. 24 (interfaced system 11) or Count-Complete screen 1183 of FIG. 25 (non-interfaced system 11) is shown on display 37. Prescription Status Indicator fields 79, 1079 remain set to "Verified" providing continued indication to the user that correct container 175 was selected. Main Instructions fields 91, 1091 instruct the user that the count is complete and prompts the user to remove tray 45 so that the counted tablets can be poured from tray 45 into a vial, bottle or other container for the patient's prescription. Speaker 63 may generate an audible signal indicating that the correct count has been made.

At decision point 231, an undercount could occur if the user removes tray 45 before the required quantity of tablets is counted. An undercount may also occur if too much time elapses, i.e., because the count was not completed within a user-configurable time interval, such as 5 minutes, if, for example, a user might be asked to assist with another task in the pharmacy before completing the count. An undercount message indicating the undercount is provided in Main Instructions field 91, 1091. An audible signal generated by speaker 63 would also indicate an undercount condition to the user. If an undercount occurs at decision point 231 of FIG. 14B, then additional tablets are poured from container 175 into funnel 41 until the actual count equals the required count at block 233. The count is displayed in Count Status field 95, 1095.

If an overcount occurs at decision point 235, then the user is notified of the overcount by a message in Main Instructions field 91, 1091 and an audible signal from speaker 63. The user is prompted to manually adjust the count by removing tablets or to re-pour the tablets through tablet counter 15 until the actual count equals the expected count as indicated in Count Status field 95, 1095.

If the tablets are poured too rapidly into tablet counter 15, then an overspeed error condition can occur (step 517 of FIG. 11B) indicating that the tablets passing by collimated IR sources 308a, 308b and sensors 307a, 307b were not accurately counted. If an overspeed error occurs, then the user is prompted by an audible signal from speaker 63 and an overspeed message (not shown) is presented on display 37. The user is prompted to re-pour the tablets through tablet counter 15 until the actual count equals the expected count as indicated in Count Status field 95, 1095.

The result of blocks 225, 227, 233 and 237 of FIGS. 14A and 14B is that the correct quantity of tablets has been counted and the counted tablets are in tray 45.

Figure 26:
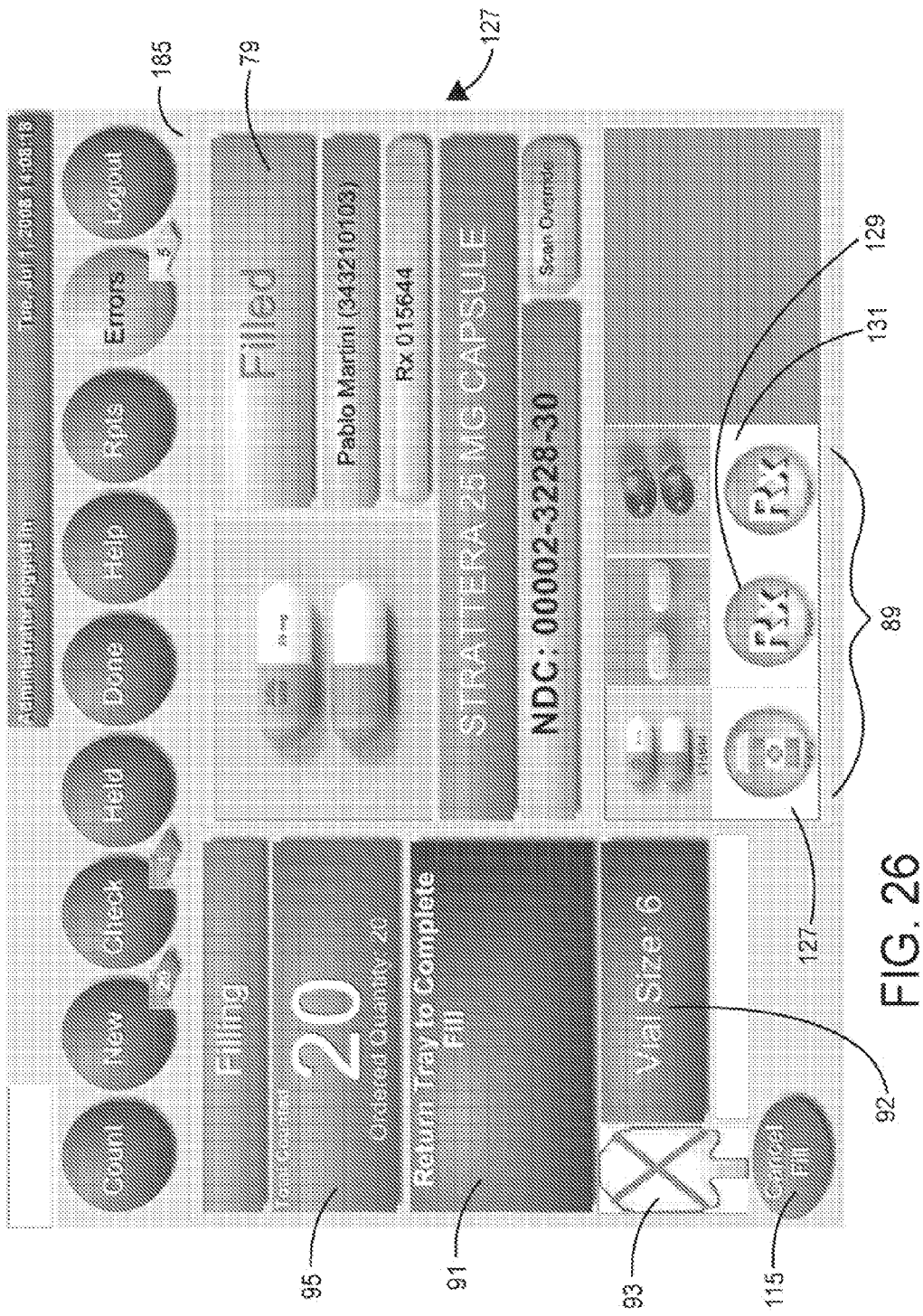
Figure 27:
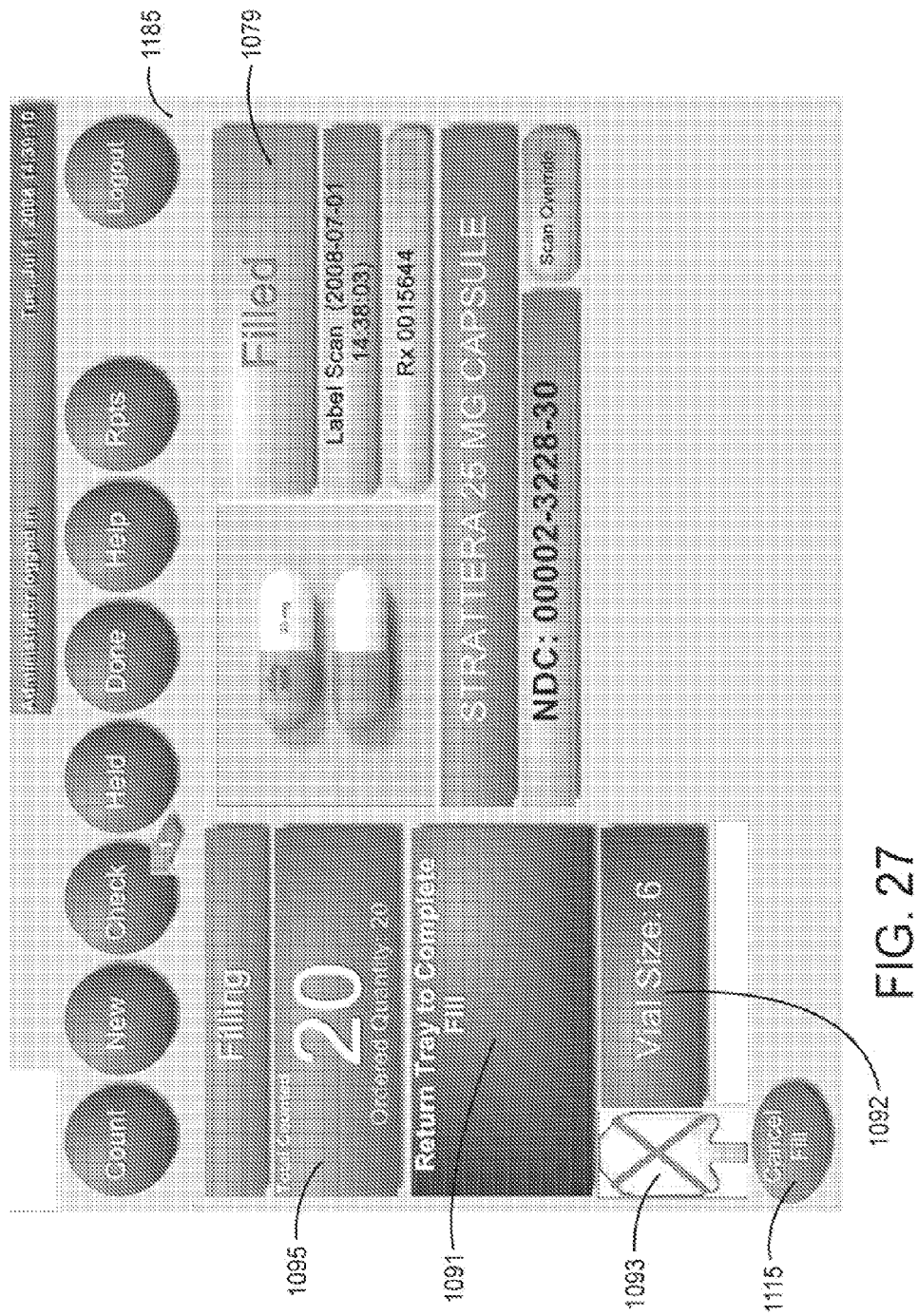

Referring again to FIG. 14B and to the screen displays of FIGS. 26, 27, at block 229, tray 45 is removed and the tablets in tray 45 are poured into a patient medication container, such as a bottle or vial (not shown). Removal of tray 45 triggers display of "Filled" screen 185 of FIG. 26 (interfaced system 11) or "Filled" screen 1185 of FIG. 27 (non-interfaced system 11) indicating that the prescription status is considered to be "Filled" as indicated in field 79, 1079. Tray Status field 93, 1093 includes an "x" symbol indicating removal of tray 45. For interfaced system 11, prescription 127 in Collated Order field 89 of Filled screen 185 (FIG. 26) changes to "Filled" indicating that the required tablets were counted and removed from the system 11. For interfaced systems, prescription orders 129, 131 await fulfillment as indicated by the two occurrences of the word "New" in Collated Order field 89. Selected prescription 127 has been correctly counted, and the counted tablets in tray 45 are poured from tray 45 into a patient container, such as a vial or bottle.

At block 239, tray 45 is returned to bay 47. Return of tray 45 to bay 47 is detected by system 11 and represents the terminal point of the filling process for that prescription. An optional verification process described in connection with blocks 241-251 of FIG. 14B may be subsequently performed for the prescription as described below.

If system 11 is interfaced to PMS 21, then at decision point 241, system 11 determines whether additional prescriptions must be filled for the patient (e.g., prescriptions 129, 131). If so, the process of steps 213-241 (FIGS. 14A, 1413) are repeated resulting in all prescriptions for the patient being filled.

If system 11 is non-interfaced, the user may move to the optional verification process enabled at decision point 243 and executed in blocks 247-249. If verification is not selected at point 243, then the process is Done at block 245.

Next, optional verification can occur if verification is enabled at point 243. Verification by a registered pharmacist using system 11 is useful to provide further assurance that the prescriptions (e.g., prescriptions 127-131) were filled accurately before the prescription order is made available to the patient. Verification can be performed as each prescription (e.g., prescriptions 127-131) is fulfilled or after all prescriptions of a prescription order are fulfilled. Once all prescriptions are optionally verified, the prescription order is confirmed as done.

As illustrated in the interfaced system 11 screen display of FIG. 24 and FIGS. 28-31, verification is made easier and more efficient because interfaced system 11 can present all prescriptions to be verified collated by patient in Collated Order field 89 (FIGS. 24 and 28-31). The pharmacist or other user is able to quickly and easily access all prescriptions for any patient in order to complete the verification process. Patient care is improved because order verification is made more accurate and the chance that a patient might accidentally not receive all required prescriptions is diminished.

Referring to FIG. 14B, blocks 247 and 249 illustrate steps of an optional verification process. Verification is available once tray 45 is inserted into bay 47 and verification is enabled at point 243. Verification is preferably enabled by the administrator of system 11 as a user-configurable option.

Figure 28:
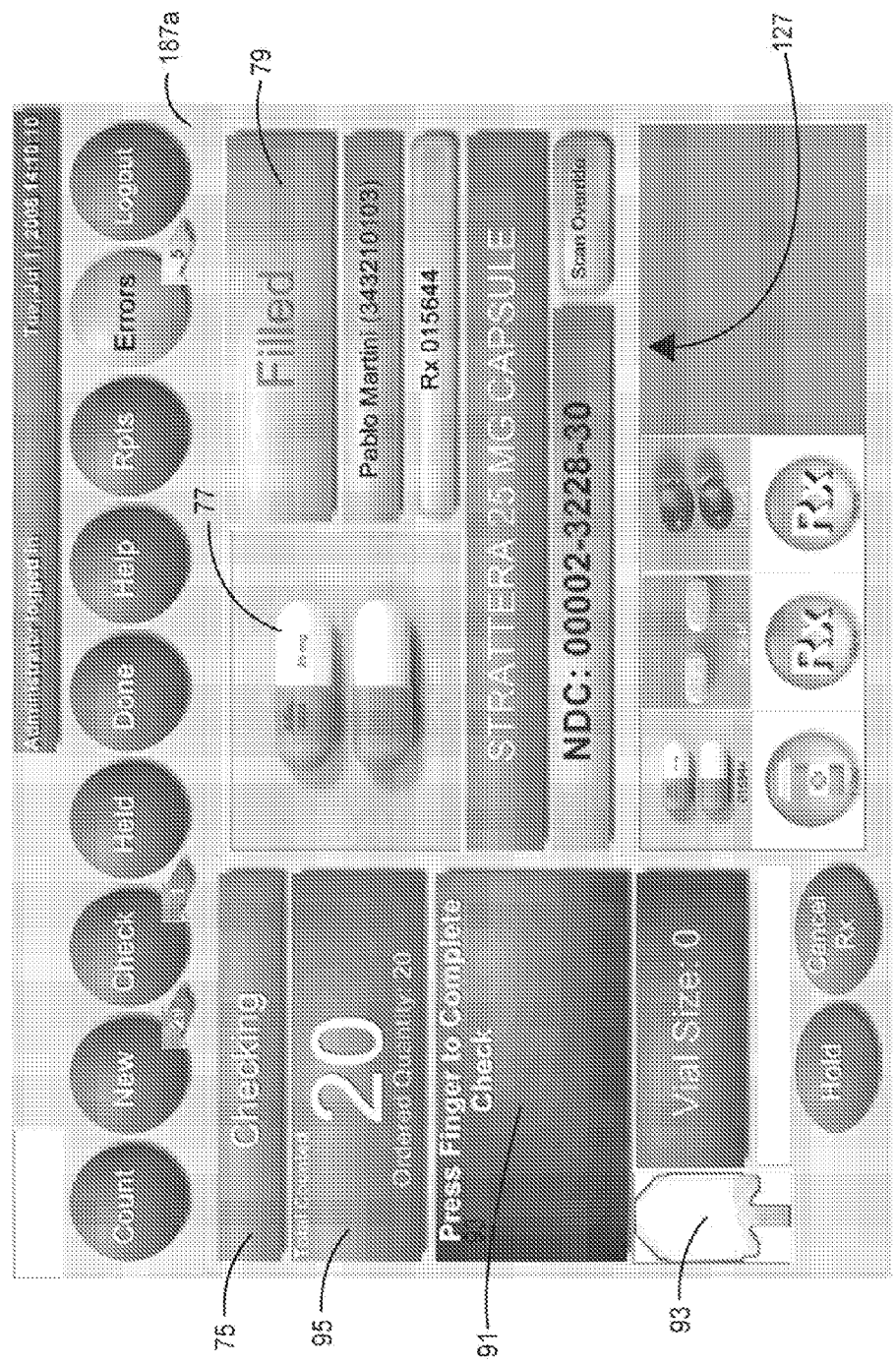
Figure 29:
Figure 30:
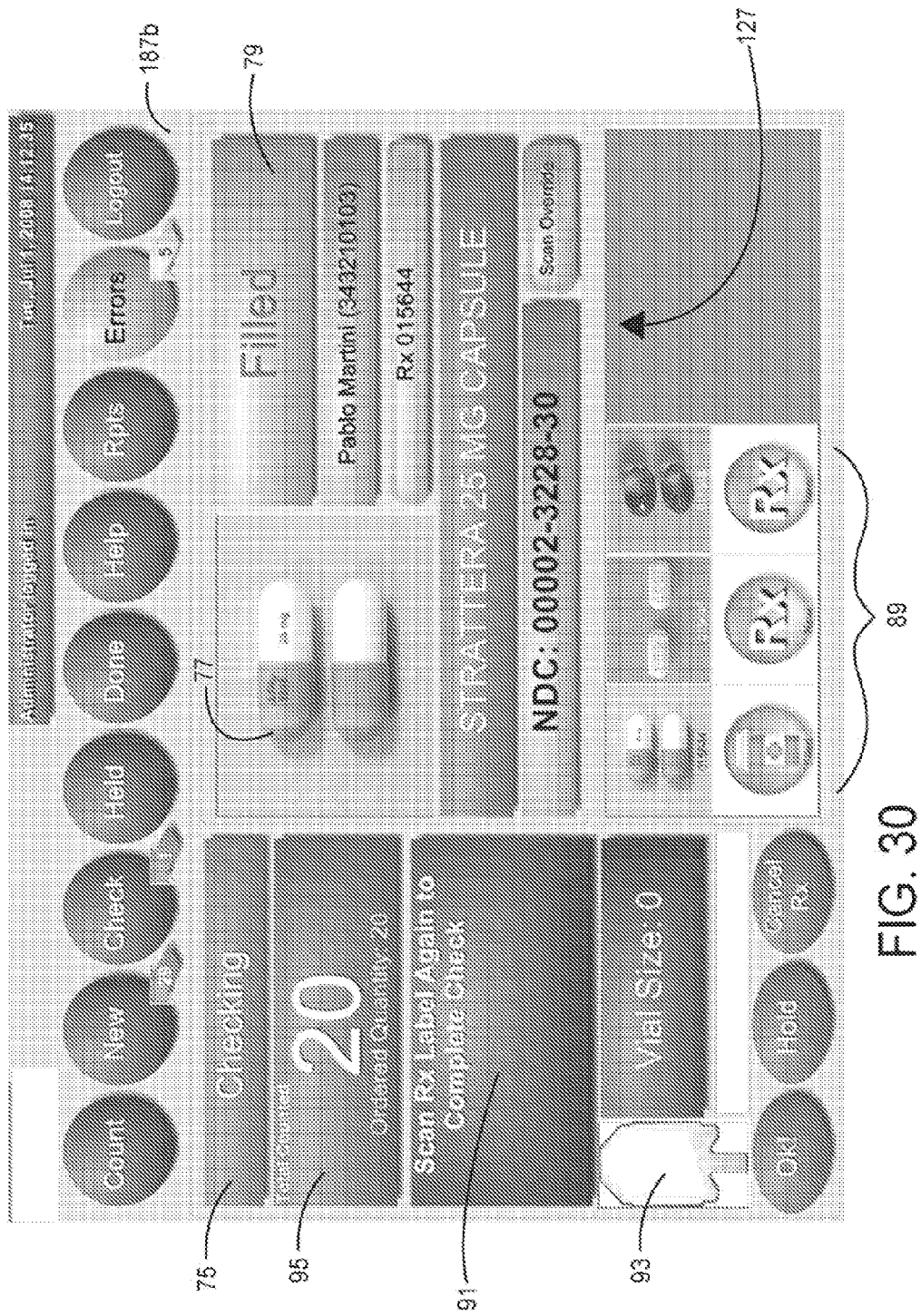
Figure 31:
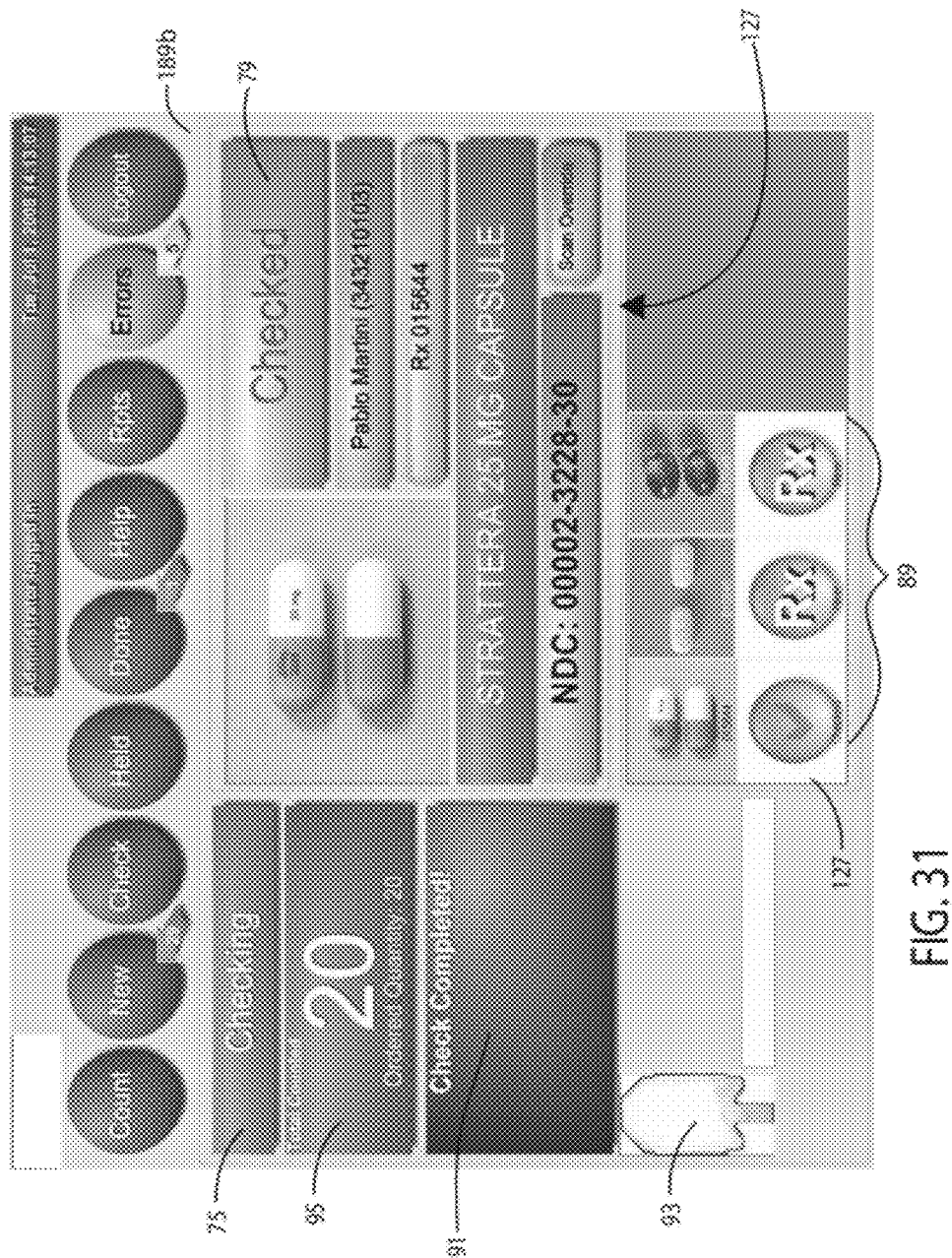

For both the exemplary interfaced and non-interfaced systems 11, two alternative processes are available to perform optional prescription verification in blocks 247 and 249. Verification may be controlled by means of a fingerprint scan process or by a barcode scan process. FIGS. 28 and 29 illustrate exemplary screen displays for a fingerprint-controlled verification process for interfaced system 11 and FIGS. 30 and 31 illustrate exemplary screen displays for a barcode scan-controlled verification process for an interfaced system 11. Enablement of verification at point 243 and selection of the type of scan may be based on preferences selected by the user, for example, in a system setup procedure executed after login at block 205 (FIG. 14A). For each of the examples of FIGS. 28-31, the verification process is being performed following partial fulfillment of prescription 127 and before fulfillment of prescriptions 129, 131 as indicated by the word "New" in Collated Order field 89 for prescriptions 129, 131.

Referring to FIGS. 28 and 29, for the fingerprint-controlled scan verification process, the pharmacist scans label barcode 145 which has been applied to the patient medication container or touches display 37 proximate displayed prescription 127 (e.g., prescriptions 127-131). Block 247 is entered and Verification screen 187a (FIG. 28) is shown on display 37. Prescription Status Indicator field 79 remains set to "Filled" indicating to the user that the prescription has been fulfilled. Main Instructions field 91 prompts the user to begin the optional verification process. The medication image is displayed in field 77. The user manually checks the information on screen 187a against the physical appearance of the tablets in the patient's container and against the information provided on prescription order paperwork 147.

If the correct medication has been loaded in the patient container, then in block 249 (FIG. 14B), the user places a finger against biometric sensor 55 to confirm the verification to interfaced system 11. Check Completed screen 189a (FIG. 29) appears on display 37 for interfaced systems, and a check mark appears for the verified prescription 127 in Collated Order field 89. Activity field 75 is set to "Checking" indicating that verification is being performed and Prescription Status Indicator field 79 is set to "Checked" indicating that the prescription has been checked and verified as indicated by placement of the user's finger on sensor 55. Main Instructions field 91 is set to "Check Completed" also indicative of completed verification for prescription 127.

Referring now to FIGS. 14B, 30 and 31, the process for barcode scan-controlled verification at blocks 247, 249 is essentially the same as described for the fingerprint-controlled process. Block 247 is entered and Verification screen 187b (FIG. 30) is shown on display 37. Prescription Status Indicator field 79 remains set to "Filled" indicating to the user that the prescription has been fulfilled. Main Instructions field 91 prompts the user to scan label barcode 145. At block 247, the user then scans selected label barcode 145 of the prescription to initiate verification.

The user then manually checks the information on screen 187b against the physical appearance of the tablets in the patient's container and against the information provided on prescription order paperwork 147.

If the correct medication has been loaded in the patient's container, then at block 249, the user scans label barcode 145 of the prescription for a second time to confirm the verification. Check Completed screen 189b (FIG. 31) appears on display 37 for interfaced systems 11 and a check mark appears for verified prescription 127 in Collated Order field 89. The Activity field 75 is set to "Checking," indicating that verification is being performed and Prescription Status Indicator field 79 is set to "Checked," indicating that the prescription has been checked and verified as indicated by placement of the user's finger on sensor 55. Main Instructions field 91 is set to "Check Completed" also indicative of completed verification for prescription 127.

Figure 32:
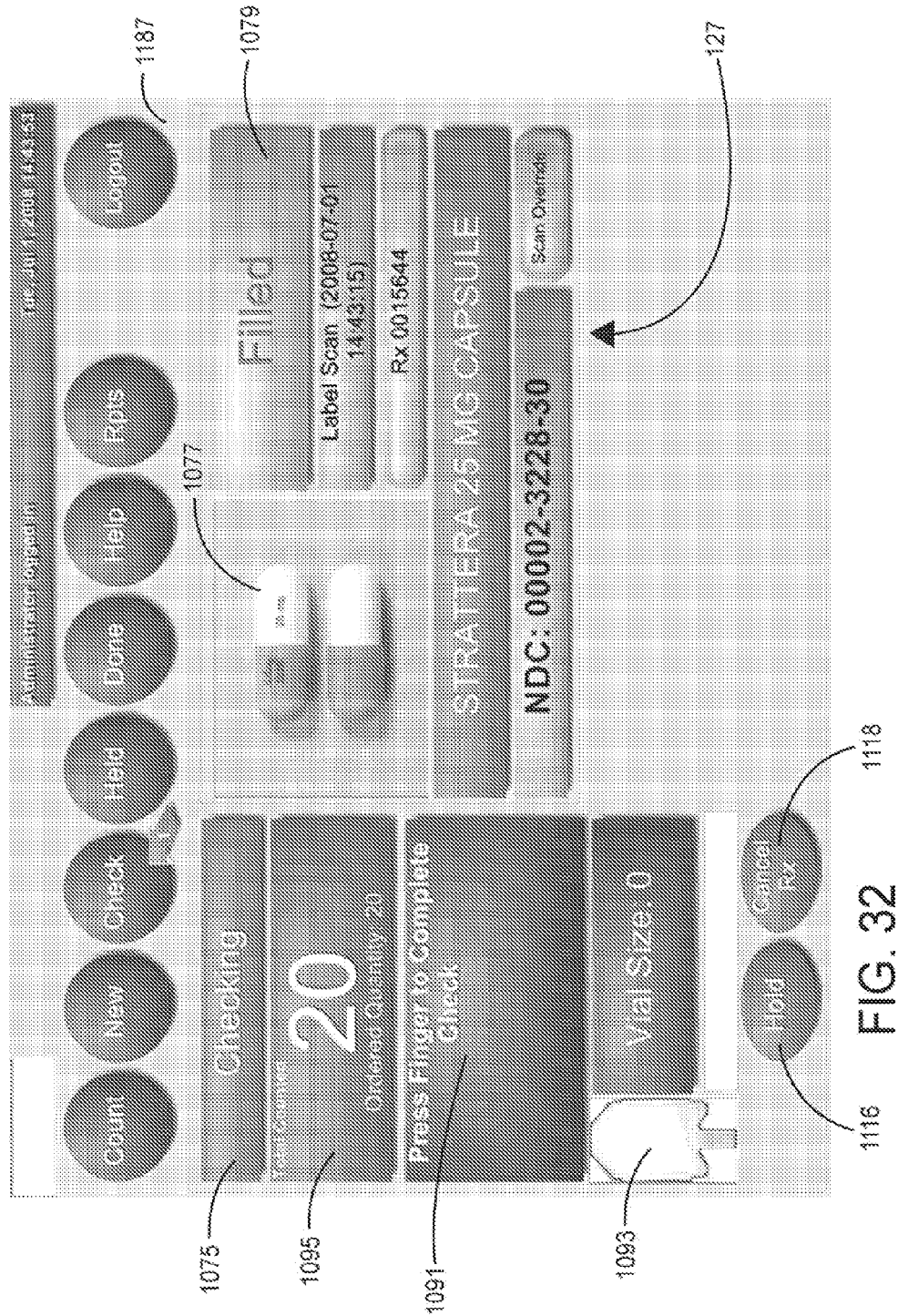
Figure 33:
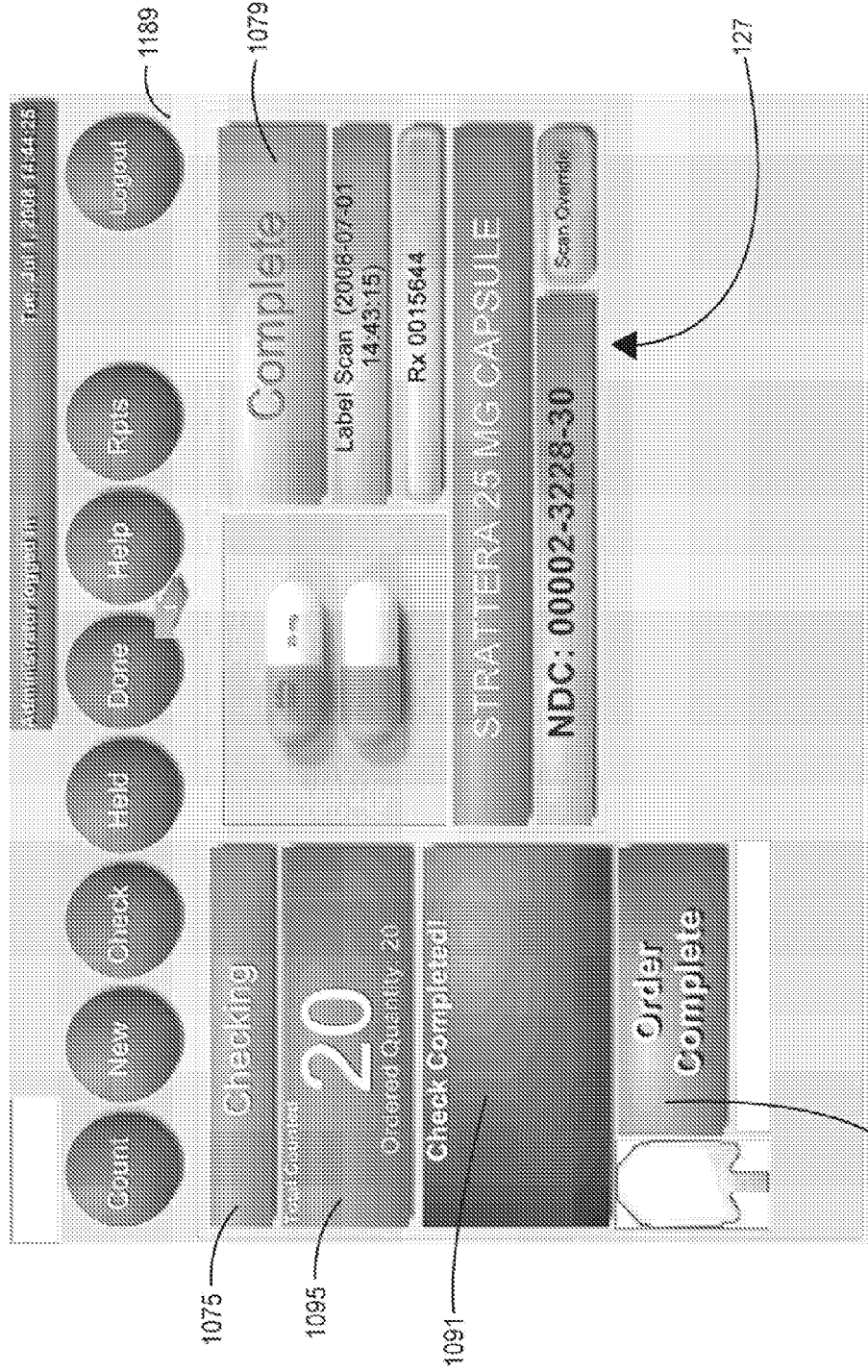

Referring to FIGS. 14B, 32 and 33, verification for non-interfaced systems 11 at blocks 247, 249 is much the same as previously described for interfaced system 11, except that the user has the option of verifying only the single prescription being fulfilled. The user has the ability to control verification by fingerprint or by scanning as described above for interfaced system 11 and such description is incorporated herein by reference. For simplicity and brevity, fingerprint-controlled verification is described herein, it being understood that barcode-controlled verification merely substitutes barcode scanning for placement of a finger on biometric sensor 55.

Turning then to FIGS. 32 and 33, Verification screen 1187 (FIG. 32) appears on display 37 for fingerprint-controlled verification on non-interfaced system when the pharmacist or other user scans barcode 150 on paperwork 147 to initiate verification. The user then manually checks the information on screen 1187 against the physical appearance of the tablets in the patient's container and against the information provided on prescription order paperwork 147. Based on the NDC in barcode 150, the medication image is retrieved from the medication image database in storage 61 and displayed in field 1077.

If the correct medication has been loaded in the patient container as determined at block 249 (FIG. 14B), the user places a finger against biometric sensor 55 to confirm the verification. Check Completed screen 1189 (FIG. 33) appears on display 37 for the non-interfaced system 11. Prescription 127 for non-interfaced system 11 is now complete as indicated by Prescription Status Indicator field 1079 being set to "Complete" and the Main Instructions field 1091 being set to "Check Completed!." Vial Size field 1092 is set to display the message "Order Complete" also indicating that the prescription has been verified.

A record 70a indicating that single prescription 127 has been fulfilled and verified is stored in the prescription record database of non-volatile data storage 61. The record corresponding to prescription 127 includes the prescription number, NDC, medication name, medication quantity, date and time the medication was counted and the date and time that the prescription was verified. This information allows the pharmacy to reconstruct fulfilment of the prescription 127. The record for prescription 127 includes all of the information shown on Check Completed screen 1189 of FIG. 33. And, the record for the non-interfaced system 11 could include a collation of all prescriptions fulfilled for patient Pablo Martini, including prescriptions 129 and 131 once those prescriptions 129, 131 are verified. For the non-interfaced system 11, the status of the prescription 127 is set as Done in block 253.

Figure 34:
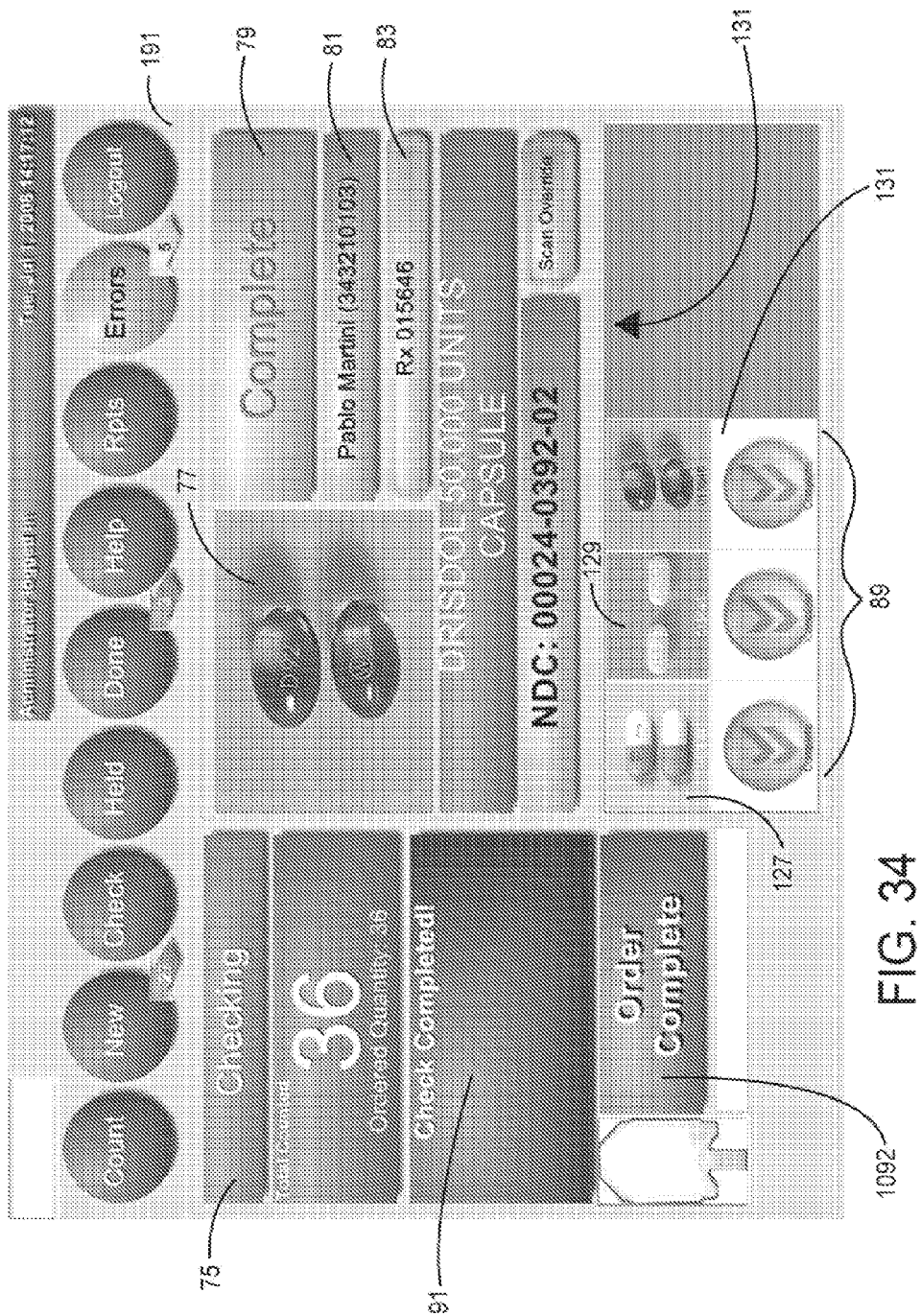

Referring again to the interfaced system 11 and FIGS. 14B and 34, at decision point 251 it is determined whether all prescriptions (e.g., prescriptions 127-131) for the patient have been filled and verified. If all prescriptions have been verified, Order Complete screen 191 illustrated in FIG. 34 is shown on display 37. Prescription Status Indicator field 79 is set to "Complete", and Main Instructions field 91 is set to "Check Completed" indicating that the verification of all the collated prescriptions 127, 129, 131 has been completed. All prescriptions 127-131 are indicated as verified by the double check marks and setting of the word "Complete" in Collated Order field 89.

The prescription order including all prescriptions 127-131 for fictitious patient Pablo Martini are now fulfilled and the order status is set to Done in block 253.

Figure 35:
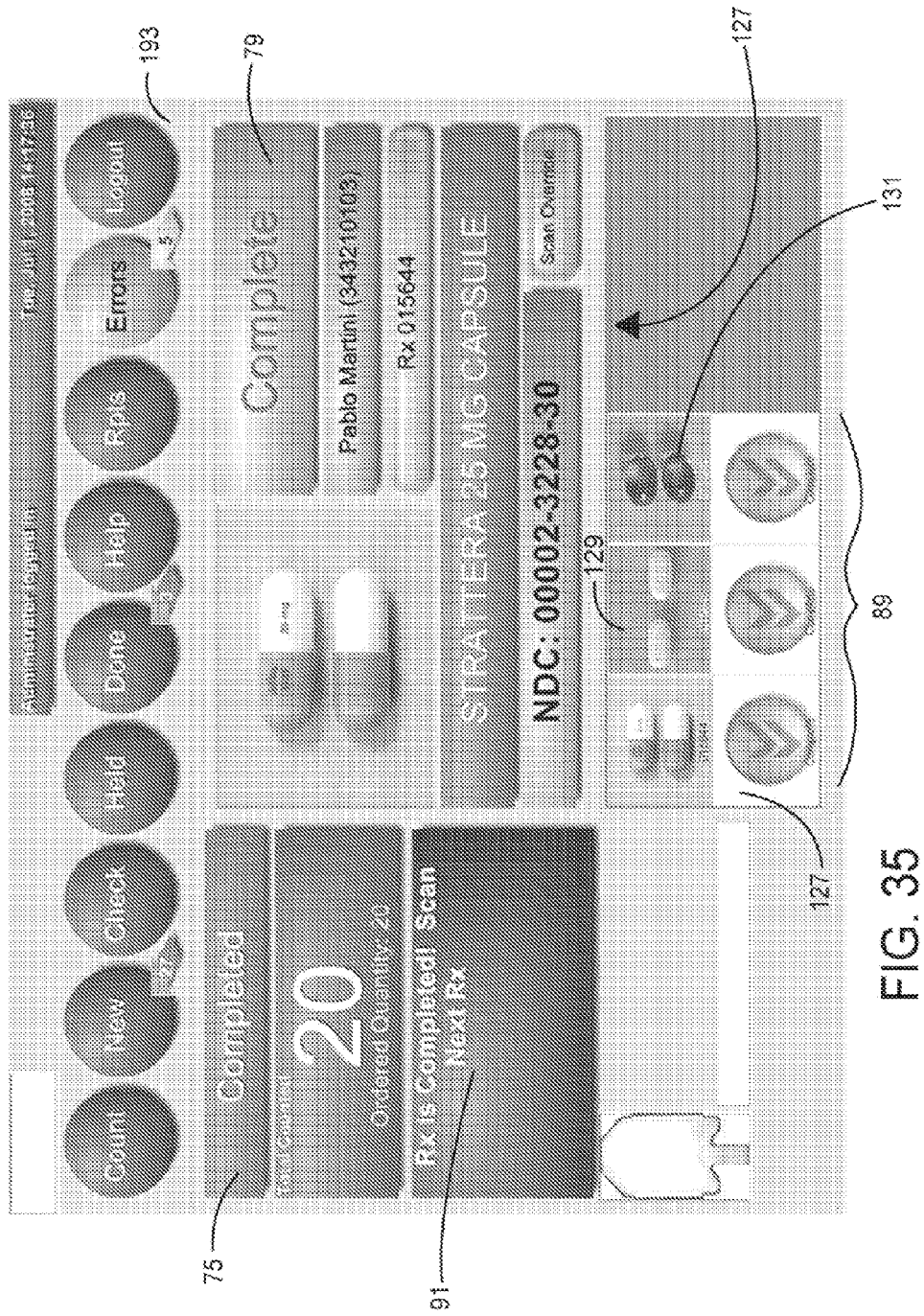

Referring now to FIGS. 35 and 37B, interfaced system 11 creates record 70b of each prescription filled collated by patient. FIG. 35 illustrates a Completed Order Record screen 193 generated by interfaced system 11 for fictitious patient Pablo Martini after each of prescription 127, 129, 131 is fulfilled and verified. All prescriptions 127-131 are collated by the patient's name for convenience. Activity field 75 and Prescription Status Indicator field 79 are set to "Completed" and "Complete" indicating that the prescriptions 127-131 are complete and have been verified. The double check marks and word "Complete" for each prescription 127-131 in Collated Order field 89 is further indicating that the three prescriptions in the example have been completed and verified. Main Instructions field 91 informs the user that the system 11 is ready to begin a new counting process indicated by the text "Scan Next Rx."

Referring to FIG. 37B, the information shown on Completed Order Screen 193 is maintained in prescription record database stored in non-volatile data storage 61 as record 70b that the prescriptions (e.g., prescriptions 127-131) of the prescription order were fulfilled and verified. Record 70b includes all prescriptions 127-131 collated for patient Pablo Martini. Record 70b (FIG. 37B) and display of Completed Order Record screen 193 (FIG. 35) can be called by selecting Done push button 105 and then selecting the patient's name from the universe of patient names within system 11 data storage 61. A user would want to access Completed Order Record screen 193 to further verify each prescription fulfilled using system 11.

Referring now to FIGS. 14A and 14C, the scan override mode of tablet counting may be entered at entry block 255 by selecting Scan Override push button 117, 1117 for example on Start screen 73 or 1073 (FIGS. 15, 16). Scan override mode is optionally provided should the user wish to perform only a tablet count. Scan override would be desirable, for example, to count tablets for a patient prescription order, to count tablets as part of an inventory procedure, or to confirm that a hand count of tablets was accurate.

Once scan override is entered (entry block 255), the user delivers tablets to feeder device 19 for a count in block 257. In the example of FIGS. 1-5, this is done by pouring tablets into funnel 41 for counting by tablet counter 15. Scan override is also useful for counting non-prescription objects such as vitamins, nutriceuticals or supplements.

At decision point 259 (FIG. 14C), it is determined whether the user has enabled optional verification. If verification is not enabled, the prescription is considered to be done at block 261.

If verification is enabled at decision point 259, the process moves to block 263 to initiate verification. The verification process is the same as described in connection with blocks 247 and 249. If verification is enabled at decision point 259, the user scans label 143 barcode 145 (or barcode 150) to initiate verification in block 263. The user then manually checks the prescription to confirm that the prescription was filled correctly. If the correct medication has been loaded in the patient container, then at block 265, the user places her finger against biometric sensor 55 or scans label barcode 145 of the prescription for a second time to confirm the verification. The order status is set to done at block 267. A record (e.g., record 70a of FIG. 37A) of the completed order is stored in prescription record database in non-volatile data storage 61.

Figure 36:
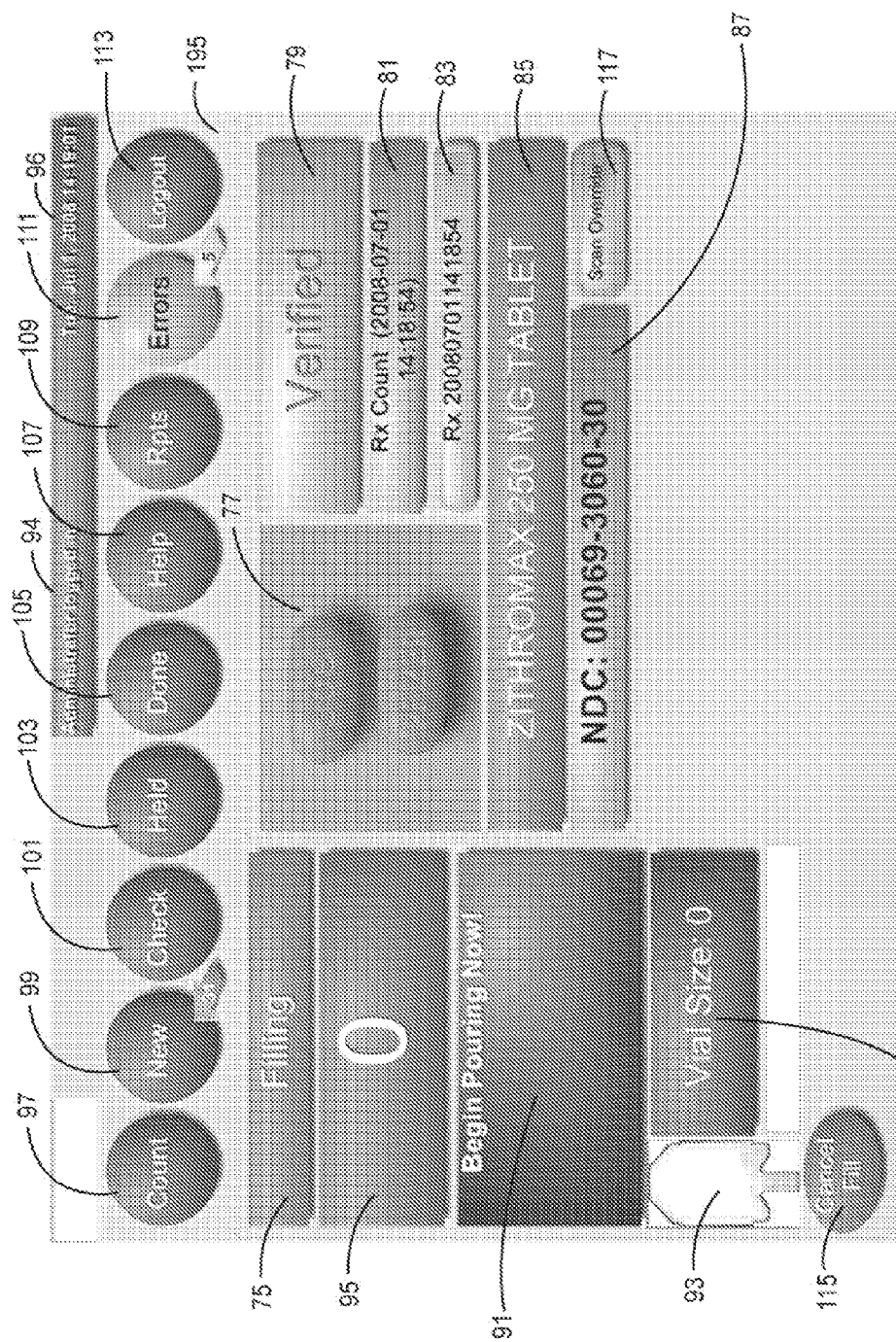
Figure 39:
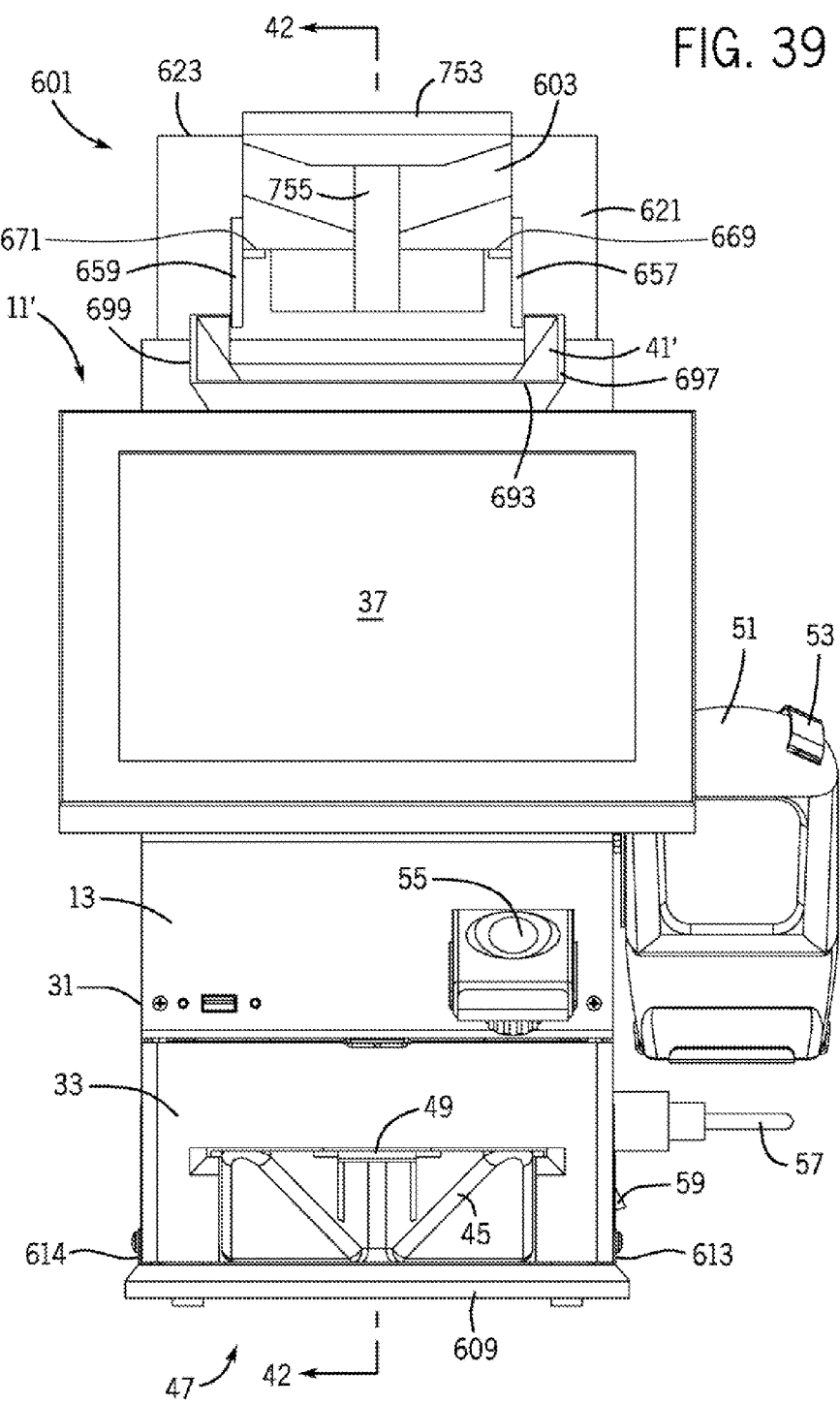
FIG. 39 is a front elevation view of the exemplary system of FIG. 38.
Figure 40:
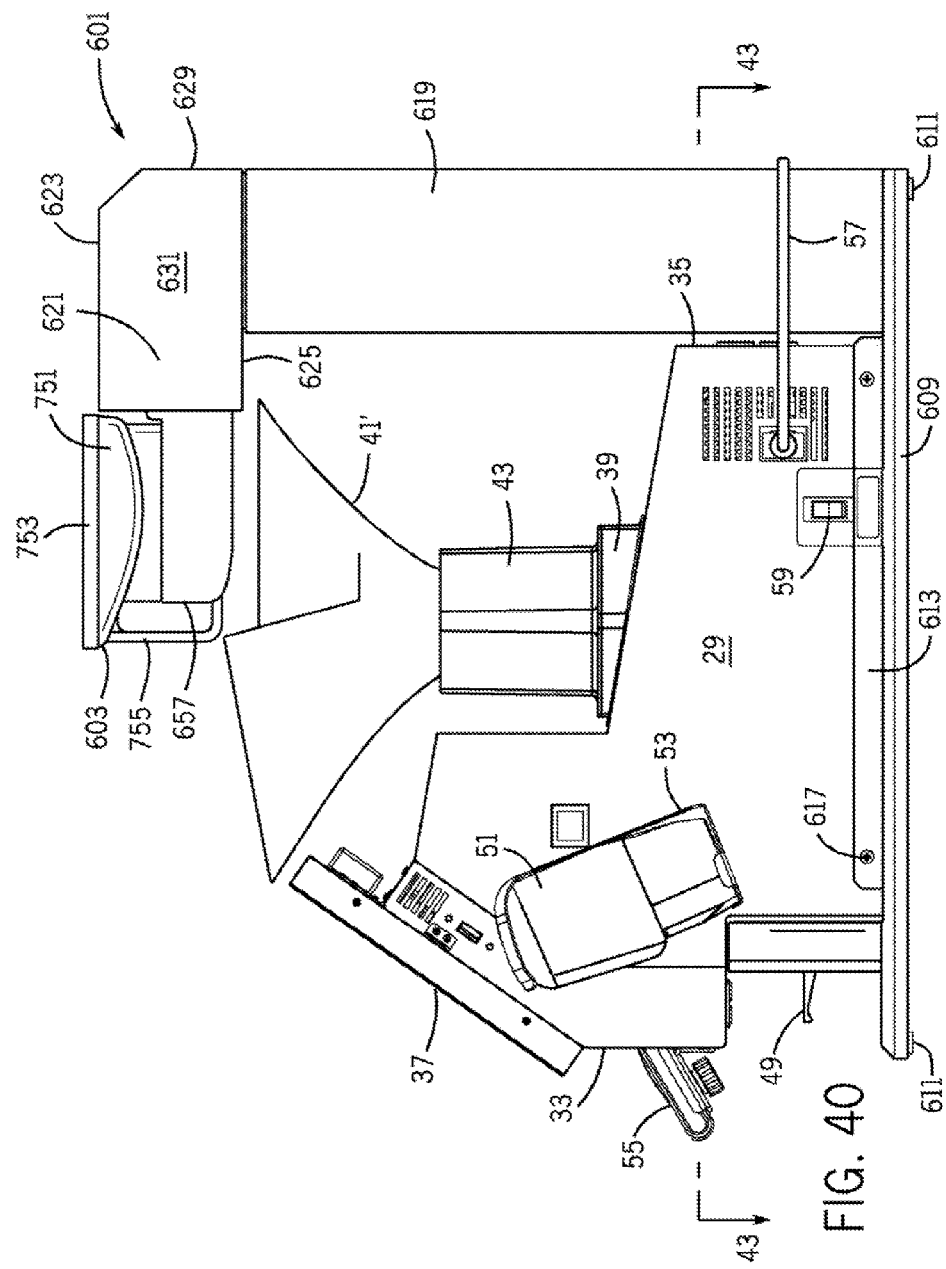
FIG. 40 is a right side elevation view of the exemplary system of FIG. 38.
Figure 41:
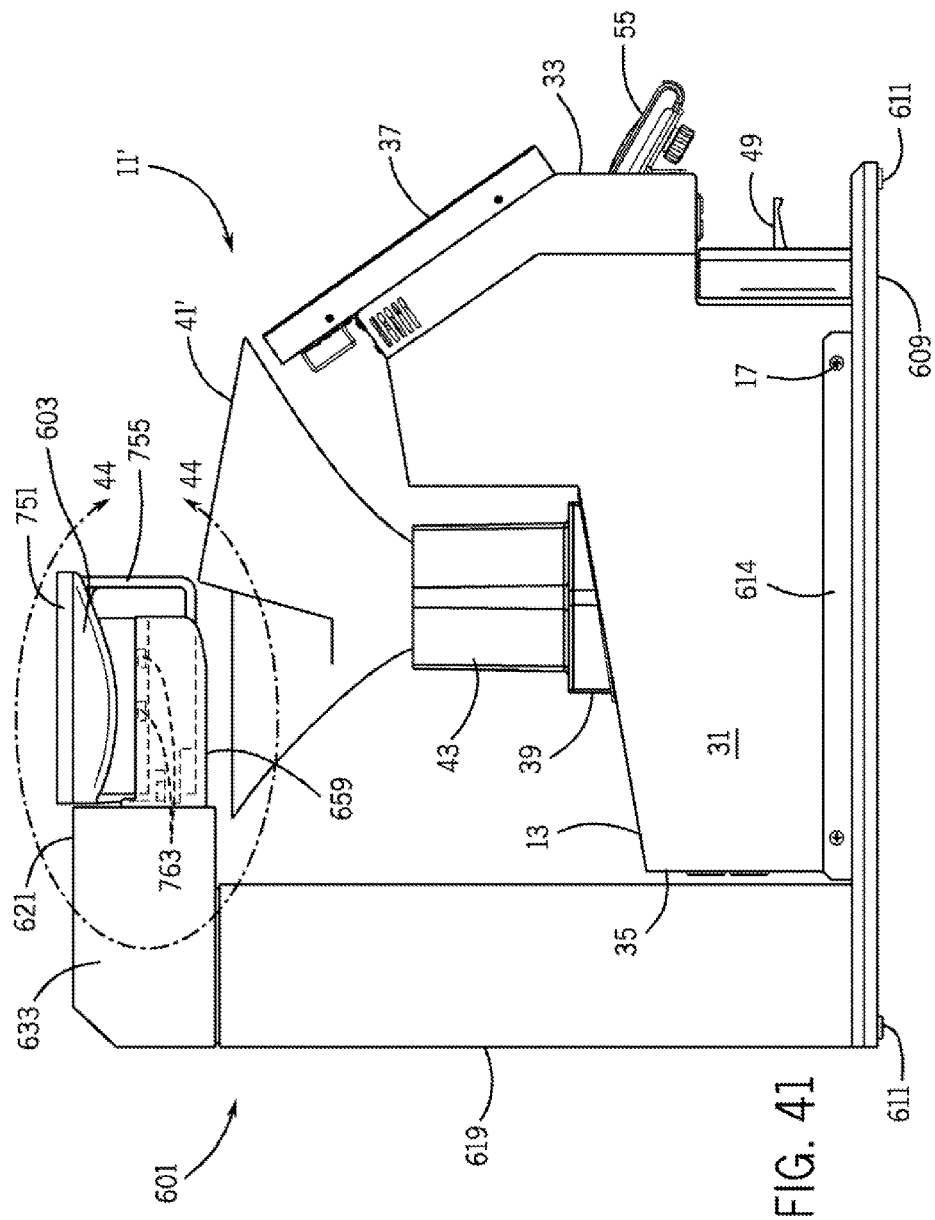
FIG. 41 is a left side elevation view of the exemplary system of FIG. 38.

Referring again to FIGS. 14A and 14C and to FIG. 36, the optional UPC scan mode of tablet counting may be entered at entry block 269. In block 271, container 175 including UPC barcode 173 is selected. In block 273, UPC barcode 173 is scanned with scanner 51. Scanning of UPC barcode 173 as the first step of the process initiates the UPC scan mode. Scanning of UPC 173 causes a UPC Start screen 195 to appear on display 37 as illustrated in FIG. 36. UPC scan mode Start screen 195 is for interfaced system 11. All of the fields and controls described in connection with Start screen 73 (FIG. 15) are provided, and the description of such fields and controls is incorporated by reference herein.

Fields illustrated on Start screen 195 (FIG. 36) include: an Activity field 75, a Medication Image field 77 and a Prescription Status Indicator field 79. Since no patient or prescription information is known for a UPC scan mode count, Customer/Patient field 81 and Prescription Number field 83 show the date and time of day of the UPC scan count. Other fields are a Medication Description field 85, a Medication NDC field 87, a Main Instructions field 91, a Vial Size field 92, a Tray Status field 93 and a Count Status field 95. Fields for the User Name 94 and Date and Time of Day 96 are provided. No Collated Prescription field is required because the UPC scan mode is based on a count of a single medication and is not tied to a specific prescription.

Control push buttons on Start screen 195 (FIG. 36) include: a Count push button 97, a New push button 99, a Check push button 101, a Held push button 103, a Done push button 105, a Help push button 107, a Rpts (reports) push button 109, an Errors push button 111 and a Logout push button 113. Additional control push buttons can include a Cancel Fill push button 115 and a Scan Override push button 117. These controls function as described in connection with screen 73. Hold and Cancel Rx push buttons (not shown) may also be provided on display 37 for the purpose described in connection with Hold and Cancel Rx push buttons 1116, 1118.

In block 257 the tablets are counted by tablet counter 15. Once again, in the examples of FIGS. 1-5, this is accomplished by pouring the tablets from container 175 into feeder device 19 through funnel 41. Blocks 259, 261, 263, 265 and 267 described in connection with scan override counting mode are repeated for the UPC counting mode providing the opportunity for the user to verify and check the prescription for accuracy. The order status is set to Done at block 267 if verification is enabled. A record such as record 70a (FIG. 37A) of the completed order is stored in prescription record database in non-volatile data storage 61.

System 11 can also be configured to fulfill prescription orders for medication and other health-care-related products not requiring counting by tablet counter 15, thereby providing a more comprehensive tool with which to manage pharmacy workflow. For example, a patient prescription order may require an ointment or other product not requiring tablet counting as represented by box 174 illustrated in FIG. 12B. Box 174 includes a UPC barcode 176.

For interfaced systems 11, the medication or product contained in box 174 can appear as a separate prescription on New Order screen 119 (FIG. 17). The patient name 121, prescription number 135, medication name, strength and form 137, count 139, image 138 and status 140 information can be provided for the medication or product in box 174. Barcode 176 can be scanned with scanner 51 and the UPC verified to confirm that the box contains the medication or other product required by the prescription. The medication in box 174 can then be verified as described in connection with blocks 247 and 249.

Accordingly, patient prescription order workflow for a wide-range of medications can be easily managed by system 11. Accuracy in prescription order fulfillment is improved by providing a greater level of certainty that the patient is receiving all of the medication required by the patient's prescription order and that the selected medication is correct. Because system 11 reduces the time required to fulfill patient prescription orders, the pharmacist is free to perform other valuable tasks such as counseling patients. The result of system 11 implementation is an improvement in pharmacy management and in the general level of patient care.

Workflow Management System 11'

FIGS. 38-49 illustrate a further embodiment of an exemplary pharmacy workflow management system 11'. System 11' includes automatic tablet counter 15 and is fully capable of operating as a pour-through tablet counter as described and illustrated in connection with system 11.

System 11' differs from workflow management system 11 in that system 11' combines automatic tablet counter 15 with a second automatic tablet counter 615 of tablet feeder 19 thereby providing system 11' with a cassette-based dispensing capability.

In the example of system 11', each tablet counter 15, 615 represents a system comprising apparatus and code. With respect to system 11', tablet counter 15 is referred to herein as a first tablet counter and tablet counter 615 is referred to herein as a second tablet counter. Tablet counters 15, 615 are also referred to as object counters because counters 15, 615 can count objects generally. The combination of first and second tablet counters 15, 615 and other component parts described herein provides pharmacy personnel with improved control over counting tablets required for prescription fulfillment. It will be understood that first and second tablet counters 15, 615 are described in the context of prescription fulfillment but can count objects in applications other than prescription fulfillment.

In the embodiment of system 11', tablet feeder 19 comprises a cassette dispenser 601 capable of automatically feeding tablet-form medication (e.g., tablets 321-327) and other objects from a cassette 603 mounted to the mounting assembly 601. In the example, tablets 604, 606, 608, 610 are fed from cassette 603 into funnel 41' and chute 43 portions of tablet feeder 19 for delivery to first tablet counter 15.

Cassette 603 may be rapidly mounted to, and removed from, cassette dispenser 601. In the example, second tablet counter 615 includes a detector 605 (FIGS. 44-46), supported by cassette dispenser 601 and further includes a controller 607 (FIG. 42) which increments a tablet count as each tablet (e.g., tablet 604) is fed from a mounted cassette 603 by cassette dispenser 601. In the example, data processing platform 17 controls operation of cassette dispenser 601 and feeding of tablets from cassette 603 mounted thereto. In the example, the tablet count displayed to a user is provided by first tablet counter 15.

In the example, the count from first tablet counter 15 is compared in real time by data processing platform 17 with the count from second tablet counter 615 to confirm the quantity of tablets fed from cassette 603 and counted by first tablet counter 15. The comparison can be used for various purposes, including to confirm that tablets are moving freely through funnel 41' and chute 43 and to confirm that the correct quantity of tablets has been dispensed as required by the prescription being fulfilled.

Systems 11 and 11' share many components, video display screens and operational steps. For convenience and brevity and to facilitate ease of understanding, reference numbers and figures used previously to describe components and operational steps of system 11 are used to describe like components and operational steps of system 11', it being understood that the date and time stamps of the figures from system 11 are not sequential with the date and time stamps of the figures from system 11'.

Turning then to FIGS. 38-49, system 11' includes a housing 13 that houses first tablet counter 15 and a data processing platform 17. Data processing platform 17 includes all components necessary for data processing (e.g., one or more printed circuit boards that include a microprocessor, memory and interface circuitry mounted thereon). Accordingly, a data processing platform 17 includes any number of components performing some or all of the data processing.

In the example, data processing platform 17 interfaces to first tablet counter 15 and cassette dispenser 601 controller 607 of tablet feeder 19 to control the operations of system 11' during the pharmacy workflow management operations carried out by system 11'. These operations include control of pharmacy workflow involving fulfillment of prescriptions which require tablet counting and, in embodiments, may also include control of pharmacy workflow involving fulfillment of prescriptions for other medication types such as unit-of-use medications, pre-packaged medications and things (e.g., ointments, syringes, inhalers, etc.).

Data processing platform 17 may interface with a Pharmacy Management System (PMS) 21 as described and illustrated previously in connection with system 11. Data processing platform 17 may be connected to PMS 21 through a communication link represented by line 23 in FIG. 49 providing a means for data transmission back-and-forth between PMS 21 and system 11'. An interface between system 11' and PMS 21 may be provided by means other than link 23, such as by batch delivery of prescription orders from PMS 21 to system 11' via a portable non-volatile memory device (not shown). Prescription order data downloaded onto the memory device could then be transferred to system 11' by pharmacy personnel.

As with system 11, validated prescription orders consisting of one or more prescriptions are transmitted electronically from PMS 21 via link 23, or by batch, to data processing platform 17 of system 11' for managed prescription order fulfillment as described in detail below. Following prescription order fulfillment by a pharmacy technician and/or registered pharmacist utilizing system 11', a record of each completed prescription order may be sent by system 11' back to PMS 21 providing confirmation of prescription order fulfillment.

System 11' can also function as a stand-alone system which is not interfaced with PMS 21 as is the case with the example of system 11 described previously. For non-interfaced embodiments of system 11', PMS 21 provides instructions and information for fulfillment of separate prescriptions. This information may be in the form of prescription order paperwork 147 (FIG. 13) which includes all information required to fulfill a validated prescription as described herein.

Systems 11 and 11' share other hardware, database, storage and code components described now in connection with FIGS. 38-49. System 11' includes top 25 and bottom walls 27, sidewalls 29, 31 and front 33 and rear walls 35. System 11' includes a display 37 mounted to housing 13 front wall 33 and interfaced with data processing platform 17. Display 37 outputs information to a user of system 11', such as a pharmacy technician or pharmacist. Display 37 preferably provides status messages to the user, including information relevant to the management of pharmacy workflow, the number of tablets counted by first tablet counter 15 and prescription status. First tablet counter 15 provides this information in real time, including near-instantaneous display of counted tablets in the Count field 95, 1095 (e.g., FIGS. 24, 25, 60, 61). Examples of screen displays are discussed in connection with FIGS. 55-75 and 20-36.

As in system 11, display 37 of system 11' is preferably a flat panel liquid crystal display (LCD). It is preferred that display 37 is a touch-screen-type display thereby enabling display 37 to also serve as an input device for transmission of information from the user to data processing platform 17. Data is transmitted from display 37 to data processing platform 17 of the second embodiment 11' when a user touches display 37 proximate information or an image shown on display 37. A touch-screen-type display may display an image of a QWERTY-type 65 (e.g., FIG. 70) or ABC-type keypad which enables a user to input information to data processing platform 17 by touching keys of the keypad. Such a keypad would be useful for inputting information to data processing platform 17, for instance user login information, prescription number information or NDC information. Numeric keypads may also be provided to input information to data processing platform 17 as described below. Other types of displays, such as a cathode ray tube (CRT) or digital numeric display, may be used. System 11' could optionally utilize an external keyboard and mouse (not shown) connected to a universal serial bus port (USB) of system 11' (not shown) if a touch-screen-type display is not used.

Funnel 41' is provided to receive tablet-form medications and other objects poured by a user from a bulk storage container 175 (FIG. 12A) or fed from a cassette 603. Funnel 41' is attached to vertically-oriented chute 43 which is removably seated in mount 39 on housing top wall 25. Tablet-form medications and other objects fall by means of gravity through funnel 41' chute 43, past tablet counter 15 into a tray 45 removably positioned in tray bay 47 provided in housing front wall 33. Tray 45 may be removed from housing 13 bay 47 by grasping and pulling tray handle 49, thereby permitting medication in tray 45 to be conveniently poured into a container (not shown) such as a vial or bottle which is subsequently provided to the patient.

Referring further to FIGS. 38-43, system 11' includes other external and internal components as described in connection with the example of system 11. These components include a barcode scanner 51 input device secured to housing 13 sidewall 31 by support 53 as previously described. As described in connection with the first embodiment 11, other types of code readers, such as a radio frequency identification tag (RFID) reader (not shown) may be utilized separately or in combination with barcode scanner 51. In the example, a biometric sensor 55 is mounted to housing 13 front wall 33 as described in connection with system 11. Data processing platform 17 interfaces with both barcode scanner 51 and biometric sensor 55.

Power cord 57 supplies electrical power to power supply 58 of system 11'. A rocker-type ON/OFF switch 59 is provided along housing 13 sidewall 31 to control the electrical power delivered to power supply 58.

Figure 49:
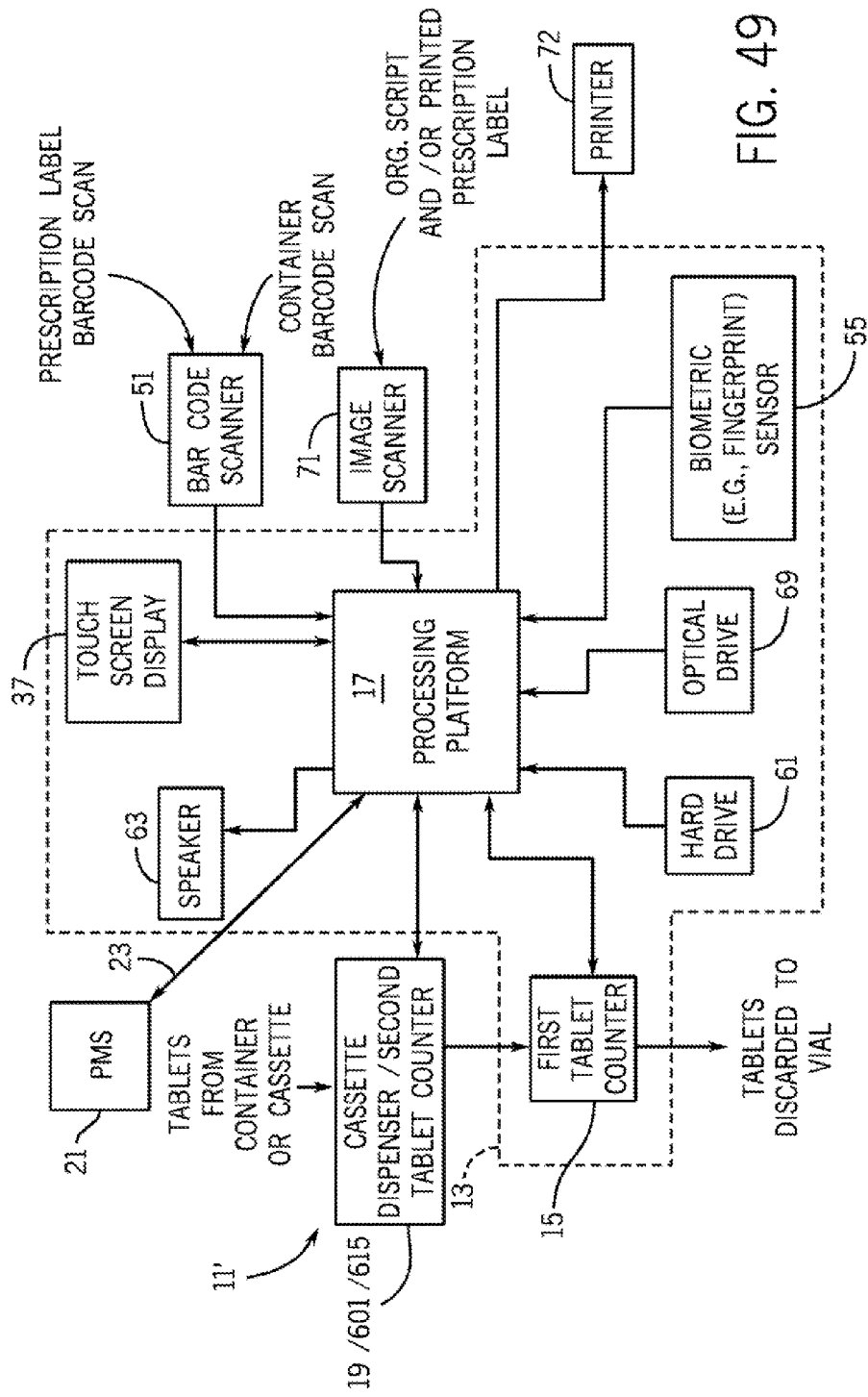
FIG. 49 is a schematic block diagram showing an exemplary data processing platform for use with the exemplary system of FIG. 38, together with other components.

Referring now to FIG. 49, data processing platform 17 interfaces to a number of components that are housed within system housing 13, including non-volatile data storage 61 (which may be realized by a hard drive, flash memory or other suitable non-volatile memory means), an audio speaker 63 and touchscreen-type display 37. Data processing platform 17 executes operating system and application logic that is persistently stored in the non-volatile data storage 61 and loaded onto the data processing platform 17 for execution thereon. Such execution provides for automatic control over system 11' in accordance with the operations described herein (FIGS. 50-53A and 54A-54D).

Figure 70:
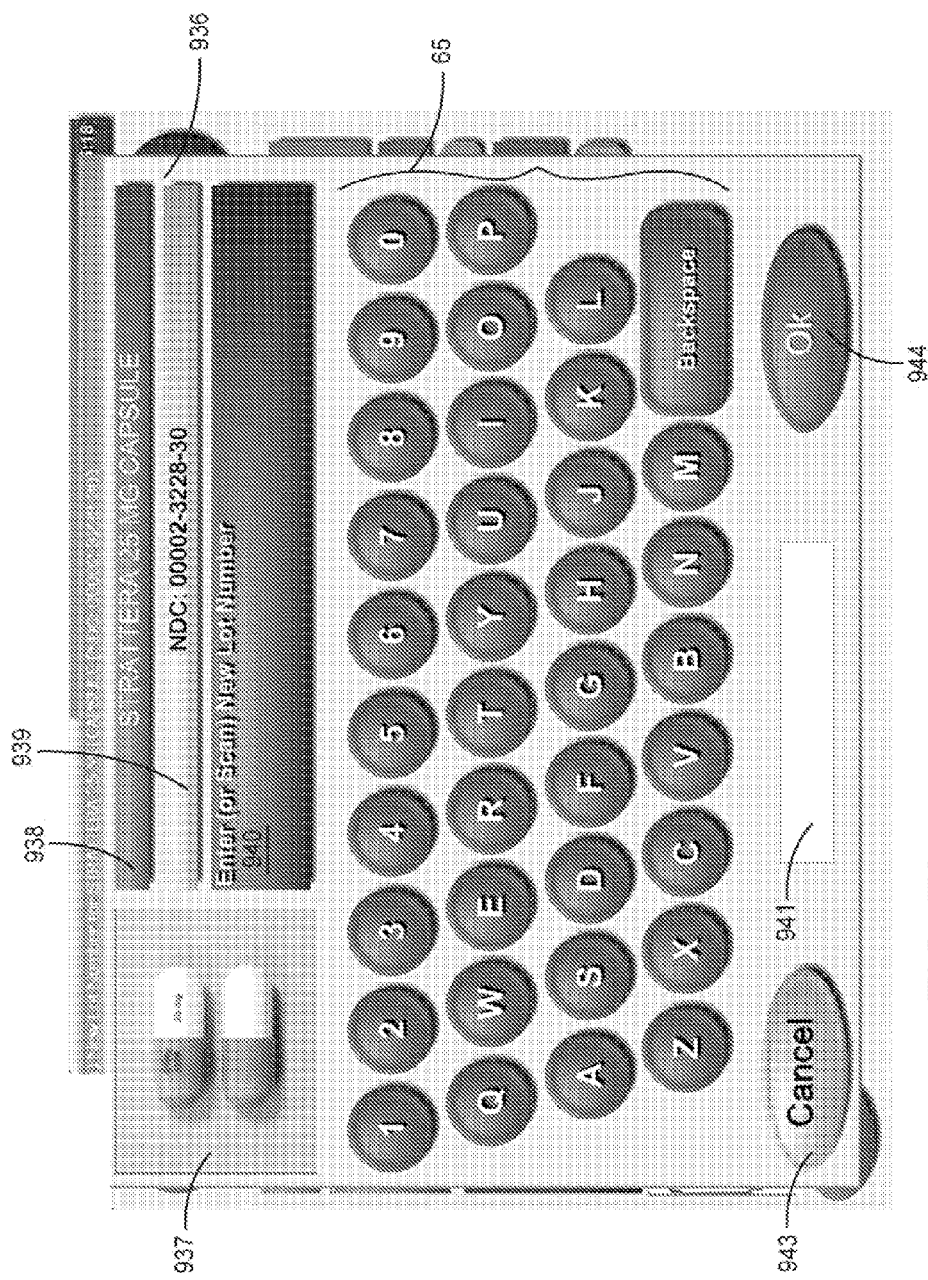

As previously described, information may be input by a user to data processing platform 17 through a touch-screen-type keypad 65 shown on display 37 (an example of which 65 is illustrated in FIG. 70) and/or barcode scanner 51 also as previously described. In other systems, information may be provided from another data processing system that is coupled to system 11' over a communication link therebetween. An optional keyboard and mouse (not shown) may also be used to input information to data processing platform 17.

Data processing platform 17 also preferably interfaces to an optical drive 69 (which may be realized by a CDROM drive, DVD-ROM drive or other suitable device) and an image scanner 71. Optical drive 69 can be mechanically supported in an independent housing and interfaced to data processing platform 17 through suitable connection means. Barcode scanner 51 and image scanner 71 are preferably mechanically supported in independent housings and interfaced to data processing platform 17 through suitable connections (such as a wired or wireless data link therebetween). Alternatively, barcode scanner 51 and/or image scanner 71 can be housed within housing 13. In addition, system 11' may include a printer 72 that prints a prescription label 143 and prescription order paperwork 147 for each prescription of a prescription order. System 11' may also include a connection such as a USB port or other similar connection to enable batch prescription data to be transferred to/from system 11'.

Non-volatile data storage 61 stores an image database that maintains image files for a large number of commercially-available medications indexed by NDC number (hereinafter referred to as the "medication image database"). Each image file is an electronic image of a particular medication as identified by its corresponding NDC number. Exemplary image files from medication image database shown on display 37 are illustrated in Medication Image field 77, Image field 138 and Collated Order field 89 of the interfaced system 11' screen displays (e.g., FIGS. 57-58, 60, 62-64, 66-71, 73, 75) and Medication Image field 1077 of the non-interfaced system 11' screen displays (e.g., FIGS. 59, 61, 65, 72, 74). The medication image database is updated periodically by loading updated files stored on an optical disk into the system via optical drive 69 or via updates from PMS 21 via link 23. Alternatively, the medication image database may be updated from a remote computer system coupled thereto over a network link (e.g., over a LAN or WAN/Internet), for example, from a database provider such as First DataBank® of San Bruno, California or Medi-Span® of Indianapolis, Ind.

Non-volatile data storage 61 may also store a database of records indexed by prescription numbers (hereinafter referred to as the "prescription record database"). A prescription number is a unique number assigned by the pharmacy to each prescription. Exemplary prescription numbers can be seen in Prescription Number field 135 of New Order screen 119 of FIG. 57. The unique prescription number is used to track all information related to fulfillment of the prescription. The prescription record database may be local on storage 61 for systems which are interfaced with PMS 21 and for stand-alone systems 11' which are not interfaced with PMS 21. Alternatively, the prescription record database could be maintained by PMS 21 and accessed by system 11' via link 23.

Figure 57:
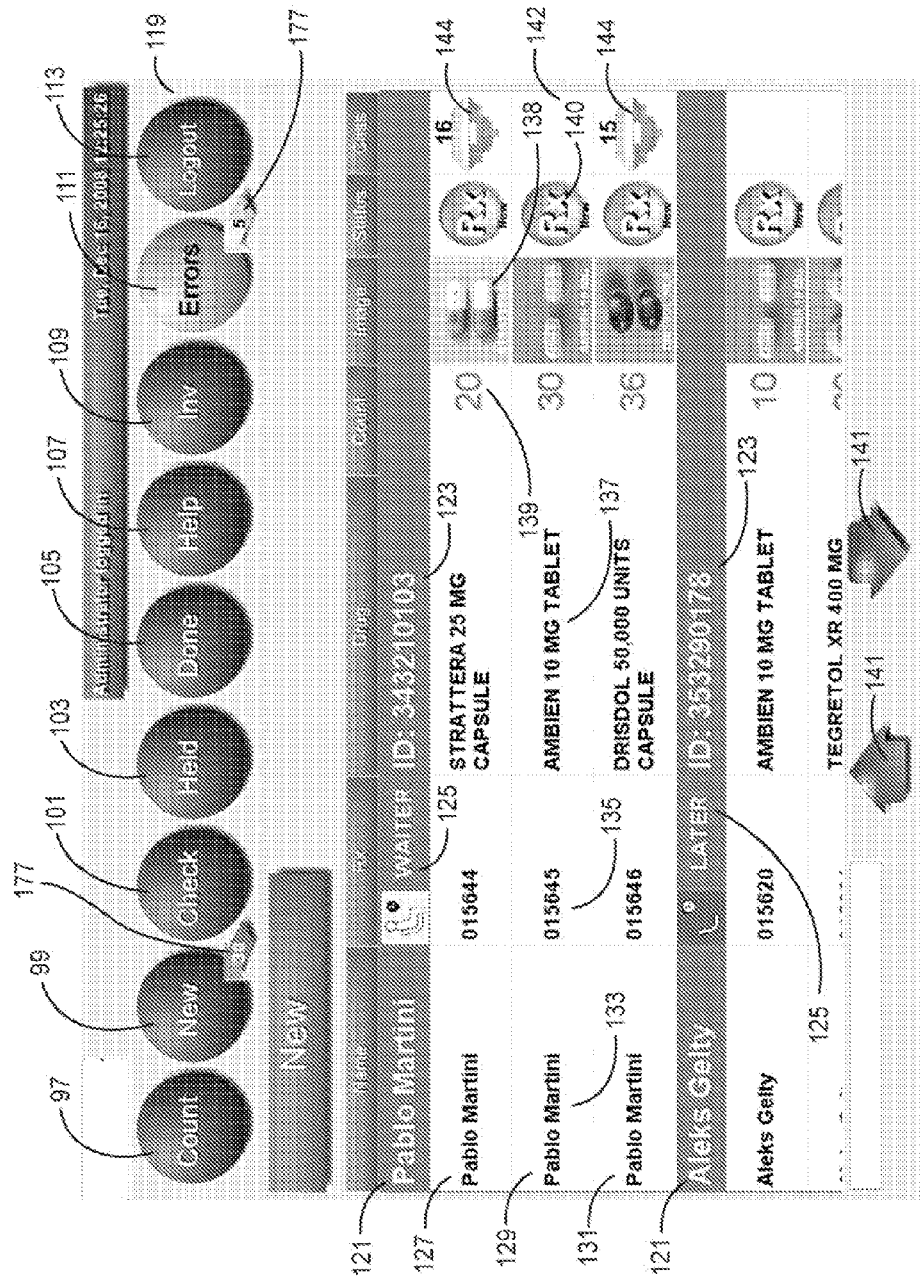
Figure 58:
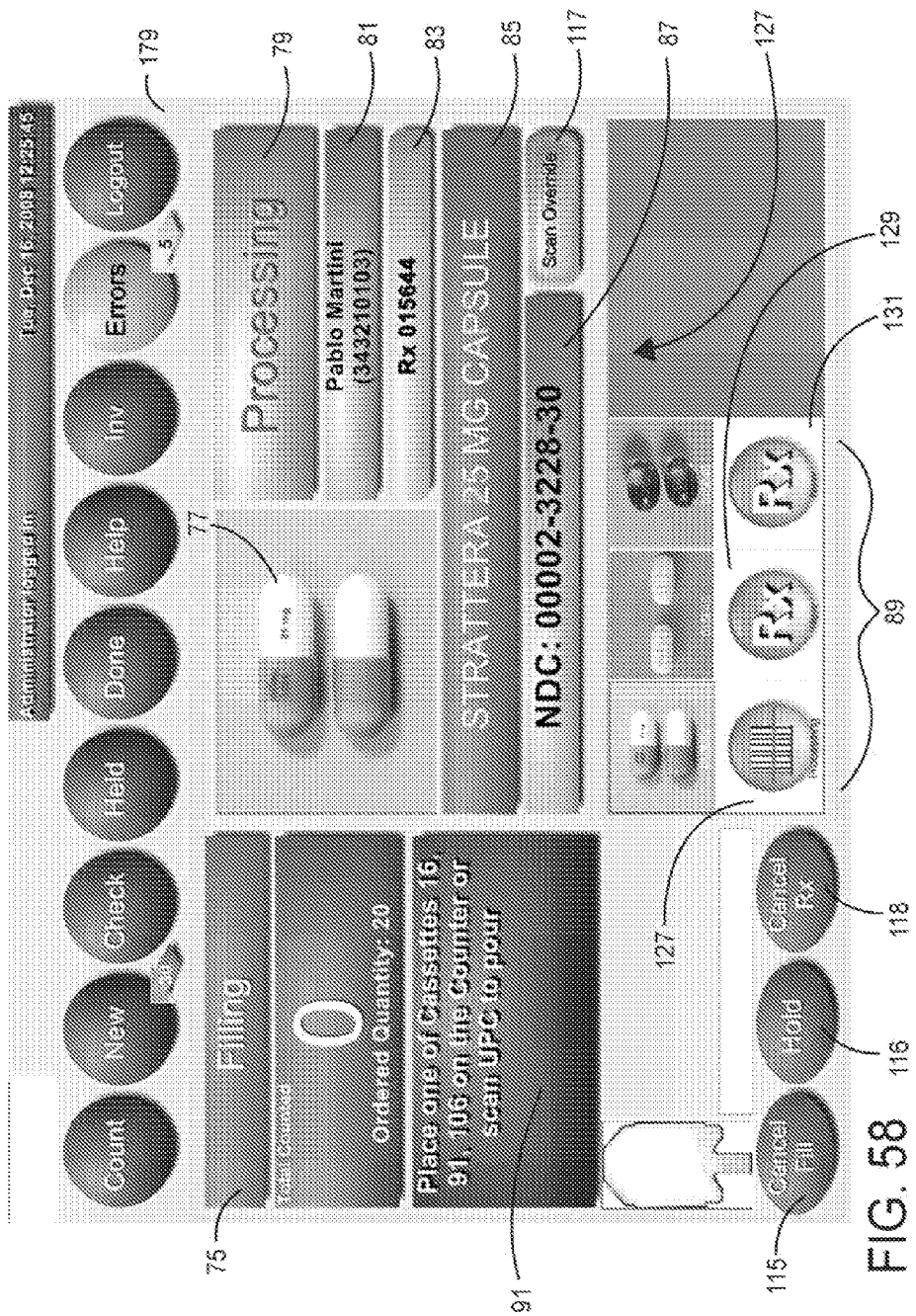

As described below, the prescription record database for an interfaced system 11' may include a record of each prescription awaiting fulfillment, examples of which (prescriptions 127, 129, 131) are seen, for example, on New Order screen 119 (FIG. 57) and Prescription Filling screen 179 (FIG. 58). The information in the prescription record database could include patient name, prescription number, medication type, strength and form, and required medication quantity. Other information in prescription record database for each prescription may include the status of each such prescription (e.g., fully or partially fulfilled, held because medication is not available, held because of a prescription data error, etc.).

The prescription record database for a non-interfaced system 11' may include a record of each prescription for which fulfillment has been initiated as well as the status of each such prescription (e.g., fully or partially fulfilled, held because medication not available, held because of an error, etc.). The record could include the NDC, the prescription number, the medication type, strength and form, and the required medication quantity.

The prescription records in the prescription record database may also include, for each prescription number, an image file of the original script of the prescription (as written by the doctor) and an image file of the printed prescription label for the prescription number. These image files are output to system 11' prescription record database from PMS 21 or may be loaded into the prescription record database by means of image scanner 71.

The prescription record database for each prescription number is updated following prescription fulfillment with a record such as record 70a (FIG. 37A) for a single prescription or record 70b (FIG. 37B) for all prescriptions collated by patient including all desired information relating to the fulfillment transaction. Record 70a or 70b of prescription fulfillment may be accessed from non-volatile data storage 61 for a user-determined amount of time.

For interfaced systems 11', a prescription record database maintained by PMS 21 may also be updated following prescription fulfillment with a record including all desired information relating to the fulfillment transaction. Such record is maintained for archival purposes.

Non-volatile data storage 61 may also store a database of records indexed by cassette 603 (hereinafter referred to as the "cassette record database"). The cassette record database tracks each cassette 603 of system 11' by a unique cassette code embedded in a barcode 760 on cassette sidewall 759 (FIG. 46A, barcode 760 location indicated in FIG. 46) which is detected and passed to data processing platform 17 when cassette 603 is fully mounted on cassette mount 621. The unique cassette code embedded in barcode 760 is displayed to a user on display 37 (e.g., icons 144, 146, 1146, FIGS. 57, 60-61) to assist the user in selecting the correct cassette 603.

The unique cassette code is used to track all information related to medication or other product in each cassette 603. The cassette record database tracks the type and quantity of medication or product loaded in each cassette 603. The cassette record database may also track the medication strength, lot number, expiration date and medication physical form. The cassette record database preferably also tracks cassettes 603 which are confirmed as having been properly loaded and verified by a registered pharmacist and therefore are available for use with system 11'. The cassette record database is updated following prescription fulfillment to track the inventory of medication available to system 11'. This information can be utilized for reordering of medication when the inventory becomes low. Other information about each cassette 603 can be stored in the cassette record database based on user requirements. Therefore, the cassette record database tracks all medication or other product in the inventory of cassettes 603.

The cassette record database may be local on storage 61 for systems which are interfaced with PMS 21 and for stand-alone systems 11' which are not interfaced with PMS 21. Alternatively, the cassette record database could be maintained by PMS 21 and accessed by system 11' via link 23.

Figure 42:
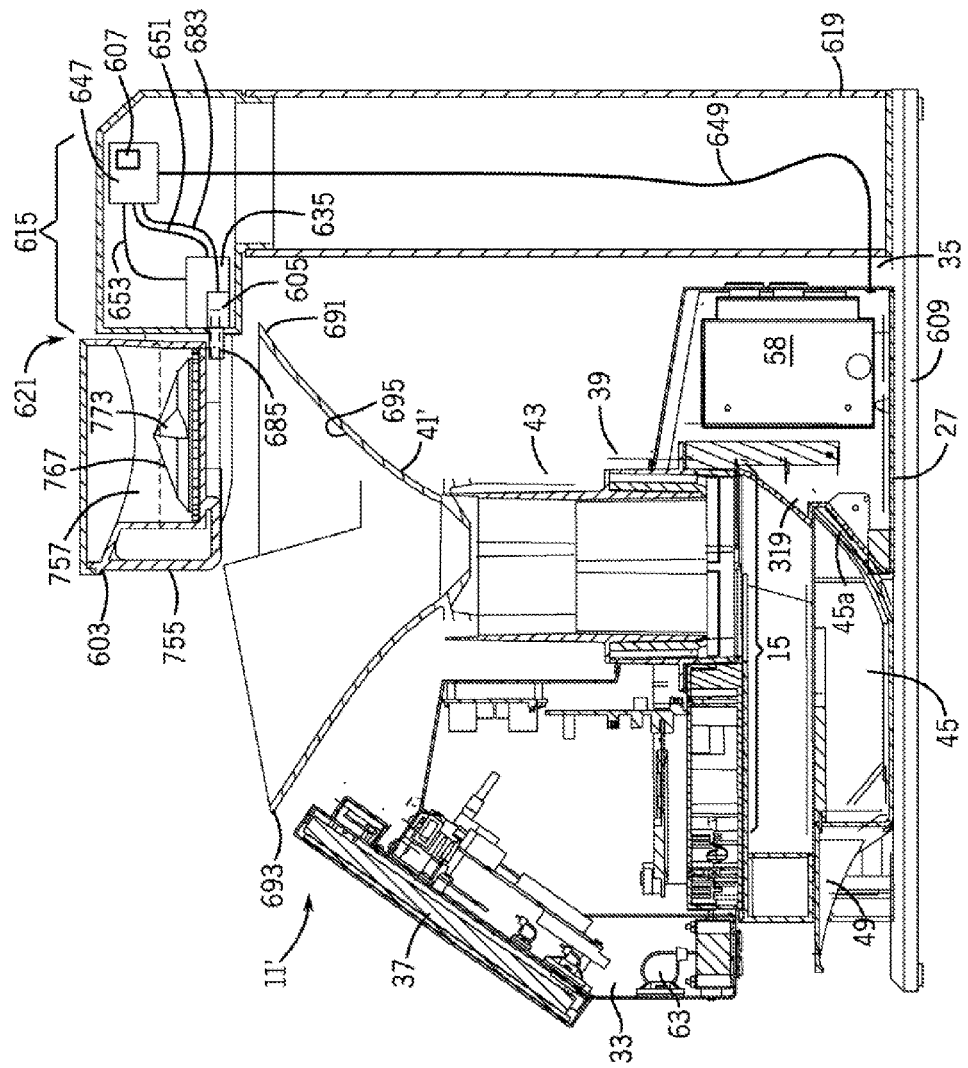
FIG. 42 is a side section view taken along section 42-42 of FIG. 39 showing a tablet counter, cassette dispenser and other internal components.
Figure 43:
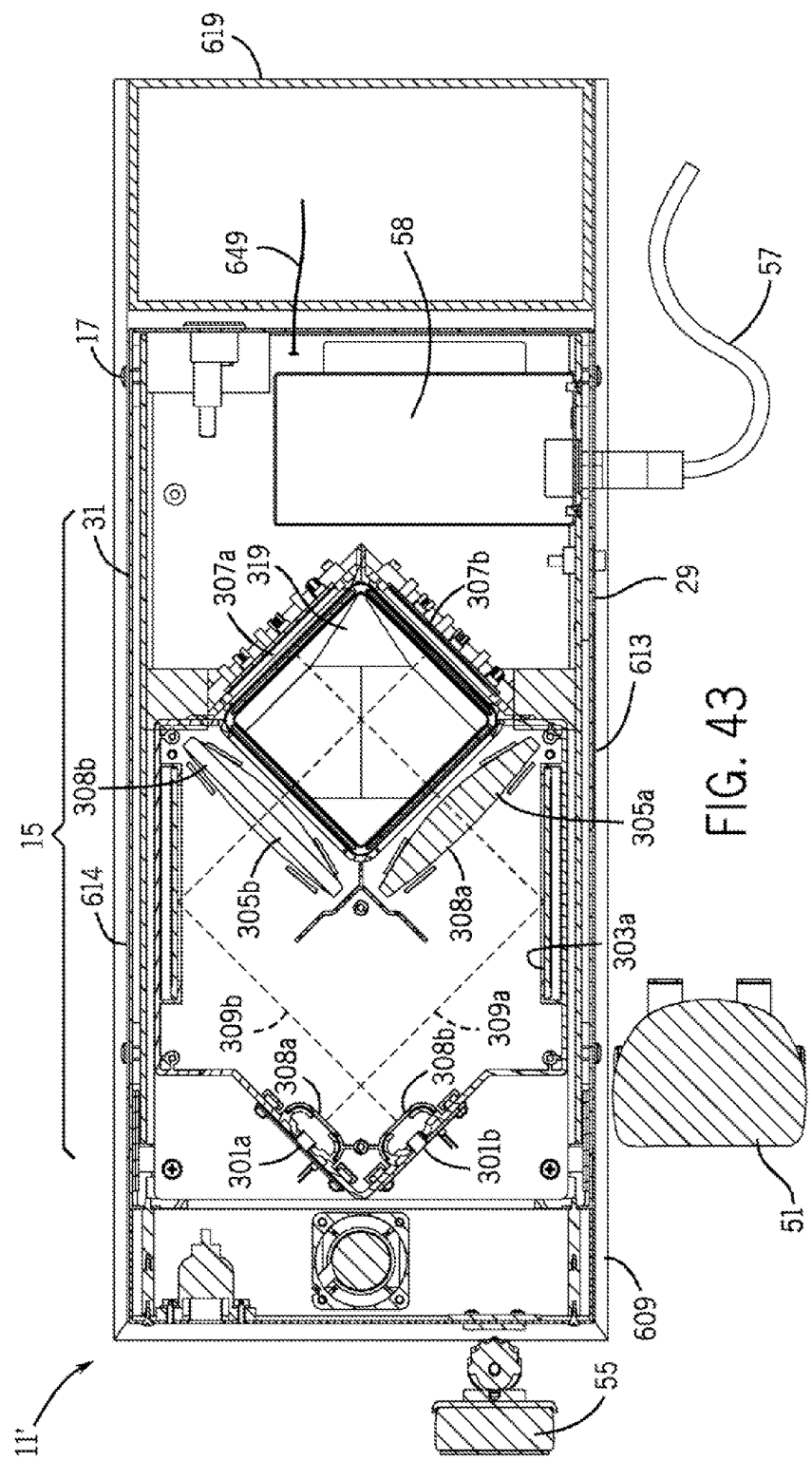
FIG. 43 is a section view taken along section 43-43 of FIG. 40 showing tablet counter, cassette dispenser and other internal components.

Referring now to FIGS. 42-43 and 49, first tablet counter 15 of second system embodiment 11' is preferably identical to the optical system described in connection with first tablet counter 15. The first tablet counter 15 is capable of automatically counting tablets and other types of discrete objects. (Such discrete objects, could include, for example, non-prescription objects such as vitamins, nutriceuticals, supplements, jewelry, parts or other countable things.) Accordingly, the description of automatic tablet counter 15 set forth above (including FIGS. 4, 5, 6, 7, 8, 9, 10A, 10B, 10C-1, 10C-2, 11A and 11B) is incorporated herein by reference in its entirety to describe and illustrate first tablet counter 15 of system 11'. A summary of the previously-described structure and operation of tablet counter 15 follows as adapted for use as first tablet counter 15 of system 11'.

Referring to FIGS. 42-43 and FIGS. 7-11B, first tablet counter 15 of system 11' preferably includes infra-red (IR) emitters 301a, 301b, mirrors 303a, 303b, collimating lenses 305a, 305b, and IR sensor linear arrays 307a, 307b all as described and illustrated in connection with tablet counter 15 of system 11. As illustrated in FIG. 7, sensor arrays 307a, 307b are coupled to a microprocessor-based controller 311 which is also coupled to collimated IR sources 308a, 308b. Controller 311 is preferably bidirectionally coupled to microprocessor-based master controller 313 which provides output to display 37 and operates speaker 63 to generate audible alarm 315. Controller 311 strobes IR emitters 301a, 301b at a relatively high rate and preferably alternatingly so that only one IR emitter 301a or 301b is activated at any instant. Each mirror 303a or 303b directs light 309a, 309b from a corresponding IR emitter 301a, 301b to a respective lens collimating lens 305a, 305b beneath chute 43. In the example, mirrors 303a, 303b deflect light 309a, 309b approximately 90 degrees. As with system 11, this arrangement permits housing 13 to be more compact because the focal length of lenses 305a, 305b is traversed in two orthogonal segments, and IR emitters 301a, 301b therefore need not be placed so far away from lenses 305a, 305b.

As tablets pass between each sensor array 307a, 307b and its respective collimated IR source 308a, 308b, shadows will be cast on one or more of the forty-eight sensors in each array 307a, 307b. This information is processed as described above in connection with FIGS. 8 through 11B, resulting in updating of the count at block 513 of FIG. 11A and display of the count to a user in the count field 95, 1095 of a screen display as shown, for example, in the screen displays of FIGS. 24, 25, 60 and 61. Processing of the data can also provide an alarm 315 and/or indication on display 37 if an overspeed condition (i.e., a pour-too-fast condition) exits which prevents accurate counting as at block 517 of FIG. 11B.

As described below in connection with FIGS. 50-53B, data processing platform 17 compares the count from the first tablet counter 15 in real time with the count from the second tablet counter 615 to provide control over the quantity of tablets fed from cassette 603 and counted by first tablet counter 15.

Like system 11, system 11' includes a deflector 319 which is provided below sensor arrays 307a, 307b for deflecting tablets into the removable tray 45. Tray 45 preferably includes a curved inner-surface portion 45a which cooperates with and continues from deflector 319. Deflector 319 and curved surface portion 45a of the tray 45 together present a surface which prevents tablets which are falling into tray 45 from bouncing up into chute 43 and being recounted. It will be appreciated that the deflector 319 is housed in system 11 housing 13.

Referring next to FIGS. 38-49, an exemplary cassette dispenser 601 is shown. Cassette dispenser 601 supports second tablet counter 615 and a removable, tablet-containing, cassette 603 mounted to cassette dispenser 601. Each cassette 603 may be rapidly coupled to, and decoupled from, cassette dispenser 601 permitting a pharmacy to rapidly count and dispense different types of tablet-form medication from a cassette 603. Certain users may prefer to utilize cassettes 603 as an alternative to use of a container from the manufacturer (e.g., container 175, FIG. 12A), particularly for more frequently-used tablet-form products.

Cassette dispenser 601 of system 11' controls feeding of tablets from a mounted cassette 603 and second tablet counter 615 provides a second tablet count. Comparison of the counts from the first and second tablet counters 15, 615 by data processing platform 17 provides assurance that the correct quantity of tablets have been dispensed. The count redundancy provided by first and second tablet counters 15, 615 overcomes inaccurate counts associated with prior cassette counters which would fail to detect that too many tablets had been dispensed if two tablets (e.g., tablets 321, 323) were fed simultaneously from the cassette (essentially "giving away" the medication) and which would fail to detect that insufficient tablets were dispensed if a tablet fragment were dispensed from the cassette, thereby failing to meet the patient's prescription needs. And, use of cassettes 603 is convenient and efficient. Therefore, cassette dispenser 601 provides improved control over dispensing and counting of tablet-form medication and other products.

A pharmacy may utilize any number of cassettes (e.g., cassette 603). Each cassette is loaded with one type of tablet-form (e.g., tablet 321 or 604) medication or other product. Each cassette 603 has an identical mating structure enabling any cassette 603 to be rapidly coupled to, and decoupled from, cassette dispenser 601. Each cassette 603 may be calibrated for a particular size and shape of tablet or may have a single design provided to accommodate only one tablet size or shape. When not coupled to cassette dispenser 601, each cassette may be stored at a storage location (not shown) convenient to the tablet counter system 11'.

The exemplary cassette dispenser 601 will now be described with reference to FIGS. 38-49 followed by description of an exemplary cassette 603 suitable for use with cassette dispenser 601. In the embodiment, cassette dispenser 601 includes a base 609 with feet (one indicated by reference number 611). Feet (e.g., foot 611) may be made of a tactile material permitting adapter 601 to rest firmly on a bench or desktop surface (not shown). In the example, system 11' is supported on base 609. Flanges 613, 614 extend away from base 609 and are secured to a respective tablet counter sidewall 29, 31, for example by fasteners such as machine screws (each indicated by reference number 617). Support column 619 is rigidly attached to base 609 and extends upward from base 609 in the example.

Referring to FIGS. 38-48, cassette mount 621 is rigidly supported on an upper end of column 619. Cassette mount 621 is provided to receive and support a tablet-containing cassette 603 in position to feed tablets into funnel 41', chute 43 and first tablet counter 15. Thus, tablets are provided to first tablet counter 15 through the intermediate funnel 41' and chute 43 parts of tablet feeder 19 in the example. Cassette mount 621 permits rapid and secure coupling and decoupling of cassettes (e.g., cassette 603) thereto.

Referring to FIGS. 38-42 and 44-48 cassette mount 621 includes top 623, bottom 625, front 627, rear 629 and side walls 631, 633 defining a housing which forms an enclosure for cassette-drive motor 635 with a drive shaft 637, micro-switch 639 with a switch arm 641, reader 645 and printed circuit board 647, including cassette dispenser controller 607. Controller 607 may be an off-the-shelf microcontroller, many variants of which are commonly available for use in controlling devices similar to cassette dispenser 601.

Cassette dispenser 601 base 609, column 619 and mount 621 walls 623-633 may be made of any suitable material having sufficient rigidity and strength. Support column 619 of the example is preferably fabricated of lightweight rectangular tubing, or other suitable material.

Exemplary cassette dispenser 601 motor 635 is a DC motor which powers operation of a cassette 603 when the cassette 603 is mounted on cassette mount 621. Motor drive shaft 637 is couplable (i.e., capable of being coupled) to a linkage in a cassette 603 mounted on cassette mount 621. Motor 635 and motor drive shaft 637 are referred to herein collectively as a "drive system." Other systems for powering operation of a cassette 603 may be utilized (e.g., gears, belts, etc.). Micro-switch 639 is closed by contact between switch arm 641 and cassette cam 765. Closure of switch 639 generates a signal to controller 607 indicative that a cassette 603 is completely coupled to mount 621.

Reader 645 detects barcode 760 (FIG. 46A) on each cassette 603 when cassette 603 is fully mounted as illustrated in FIGS. 44 and 46-48. Reader 645 is preferably a binary optical sensor. In the example, each cassette 603 includes a barcode 760 on cassette sidewall 759 and the barcode 760 is positioned in the path of reader 645 when cassette 603 is fully mounted on cassette mount 621. The barcode 760 is detected by reader 645 and reader 645 generates a signal to data processing platform 17 uniquely identifying the cassette 603 from records in the cassette record database thereby enabling system 11' to immediately identify the contents of any cassette 603 once mounted on mount 621. Any type of machine-readable code may be used. Therefore, an RFID tag could be used in place of barcode 760 and reader 645 could be an RFID tag reader.

Figure 50:
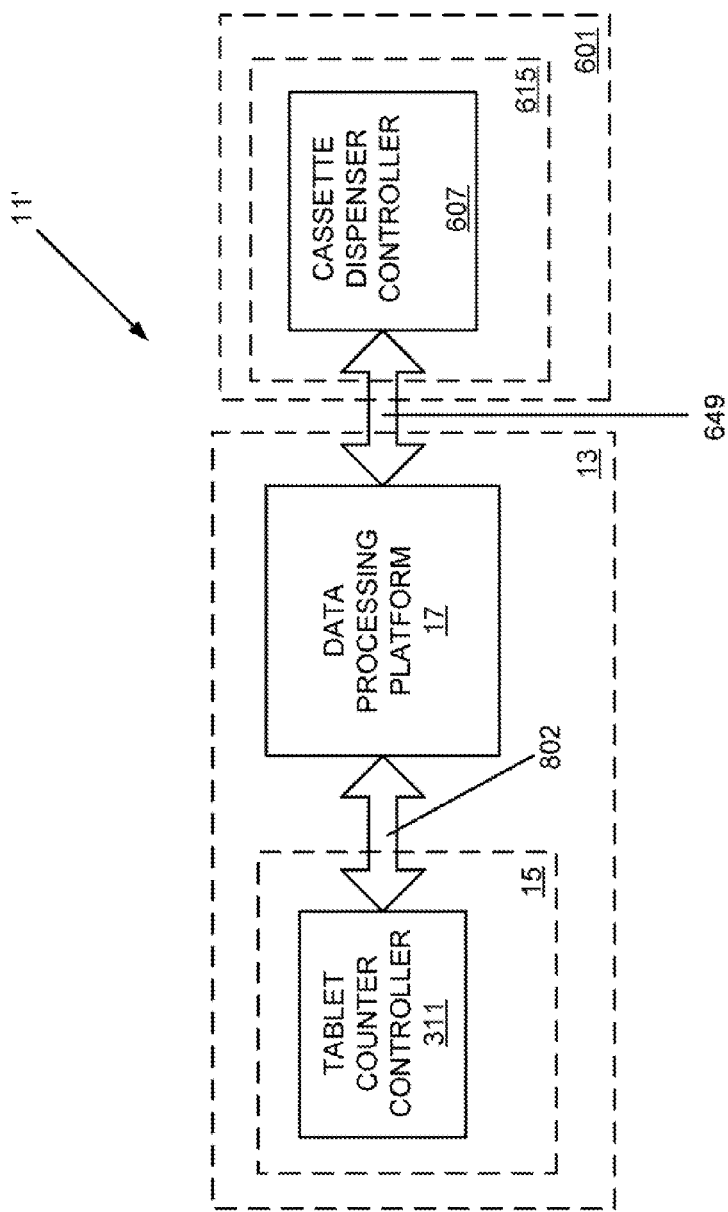
FIG. 50 is a schematic block diagram showing system logical component interaction for the comparison of tablet counts in an embodiment of the inventive system for feeding and counting discrete objects.

Cassette dispenser 601 controller 607 is operatively connected to data processing platform 17, preferably by an RS 232 serial connection 649 (shown schematically in FIGS. 24 and 50), permitting data communication between data processing platform 17 and controller 607 as indicated by the dual-headed arrow 649 in FIG. 50. Controller 607 is operatively connected to motor 635, switch 639 and reader 645 by means of respective conductors 651, 653, 655. Electrical power is supplied to controller 607, motor 635, switch 639 and reader 645 from power supply 58.

As illustrated in FIGS. 38-42 and 44-46, cassette mount 621 includes a pair of fixed-position elongate receivers 657, 659. Each receiver includes a pair of spaced apart walls 661 (outer), 663 (inner) and 665 (outer), 667 (inner), a bottom wall 669, 671 and stop walls 673, 675 forming a female opening 677, 679 therebetween for snugly receiving a cassette 603 male sidewall portion 759, 761 thereby supporting a cassette 603 at cassette mount 621. Walls 661-675 limit lateral and downward movement of a cassette 603 coupled to mount 621. Cassette mount 621 is a "universal" mount in that any cassette (e.g., cassette 603) may be mounted and supported thereon.

Referring to FIGS. 42, 44 and 46-48, detector 605 is supported on mount 621 in the path 681 of tablets fed from cassette 603 as described below. Detector 605 is operatively connected to cassette dispenser controller 607 through a suitable conductor 683. Detector 605 includes an emitter 685 which may emit an infra-red (IR) energy beam 687 and a receiver 689 onto which the IR energy beam 687 is directed. Passage of a tablet (e.g., tablet 321 or 604) along path 681 in the direction of arrow 690 (FIG. 48) between emitter and receiver 685, 689 momentarily breaks beam 687 causing receiver 689 to generate a signal which is indicative of a tablet falling along path 681 and toward funnel 41'. The signal generated by receiver 689 of detector 605 is received by cassette dispenser controller 607 causing controller 607 to increment a tablet count 830 (FIG. 52) by one tablet. As described in connection with FIGS. 50-53B, the tablet count 830 from controller 607 of the second tablet counter 615 is compared with the tablet count 814 from first tablet counter 15.

Figure 44:
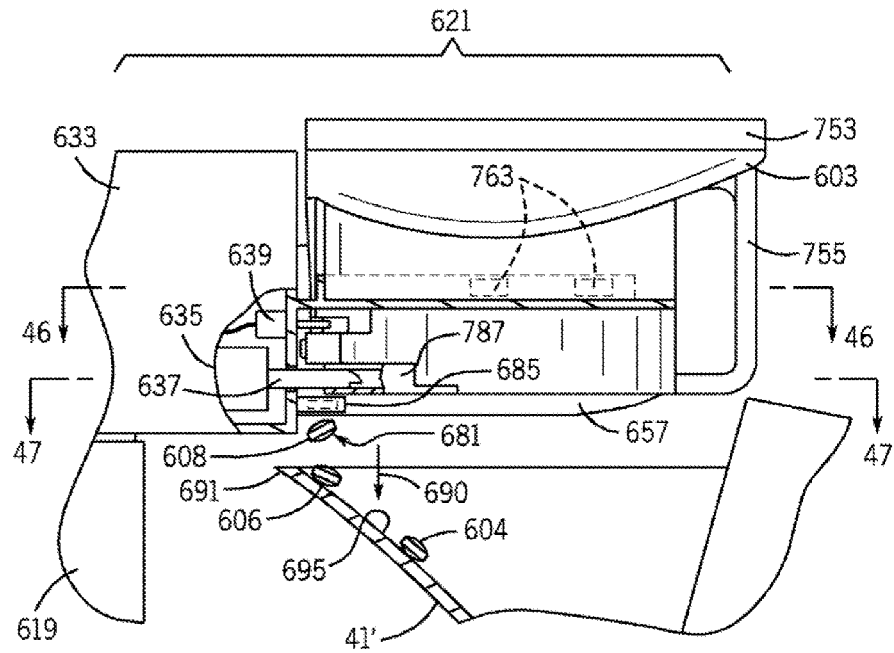
FIG. 44 is an enlarged partial view of an exemplary cassette dispenser cassette mount with a cassette mounted thereto taken along portion 44-44 of FIG. 46.
Figure 45:
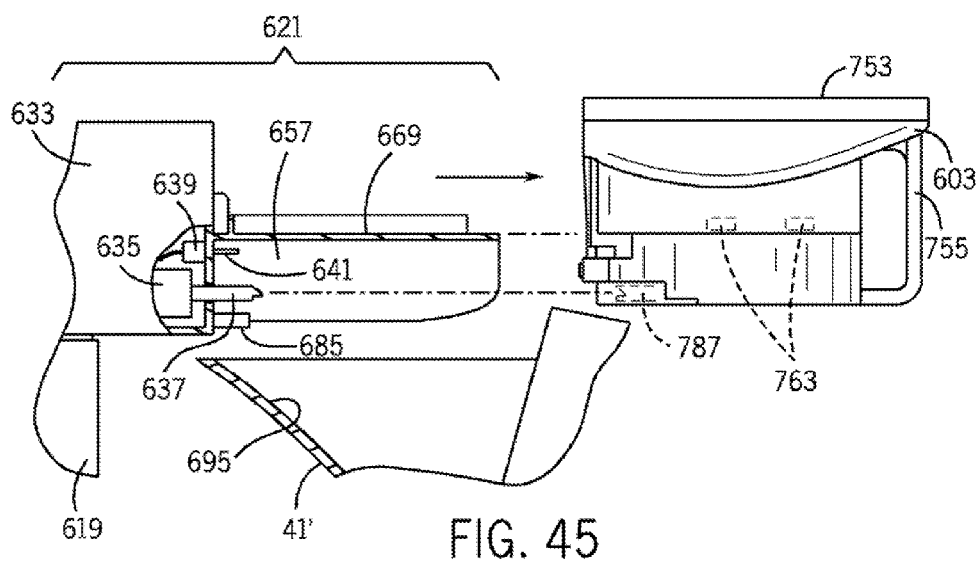
FIG. 45 is a further view of the cassette dispenser and cassette mount of FIG. 44 but with the cassette being demounted.

Tablets fed from cassette 603 (or manually poured from a container 175) fall into funnel 41'. In the example, funnel 41' has a somewhat rectangular cross-sectional area at the upper open end of funnel 41' as illustrated in FIGS. 38-42. This shape makes it easy for a user to manually pour tablets into funnel 41' without removing a mounted cassette 603 as well as to feed tablets from mounted cassette 603. Funnel 41' includes a rear portion 691 and a front portion 693. Funnel rear portion 691 includes a sloped surface 695 proximate path 681 as illustrated in FIGS. 44-45 and directs tablets from cassette 603 toward chute 43. Funnel 41' sidewalls 697, 699 along front portion 693 are relatively higher than sidewalls 697, 699 along rear portion 691 to facilitate manual pouring of tablets into funnel 41' by a user and to direct tablets to chute 43 without spilling of tablets out of funnel 41'.

Tablets (e.g., tablet 321 or 604) fall through funnel 41' and into vertically-oriented chute 43. Tablets are then counted by first tablet counter 15 as they fall past sensors 307a, 307b.

Tablets (e.g., tablets 321 or 604) fall into tray 45. Deflector 319 and tray curved inner portion 45a help to guide tablets into tray 45 and to limit any bouncing of tablets back past sensor arrays 307a, 307b to avoid an overcount. Tray 45 may be removed from housing 13 bay 47 and the tray tablet contents poured into a vial, bottle or other container.

Turning now to FIGS. 38-42 and 44-48, there is shown an exemplary cassette 603 capable of being mounted on cassette dispenser 601 to feed tablets past second tablet counter 615, into funnel 41' and to first tablet counter 15. In the example, each cassette 603 includes a case 751 which defines an opening for receiving tablets and a removable lid 753 over the opening. Case 751 and lid 753 are preferably made of plastic materials but may be made of any suitable materials or materials. Case 751 includes a handle 755 which can be grasped by the hand of a user to mount a cassette 603 on cassette mount 621 of cassette dispenser 601, to remove a cassette 603 from cassette mount 621 of cassette dispenser 601 or otherwise handle or transport cassette 603. Case 751 includes a hopper 757 which holds a plurality of bulk-form tablets. Removal of lid 753 permits tablets to be poured into hopper 757 through a top opening defined by case 751.

As previously described, cassette 603 includes elongate male sidewall portions 759, 761. Sidewall portion 759 preferably includes a barcode 760 which is read by reader 645 to uniquely identify the cassette 603 to system 11' by data processing platform 17. Inwardly-facing resilient fingers (each indicated by 763) are urged against a respective receiver inner wall 663, 667 to snugly couple cassette 603 to receivers 657, 659 of cassette mount 621. Sidewall portions 759, 761 abut a respective stop wall 673, 675 when cassette 603 is fully coupled to mount 621. Cam 765 acts on switch arm 641 to close switch 639 when cassette 603 is fully coupled to cassette mount 621. Closure of switch 639 generates a signal to controller 607 indicative that cassette 603 is coupled as previously described.

Rotor 767 is provided in hopper 757 mounted on a shaft 769. Rotor 767 has a top surface 771 with a conical shape. In the example, three vanes (each indicated by 773) extend outwardly from the rotor 767 top surface 771. Vanes 773 are pitched so as to push tablets toward the outer circumferential surface 775 of rotor 767 (i.e., periphery of rotor 767) during rotor 767 rotation in the direction of arrow 777.

Figure 46:
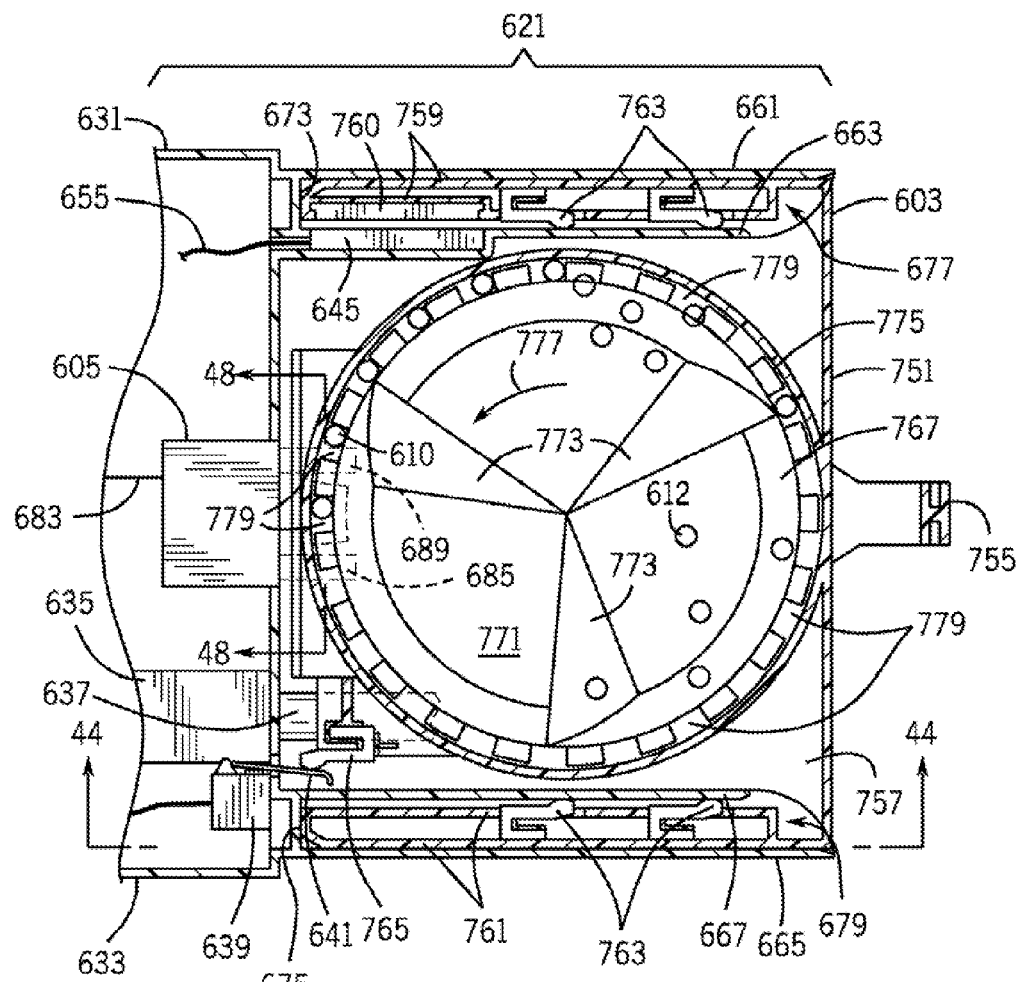
FIG. 46 is a section view taken along section 46-46 of FIG. 44 showing the exemplary cassette dispenser and cassette mount of FIG. 38 with a cassette mounted thereto.
Figure 46A:
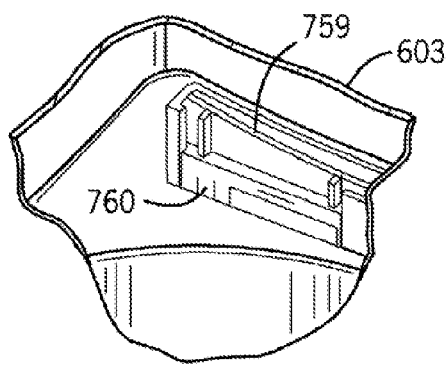
FIG. 46A is a partial view of the cassette of FIG. 46 showing an exemplary cassette barcode in which a unique cassette-identification code is embedded.
Figure 47:
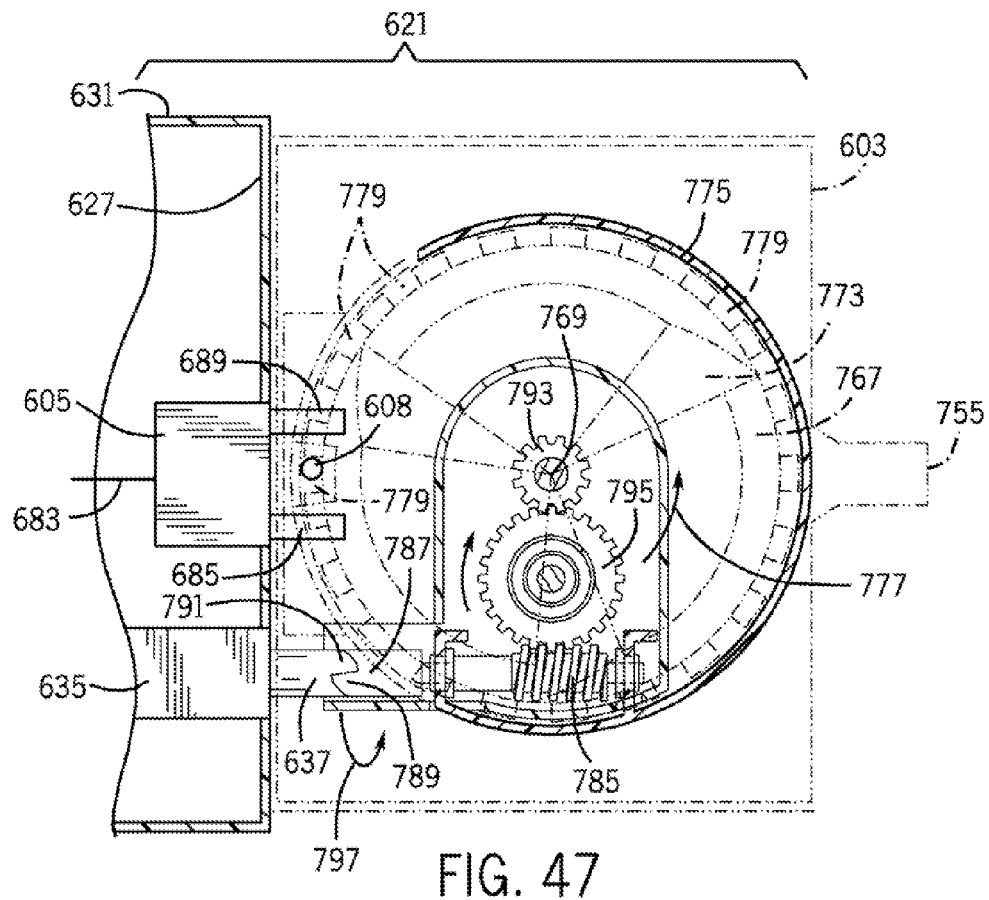
FIG. 47 is a section view taken along section 47-47 of FIG. 44 showing a mounted cassette and an exemplary drive mechanism enabling cassette rotor rotation.
Figure 48:
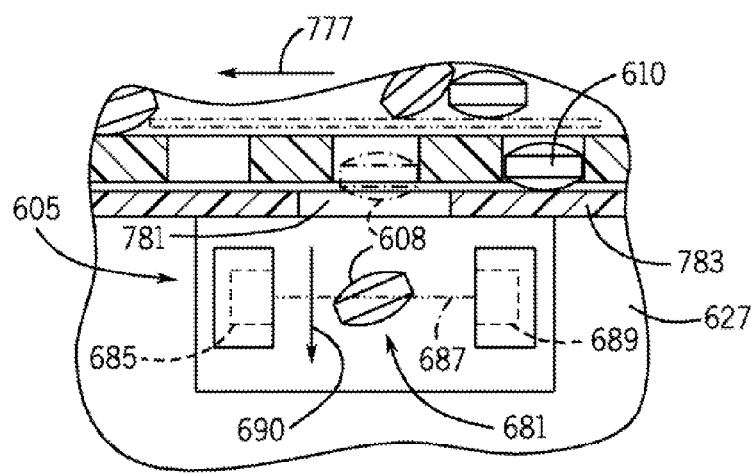
FIG. 48 is an enlarged partial section view taken along section 48-48 of FIG. 46 showing an exemplary optical-type detector which detects objects fed from a mounted cassette.

Referring to FIGS. 46-47, a plurality of pockets, several of which are indicated by reference number 779, are spaced apart at equal angular intervals in a radially-outward direction along rotor circumferential surface 775. Each pocket 779 has a width, depth and height that allows it to hold only one tablet (e.g., tablet 321 or 604). As illustrated in FIG. 48, an opening 781 is provided in a bottom wall 783 of cassette case 751 hopper 757. Opening 781 has a cross-sectional area which permits alignment of only one pocket 779 of rotor 767 above opening 781 as illustrated in FIG. 48.

Cassette drive system consisting of motor 635 and motor shaft 637 powers rotor 767 rotation through a cassette linkage consisting of worm gear 785, coupling 787, pinion 793 and intermediate gears 795 in the example. Coupling 787 is coupled to motor drive shaft 637. Coupling teeth 789 mesh with complementary teeth 791 of motor drive shaft 637 when cassette 603 is fully mounted on cassette mount 621. Rotation of motor drive shaft 637 in the direction of the arrow 797 proximate shaft 637 (FIG. 47) causes worm gear 785 to drive pinion gear 793 on rotor shaft 769 through intermediate gear 795. The cassette drive system consisting of motor 635 and drive shaft 637 causes rotor 767 to rotate in the direction of arrow 777 in FIGS. 46-48. Vanes 703 push tablets outward on the rotor 767 conical top surface 771. One tablet (e.g., tablet 321 or 604) falls into each pocket 779. One tablet is fed from cassette 603 as the tablet 608 in a pocket 779 is aligned with opening 781. Each tablet 604, 606, 608, 610 (or tablet 321) fed from the cassette 603 falls along path 681 and past detector 605 in the direction of arrow 690 (FIG. 48). Breaking of beam 687 registers a count by controller 607 of second tablet counter 615 as previously described.

Controller 607 of second tablet counter 615 controls motor 635 operation, turning motor 635 "on" to rotate rotor 767 to feed tablets from cassette 603 and turning motor 635 "off" once the required quantity of tablets have been detected by detector 605 and counted by controller 607 of second tablet counter 615. Motor 635 is capable of powering rotor 767 at a high rate of revolutions per minute (RPM) for rapid dispensing of tablets from cassette 603. By way of example only, motor 635 can power rotor 767 so that thirty tablets are fed from cassette 603 in four seconds or less.

As illustrated in FIG. 44, singulation of tablets (e.g., tablets 604, 606, 608, 610) fed from cassette 603 facilitates accurate counting by first tablet counter 15. Singulation provides spacial separation between tablets dispensed from cassette one-after-the-other so that separate tablets fall past sensors 307a, 307b. Separate tablets are more accurately detected by first tablet counter 15 improving the accuracy of the tablet count. Singulation also facilitates avoidance of an overspeed condition and a "Pour is Too Fast! Count Failed" message as described above in connection with FIG. 11B, thereby avoiding the necessity for a re-pour of tablets (e.g., tablets 604, 606, 608, 610) into first tablet counter 15. (An overspeed condition can exist where multiple tablets pass sensors 307a, 307b simultaneously, preventing identification of discrete tablets by first tablet counter 15. This is an error condition.) By providing spacial separation between tablets (e.g., tablets 604, 606, 608, 610), the overspeed condition is avoided and a more accurate count by first tablet counter 15 is produced.

According to a preferred aspect of system 11', logic of controller 607 can regulate motor 635 speed. In the example, controller 607 regulates motor 635 to provide six different RPM settings, from 1 to 6. Speed setting 1 is the highest RPM setting and speed setting 6 is the lowest RPM setting. Tablets which are harder can be fed from a cassette 603 at a relatively faster rate whereas tablets which are softer and may stick to the hopper 757 (e.g., gel caps) or which are more fragile and may break are preferably dispensed at a relatively slower rate. Speed setting 4 may be set as a default speed setting. The user can set a speed setting from one to six for each cassette 603 through touch screen display 37 as described below in connection with cassette-empty window 901 of FIG. 66 or cassette count window 945 of FIG. 75.

Controller 607 sets motor 635 to the highest designated setting for the cassette 603 to commence feeding of tablets from the cassette 603. As the count from second tablet counter 615 approaches the required count (point 829, FIG. 52), controller 607 decreases motor 635 RPMs to a lower speed setting slowing rotation of rotor 767 and the rate at which tablets are fed from cassette 603. This speed control feature avoids excessive rotation of rotor 767 as the required tablet count is approached, thereby avoiding the feeding of tablets in excess of the quantity required from cassette 603 and substantially preventing unwanted tablet overcounts by second tablet counter 615.

Referring next to FIGS. 50-53B, there are shown block diagrams which illustrate the logical flow of information and logical decisions made within system 11' in order to count tablets with first and second tablet counters 15, 615 and to compare the counts. The instructions which carry out such logical flow and decisions may reside in firmware or software without limitation, depending on the specific hardware which is utilized within an embodiment. In system 11', the instructions may reside in both forms within the various elements of system 11'.

FIG. 50 is a schematic block diagram showing system logical component interaction for the comparison of tablet counts as well as other elements of system control. First tablet counter 15 includes tablet counter controller 311, instructions for which reside in firmware within controller 311. Cassette dispenser 601 (indicated as "CD" in FIGS. 52 and 53B) includes second tablet counter 615 which in turn includes cassette dispenser controller 607. Instructions for controller 607 reside in firmware within controller 607. In the example of system 11', first tablet counter 15 and data processing platform 17 are within housing 13, and second tablet counter 615 is associated with cassette dispenser 601 as represented by the dotted line boxes in FIG. 50.

Processing platform 17 includes software instructions which carry out the logical flow and decisions which utilize information and commands from both first tablet counter and second tablet counter 15, 615. The instructions enable counting with the first and second tablet counters 15, 615 of the quantity of tablets required by the prescription being fulfilled. Information is passed bi-directionally between processing platform 17 and the first and second tablet counters 15, 615 via two data connections 802 and 649, respectively as represented by the dual-headed arrows in FIG. 50. Data connections 802 and 649 may be, for example, standard RS232 serial port connections.

Figure 51:
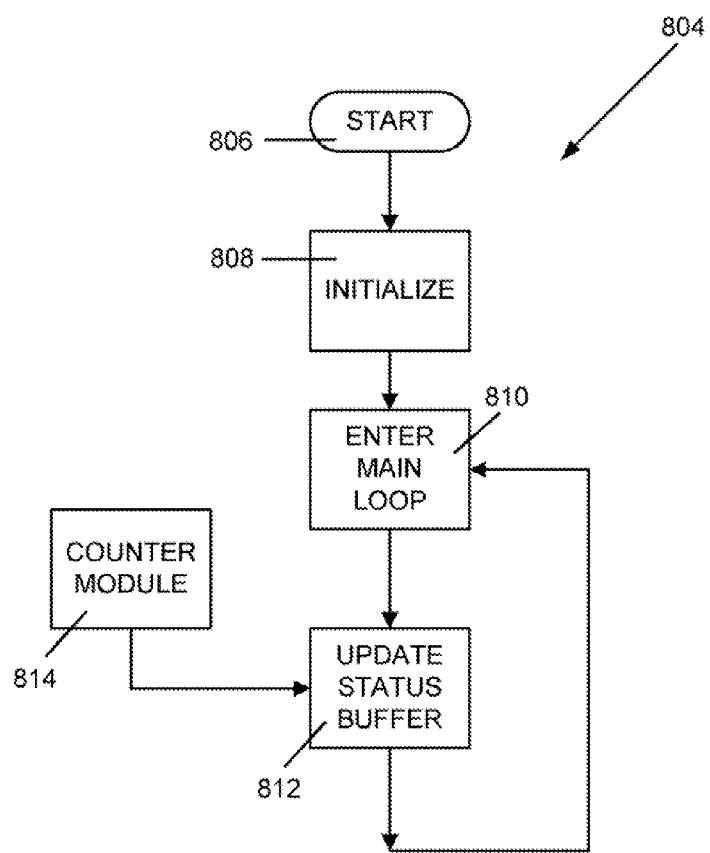
FIG. 51 is a high-level logic flow diagram of a first tablet-counting device, illustrating tablet counting and the handling of data to be used in the embodiment of FIG. 50.
Figure 52:
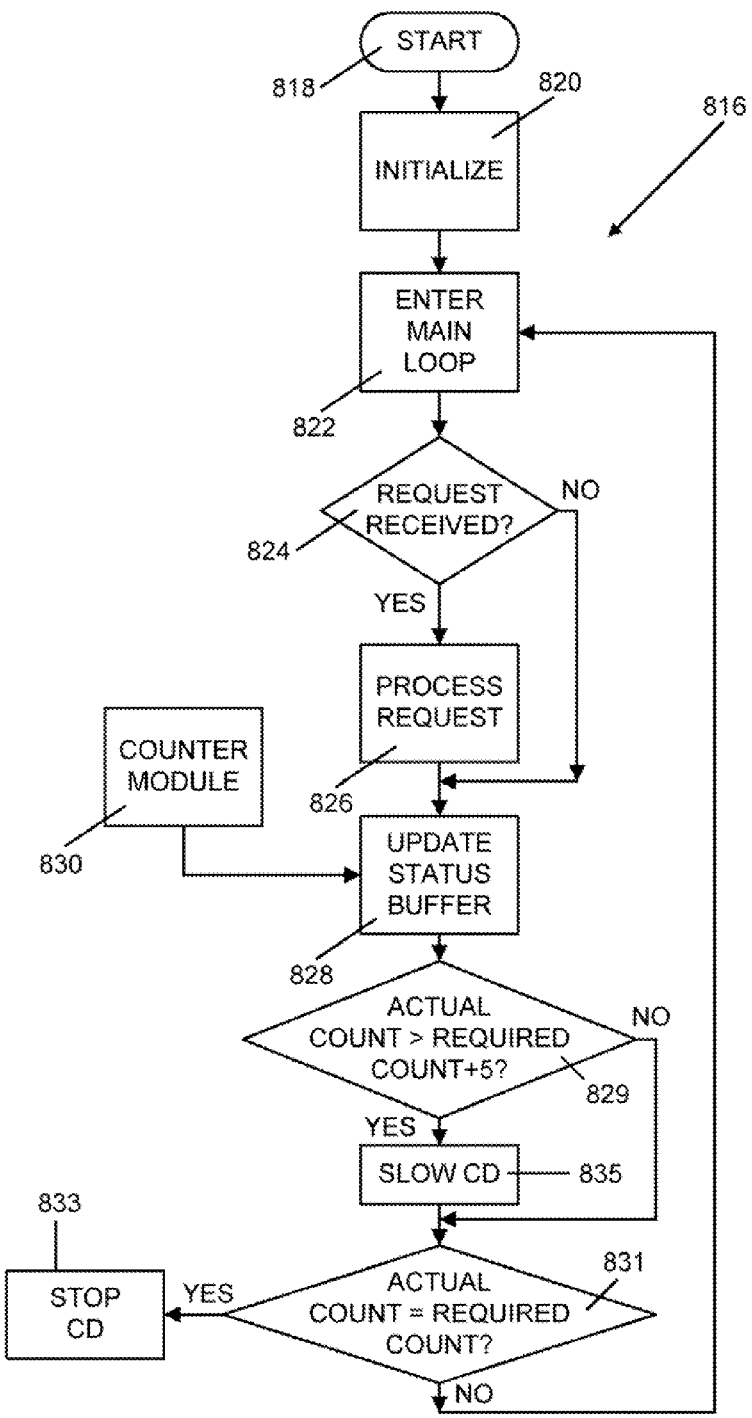
FIG. 52 is a high-level logic flow diagram of a second tablet-counting device, illustrating tablet counting and the handling of data to be used in the embodiment of FIG. 50.

Logical flow of information and logical decisions within system 11' occur in four cooperating portions, illustrated in FIGS. 51-53B. FIG. 51 is a high-level logic flow diagram of first tablet counter controller 311; the logic flow within controller 311 is indicated by reference number 804. FIG. 52 is a high-level logic flow diagram of cassette dispenser controller 607; the logic flow within controller 607 is indicated by reference number 816.

Figure 53A:
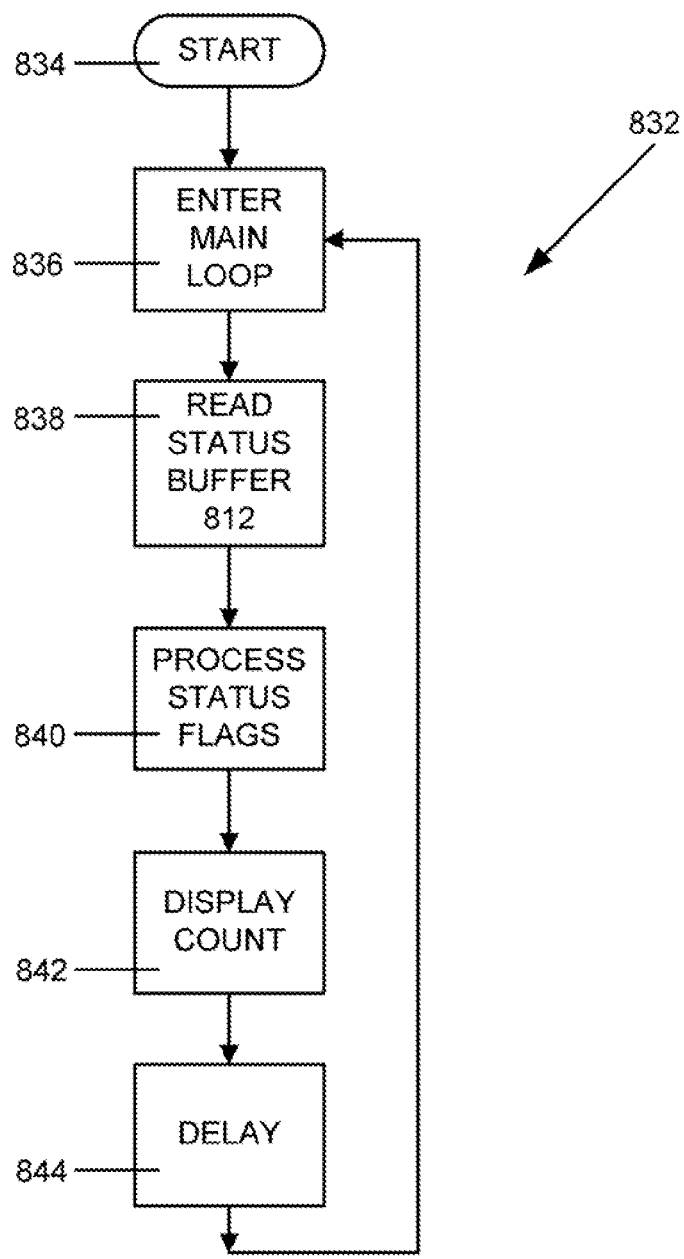
FIG. 53A is a high-level logic flow diagram illustrating software operation for data handling and for displaying the tablet count of the first tablet-counting device in the embodiment of FIG. 50.
Figure 53B:
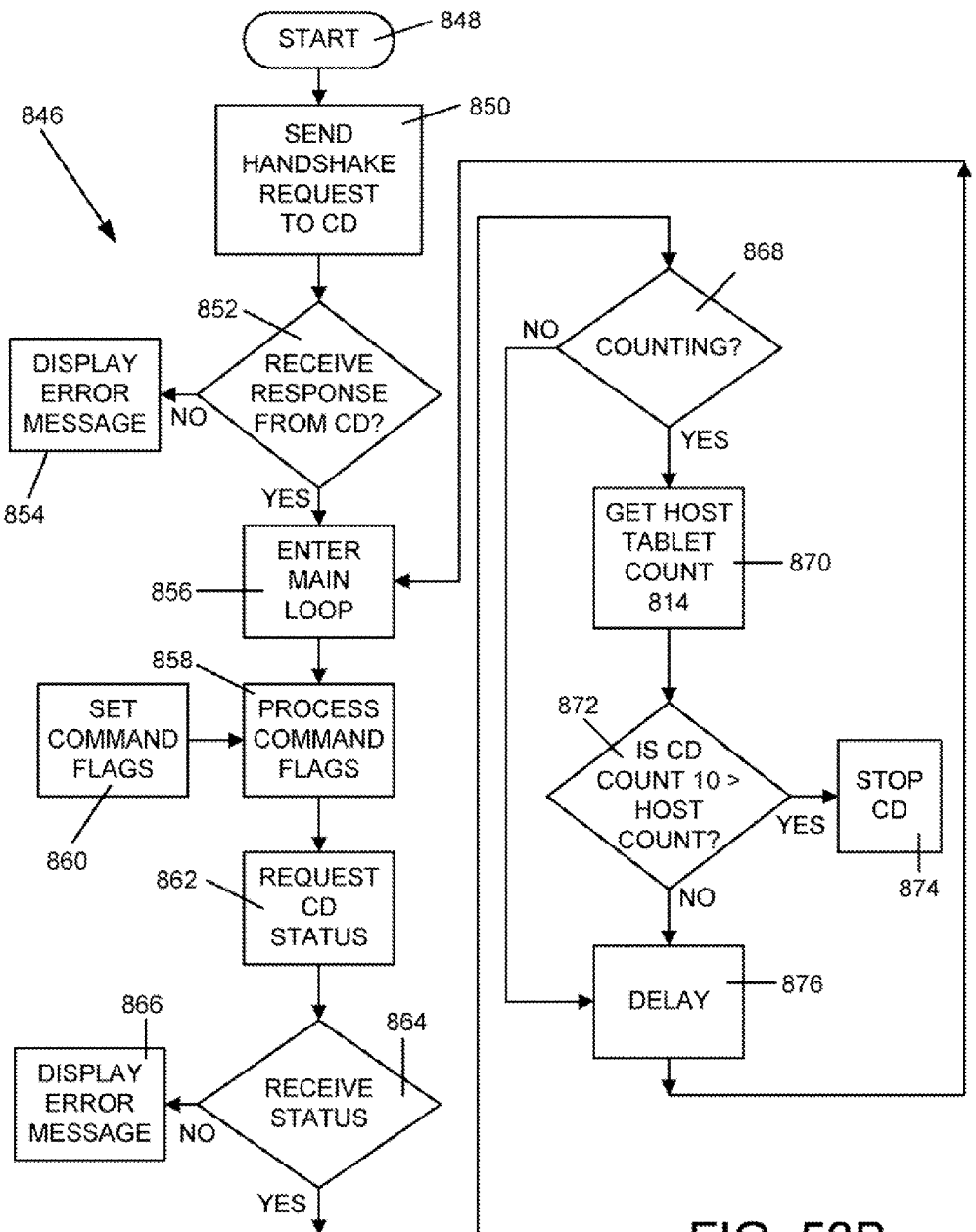
FIG. 53B is a high-level logic flow diagram illustrating software operation for data handling of the second tablet-counting device, for comparing the counts of the first and second tablet-counting devices, and for controlling the second tablet-counting device in the embodiment of FIG. 50.

FIG. 53A is a high-level logic flow diagram illustrating software operation for data handling and for displaying the tablet count of first tablet counter 15; the logic flow within this portion of the instructions within data processing platform 17 is indicated by reference number 832. FIG. 53B is a high-level logic flow diagram illustrating software operation for data handling and for displaying the tablet count of second tablet counter 615; the logic flow within this portion of the instructions within data processing platform 17 is indicated by reference number 846.

The four logic flow portions 804, 816, 832, and 846 are only partial representations of the logical operations which are performed within tablet counter controller 311, cassette dispenser controller 607, and data processing platform 17. Many other specific functions may be included to enhance the performance of a product which includes the inventive system utilizing two tablet counters 15, 615 but which are not essential to the cooperating operation of the two tablet counters 15, 615. The logical flow elements depicted in such four logic flow portions describe the flow of information and the logical decisions within system 11' necessary for such cooperating operation.

These four portions 804, 816, 832, 846 of the logical flow of information and logical decisions within system 11' operate in parallel and cooperate together via firmware and software instructions and device connectivity, as follows. Referring first to FIG. 51 illustrating logic flow portion 804 of tablet counter controller 311, upon start-up (power-up or restart), controller 311 enters the logic flow at start-up block 806 and proceeds to initialize logic flow portion 804 at initialization block 808. Initialization includes allowing controller 311 to establish normal operating voltage levels and resetting internal variables. Logic flow portion 804 then enters its main loop at block 810. Logic flow portion 804 then sequentially loops through its main loop, the principal task of which is to update a status buffer 812 at block 812. (In this description of logic flows, the reference number of a logic flow block may be used to refer both to the process occurring within the block as well as the variable, such as, in this case, a status buffer which is set by such process.)

During status buffer 812 updating, an actual tablet count 814 from a counter module 814 within controller 311 is passed to status buffer 812. Thus, as the main loop within logic flow portion 804 of controller 311 continues to cycle, status buffer 812 maintains an up-to-date value for actual tablet count 814 of first tablet counter 15. Tablet count 814 is sometimes referred to herein as the "host" count, indicating that such count is obtained from the first tablet counter 15 which is "hosting" the second tablet counter 615.

In a similar fashion, cassette dispenser controller 607 of second tablet counter 615, maintains an up-to-date value of its own tablet count. Referring to FIG. 52 illustrating logic flow portion 816 of cassette dispenser controller 607, upon start-up (power-up or restart), controller 607 enters the logic flow at start-up block 818 and proceeds to initialize logic flow portion 816 at initialization block 820. As with controller 311, initialization includes allowing controller 607 to establish normal operating voltage levels and to reset internal variables. Logic flow portion 816 then enters its own main loop at block 822, the principal tasks of which are to receive and process requests and to update a status buffer 828 and block 828. Controller 607 is configured to receive requests from data processing platform 17 at decision point 824. Point 824 includes a logical decision to direct logic flow based on whether or not such a request has been received. Such requests include but are not limited to (1) a request from data processing platform 17 to simply acknowledge that the controller 607 is active, (2) a request to commence operation of cassette dispenser 601 to count a required amount of tablets needed to fulfill a prescription, (3) a status request, and (4) other requests such as cancelling, pausing, and resuming a fill request, and emptying a cassette.

If a request has been received at block 824, all such requests are processed in block 826 (through a "YES" decision at point 824) and involve the setting of a portion of a status buffer 828 at update status buffer block 828. For example, if a prescription fulfillment request is received from data processing platform 17 and the proper cassette 603 is mounted to cassette dispenser 601, processing of such prescription fulfillment request initiates operation of cassette dispenser 601 including starting motor 635. If no request has been received at point 824, request processing block 826 is bypassed through a "NO" decision at point 824.

During status buffer 828 updating, an actual tablet count 830 from a counter module 830 within controller 607 is passed to status buffer 828. This actual tablet count 830 is incremented when detector 605 detects a tablet fed from cassette 603 and detector receiver 689 sends a signal to controller 607 indicative of the tablet detection. Thus, as the main loop within logic flow portion 816 of controller 607 continues to cycle, status buffer 828 maintains an up-to-date value for the actual tablet count 830 of second tablet counter 615 and requests for fulfillment of a prescription are processed as they are received.

The main loop of logic flow portion 816 then continues with decision point 829 which determines if the actual tablet count 830 is approaching the required count. A predetermined value defines a difference between the actual and required tablet counts in order for the counts to be considered to be "close." In system 11', this preset value is shown as 5 at decision point 829 of FIG. 52, but other values may be used depending on a variety of parameters. At point 829, if the actual count 830 approaches the required count such that the difference between the counts is four (4) or fewer, then a "YES" decision at point 829 is reached and logic flow portion 816 proceeds to slow cassette dispenser 601 motor 635 (slowing rotor 767) in block 835 to facilitate accurate dispensing of tablets by cassette dispenser 601.

If a "NO" decision is reached at decision point 829, block 835 is bypassed and logic flow portion 816 continues with decision point 831 at which point the actual count 830 is compared with the required count to determine if counting is complete. If the actual count 830 equals the required count resulting in a "YES" decision at point 831, then drive motor 635 is stopped, ceasing dispensing operation of cassette dispenser 601. If the required count has not been reached, a "NO" decision is reached at decision point 831 and the main loop of logic flow portion 816 within controller 607 continues to its next cycle.

Logic flow portions 832 and 846 are programmed to operate in parallel within data processing platform 17 and are described in FIGS. 53A and 53B. FIG. 53A illustrates logic flow portion 832, the main tasks of which are to communicate with controller 311 of first tablet counter 15 in order to display and make available tablet count 814 from first tablet counter 15. Logic flow portion 832 accomplishes these tasks by regularly reading status buffer 812 within its own main loop. Among other information, status buffer 812 contains tablet count 814 of first tablet counter 15.

Upon start-up (power-up or restart) at start-up block 834, logic flow portion 832 enters its main loop at block 836. Logic flow portion 832 cycles through this main loop by sequentially reading status buffer 812 at block 838, processing status flags at block 840, displaying tablet count 814 on display 37, and looping back through the main loop through a delay block 844 which can be set to slow the rate at which the main loop is cycled. Status flags include but are not limited to indication of the operation of the first tablet counter 15 and various error conditions which may exist.

FIG. 53B illustrates logic flow portion 846 operating in parallel with logic flow portion 832 within data processing platform 17. Upon start-up (power-up or restart) at start-up block 848, logic flow portion 846 sends a handshake request at block 850 to cassette dispenser 601 to determine whether cassette dispenser 601 is ready to operate. Decision point 852 determines whether or not a handshake response is received from dispenser 601. A "NO" decision at point 852 displays an error message at block 854 and ends the logic flow accordingly. An error message could be displayed in Main Instructions field 91, 1091 at block 854. A "YES" decision at point 852 permits logic flow portion 846 to enter its own main loop at block 856. The main loop of logic flow portion 846 cycles with the principal tasks of processing commands and making a determination whether or not the tablet count 814 from first tablet counter 15 and tablet count 830 from second tablet counter 615 are within a predetermined number of each other.

Upon entering the main loop of logic flow portion 846, any command flags which are set at block 860 are processed in block 858. Command flags include, but are not limited to, information related to a request to fulfill a prescription (e.g., prescription 127) to be sent to cassette dispenser 601 and the other types of requests listed above which may be received by controller 607.

In block 862, logic flow portion 846 requests the status of second tablet counter 615. If this request is not answered at decision point 864, a "NO" decision triggers the display of an error message in Main Instructions Field 91, 1091 on display 37 and ends the logic flow in block 866. A "YES" decision at point 864 continues logic flow portion 846 to another decision point 868 which simply determines if counting is taking place by second tablet counter 615. The status information obtained from the status request of block 862 contains, among other information, the actual tablet count 830 from second tablet counter 615.

A "NO" decision at point 868 sends the logic flow through a delay block 876 which cycles the logic flow back to the entry block 856 of the main loop after a delay in block 876 to control the cycle time of the main loop of logic flow portion 846. A "YES" decision at point 868 results in logic flow portion 846 obtaining tablet count 814 in block 870.

At decision point 872, a comparison is made between tablet count 814 from first tablet counter 15 and the actual tablet count 830 from second tablet counter device. The comparison determines if the cassette dispenser 601 actual count 830 exceeds the host tablet count 814 by more than a predetermined amount. FIG. 53B shows a value of 10 for such predetermined amount, but other values for the predetermined amount may be used depending on the desired performance of system 11'.

If the actual count 830 of the cassette dispenser 601 exceeds the host count 814 by more than 10 (a "YES" decision at point 872), then a signal is generated by data processing platform 17 which stops the operation of cassette dispenser 601 at block 874. The signal turns off motor 635 and displays a visual message to the user on display 37. The signal-generated message alerts the user that an error condition exists and that corrective action should be taken. An error condition could exist, for example, if there is a tablet jam in funnel 41' such that tablets fed from cassette 603 and counted by second tablet counter 615 remain in funnel 41' and do not flow freely to first tablet counter 15. The signal-generated visual message (e.g., "Count differential exceeded. Attention required.") could be displayed in Main Instructions field 91,1091 on display 37, shown in FIGS. 60 and 61.

A "NO" decision at decision point 872 allows the main loop to cycle through delay block 876 to control the rate at which logic flow portion 846 cycles.

Referring now to FIGS. 54A, 54B, 54C, 54D, system 11' is capable of performing pharmacy workflow management in a manner similar to that described in connection with system 11 and FIGS. 14A, 14B and 14C in which tablets are manually poured into funnel 41 for counting by first tablet counter 15, but with the enhanced capability of automatic cassette-based dispensing and dual counting provided by tablet counters 15, 615. Therefore, many of the processes performed in connection with FIGS. 14A-14C are performed in connection with the processes described in connection with FIGS. 54A-54D and the related exemplary screen displays of FIGS. 55-75 and 20-36. References to screen displays associated with FIGS. 14A-14C are made as appropriate to describe the workflow of FIGS. 54A-54D.

The pharmacy workflow management executed by system 11' as shown in the examples of FIGS. 54A-54D and the screen displays of FIGS. 55-75 and 20-36 is enabled by a program of instructions (e.g., instructions according to the logic of FIGS. 50-53B) residing in non-volatile data storage 61 of data processing platform 17. When executed, the instructions enable system 11' to perform the pharmacy workflow management described herein. For interfaced systems 11', the instructions enable system 11' to receive prescriptions from PMS 21. The prescriptions may be stored in prescription record database in non-volatile storage 61. The instructions further enable a user to select one of the stored prescriptions for fulfillment and for the selected prescription to be retrieved. The instructions enable required medication to be counted and can create a record (e.g., FIGS. 37A, 37B, record 70a or 70b) that the quantity of the medication required by the retrieved prescription has been counted. For non-interfaced systems 11', the instructions enable counting and verification of prescriptions as described herein.

System 11' provides the user (e.g., a registered pharmacist, a pharmacy technician or other authorized person) with a powerful tool which enables control of pharmacy workflow directly from system 11' and fulfillment of one or more prescriptions of a prescription order by cassette dispensing or by manual pouring. System 11' enables counting of any tablet-form product including medications, nutriceuticals, and supplements and could be used for counting other discrete object types. System 11' can also manage workflow involving containers not requiring tablet counting, such as a medication-containing box 174 as will be described.

Figure 54A:
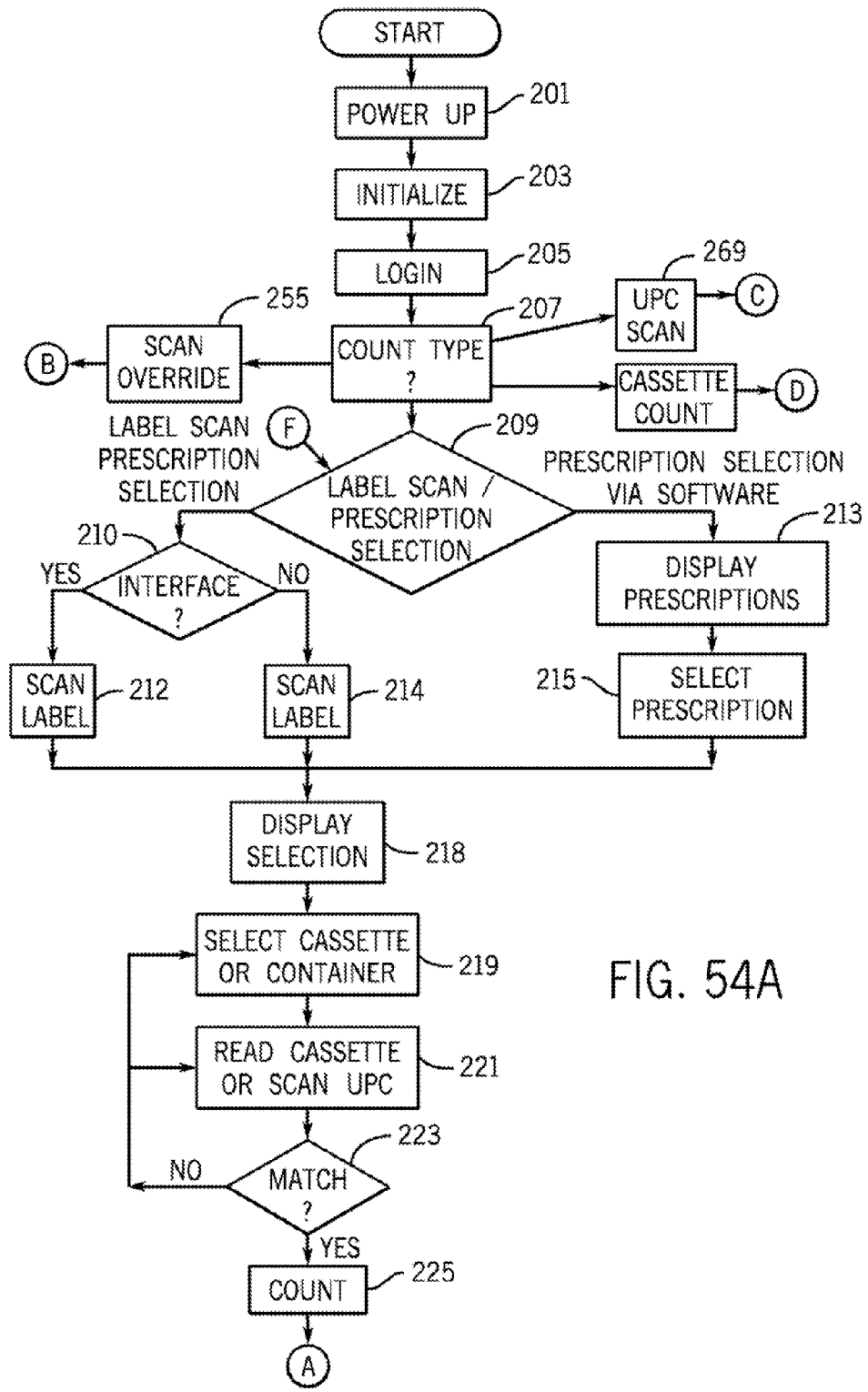
FIGS. 54A-54D are flow diagrams showing exemplary steps of a pharmacy workflow management process capable of being performed by the system of FIG. 38.

Referring to FIG. 54A, the operations for system 11' begin at block 201 when the user places an on/off switch 59 in the "on" position if system 11' is not already operating. In block 203, data processing platform 17 is initialized and system 11 is placed in a ready state.

During initialization, a check is performed to determine whether system 11' is interfaced with PMS 21. If an interface with PMS 21 does not exist, system 11' is operable as a stand-alone system. Prescription order fulfillment processing steps are described herein for both interfaced and non-interfaced systems 11'. If an interface is present, all prescription orders which have been validated by PMS 21 are sent to system 11' via communication link 23 and are stored in prescription record database in files organized by prescription number in non-volatile data storage 61 awaiting fulfillment. Alternatively, validated prescription orders may be delivered to system 11' via batch data delivery as previously described.

In block 205, a user is authenticated and logs into system 11'. In the example, user authentication and login can occur in several ways. For example, a user can enter a user ID (name and password in the example) into system 11' by means of a QWERTY-type keypad 65 (e.g., FIG. 70) displayed on touch-screen-type display 37, by means of an external keyboard or mouse (not shown), or by means of biometric sensor 55. The user ID is received by data processing platform 17.

Biometric sensor 55 of system 11' is a fingerprint sensor as described with respect to system 11. The user places his or her finger against the sensor 55 and, if the presented fingerprint matches a stored fingerprint, biometric sensor 55 communicates the user ID associated with the stored fingerprint to processing platform 17. If the presented fingerprint fails to match a stored fingerprint, biometric sensor 55 communicates an error message to processing platform 17.

If the user ID keyed in by the user or output from biometric sensor 55 to processing platform 17 is valid, processing platform 17 identifies the user and permits user login, enabling continued processing (blocks 207 and on). If the user ID is incorrect or if an error message is transmitted from biometric sensor 55, then data processing platform 17 denies user access and the continued operations of blocks 207 and on are not performed. In this manner, only authenticated users can use system 11 for its intended purpose. Similar authentication operations may be performed for other biometric sensor types. Alternatively, user authentication can be accomplished by other known means, such as a smart card reader or an RFID reader.

Figure 55:
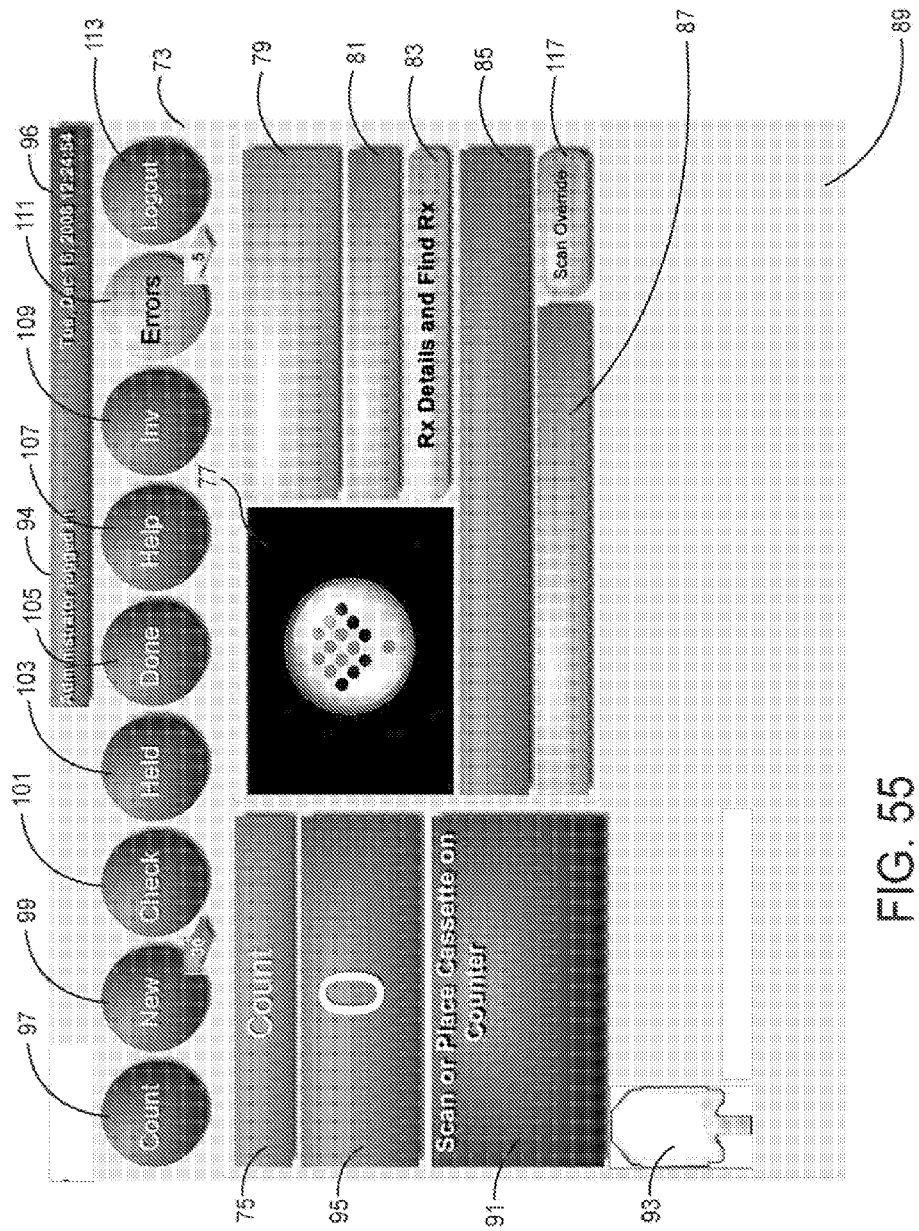
FIGS. 55-75 are exemplary images of various user interfaces for the software of the system of FIG. 38 separately shown for (a) the system when interfaced with a Pharmacy Management System and (b) for the system when not interfaced with a Pharmacy Management System.
Figure 56:
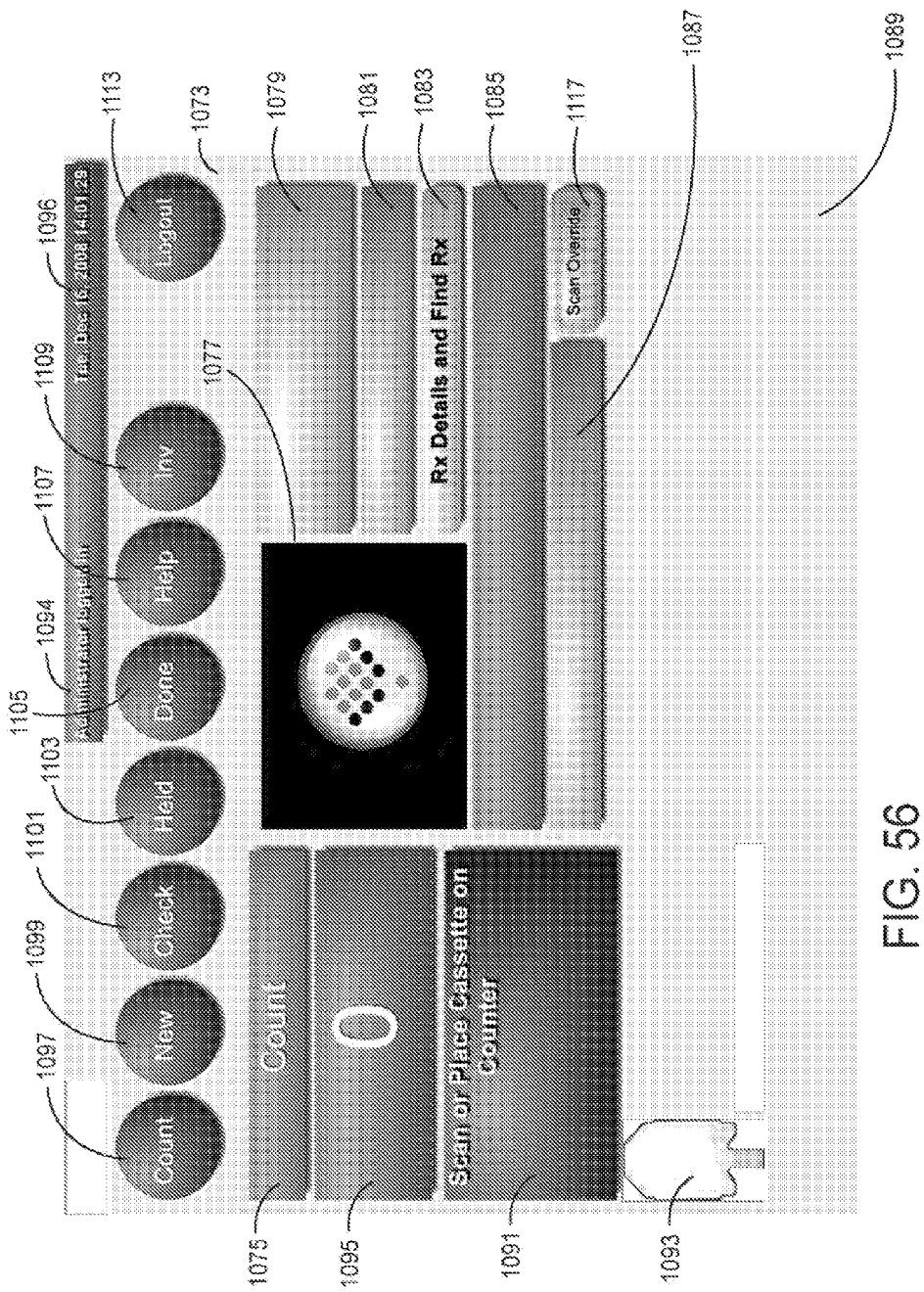

For system 11', following successful login at block 205, a Start screen 73 is shown on touch-screen-type display 37 as illustrated in FIG. 55. In the example, the Start screen 73 is preferably the same for both interfaced and non-interfaced systems 11'. FIG. 56 described below illustrates a Start screen 1073 which could appear for a non-interfaced system 11', indicative of the similarity between Start screens 73, 1073. As with system 11, Start screen 73 of system 11' includes controls in the form of graphical user interfaces (GUIs) which permit the user to select from several processing options. Information-displaying fields are also provided. The controls and fields shown on Start screen 73 and on the further displays of FIGS. 55-75 and 18-36 are non-limiting examples provided for purposes of illustration only. It should further be recognized that the screen displays shown in FIGS. 55-75 and 18-36, and the sequence of the screen displays are illustrative and are not intended to be limiting.

In the example of system 11', Start screen 73 (FIG. 55) provides information indicating that four counting modes are available. The counting modes are: (1) a customer label scan/prescription selection counting mode (blocks 209-253), (2) a scan override counting mode (blocks 255-267), (3) a Universal Product Code (UPC) barcode scan counting mode (blocks 269, 271, 273 and 257-267) and (4) a cassette count mode (blocks 298-300 and 257-267). Each counting mode can be performed by either interfaced or non-interfaced systems 11' except that non-interfaced systems do not receive validated prescriptions orders directly from PMS 21 via link 23 or batch delivery. Each counting mode is described below.

Exemplary Start screen 73 of interfaced system 11' illustrated in FIG. 55 shows exemplary fields and controls similar to those of Start screens 73, 1073 illustrated in FIGS. 15 and 16 but with a further prompt that the process may include cassette 603 usage. The fields and controls which are active on a particular screen correspond to the particular action then in process. Fields include: an Activity field 75, a Medication Image field 77, a Prescription Status Indicator field 79, a Customer/Patient field 81, a Prescription Number field 83, a Medication Description field 85, a Medication NDC field 87, a Collated Prescription Status field 89, a Main Instructions field 91, a Tray Status field 93 and a Count Status field 95. Start Screen 73 of interfaced system 11' differs from Start screens 73, 1073 in that Count Status field 95 would include a cassette icon 144 if a cassette 603 is fully mounted on cassette dispenser 601. Start screen Fields for the User Name 94 and Date and Time of Day 96 are also provided. In the example, the user name is shown as "Administrator" indicating that the logged-in user is also system Administrator. System 11' may be configured to display the user's given and surnames in field 94, if desired.

Activity field 75 shows the current system 11' operation. Medication Image field 77 shows a graphic image of the color, shape, markings and form of the medication required by the prescription being fulfilled. Each image is retrieved from the medication image database based on the NDC number of the medication required by each prescription. Prescription Status Indicator field 79 indicates the status of the prescription in the workflow. Customer/Patient field 81, Prescription Number field 83, Medication Description field 85 and NDC field 87, respectively, provide information about the patient name, prescription number, medication description and medication NDC for the selected prescription. Collated Prescription Status field 89 shows the status of all prescriptions grouped together for the patient and may include an image of each medication required by the prescription.

Main Instructions field 91 prompts the user to take an action. As shown on Start screen 73 of FIG. 55, Main Instructions field 91 includes a prompt to scan a prescription label or a UPC barcode on a medication package to initiate one of the first two counting modes. Tray Status field 93 indicates whether a tray 45 is detected in bay 47. Tray 45 is shown as detected in Start screen 73 because no "x" symbol is imposed over the tray icon. Vial size field 92, 1092 indicates a recommended vial size suitable to hold the counted tablets. The recommended vial size may be based on the size of the tablets and count. Finally, Count Status field 95 indicates the quantity of tablets counted by first tablet counter 15. Start screen 73 displays a 0 in Count Status field 95 indicating that no count has yet occurred.

Referring further to FIG. 55, controls include: a Count push button 97, a New push button 99, a Check push button 101, a Held push button 103, a Done push button 105, a Help push button 107, an INV push button 109, an Errors push button 111 and a Logout push button 113.

Figure 60:
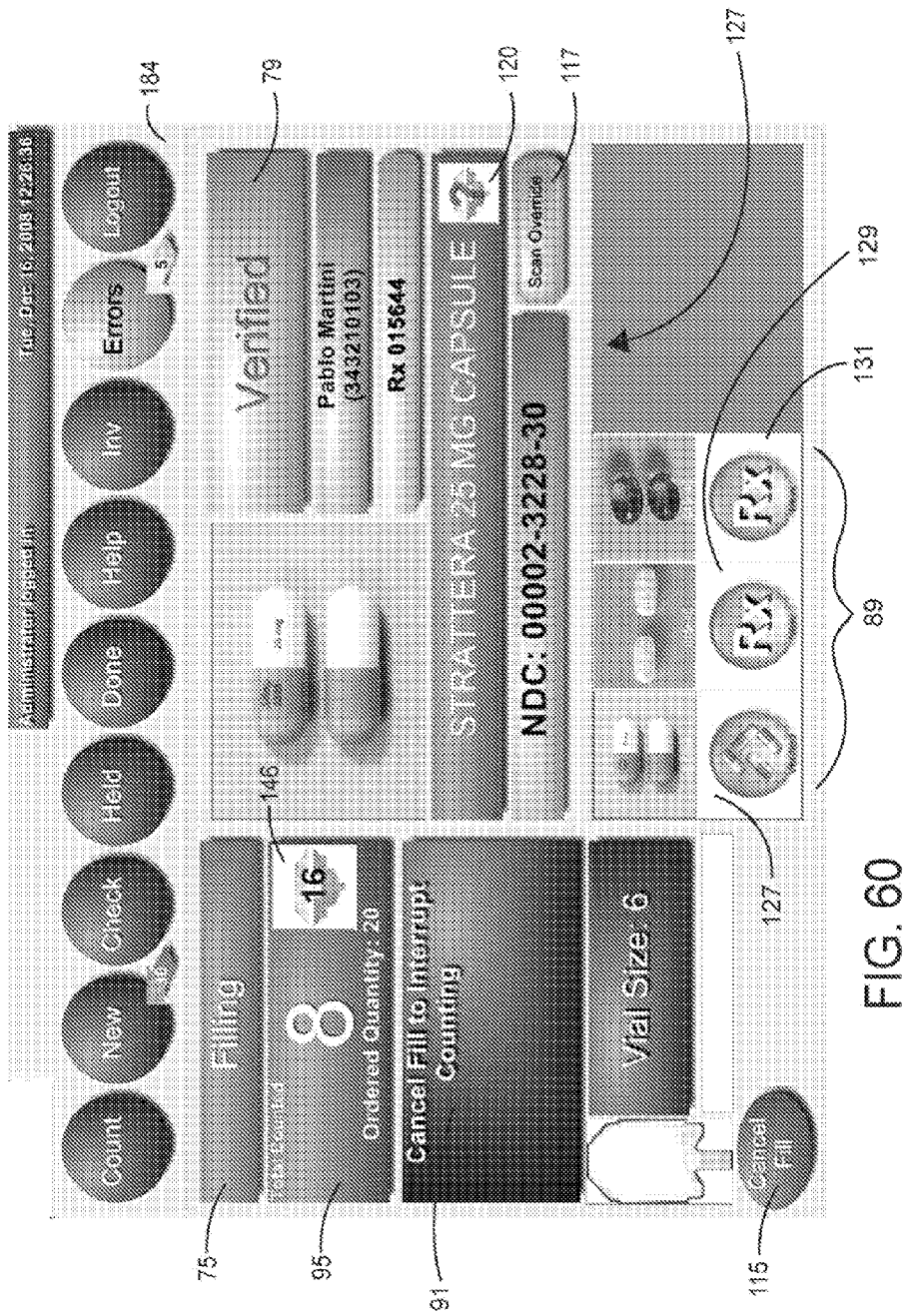
Figure 62:
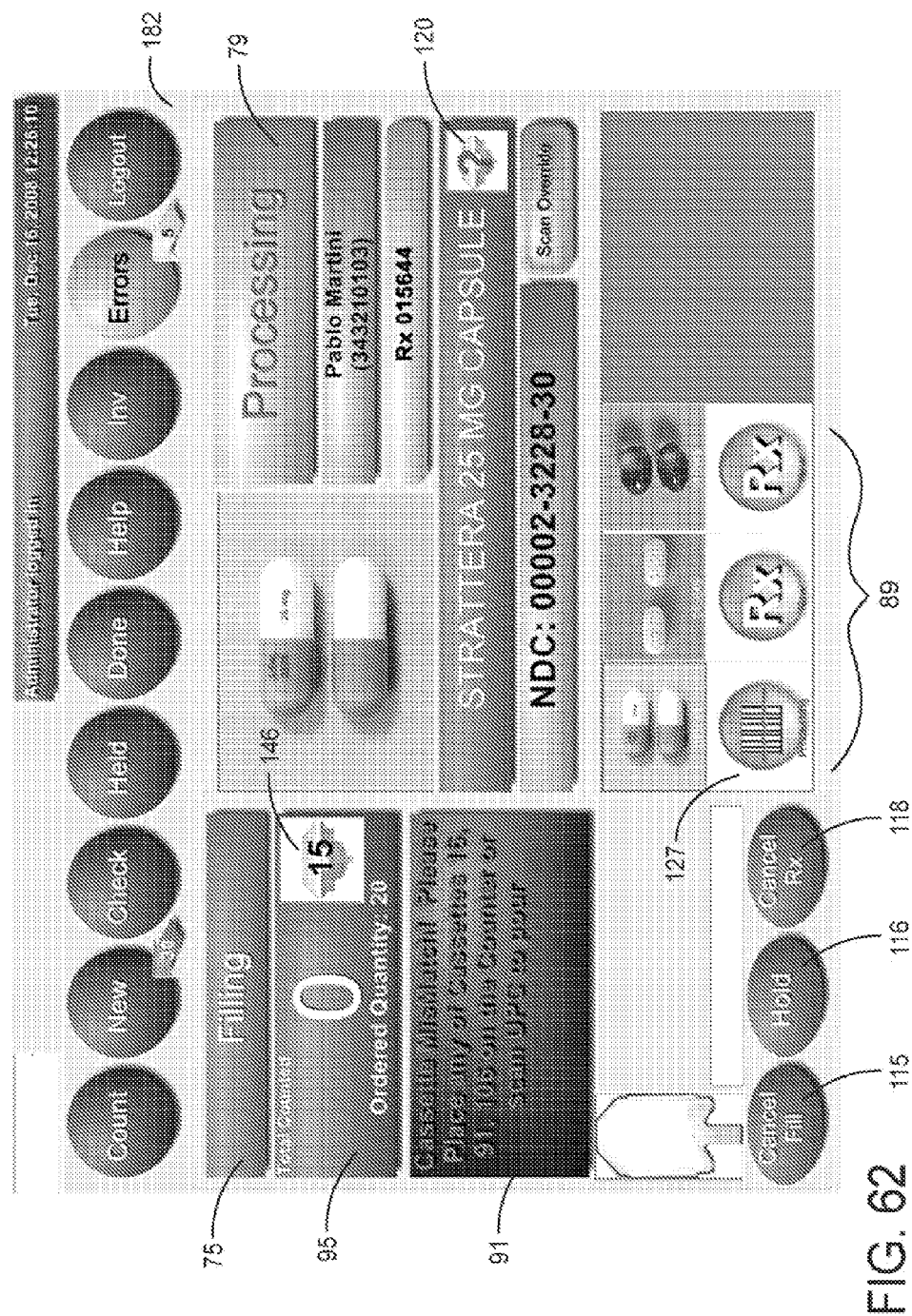
Figure 64:
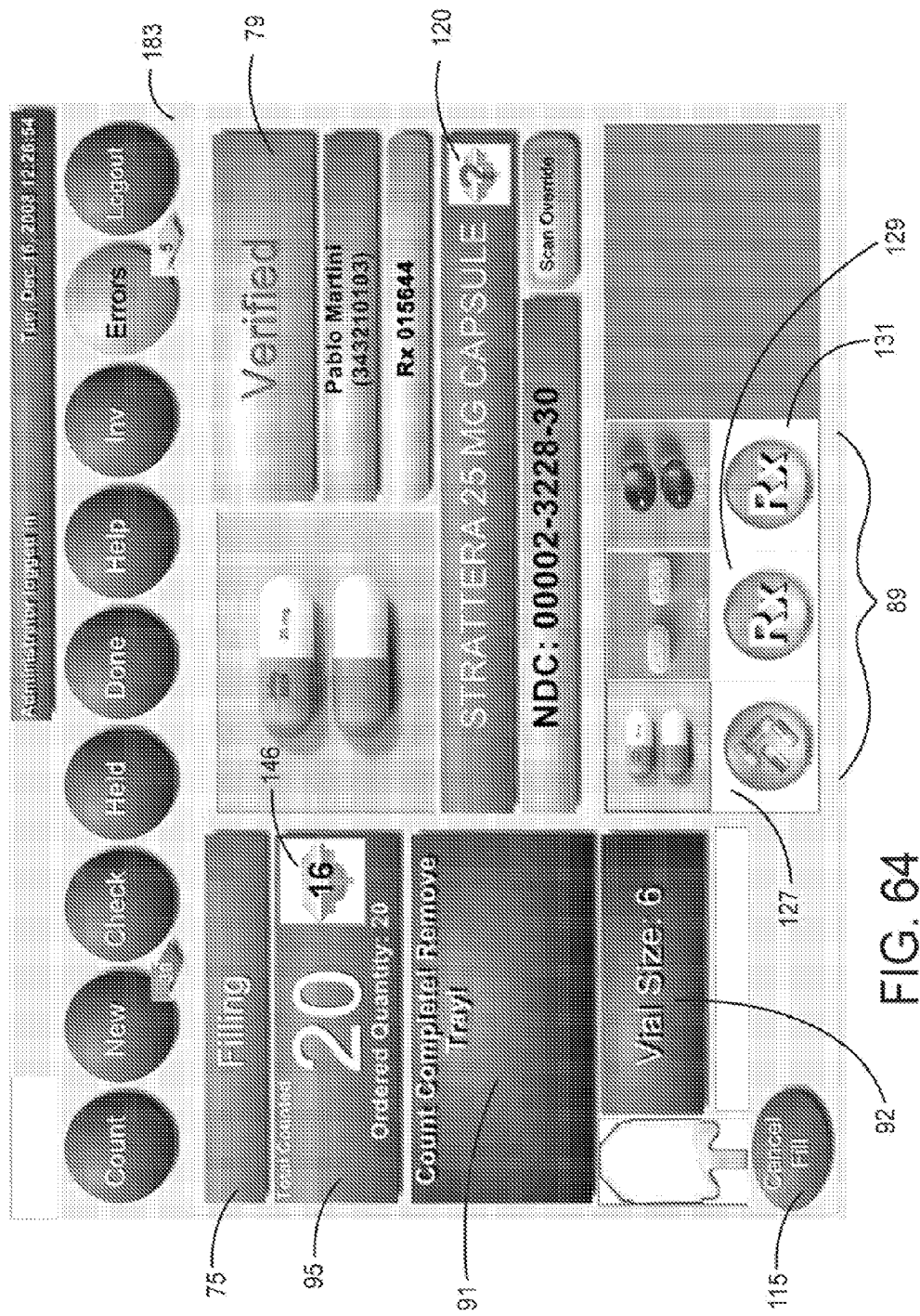

As illustrated, for example, in FIGS. 55 and 58 additional control push buttons can include a Cancel Fill push button 115, a Scan Override push button 117 and a Registered Cassette Query push button 120 (e.g., FIGS. 60, 62, 64).

Selection of Count push button 97 clears the current screen for a new count while selection of New push button 99 causes system 11' to display any existing prescription orders in non-volatile data storage 61 that await selection for fulfillment (block 213).

Selection of Check push button 101 causes system 11 to display any prescription orders that have been counted using system 11, but which await final checking and verification by a registered pharmacist (blocks 247-251).

Selection of Held push button 103 shows any prescriptions that have been placed on hold and have not been fulfilled. Prescriptions may be placed on hold, for example, if medication is not available to fulfill the prescription.

Selection of Done push button 105 causes system 11' to display any existing prescription orders that have been fulfilled using system 11'. If an interface with PMS 21 is provided, prescriptions are preferably collated by patient for ease of review by the user.

Selection of Help push button 107 provides access to support, system setup and configuration details, user and medication database maintenance as well as technical resources. Selection of Help push button 107 also takes the user to a list of available reports which can be sorted by category and viewed on display 37 or printed with printer 72. For example, the reports include a record (e.g., record 70a or 70b of FIGS. 37A, 37B) of each prescription fulfilled by system 11'.

Selection of Inv (inventory) push button 109 allows a user to perform inventory-related tasks.

Errors push button 111 appears if system 11' has determined that data received from PMS 21 cannot be processed. Selection of Errors push button 111 displays prescriptions flagged with the error so that the user can determine the source of the error and make appropriate corrections so that the prescription can be fulfilled using system 11'. Errors push button 111 can appear for other reasons, such as if a barcode 145 falsely indicates that 0 tablets are required for a prescription.

Selection of Logout push button 113 permits the user to log off system 11'.

Selection of the Cancel Fill push button 115 (e.g., FIGS. 59, 60) permits a user to interrupt any process at any time. The Cancel Fill push button 115 can be selected once a prescription is selected for processing, or counting has begun, or at any time the Cancel Fill button is visible. Interrupting a process may be useful if the user wishes to start over or stop use of system 11' to perform a task unrelated to system 11'.

Scan Override push button 117 (e.g., FIG. 55) permits a user to proceed directly to tablet counting without any preliminary processing steps (blocks 255-267). For example, Scan Override 117 can be selected when only a tablet count is required as part of managing inventory by counting tablets in inventory.

Registered Cassette Query push button 120 (e.g., FIGS. 60, 62, 64, 67, 71, 73) is provided to query system 11' for identification of all cassettes 603 including a particular medication type. This push button 120 appears in the Medication Description field 85 next to the medication description. Registered Cassette Query push button 116 can be selected to display a window 188 (FIG. 63) showing all cassettes 603 registered as containing the type of medication described in Medication Description field 85. This feature is useful to assist the user in selecting the required cassette 603 from a group of cassettes at a pharmacy.

Referring next to FIG. 56, Start screen 1073 which could appear on a non-interfaced system 11' is shown. Start screen 1073 includes information-providing fields and user-selectable control push buttons as described in connection with the like fields and controls of Start screen 73. Fields include: an Activity field 1075, a Medication Image field 1077, a Prescription Status Indicator field 1079, a Customer/Patient field 1081, a Prescription Number field 1083, a Medication Description field 1085, a Medication NDC field 1087, a Main Instructions field 1091, a Tray Status field 1093 and a Count Status field 1095. These fields are identical, respectively, to fields 75, 77, 79, 81, 83, 85, 87, 91, 93, 95 described previously. Fields for the User Name 1094 and Date and Time of Day 1096 are provided. No Collated Prescription field 89 is required because the non-interfaced system 11' does not access PMS 21 to receive and manage collated prescriptions.

Control push buttons on Start screen 1073 include: a Count push button 1097, a New push button 1099, a Check push button 1101, a Held push button 1103, a Done push button 1105, a Help push button 1107, an Inv (inventory) push button 1109 and a Logout push button 1113 as described previously in connection with respective push buttons 97, 99, 101, 105, 107, 109, 113. Additional control push buttons include a Cancel Fill push button 1115 (e.g., FIGS. 21, 23, 25, 27, 59, 61, 65, 72, 74), a Registered Cassette Query push button 1120 (e.g., FIGS. 61, 65, 72) and a Scan Override push button 1117 (e.g., FIGS. 56, 59). These controls function as described in connection controls 115, 117, 120 of interfaced system 11'. A Hold 1116 and a Cancel Rx 1118 push button (e.g., FIGS. 32, 62) may be provided to place the prescription into a hold status for fulfillment at a future time or to terminate the prescription. If desired, a single prescription or even an entire prescription order can cancelled by pushing Cancel Rx button 1118. This status will complete the processing for the prescription (e.g., prescription 127) and require nothing further. Hold and Cancel Rx push buttons (identical to buttons 1116, 1118) may also be provided on displays for interfaced systems 11.

While not shown in the non-interfaced screen displays (FIGS. 56, 59, 61, 65, 72, 74), an Errors push button identical to Errors push button 111 and located in the same position as button 111 can appear. An Errors push button for a non-interfaced system could include information about a previous prescription which could not be completed, for example, if a barcode (e.g., barcode 150, FIG. 13) was scanned requesting a count of 0 tablets. Selection of Errors push button displays prescriptions flagged with the error so that the user can determine the source of the error and make appropriate corrections so that the prescription can be fulfilled using system 11'.

Referring again to the flow diagram of FIG. 54A, the user determines the type of counting mode at point 207. The process proceeds to enter decision point 209 if the user selects the customer label scan/selection via software counting mode, to entry block 269 if the user selects the medication container UPC barcode scan counting mode, to entry block 255 if the user selects the scan override counting mode or to entry block 298 if the user selects the cassette-count mode.

Figure 54B:
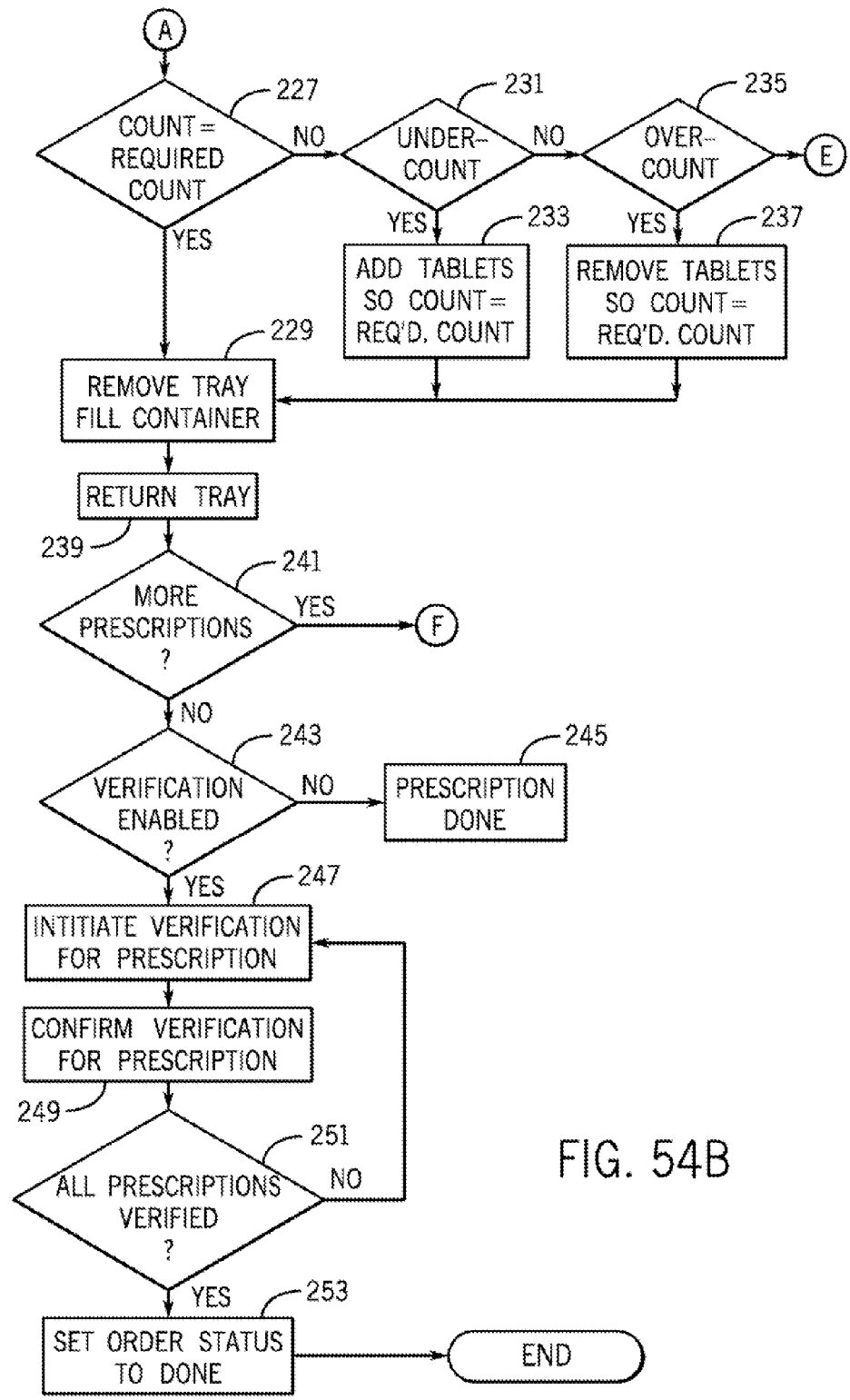

Referring to FIGS. 54A and 54B, exemplary steps of the customer label scan/selection via software counting mode are now described with respect to blocks/decision points 209-253. At decision point 209, the user selects a prescription by label scan selection or by selection via software.

If the prescription selection is via software, the user pushes New button 99 and enters block 213 which results in display of prescriptions which await fulfillment on New Order screen 119 illustrated in FIG. 57. The prescriptions received from PMS 21 are retrieved from the prescription record database residing in non-volatile data storage 61.

New Order screen 119 of FIG. 57 contains fields which provide information for the user regarding each prescription and the prescription order. Fields include: a Patient Name field 121, a Pharmacy-Assigned Patient Identification Code field 123 and a Delivery-Status field 125 indicative of whether the patient is waiting for the prescription or will pick up the prescription later.

New Order screen 119 of FIG. 57 also shows one or more prescriptions for each patient. The prescriptions are preferably collated by patient as illustrated in FIG. 57. Grouping together of pending prescriptions by patient makes it easier for the pharmacist or pharmacy technician to fulfill all prescriptions of all prescription orders pending for each patient. As illustrated in FIG. 57, three prescriptions 127, 129, 131 are shown for fictitious patient Pablo Martini. Each prescription 127-131 shown includes fields for the patient's name 133, pharmacy-assigned prescription number 135, medication name, strength and form information 137, medication quantity 139, medication image 138 and status as a new or previously-fulfilled prescription 140. Collectively, prescriptions 127-131 may represent a single prescription order if placed for fulfillment together or may represent separate prescription orders if placed separately. Touching one of the up/down arrows 141 permits the user to scroll up or down to view pending prescriptions for patient Gelty and others.

New Order screen 119 for system 11' also contains a field of information 142 alerting the user that medication for a prescription (e.g., prescription 127, 129 or 131) is available from a cassette 603. The availability of a cassette 603 containing the required tablets is represented by cassette icon 144 in field 142. The user can select the identified cassette or select a container 175 (FIG. 12A) in order to fulfill the prescription.

In FIG. 57, new order screen 119 displays two cassette icons (each represented by 144 in field 142). As illustrated in FIG. 57, the numbers "16" and "15" appearing with the cassette icons 144 are the unique identifier for each cassette 603 from cassette record database. Each cassette 603 is marked with the unique identifier in human-readable form to enable the user to select the correct cassette. Cassette record database in non-volatile memory 61 is programmed to associate the number of each cassette 603 with a particular tablet loaded in that cassette 603 during cassette 603 replenishment and registration as described below.

New Order screen 119 of FIG. 57 may also include some or all of the control push buttons 97-113 described above in connection with Start screen 73. New Order screen 119 may also include User Name and Date/Time fields 94, 96 or other information fields.

In block 213 of FIG. 54A, a user may display New Order screen 119 and retrieve a prescription for fulfillment in subsequent block 215. The user may select New push button 99 on any screen on which New push button 99 is displayed. This will call up the New Order screen 119 of FIG. 57. The user may then touch one of the prescriptions to select a prescription for fulfillment at block 215 and trigger retrieval of the selected prescription from non-volatile storage 61. The selected prescription is displayed in block 218 as described below.

Referring further to New Order screen 119 of FIG. 57, an arrow 177 may appear on any screen pointing to one of the control push buttons 97-113. A number in such arrow 177 is indicative of the number of prescriptions residing in each control category. For example, arrow 177 pointing to New push button 99 indicates that there are 30 new prescriptions awaiting fulfillment, and arrow 177 pointing to Errors push button 111 indicates that there are five prescriptions with errors that require attention. The number in each arrow 177 is incremented or decremented as new prescriptions are added or removed from each control push button category.

Therefore, New Order screen 119 of interfaced system 11' (FIG. 57) provides the user with a centralized point of control including user access to all information required to fulfill any pending validated prescription order. The user may scroll up or down using arrows 141 to access any of the pending validated prescription orders. Access to the entirety of the pending validated prescription orders through system 11' provides the user with an improved level of control over pharmacy workflow because, for example, the user may fulfill any prescription in any sequence that is most efficient and is no longer required to wait for physical delivery of prescription order paperwork (e.g. paperwork 147) from pharmacy PMS 21. For instance, the user can advance the order for fictitious patient Martini past an order for fictitious patient Gelty because patient Martini is indicated to be waiting for his order as indicated in field 125, whereas patient Gelty will pick up his order at a later time as indicated in field 125 next to his order on New Order screen 119.

As an alternative to prescription selection via software, the user may select the prescription by label scan at decision point 209.

If system 11' is interfaced at point 210, scanning of a prescription label 143 barcode 145 with scanner 51 at block 212 triggers prescription selection. Selection by scanning at block 212 triggers retrieval of the selected prescription and all other prescriptions collated for the patient from non-volatile storage 61. In the label scan prescription selection mode, system 11' bypasses New Order screen 119 and proceeds directly to fulfillment of the selected prescription corresponding to the scanned label as illustrated in connection with FIG. 58.

If system 11' is not interfaced at point 210, scanning of prescription paperwork barcode 150 with scanner 51 at block 214 triggers prescription selection. System 11' proceeds directly to fulfillment of the selected prescription corresponding to the scanned label as illustrated in connection with FIG. 59.

Exemplary label scan mode prescription selection for an interfaced system 11' is entered at steps 209, 210 and 212 and operates in the following manner.

In the example, the label 143 which is scanned is part of the prescription order paperwork 147. Label 143 is generated by PMS 21 as prescription order paper work 147 for each prescription for each patient. The user is provided with paperwork 147 for each prescription to be fulfilled with system 11'. Prescription label 143 includes machine-readable indicia in the form of barcode 145. Prescription label 143 of prescription order paperwork 147 is adhesive-backed and is peeled off paperwork 147 and applied to the patient prescription container (not shown) for the patient's prescription.

If system 11' is interfaced to PMS 21, then barcode 145 need only include a prescription number 149 which matches the prescription number (e.g. prescription number 015644 in Field 135) in the prescription record database in data storage 61. The record of the prescription in the prescription record database will include the data expected to be embedded in the UPC barcode 173 or other container identification code of the container 175 (FIG. 12A) for the medication called for in each prescription being filled. The UPC barcode 173 or other expected container identification code may be provided by means of a relational database or other suitable database type, such as a hierarchical database.

Scanning of barcode 145 at block 212 retrieves the corresponding prescription from prescription record database in storage 61 and further results in retrieval of all other prescriptions for that patient so that all prescriptions for that patient are collated together and can be easily fulfilled by the user. Processing of the prescription corresponding to the scanned label is commenced immediately by system 11' as described below in connection with FIG. 58. At block 218, the selected prescription is displayed to the user on display 37 as described in detail below.

System 11' can permit other information to be present on the prescription paperwork 147. As described previously, this information can include: pharmacy identification information 151, prescribing physician name 153, patient name 155, medication name 157, NDC 159, medication quantity 161, prescription expiration date 163, and prescription price 165. Paperwork 147 may also include a receipt 169 with information corresponding to that of prescription label 143.

Exemplary label scan mode prescription selection for a non-interfaced system 11' is entered at steps 209, 210 and 214 and operates in the following manner.

In the example, the label which is scanned is the receipt portion 169 of prescription order paperwork 147 illustrated in FIG. 13. Receipt 169 includes a barcode 150. Embedded in barcode 150 are three fields of information 152 shown next to barcode 150 including the 11-digit NDC used by the pharmacy (00002-3228-30), the pharmacy-assigned prescription number (015644) and the quantity of tablets required by the patient's prescription (0020).

For non-interfaced systems 11, the NDC number in barcode 150 can be used with a commercially-available database provided in non-volatile storage 61 to look up UPC 173 (or other identification code) of container 175 in storage 61 for subsequent scan verification and can be used to retrieve a reference image of the medication from non-volatile storage 61 in Medication Image field 1077 as described herein. The database including the expected UPC 173 may be a relational database, or other suitable database type (i.e. a hierarchical database). As previously described, each NDC identifies the medication source, medication type and strength and package type and medication quantity. The relational database will include the specific UPC code 173 or other code on the container 175 for the medication identified by the NDC.

Also for non-interfaced systems 11, the NDC number in barcode 150 can be used with cassette record database in non-volatile storage 61 to look up the cassette 603 identification code (which corresponds to the code embedded in barcode on cassette sidewall 759) for the cassette 603 containing the required medication should the user prefer to dispense the medication from a cassette 603 rather than by manual pouring from a manufacturer's container 175.

If barcode 150 on paperwork 147 receipt 169 is scanned, then the non-interfaced system 11 immediately begins to process that prescription (e.g., prescription 127) resulting in selection of the prescription at block 214 and retrieval of the UPC 173 or cassette identification code (icons 144, 146, 1146) and reference image information from non-volatile storage 61.

Fulfillment of prescription 127 requiring 20 capsules of 25 mg Eli Lily & Co. Strattera medication for fictitious patient Pablo Martini is described below for both interfaced and non-interfaced systems 11'. Fulfillment of prescriptions 129, 131 for patient Martini would occur in the same manner, providing that medication is available in a cassette 603.

Referring to FIG. 54A, block 218 is entered to display information relating to the selected prescription for both interfaced and non-interfaced systems 11'.

If system 11' is interfaced, prescription selection via software at block 215 or by label scan at block 212 results in appearance of Prescription Filling screen 179 (FIG. 58) on display 37 and all relevant information pertaining to fulfillment of prescription 127 is presented to the user. Prescription Filling screen 179 illustrated in FIG. 58, Activity field 75 is set to "Filling" and Prescription Status Indicator field 79 is set to "Processing" to indicate that fulfillment of the prescription is in process. Patient name field 81 is set to show the patient name and the prescription number of the prescription being fulfilled is shown in field 83. The prescribed medication image, medication name, strength and form and NDC number are set in respective fields 77, 85, 87. All three prescriptions 127, 129, 131 are collated together in Collated Order field 89 with prescription 127 indicated as being in a "Processing" mode.

If the required medication is available in a cassette 603 or a container 175, the user is able to choose whether to fulfill the prescription 127 from the cassette 603 or by manually pouring the medication through the system 11'. For system 11', Main Instruction field 91, prompts the user to select a cassette 603 or container 175 to fulfill the prescription. In the example, three cassettes 603 are designated as containing the required Strattera tablets (i.e., cassettes "16", "91", "106"), and the user is prompted to select any one of the three cassettes 603.

Figure 59:
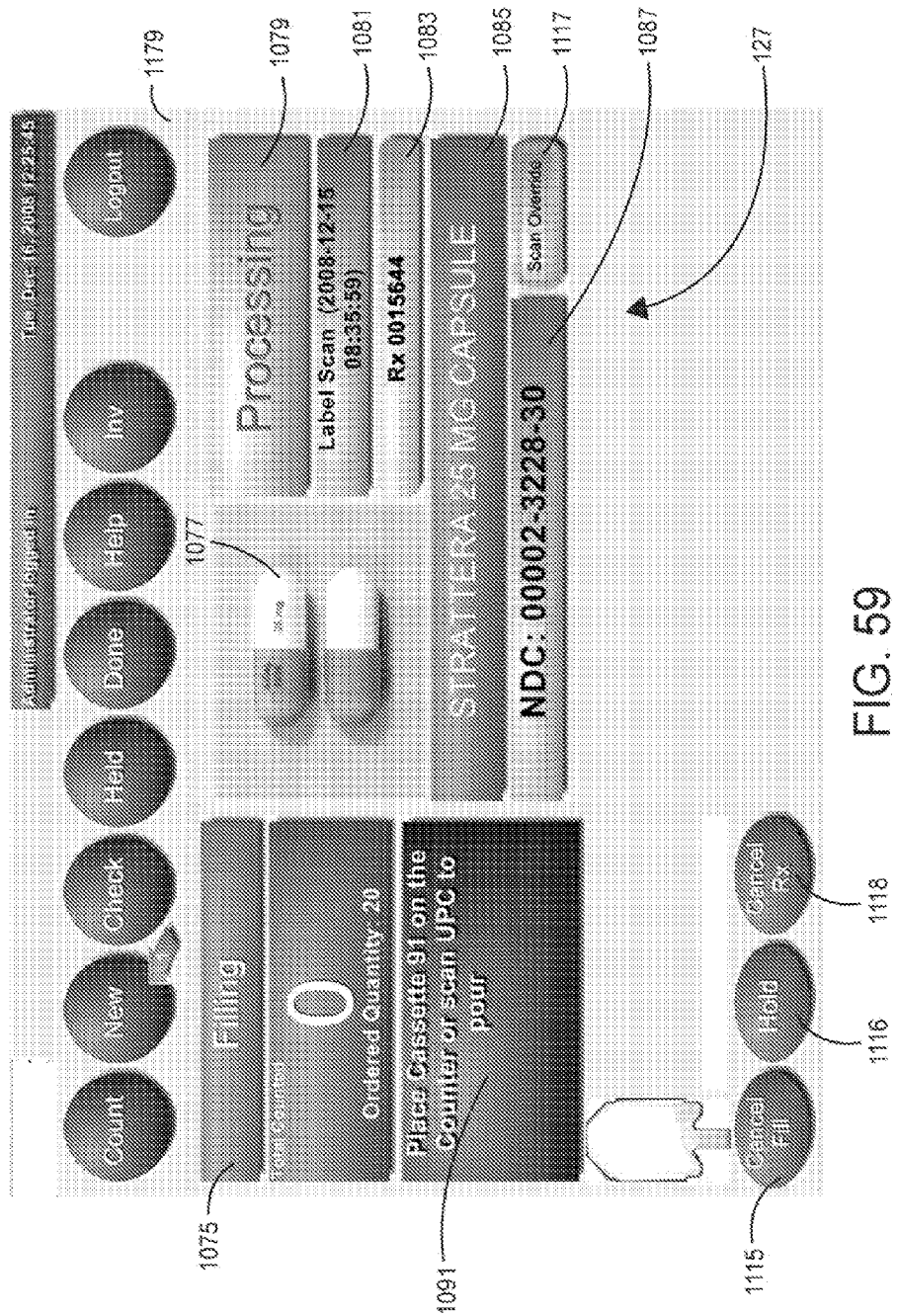

If system 11' is non-interfaced, prescription selection by label scan at block 214 results in display of the selected prescription at block 218. Entry of block 218 for non-interfaced system 11' by scanning barcode 150 during the label scan selection process block 214 causes Start screen 1073 (FIG. 56) to be replaced with Prescription Filling screen 1179' (FIG. 59). As illustrated in FIG. 59, Prescription Filling screen 1179 Activity field 1075 is set to "Filling" and Prescription Status Indicator field 1079 is set to "Processing" to indicate that fulfillment of the prescription is in process.

Because the patient name and prescription number are not known from scanning barcode 150, patient name field 1081 and prescription number field are set to show the date and time of day. The medication image, medication name, strength and form and NDC number for the Strattera medication required by prescription 127 are again set in respective fields 1077, 1085, 1087. This information is retrieved from a relational database corresponding to the NDC number in barcode 150 from non-volatile data storage 61.

Also retrieved from the relational database is UPC barcode 173 expected to be on container 175 and the cassette identification code for the cassette 603 or cassettes containing the required medication as previously described. The expected UPC barcode and cassette identification code are related directly to the NDC number embedded in barcode 150. Single prescription 127 being filled is shown with prescription 127 indicated as being in a processing mode in field 1079.

If the required medication is available in a cassette 603 or a container 175, the user is able to choose whether to fulfill the prescription 127 from the cassette 603 or by manually pouring the medication through the system 11'. For non-interfaced system 11', Main Instruction field 91, prompts the user to select a cassette 603 or container 175 to fulfill the prescription. In the example of FIG. 59, one cassette 603 is designated as containing the required Strattera tablets (cassette "91"), and the user is prompted to select the designated cassette 603.

Block 219 of FIG. 54A is entered next for both interfaced and non-interfaced systems 11'. In block 219, the user selects a cassette 603 or a container 175 containing tablet-form medication required by the prescription (e.g., prescription 127).

If a cassette is selected at block 219, the user mounts cassette 603 on cassette dispenser 601. In the interfaced system 11' example of FIG. 60, cassette 603 with cassette identification code "16" is selected by the user from a storage location (not shown) and is mounted on cassette mount 621. In the non-interfaced system 11' example of FIG. 61, cassette 603 with cassette identification code "91" is selected by the user from the storage location (not shown) and is mounted on cassette mount 621. In the examples, cassette identification codes "16" and "91" are embedded in a respective barcode 760.

At block 221 of FIG. 54A, reader 645 reads the barcode 760 (FIG. 46A, barcode 760 location indicated in FIG. 46) on the mounted cassette 603, and a signal corresponding to the cassette identification code is transmitted to data processing platform 17 via serial connection 649. A cassette icon 146, 1146 appears in Main Instructions field 91, 1091 corresponding to the unique cassette identification number of mounted cassette 603 as detected by reader 645. The cassette icon 146, 1146 remains in Main Instructions field 91, 1091 until the mounted cassette 603 is removed from cassette mount 621 as detected by opening of switch 639.

At decision point 223 of FIG. 54A, the signal including the actual cassette identification code is compared by the program of instructions operating on data processing platform 17 with the expected cassette identification code for the cassette 603 containing the required medication from the cassette record database in non-volatile data storage 61. The purpose of the comparison is to confirm that the cassette 603 including the medication required by the prescription 127 is mounted on the cassette dispenser.

Figure 61:
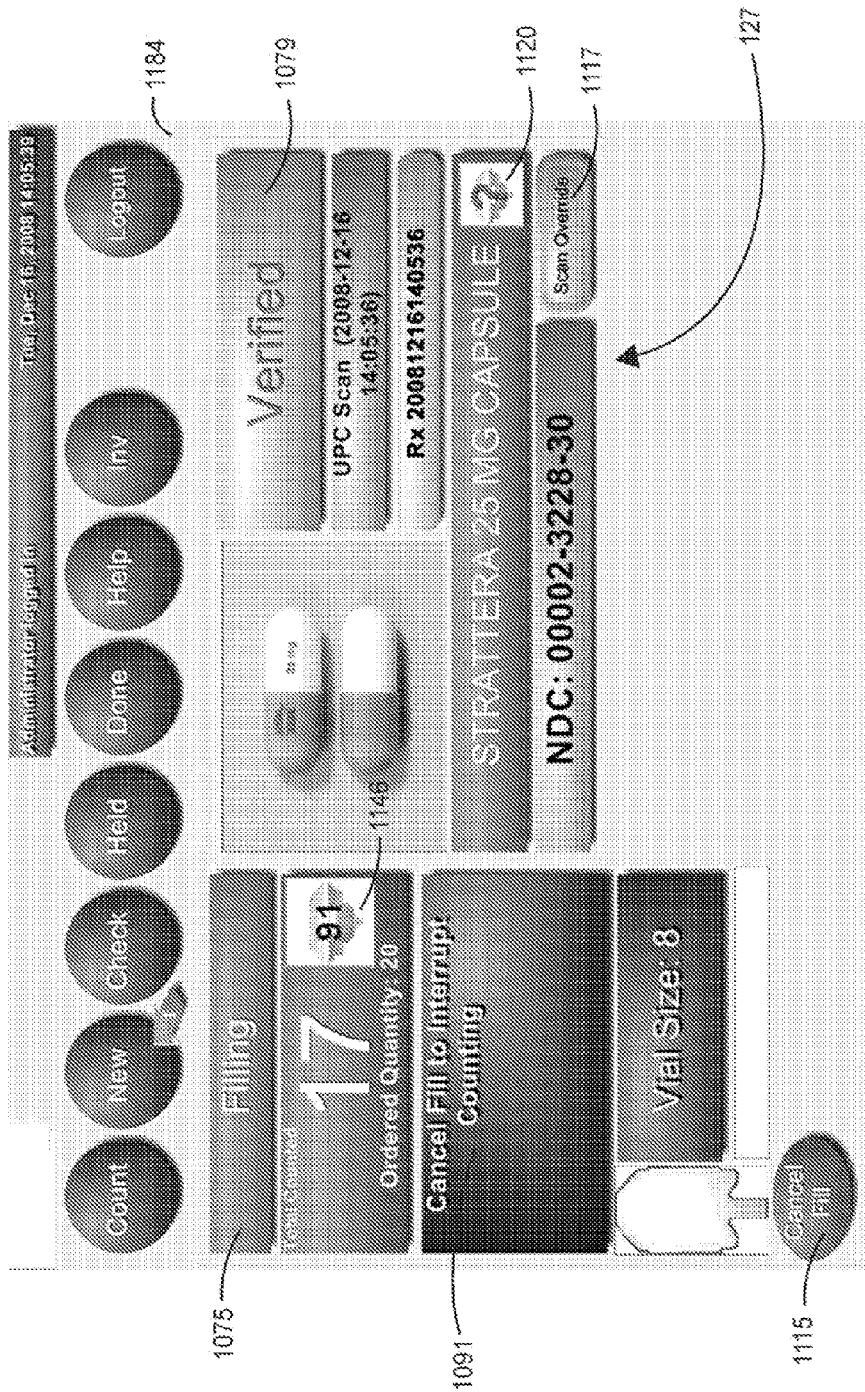

If the comparison at point 223 results in a match between the cassette identification code detected by reader 645 and expected cassette identification code, then system 11' immediately enters block 225 and commences tablet counting as described in connection with the Cassette Counting screen 184 of FIG. 60 (interfaced system 11') or 1184 of FIG. 61 (non-interfaced system 11') below.

If there is no match at point 223, the process is as follows. For the interfaced system 11', if there is no match between the mounted cassette 603 and the expected cassette at point 223, then Error screen 182 of FIG. 62 is presented to the user. In addition, speaker 63 may generate an audible signal indicating that the comparison did not result in a match. Instructions in Main Instructions field 91 indicate that an error (a cassette mismatch) has been detected to prompt the user at block 219 to select the correct cassette 603 (i.e., repeat block 219) or to remove the cassette 603 and repeat the reading process of block 221. In the example of FIG. 62, cassette "15" was erroneously mounted to cassette mount 621, and the user is prompted to select one of cassettes "16", "91" or "106" as a substitute for cassette "15". Cassettes "16", "91" or "106" are registered in cassette record database as containing the required Strattera medication. Prescription Status Indicator field 79 remains set to "Processing," and the word "Processing" also appears in Collated Order field 89 for prescription 127 because no match has occurred at point 223.

For the non-interfaced system 11', an identical error message is displayed (not shown) prompting the user to select the a replacement cassette 603 (block 219) for reading (block 221) and to determine whether the expected cassette identification code of the replacement cassette 603 matches the actual cassette identification code read by reader 645 (point 223).

Figure 63:
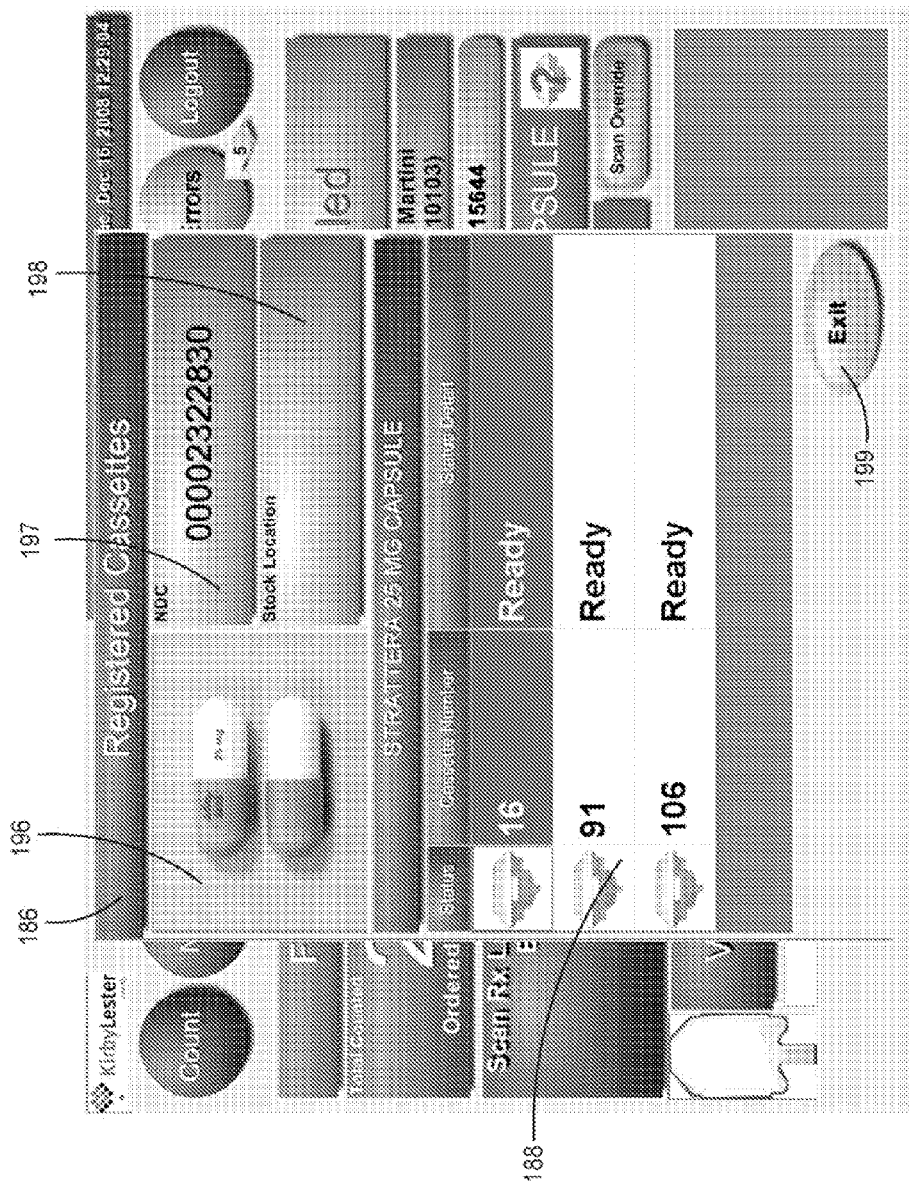

Referring to FIGS. 60 and 62-63, pressing of the Registered Cassette Query button 120 in the Medication Description field 85 brings up a Registered Cassette window 186 which informs the user of all cassettes 603 which include the medication described in the Medication Description Field 85. The information in window 186 is useful to assist the user in selecting the correct loaded cassette 603 to fulfill the prescription. In the example, window 186 includes a field 188 showing that three cassettes (numbers "16", "91" and "106") are loaded with 25 mg strength capsule-form Strattera and are registered with system 11' as being "Ready" for use. Window 186 includes an Image field 196 providing an image of the Strattera medication, an NDC number field 197 providing the NDC number of the Strattera medication and a word description of the Strattera medication. A Stock Location field 198 may be provided to indicate the storage location of a container 175 of the Strattera medication for cassette 603 replenishment. Window 186 can be accessed by pressing Registered Cassette Query button 120 on any screen on which button 120 is displayed. An Exit push button 199 is provided to exit window 186

For manual pour through of tablets from a container 175 with an interfaced system 11', the process is essentially identical to that described in connection with system 11 and results in verification that the correct container 175 has been selected to fulfill the prescription.

Block 219 of FIG. 54A is entered for both interfaced and non-interfaced systems 11'. In block 219, the user selects a medication container (e.g., container 175) containing tablet-form medication required by the prescription (e.g., prescription 127). Container 175 is retrieved from its storage location.

At block 221 of FIG. 54A, the user scans the UPC barcode 173 on container 175 with barcode scanner 51, and a signal corresponding to the actual UPC barcode 173 is transmitted to data processing platform 17.

At decision point 223 of FIG. 54A, the actual UPC barcode 173 on container 175 is compared by the program of instructions operating on data processing platform 17 with the expected UPC barcode for container 175 containing the required medication from the prescription record database in non-volatile data storage 61.

Referring to FIGS. 54A and 20-21, if the comparison at point 223 results in a match between the actual UPC barcode 173 and the expected UPC, counting of tablets is enabled and Begin-Pouring screen 181 is shown on display 37 for an interfaced system 11' and or the Begin-Pouring screen 1181 of FIG. 21 is shown on display 37 for non-interfaced system 11'.

For the interfaced system 11', if there is no match at point 223, then Error screen 182 of FIG. 22 is presented to the user. In addition, speaker 63 may generate an audible signal indicating that the comparison did not result in a match. Instructions in Main Instructions field 91 indicate that an error (a cassette mismatch) has been detected to prompt the user at block 219 to re-scan UPC 173 (repeat block 221) or to select a different container 175 (repeat block 219). Prescription Status Indicator field 79 remains set to "Processing," and the word "Processing" also appears in Collated Order field 89 for prescription 127 because no match has occurred at point 223.

For the non-interfaced system 11, if there is no match at point 223, then Error screen 1182 of FIG. 23 is presented to the user. An audible error signal can be generated by speaker 63. Instructions in Main Instructions field 1091 indicate that an error has been detected to prompt the user at block 223 to re-scan UPC 173 (repeat block 221) or to select a different container 175 (repeat block 219).

As with system 11, other error types can occur during the fulfillment process and information can be displayed to alert the user to such errors. Examples of errors can include, for example, that the medication is not in the prescription record database in storage 61, that data was erroneously entered for the prescription (for example erroneously indicating that zero tablets are required), that the UPC was not found in the relational database in storage 61, or that the lengths of barcodes 145 and 173 do not match. These and other error conditions can trigger system 11' to display instructions in Main Instructions field 91 or 1091, prompting the user to take appropriate corrective action.

At this point in the workflow for both cassette-based and manual pour-through counting, the medication has been selected and the source of the medication (cassette 603 or container 175) has been verified. Counting occurs next at block 225.

Tablet counting at block 225 is first described for cassette-based counting with reference to FIG. 54A and block 225. Cassette-based counting at block 225 is identical for interfaced and non-interfaced systems 11'. Tablet counting begins immediately once a match is determined at point 223 resulting in display of Cassette Counting screen 184 of FIG. 60 (interfaced) or Cassette Counting screen 1184 of FIG. 61 (non-interfaced). Prescription Status Indicator fields 79, 1079 of FIGS. 60, 61 are set to "Verified" indicating to the user that cassette 603 matches the expected cassette containing the medication required by prescription 127. Collated Order field 89 for interfaced system 11' is also set to "Verified" for prescription 127 also indicative of the match. (Collated Order field 89 is set to "New" for prescriptions 129 and 131 because fulfillment of these prescriptions has not yet commenced.)

Data processing platform 17 initiates operation of controller 607. Controller 607 automatically activates motor 635 resulting in rotation of rotor 767 and feeding of tablets one after the other through opening 781. Tablets 604, 606, 608, 610 fall along path 681 and past detector 605 whereupon a signal is sent via receiver 689 to controller 607 indicative of tablet detection. Controller 607 increments a count for each detected tablet as previously described. In the example of prescription 127, twenty counts would be expected corresponding to the quantity of tablets required to fill that prescription. Controller 607 stops motor 635 operation when the tablet count matches the required count. Controller 607 may slow motor 635 as the tablet count approaches the required count as previously described.

Tablets (e.g., tablet 604) fed from cassette 603 fall past detector 605 and into funnel 41' and chute 43. First tablet counter 15 automatically counts each tablet as it falls through funnel 41' and chute 43 past collimated IR sources 308a, 308b and sensors 307a, 307b and into tray 45. The system software previously described performs the count, and Count Status fields 95, 1095 of Cassette Counting screen 184 of FIG. 60 (interfaced) or Cassette Counting screen 1184 of FIG. 61 (non-interfaced) is instantaneously updated as each tablet is counted. FIGS. 60 and 61 are "snapshots" representative of the appearance of display 37 at the point at which eight and seventeen tablets of the required twenty tablets have been counted by the respective interfaced and non-interfaced systems 11'.

The tablet count from first tablet counter 15 is compared to the tablet count from the second tablet counter 615 during counting as previously described in connection with FIGS. 50-53B to ensure that the counts are within a predetermined count of the other, thereby ensuring that the required tablets are being fed out from the cassette 603.

Tablet counting at block 225 is next described for manual pour-through counting with reference to FIG. 54A. Manual pour-through counting is like that described above in connection with FIGS. 20-27. Manual pour-through counting from a container 175 at block 225 is identical for interfaced and non-interfaced systems 11'. Cassette dispenser 601 is not required for manual pour-through counting. Cassette dispenser 601 could be utilized, however, to supply any required tablets not available from container 175, for example if container 175 becomes empty before the required quantity of tablets are counted by counter 15.

Referring to FIGS. 54A and 20-21, verification of the selected container 175 in block 223 causes the "Begin Pouring Now" message to be displayed, prompting the user to manually pour tablets into funnel 41' from container 175. As illustrated in FIG. 20 (interfaced system 11) and FIG. 21 (non-interfaced system 11), Main Instructions fields 91, 1091 of the Begin-Pouring screens prompt the user to begin pouring the tablets from a container (e.g., container 175) into funnel 41' in response to the match in block 223. Prescription Status Indicator fields 79, 1079 are set to "Verified," indicating to the user that UPC 173 of container 175 matches the medication required by the prescription. Collated Order field 89 is also set to "Verified" for prescription 127, also indicative of the match. (Collated Order field 89 is set to "New" for prescriptions 129 and 131 because fulfillment of these prescriptions has not yet commenced.) Count Status field 95, 1095 are set to 0, and the tablet quantity required by the prescription (e.g., prescription 127) is displayed.

In the example of FIGS. 38-49, the user pours tablet-form medication from container 175 into funnel 41'. First tablet counter 15 automatically counts each tablet as it falls from funnel 41' past collimated IR sources 308a, 308b and sensors 307a, 307b and into tray 45. The system software previously described performs the count, and Count Status fields 95, 1095 are instantaneously updated as each tablet is counted.

Next, decision point 227 of FIG. 54B is entered and a determination is made with respect to whether the actual count equals the required count.

For cassette-based counting, the process moves to FIGS. 54B, 64 (interfaced system 11') or 65 (non-interfaced system 11') and decision point 227. At point 227, the actual tablet count made by first tablet counter 15 is compared to the required tablet count for the prescription. Tablets are fed from cassette 603 until the required quantity of tablets is counted by second counter 615. Tablets fall from cassette 603 into funnel 41' and fall past first tablet counter 15.

At point 227, the actual tablet count made by first tablet counter 15 is compared to the required tablet count for the prescription. If the actual tablet count of first tablet counter 15 equals the required tablet count, then Count-Complete screen 183 of FIG. 64 (interfaced system 11') or Count-Complete screen 1183 of FIG. 65 (non-interfaced system 11') appears on display 37.

As described in connection with FIGS. 50-53B, the actual tablet count made by both the first and second tablet counters 15, 615 is compared during counting within data processing platform 17 to provide verification that all necessary tablets are fed from cassette 603. Optionally, the total number of tablets counted by both the first and second tablet counters 15, 615 can be compared to the required count for added assurance of accuracy. For example, the count of each counter 15, 615 can be compared once the count of counter 615 equals the required count (20 counts in the example of prescription 127). If the counts of counters 15, 615 match, the process can move forward. If the counts of counters 15, 615 do not match, an error message can be presented to user in the Main Instructions field 91, 1091 of FIGS. 60-61 as described above. The error message would prompt the user to repeat the counting process or otherwise take corrective action.

Figure 65:
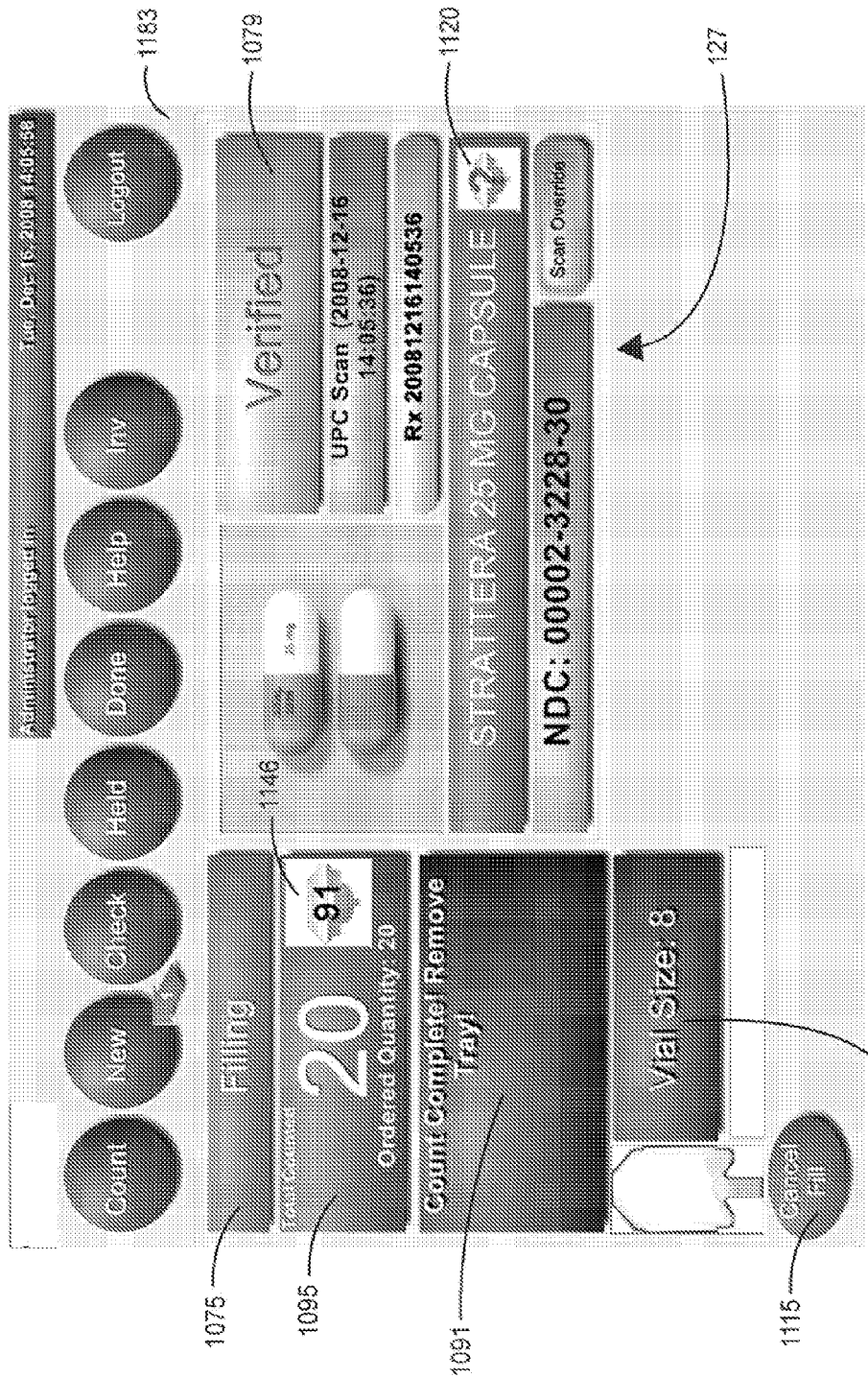

Referring further to FIGS. 64 and 65, Prescription Status Indicator fields 79, 1079 remain set to "Verified" providing continued indication to the user that correct cassette 603 or container 175 was selected. Main Instructions fields 91, 1091 instruct the user that the count is complete and prompts the user to remove tray 45 so that the counted tablets can be poured from tray 45 into a vial, bottle or other container for the patient's prescription. Vial size field 92, 1092 indicates a recommended vial size suitable to hold the counted tablets. Vial size "6" or "8" is recommended in the example. Vial size refers to the volumetric DRAM size in the example. Speaker 63 may generate an audible signal indicating that the correct count has been made.

For manual pour-through counting, the process also moves to FIGS. 54B, 24 and 25 and decision point 227. At point 227, the actual tablet count made by first tablet counter 15 is compared to the required tablet count for the prescription. Again, if the actual tablet count equals the required tablet count as determined by first tablet counter 15, then Count-Complete screen 183 of FIG. 24 (interfaced system 11') or Count-Complete screen 1183 of FIG. 25 (non-interfaced system 11') is shown on display 37. Prescription Status Indicator fields 79, 1079 remain set to "Verified" providing continued indication to the user that correct cassette 603 or container 175 was selected. Main Instructions fields 91, 1091 instruct the user that the count is complete and prompts the user to remove tray 45 so that the counted tablets can be poured from tray 45 into a vial, bottle or other container for the patient's prescription. Vial size field 92, 1092 indicates a recommended vial size suitable to hold the counted tablets. Vial size "6" is recommended in the example of FIGS. 24 and 25. Speaker 63 may generate an audible signal indicating that the correct count has been made.

For both cassette-based and manual pour-through counting, an undercount could occur at decision point 231 if the user removes tray 45 before the required quantity of tablets is counted. An undercount may also occur during manual pouring if too much time elapses, for example, because the count was not completed within a user-configurable time interval (such as 5 minutes). Such a time out could occur if, for example, a user were asked to assist with another task in the pharmacy before completing the count. An undercount message indicating the undercount is provided in Main Instructions field 91, 1091 of FIGS. 24, 25, 64, 65. An audible signal generated by speaker 63 would also indicate an undercount condition to the user. If an undercount occurs at decision point 231 of FIG. 54B, then additional tablets are poured from container 175 into funnel 41 until the actual count equals the required count at block 233. The count is displayed in Count Status field 95, 1095.

For both cassette-based and manual pour-through counting, an overcount could occur at decision point 235 if too many tablets are counted by first tablet counter 15. For example, two tablets could be ejected simultaneously from cassette 603 registering only a single count on second tablet counter 615. In this situation, the overcount would be detected by first counter 15 avoiding a situation in which potentially costly medication is essentially "given away" free of charge to the patient. If there is an overcount at decision point 235, then the user is notified of the overcount by a message in Main Instructions field 91, 1091 of FIGS. 24, 25, 64, 65 and an audible signal from speaker 63. The user is prompted to manually adjust the count by removing tablets or to re-feed tablets from cassette 603 or to manually re-pour the tablets (e.g., from tray 45) through first tablet counter 15 until the actual count equals the expected count as indicated in Count Status field 95, 1095.

If the tablets are poured too rapidly past first tablet counter 15, then an overspeed error condition can occur (step 517 of FIG. 11B) indicating that the tablets passing collimated IR sources 308a, 308b and sensors 307a, 307b were not accurately counted. If an overspeed error occurs, then the user is prompted by an audible signal from speaker 63 and an overspeed message (not shown) is presented on display 37 and the screens of FIGS. 24, 25, 64, 65. The user is prompted to re-pour the tablets through first tablet counter 15 until the actual count equals the expected count as indicated in Count Status field 95, 1095. A benefit of cassette-based tablet feeding is that overspeed conditions are avoided by tablet singulation.

Figure 54C:
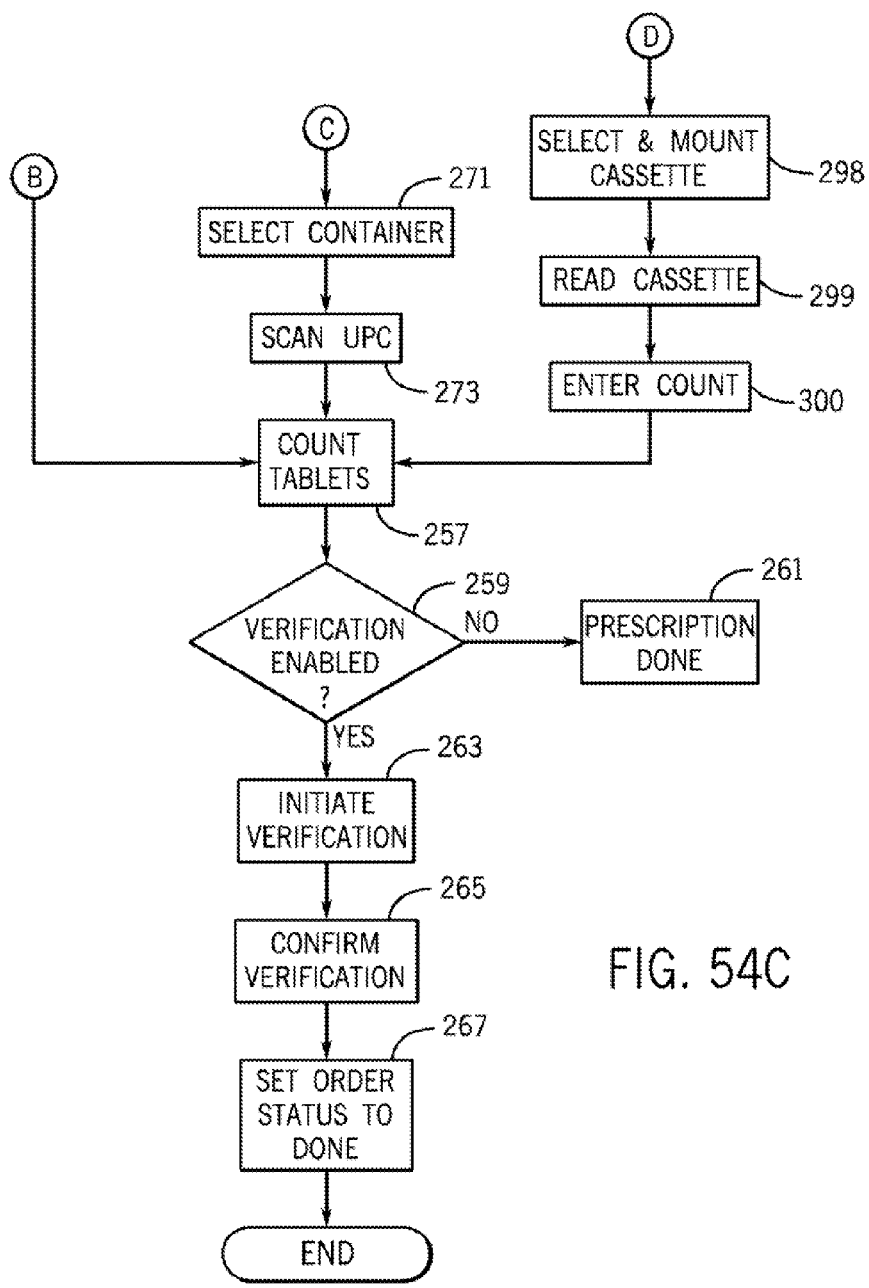
Figure 54D:
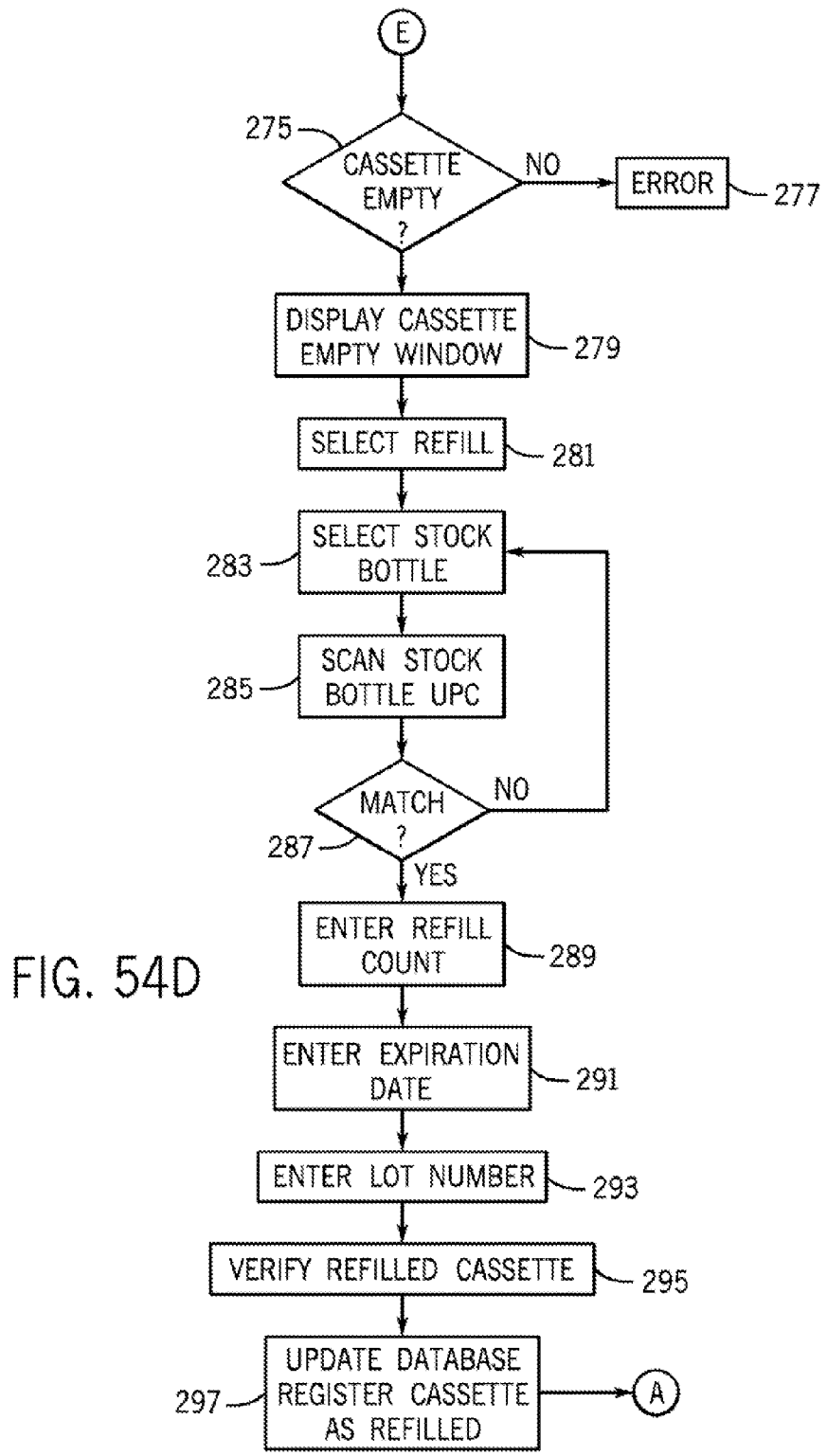

For cassette-based counting, the process moves to FIG. 54D decision point 275 if cassette 603 runs out of tablets before the tablet count of first tablet counter 15 matches the required tablet count in decision block 227. Decision point 275 is the entry step for cassette 603 replenishment or manual pouring of tablets from a container 175 to achieve the tablet count required for the prescription being fulfilled.

At decision point 275, first tablet counter 15 has not counted the required tablets (e.g., tablet 604) and has not made a count for a preset time. This condition is indicative of an empty cassette 603 or another error, such as tablets (e.g., tablets 604, 606) having become bridged or jammed in funnel 41'. In a cassette-empty state, first and second tablet counters 15, 615 have not counted the required quantity of tablets. In a jammed state, second tablet counter 615 has counted the required quantity of tablets while first tablet counter 15 has not counted the required quantity of tablets.

A tablet-jam state can exist if tablets have become jammed in funnel 41' or chute 43 and are not moving freely toward first tablet counter 15. The count comparison at point 872 (FIG. 53B) would indicate that the counts of the first and second tablet counters 15, 615 are not in agreement. If the cassette is not empty (i.e., second tablet counter 615 has counted the required tablet quantity) and there is a tablet jam, then block 277 is entered indicative that there is an error requiring user attention. An error prompt may appear in Main Instructions field 91, 1091 screens of FIGS. 64, 65 to alert the user. The user could manually clear any tablet jam and then complete the counting process.

Figure 66:
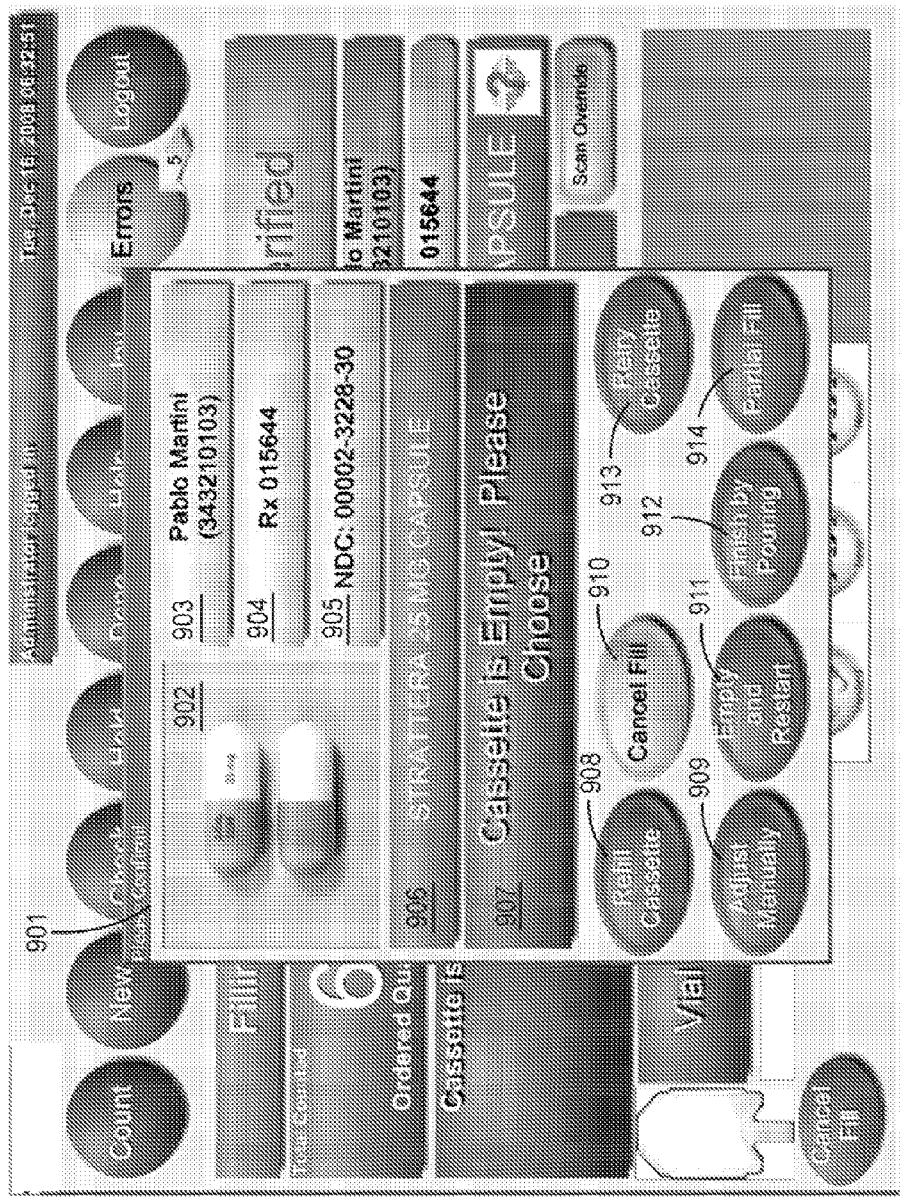

Referring to FIGS. 54D and 66, if cassette 603 is empty as indicated by both the first and second tablet counters 15, 615 not having counted the required quantity of tablets, then cassette-empty window 901 appears on display 37 at block 279 providing user options, including cassette 603 replenishment. Non-interfaced system 11' includes an identical Cassette-empty window 901 and user options. For convenience and brevity, the description of window 901 and related options for the interfaced system 11 are incorporated herein for the non-interfaced system 11'. For both interfaced and non-interfaced systems 11', the empty cassette 603 is inactivated and cannot be utilized to dispense tablets until the cassette is refilled and registered to system 11'. The empty cassette 603 can be inactivated simply by updating cassette record database in non-volatile data storage 61 to indicate that the code associated with the empty cassette 603 is not valid.

Referring to FIG. 66, window 901 of interfaced system 11 shows exemplary fields and controls. Fields include: a Medication Image field 902, a Customer/Patient identification field 903, a Prescription Number field 904, a Medication NDC field 905, a Medication Description field 906, and a Cassette Status field 907. Controls include: a Refill Cassette push button 908, an Adjust Manually push button 909, a Cancel Fill push button 910, an Empty and Restart push button 911, a Finish by Pouring push button 912, a Retry Cassette push button 913 and a Partial Fill push button 914.

In the example, information for prescription 127 for Strattera 25 mg strength capsules for fictitious patient Pablo Martini is displayed in respective fields 901-907. Cassette Status field 907 indicates that cassette 603 is empty indicative that the actual tablet count counted by first tablet counter 15 did not reach the required count at point 227 before the cassette 603 became empty.

Selection of Refill Cassette push button 908 permits the user to refill cassette 603 as described below. Adjust Manually push button 909 permits the user to manually adjust motor 635 RPM output to adjust the rate at which tablets are fed from cassette 603. This control is useful to avoid tablet jams within a cassette resulting in a false indication that the cassette is empty. Adjustment of motor 635 output has been found to be a way to improve movement of tablets out of a cassette 603. Selection of button 909 permits the user to increase or, alternatively, decrease motor RPM output 635.

Cancel Fill push button 910 permits the user to terminate the fulfilment process for prescription 127. The prescription can be filled at any time in the future. The prescription is unaffected and stays unfilled. The prescription would be added to the queue of "held" prescriptions accessible by touching the Held push button 103, 1103. Empty and Restart push button 911 permits a user to reenter block 218 and to start over. Finish by Pouring push button 912 permits a user to manually pour the required tablets from a container 175 to complete the prescription and to enter block 227. Retry Cassette push button 913 permits a user to start again from beginning, removing the tray and restarting the prescription counting from point 209. Partial Fill push button 914 permits a user to accept the counted tablets as partial fulfillment of the prescription and to finish counting manually. The counting process is terminated and it is assumed the operator will manually deliver the prescribed quantity.

Figure 67:
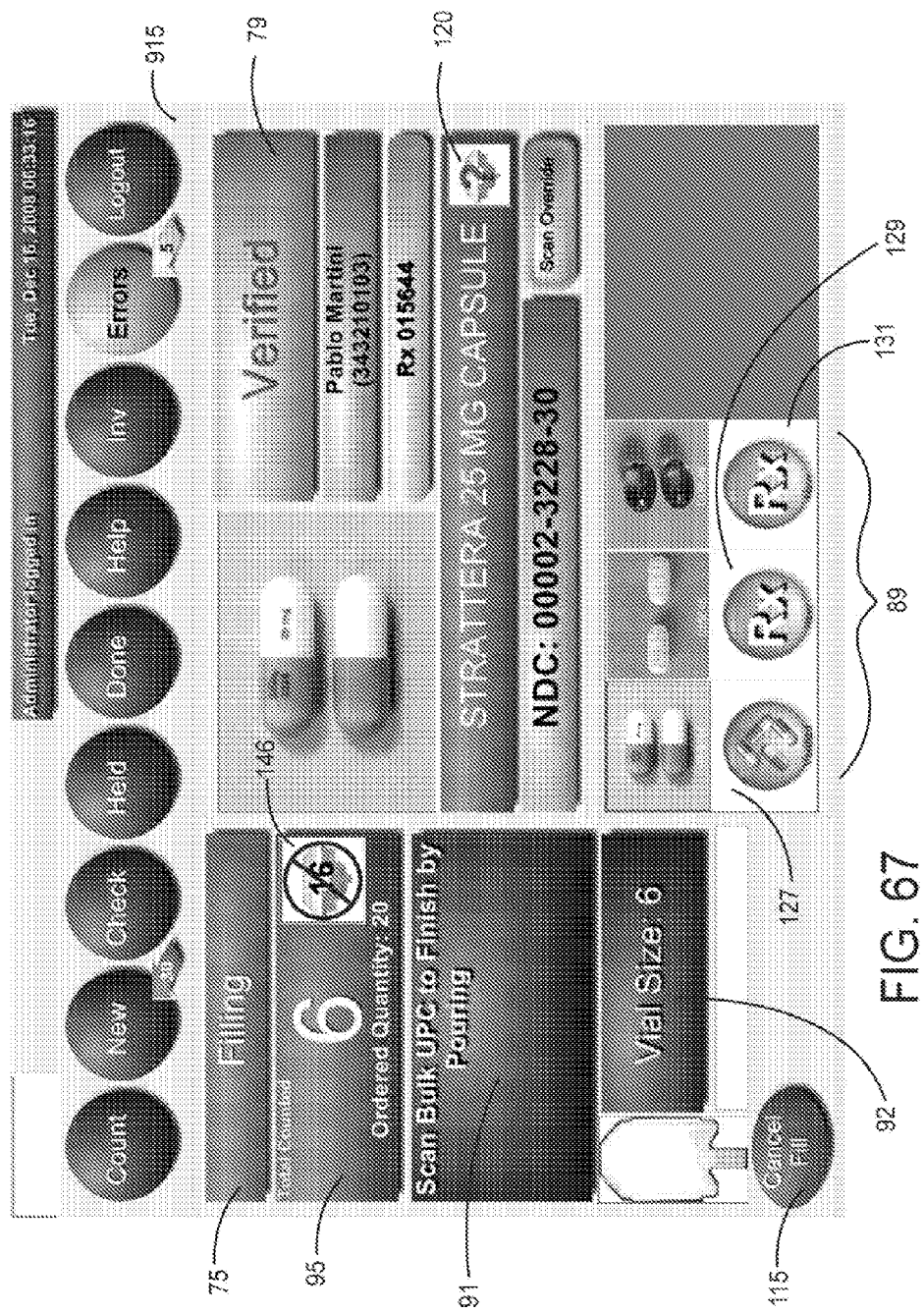

Referring next to FIG. 67, Finish by Pouring screen 915 appears on display 37 responsive to selection of push button 912. Instructions in Main Instructions field 91 prompt the user to scan the UPC barcode 173 of container 175 for the Strattera 25 mg tablets. If the information embedded in the UPC barcode 173 matches the expected UPC in database of non-volatile memory 61, the user is prompted to pour the tablets needed so that the actual count equals the required count at point 227. In the example, six of twenty tablets have been counted by first tablet counter 15 and twelve additional tablets must be poured from container 175 to fill prescription 127. Cassette icon 144 indicates that the cassette 603 from which the six tablets had been counted is now empty. The process moves to block 229 once the required tablets are poured from container 175.

Figure 68:
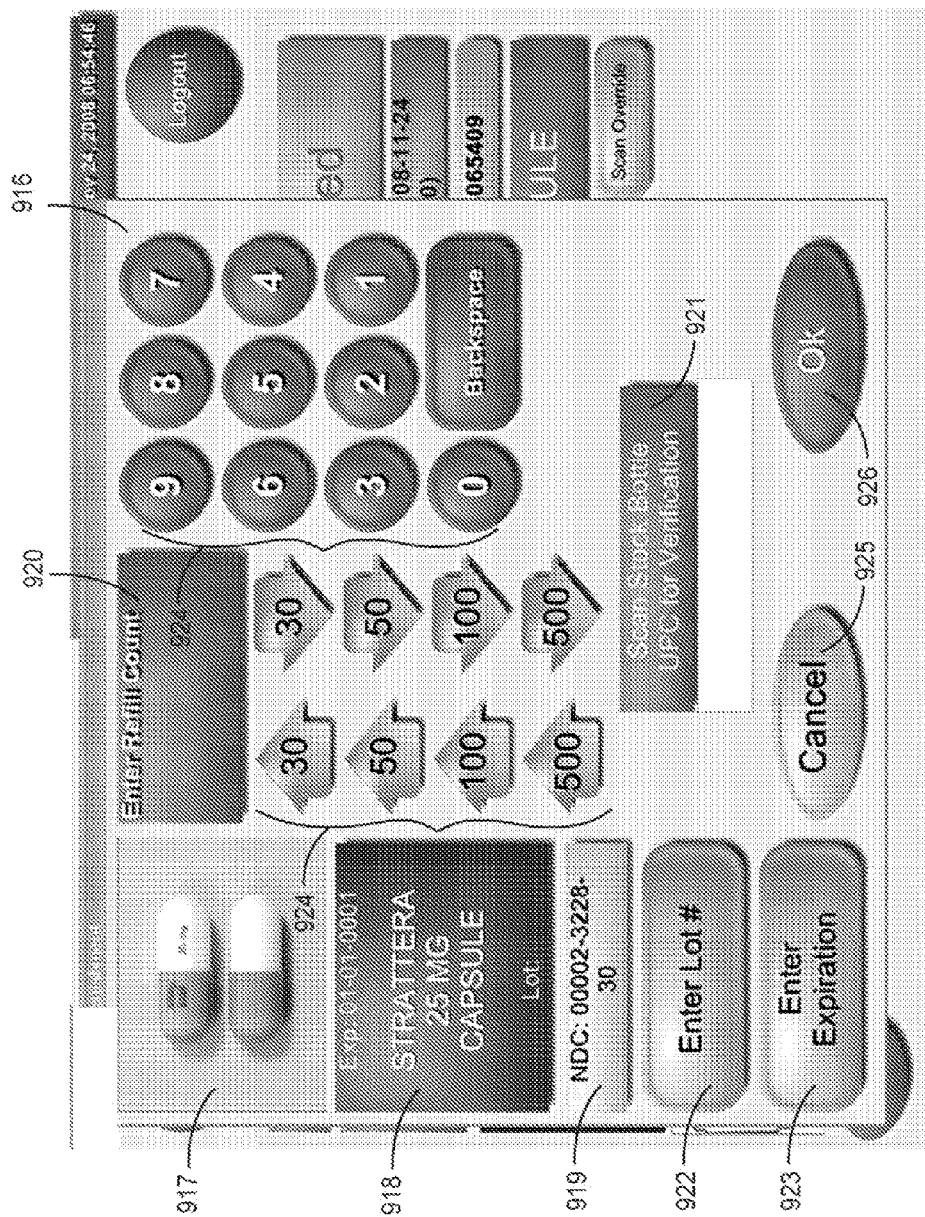

Referring next to FIGS. 54D, 68, 69 and 70, a cassette refill process is initiated at block 281 by selecting Refill Cassette push button 908 opening Refill window 916 (FIG. 68). At this point in the exemplary workflow, system 11' is in the process of filling prescription 127 with Strattera 25 mg strength capsules. Information for refilling cassette 603 number "91" with Strattera 25 mg strength capsules required to complete prescription 127 for fictitious patient Pablo Martini appears on Refill window 916. Refilling of other cassettes 603 occurs in the same manner.

Referring to FIG. 68, Refill window 916 of interfaced system 11' shows exemplary fields and controls. Fields include: a Medication Image field 917, a Medication Description field 918, a Medication NDC field 919, a Refill Count field 920 and an Instructions field 921. Controls include: a Lot Number push button 922, an Expiration Date push button 923, a keypad 924, a Cancel push button 925 and an Ok push button 926. As illustrated in FIG. 68, fields 917, 918 and 919 show information to assist the user with correctly identifying the Strattera 25 mg capsules to be loaded into cassette 603 number "91." The expiration date and lot number information in Medication Description field 918 awaits updating. Expiration date refers to the date by which the tablets should no longer be taken by a patient, and the lot number refers to the manufacturer's lot number which is used to track medication, for example for purposes of product recalls.

Referring further to FIG. 68, Instructions field 921 prompts the user to "Scan the Stock Bottle UPC for Verification." At block 283 of FIG. 54D, the user selects a container 175 with a UPC barcode 173. Preferably, container 175 should hold a sufficient quantity of medication to fully reload cassette 603.

At block 285, the user scans the UPC barcode 173 on container 175 with barcode scanner 51. At decision point 287, the actual UPC barcode 173 on container 175 is compared by the program of instructions operating on data processing platform 17 with the expected UPC for the container 175 from the cassette record database in non-volatile data storage 61. If the comparison at point 287 results in a match, refilling of cassette 603 number "91" is enabled. If the comparison at point 287 does not result in a match, an error message (not shown) in Instructions field 921 prompts the user to select a different container and to scan the UPC of the different container. The scan process of block 285 is repeated until a match is reached at point 287.

After a match at point 287, the user can enter the total number of tablets in the container 175 using key pad 924 (FIG. 68) at block 289. Alternatively, the container 175 contents could be poured into funnel 41' and counted by first tablet counter 15. The total count is then keyed into system 11' using keypad 924 at block 289. Cassette record database in non-volatile data storage 61 is updated with the count for the cassette 603. The user then selects the Ok push button 926 to complete block 289.

Figure 69:
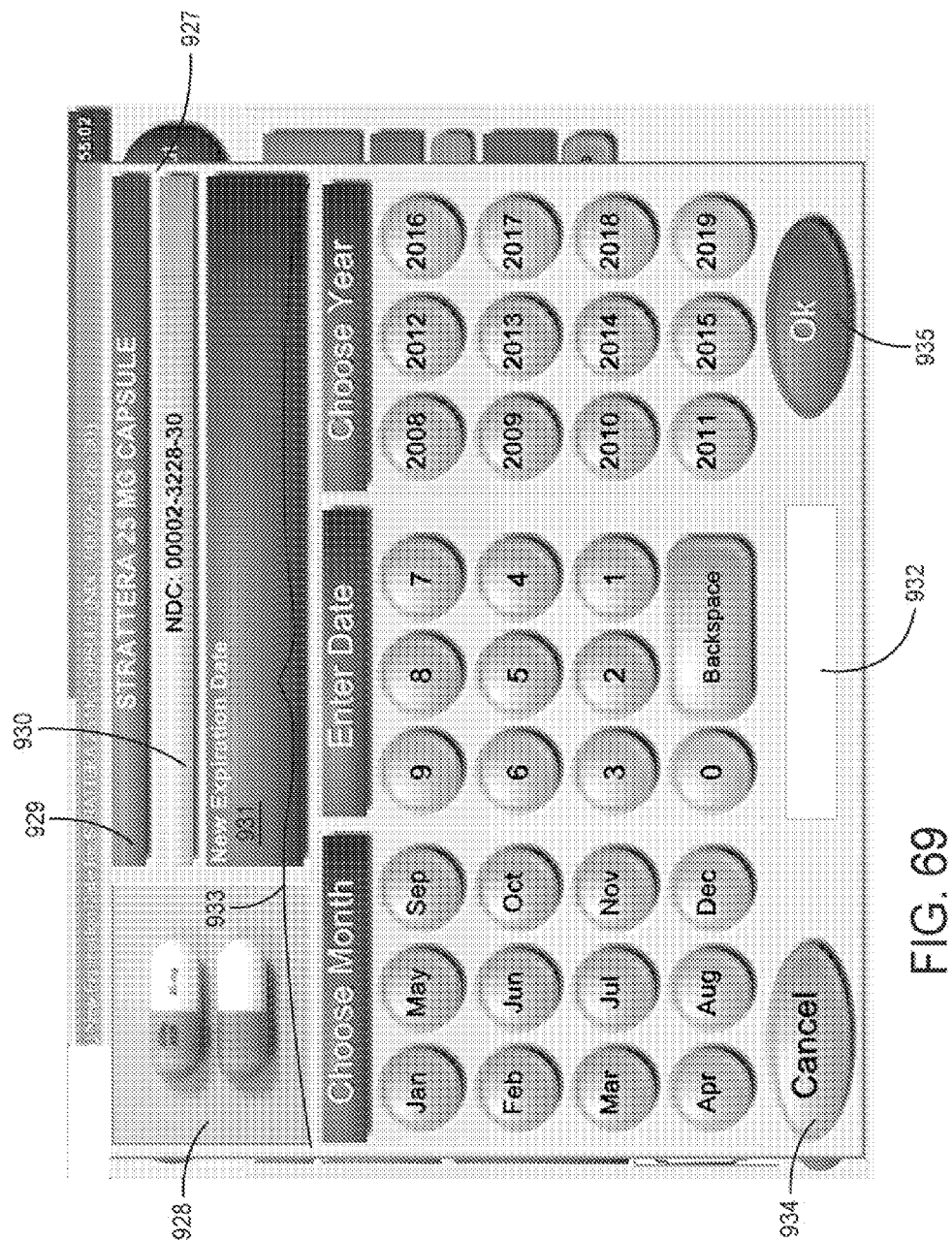

Continuing with the cassette refill process and referring further to FIGS. 54D and 69, Expiration Date window 927 appears next on display 37, permitting the user to update cassette record database in non-volatile data storage 61 with the expiration date for the tablets loaded in cassette 603 at block 291. Expiration Date window 927 of interfaced system 11' shows exemplary fields and controls. Fields include: a Medication Image field 928, a Medication Description field 929, a Medication NDC field 930, an Expiration Date Instructions field 931 and an Expiration Date Data Entry field 932. Controls include: a keypad 933, a Cancel push button 934 and an Ok push button 935. As illustrated in FIG. 69, fields 928, 929 and 930 show information to assist the user with correctly identifying the Strattera 25 mg capsules to be loaded into cassette 603 number "91." At block 291, the user enters the month, date and year of the expiration date provided on the stock bottle. This information appears in the Expiration Date Data Entry field 932. The user then selects the Ok push button 935 to complete block 291.

Continuing still further with the cassette refill process and referring to FIGS. 54D and 70, Lot Number window 936 appears next on display 37 permitting the user to update cassette record database in non-volatile data storage 61 with the lot number for the tablets loaded in cassette 603 at block 293. Lot Number window 936 of interfaced system 11' shows exemplary fields and controls. Fields include: a Medication Image field 937, a Medication Description field 938, a Medication NDC field 939, an Instructions field 940 and a Lot Number Data Entry field 941. Controls include: a QWERTY keypad 65, a Cancel push button 943 and an Ok push button 944. As illustrated in FIG. 70, fields 937, 938 and 939 show information to assist the user with correctly identifying the Strattera 25 mg capsules to be loaded into cassette 603 number "91." At block 293, the user enters the lot number provided on the container 175 using keypad 65 or by scanning the lot number from a barcode 173 on the container 175 with barcode scanner 51. This lot number information appears in Lot Number Data Entry field 941. The user then selects the Ok push button 944 to complete block 293.

At block 295, the refilled cassette 603 and its contents are verified by a registered pharmacist. In the example, the refilled cassette 603 is optionally examined by the registered pharmacist to confirm that the cassette 603 contents match the image and description in the Medication Image field 937 and Medication Description field 938. If there is match, the refilled cassette 603 is deemed verified as containing the correct medication. Such optional verification is not mandatory because of the match at point 287.

The cassette refill process is completed at FIG. 54D block 297 when the cassette record database in non-volatile data storage 61 is automatically updated with the quantity, expiration date and lot number for the tablets loaded in verified cassette 603. Cassette 603 number "16" is registered and ready for use. System 11' automatically operates the refilled cassette 603 when mounted on cassette dispenser 601 and the workflow re-enters point 227 until the actual count matches the required count.

The result of blocks 225, 227, 233, 237 and 297 of FIGS. 54A, 54B and 54D is that the correct quantity of tablets has been counted and the counted tablets are in tray 45.

For both cassette-based and manual pour-through counting, the counted tablets are next removed from tray 45. Referring to FIGS. 54B, 26-27 (manual pour through) and 71-72 (cassette dispensing), at block 229 tray 45 is removed and the tablets in tray 45 are poured into a patient medication container, such as a bottle or vial (not shown).

Figure 71:
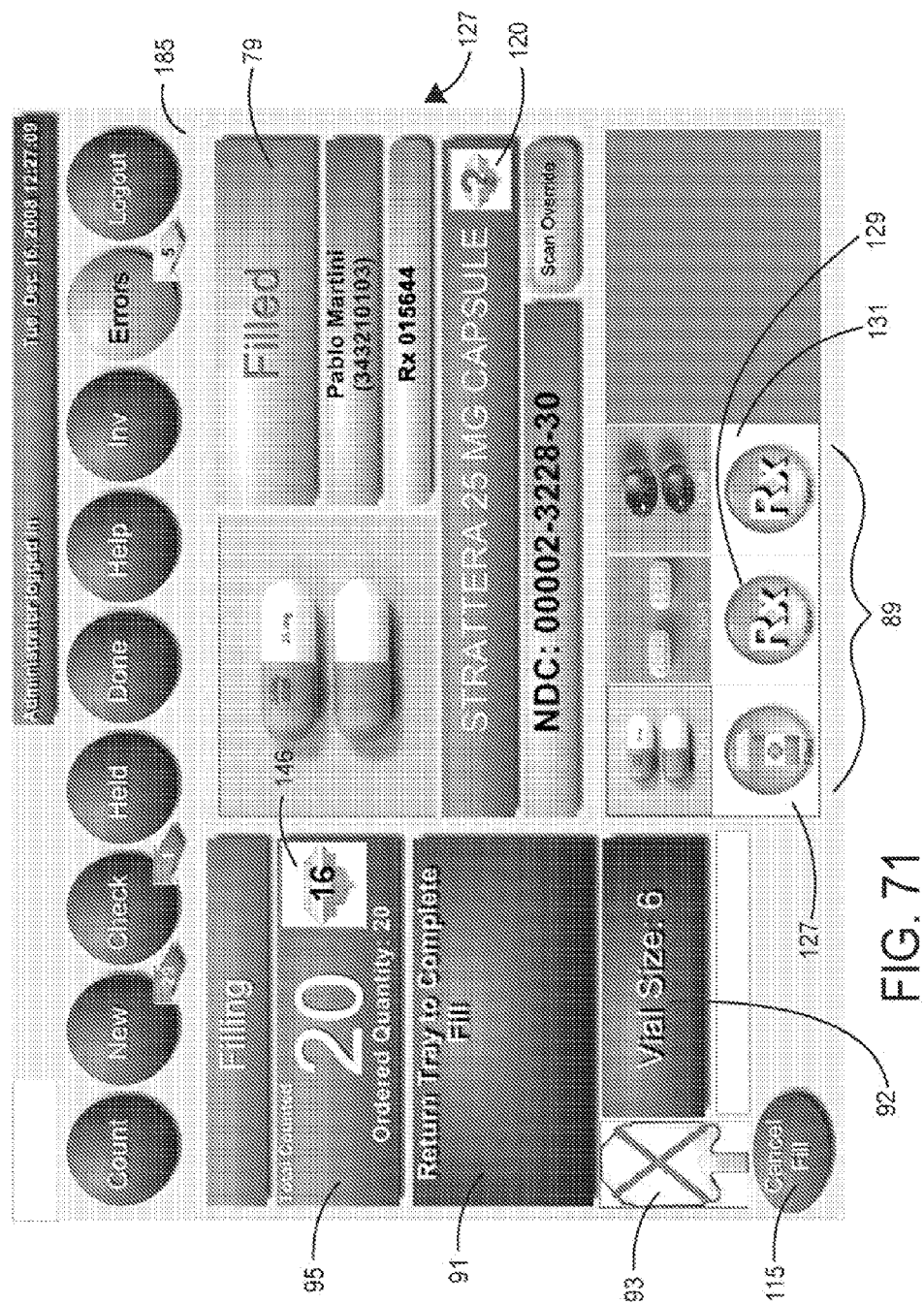
Figure 72:
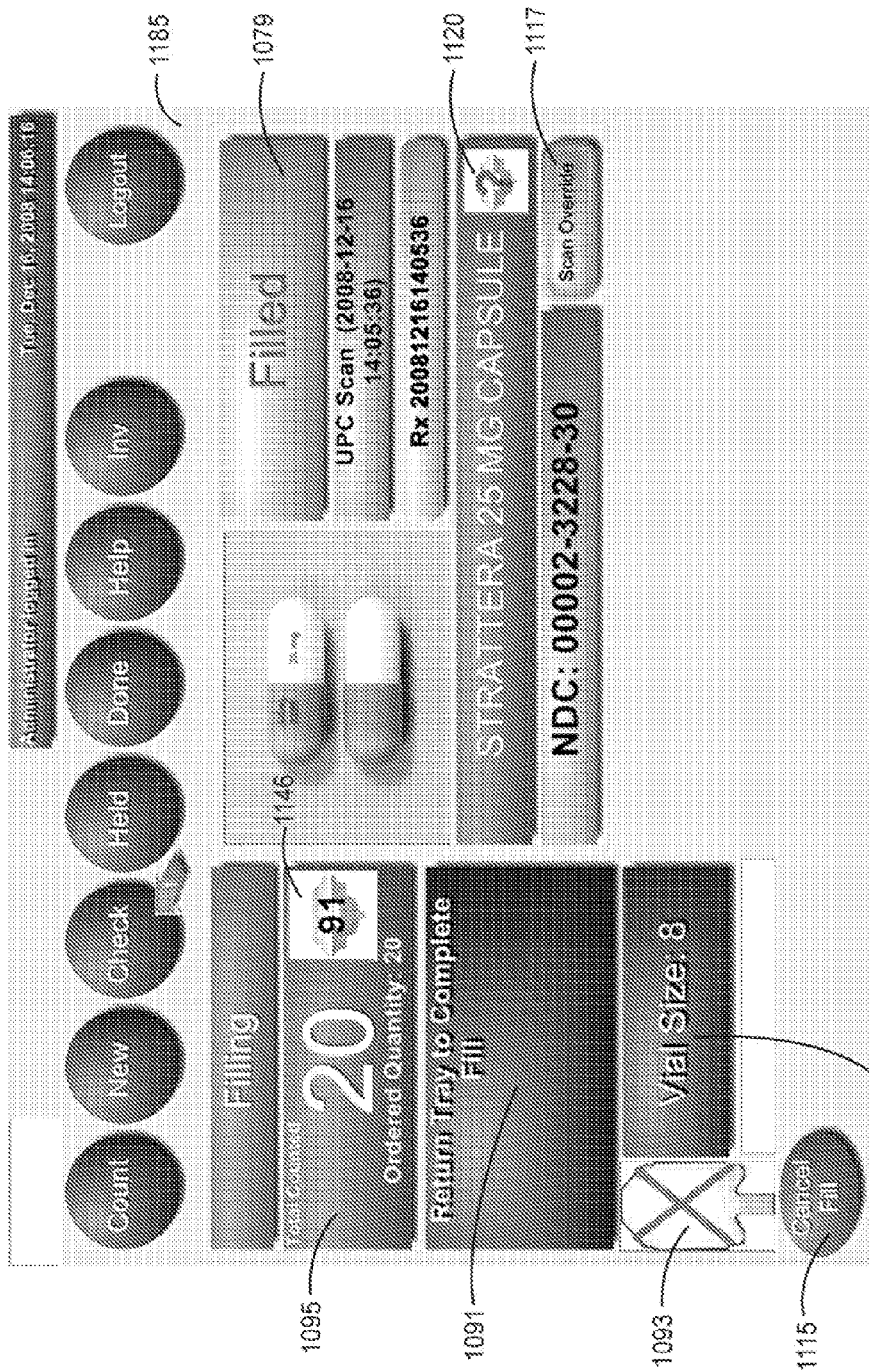

For cassette-based counting, removal of tray 45 triggers display of Filled screen 185 of FIG. 71 (interfaced system 11'), or Filled screen 1185 of FIG. 72 (non-interfaced system). For manual pour-through counting, removal of tray 45 triggers display of Filled screen 185 of FIG. 26 (interfaced system 11') or Filled screen 1185 of FIG. 27 (non-interfaced system 11'), indicating that the prescription status is considered to be "Filled" as indicated in field 79, 1079.

For both cassette-based and manual pour-through counting, Tray Status field 93, 1093 of FIGS. 26-27 (manual pour through) and 71-72 (cassette dispensing), includes an "x" symbol indicating removal of tray 45. For interfaced system 11', prescription 127 in Collated Order field 89 of Filled screen 185 (FIGS. 26, 71) changes to "Filled" indicating that the required tablets were counted and removed from the system 11'. For interfaced systems, prescription orders 129, 131 await fulfillment as indicated by the two occurrences of the word "New" in Collated Order field 89.

Figure 73:
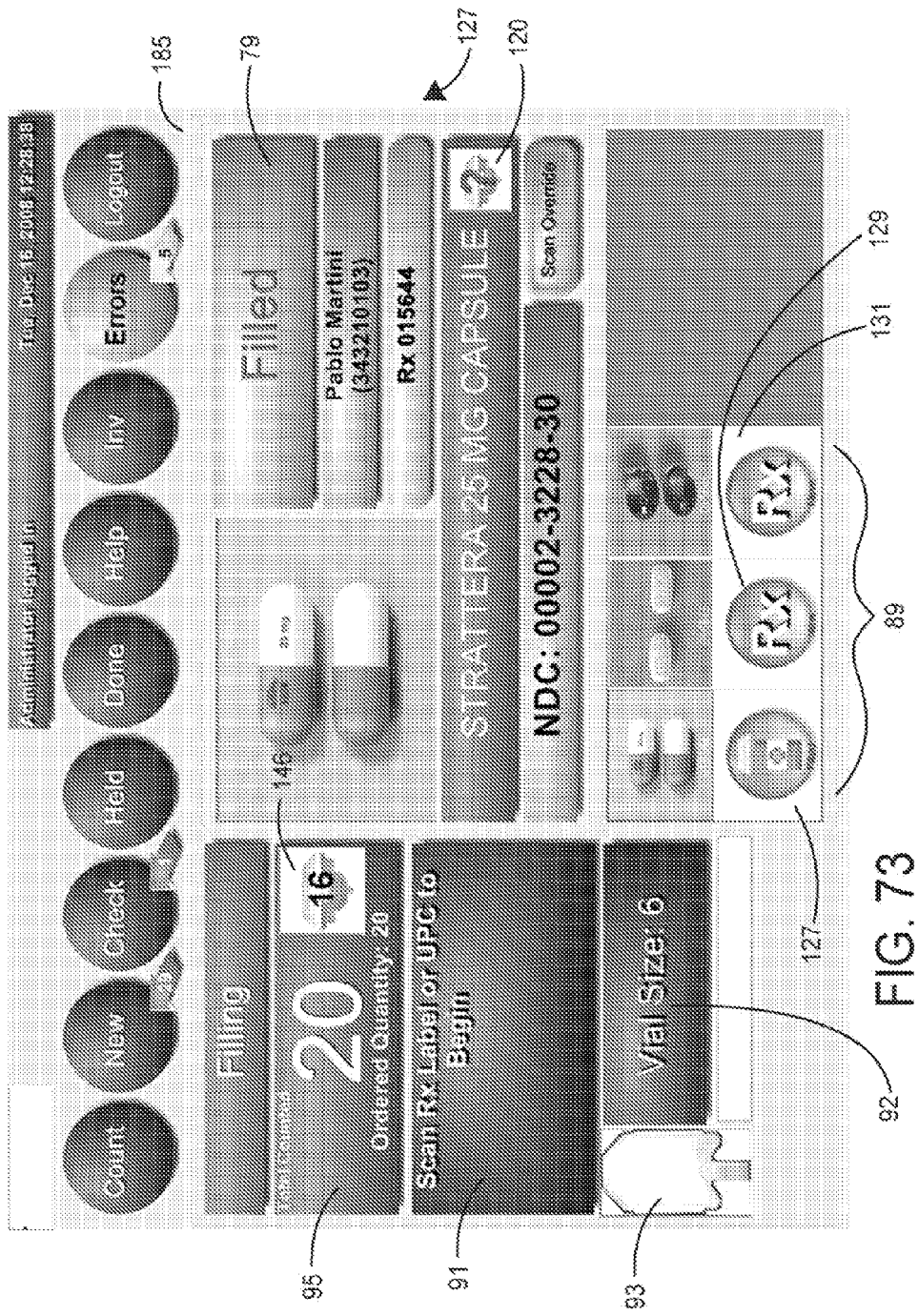
Figure 74:
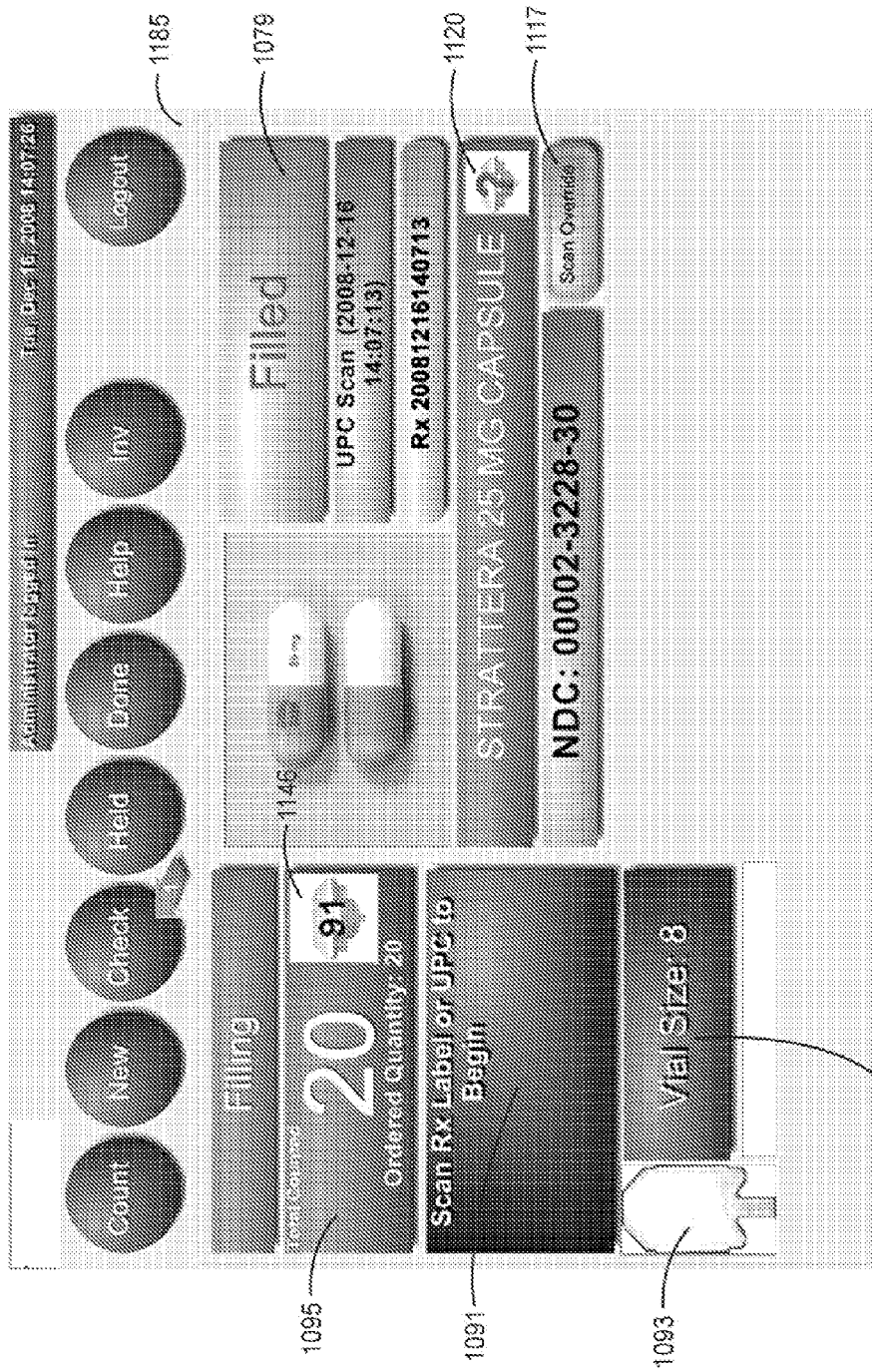

For both cassette-based and manual pour-through counting, tray 45 is returned to bay 47 at block 239 of FIG. 54B. Return of tray 45 to bay 47 is detected by system 11' and represents the terminal point of the filling process for that prescription. FIGS. 73 and 74 respectively show Filled screens 185, 1185 for interfaced and non-interfaced systems 11' after cassette 603 dispensing once tray 145 is returned to bay 47. The "x" symbol is no longer present indicative that tray 45 is fully seated in bay 47.

If system 11' is interfaced to PMS 21, then at decision point 241, system 11 determines whether additional prescriptions must be filled for the patient (e.g., prescriptions 129, 131). If so, the process of steps 209-241 (FIGS. 54A, 54B) are repeated resulting in all prescriptions for the patient being filled.

If system 11' is non-interfaced, the user may move to the optional verification process enabled at decision point 243 and executed in blocks 247-249. If verification is not selected at point 243, then the process is "Done" at block 245.

For both cassette-based and manual pour-through counting, optional verification can occur next if verification is enabled at point 243. In the example, verification is identical for both cassette counting and manual pour-through counting. Accordingly, reference is made to FIGS. 28-35 for the description of verification and prescription order completion. Verification by a registered pharmacist using system 11' is useful to provide further assurance that the prescriptions (e.g., prescriptions 127-131) were filled accurately before the prescription order is made available to the patient. Verification can be performed as each prescription (e.g., prescriptions 127-131) is fulfilled or after all prescriptions of a prescription order are fulfilled. Once all prescriptions are optionally verified, the prescription order is confirmed as "Done" in block 253.

As illustrated, for example, in the interfaced system 11' screen display of FIGS. 28-31, verification is made easier and more efficient because interfaced system 11' can present all prescriptions to be verified collated by patient in Collated Order field 89 (e.g., FIGS. 24, 29-31). The pharmacist or other user is able to quickly and easily access all prescriptions for any patient in order to complete the verification process. Patient care is improved because order verification is made more accurate, and the chance that a patient might accidentally not receive all required prescriptions is diminished.

Referring to FIG. 54B, blocks 247 and 249 illustrate steps of an optional verification process. Verification is available once tray 45 is inserted into bay 47, and verification is enabled at point 243. Verification is preferably enabled by the administrator of system 11' as a user-configurable option.

For both cassette-based and manual pour-through counting, two alternative processes are available to perform optional prescription verification in blocks 247 and 249 for interfaced systems 11'. Verification may be controlled by means of a fingerprint scan process or by a barcode scan process. FIGS. 28 and 29 illustrate exemplary screen displays for a fingerprint-controlled verification process for interfaced system 11' and FIGS. 30 and 31 illustrate exemplary screen displays for a barcode scan-controlled verification process for an interfaced system 11'. Enablement of verification at point 243 and selection of the type of scan may be based on preferences selected by the user, for example, in a system setup procedure executed after login at block 205 (FIG. 54A). For each of the examples of FIGS. 28-31, the verification process is being performed for prescription 127 and before fulfillment of prescriptions 129, 131 as indicated by the word "New" in Collated Order field 89 for prescriptions 129, 131 of interfaced system 11'.

Referring to FIGS. 28 and 29, for the fingerprint-controlled scan verification process, the user scans label barcode 145 which has been applied to the patient medication container or touches display 37 proximate displayed prescription 127 (e.g. prescriptions 127-131). Block 247 is entered and Verification screen 187a (FIG. 28) is shown on display 37. Prescription Status Indicator field 79 remains set to "Filled" indicating to the user that the prescription has been fulfilled. Main Instructions field 91 prompts the user to begin the optional verification process. The medication image is displayed in field 77. The user manually checks the information on screen 187a against the physical appearance of the tablets in the patient's container and against the information provided on prescription order paperwork 147.

If the correct medication has been loaded in the patient container, then in block 249 (FIG. 54B), the user places a finger against biometric sensor 55 to confirm the verification to interfaced system 11'. Check Completed screen 189a (FIG. 29) appears on display 37 for interfaced systems, and a check mark appears for the verified prescription 127 in Collated Order field 89. Activity field 75 is set to "Checking" indicating that verification is being performed and Prescription Status Indicator field 79 is set to "Checked" indicating that the prescription has been checked and verified as indicated by placement of the user's finger on sensor 55. Main Instructions field 91 is set to "Check Completed" also indicative of completed verification for prescription 127.

Referring now to FIGS. 54B, 30 and 31, the process for barcode-scan-controlled verification at blocks 247, 249 is essentially the same as described for the fingerprint-controlled process. Block 247 is entered and Verification screen 187b (FIG. 30) is shown on display 37. Prescription Status Indicator field 79 remains set to "Filled" indicating to the user that the prescription has been fulfilled. Main Instructions field 91 prompts the user to scan label barcode 145. At block 247, the user then scans selected label barcode 145 of the prescription to initiate verification.

The user then manually checks the information on screen 187b against the physical appearance of the tablets in the patient's container and against the information provided on prescription order paperwork 147.

If the correct medication has been loaded in the patient's container, then at block 249, the user scans label barcode 145 of the prescription for a second time to confirm the verification. Check Completed screen 189b (FIG. 31) appears on display 37 for interfaced systems 11, and a check mark appears for verified prescription 127 in Collated Order field 89. The Activity field 75 is set to "Checking," indicating that verification is being performed and Prescription Status Indicator field 79 is set to "Checked," indicating that the prescription has been checked and verified as indicated by placement of the user's finger on sensor 55. Main Instructions field 91 is set to "Check Completed" also indicative of completed verification for prescription 127.

Referring to FIGS. 54B, 32 and 33, verification for non-interfaced systems 11' at blocks 247, 249 is much the same as previously described for interfaced system 11', except that the user has the option of verifying only the single prescription being fulfilled. The user has the ability to control verification by fingerprint or by scanning as described above for interfaced system 11', and such description is incorporated herein by reference. For simplicity and brevity, fingerprint-controlled verification is described herein, it being understood that barcode-controlled verification merely substitutes barcode scanning for placement of a finger on biometric sensor 55.

Turning then to FIGS. 32 and 33, Verification screen 1187 (FIG. 32) appears on display 37 for fingerprint-controlled verification on non-interfaced system 11' for both cassette dispensing and manual pouring when the pharmacist or other user scans barcode 150 on paperwork 147 to initiate verification. The user then manually checks the information on screen 1187 against the physical appearance of the tablets in the patient's container and against the information provided on prescription order paperwork 147. Based on the NDC in barcode 150, the medication image is retrieved from the medication image database in storage 61 and displayed in field 1077.

If the correct medication has been loaded in the patient container as determined at block 249 (FIG. 54B), the user places a finger against biometric sensor 55 to confirm the verification. Check Completed screen 1189 (FIG. 33) appears on display 37 for the non-interfaced system 11. Prescription 127 for non-interfaced system 11 is now complete as indicated by Prescription Status Indicator field 1079 being set to "Complete" and the Main Instructions field 1091 being set to "Check Completed!." Vial Size field 1092 is set to display the message "Order Complete" also indicating that the prescription has been verified.

Referring again to the interfaced system 11' and FIGS. 54B and 34, at decision point 251 it is determined whether all prescriptions (e.g., prescriptions 127-131) for the patient have been filled and verified. If all prescriptions have been verified, Order Complete screen 191 illustrated in FIG. 34 is shown on display 37. Prescription Status Indicator field 79 is set to "Complete", and Main Instructions field 91 is set to "Check Completed" indicating that the verification of all the collated prescriptions 127, 129, 131 has been completed. All prescriptions 127-131 are indicated as verified by the double check marks and setting of the word "Complete" in Collated Order field 89.

The prescription order including all prescriptions 127-131 for fictitious patient Pablo Martini is now fulfilled and the order status is set to Done in block 253.

Records of the prescriptions 127-131 fulfilled by system 11' may be created as described and illustrated in connection with system 11.

For non-interfaced system 11', a record 70a indicating that single prescription 127 has been fulfilled and verified is stored in the prescription record database of non-volatile data storage 61 as represented schematically in FIG. 37A. The record 70a corresponding to prescription 127 includes the prescription number, NDC, medication name, medication quantity, date and time the medication was counted and the date and time that the prescription was verified. This information allows the pharmacy to reconstruct fulfilment of the prescription 127. The record for prescription 127 includes all of the information shown on Check Completed screen 1189 of FIG. 33. And, the record for the non-interfaced system 11' could include a collation of all prescriptions fulfilled for patient Pablo Martini, including prescriptions 129 and 131 once those prescriptions 129, 131 are verified. For the non-interfaced system 11', the status of the prescription 127 is set as Done in block 253.

Referring now to FIGS. 35 and 37B, interfaced system 11' creates record 70b of each prescription filled collated by patient. FIG. 35 illustrates a Completed Order Record screen 193 generated by interfaced system 11' for fictitious patient Pablo Martini after each of prescriptions 127, 129, 131 is fulfilled and verified. All prescriptions 127-131 are collated by the patient's name for convenience. Activity field 75 and Prescription Status Indicator field 79 are set to "Completed" and "Complete" indicating that the prescriptions 127-131 are complete and have been verified. The double check marks and word "Complete" for each prescription 127-131 in Collated Order field 89 is further indicating that the three prescriptions in the example have been completed and verified. Main Instructions field 91 informs the user that the system 11' is ready to begin a new counting process indicated by the text "Scan Next Rx."

Referring to FIG. 37B, the information shown on Completed Order Screen 193 is maintained in prescription record database stored in non-volatile data storage 61 as record 70*b* that the prescriptions (e.g., prescriptions 127-131) of the prescription order were fulfilled and verified. Record 70*b* includes all prescriptions 127-131 collated for patient Pablo Martini.

Record 70*b* (FIG. 37B) and display of Completed Order Record screen 193 (FIG. 35) can be called by selecting Done push button 105 and then selecting the patient's name from the universe of patient names within system 11' data storage 61. A user may want to access Completed Order Record screen 193 to further verify each prescription fulfilled using system 11'.

System 11' may include a scan override mode which is identical to scan override mode of system 11. The scan override mode of tablet counting may be entered at entry block 255 (FIG. 54A) by selecting Scan Override push button 117, for example on Start screen 73 (FIG. 55). In the scan override mode, system 11' is set to count tablets without regard to any particular prescription. Scan override would be desirable, for example, to count tablets for a patient prescription order, to count tablets as part of an inventory procedure, or to confirm that a hand count of tablets was accurate. Scan override mode is also useful for counting non-prescription objects such as vitamins, nutriceuticals, supplements, jewelry, parts or other countable things.

Once scan override is entered (entry block 255), the user manually pours tablets into funnel 41' for counting by first tablet counter 15. The count from first tablet counter instantaneously appears on display 37.

At decision point 259 (FIG. 54C), it is determined whether the user has enabled optional verification. If verification is not enabled, the prescription is considered to be done at block 261.

If verification is enabled at decision point 259, the process moves to block 263 to initiate verification. The verification process is the same as described in connection with blocks 247 and 249. If verification is enabled at decision point 259, the user scans label 143 barcode 145 to initiate verification in block 263. The user then manually checks the prescription to confirm that the prescription was filled correctly. If the correct medication has been loaded in the patient container, then at block 265, the user places a finger against biometric sensor 55 or scans label barcode 145 (or barcode 150) of the prescription for a second time to confirm the verification. The order status is set to done at block 267. A record (e.g., record 70*a* of FIG. 37A) of the completed order is stored in prescription record database in non-volatile data storage 61.

Referring again to FIGS. 54A and 54C and to FIG. 36, the optional UPC scan mode of tablet counting may be entered at entry block 269. UPC scan mode is provided for pouring from a container, such as container 175, which includes a UPC-type barcode 173. As previously stated, it is envisioned that codes other than UPC codes may be used with containers 175 in the future, and system 11' can be adapted to operate with such codes.

In block 271, container 175 including UPC barcode 173 is selected. In block 273, UPC barcode 173 is scanned with scanner 51. Scanning of UPC barcode 173 as the first step of the process initiates the UPC scan mode. Scanning of UPC 173 causes a UPC Start screen 195 to appear on display 37 as illustrated in FIG. 36. UPC scan mode Start screen 195 is for interfaced system 11'. All of the fields and controls described in connection with Start screen 73 (FIG. 55) are provided, and the description of such fields and controls is incorporated by reference herein.

Fields illustrated on Start screen 195 (FIG. 36) include: an Activity field 75, a Medication Image field 77 and a Prescription Status Indicator field 79. Since no patient or prescription information is known for a UPC scan mode count, Customer/Patient field 81 and Prescription Number field 83 show the date and time of day of the UPC scan count. Other fields are a Medication Description field 85, a Medication NDC field 87, a Main Instructions field 91, a Vial Size field 92, a Tray Status field 93 and a Count Status field 95. Fields for the User Name 94 and Date and Time of Day 96 are provided. No Collated Prescription field is required because the UPC scan mode is based on a count of a single medication and is not tied to a specific prescription.

Control push buttons on Start screen 195 (FIG. 36) include: a Count push button 97, a New push button 99, a Check push button 101, a Held push button 103, a Done push button 105, a Help push button 107, a Rpts (reports) push button 109, an Errors push button 111 and a Logout push button 113. Additional control push buttons can include a Cancel Fill push button 115 and a Scan Override push button 117. These controls function as described in connection with screen 73. Hold and Cancel Rx push buttons (not shown) may also be provided on display 37 for the purpose described in connection with Hold and Cancel Rx push buttons 1116, 1118.

In block 257 the tablets are counted by first tablet counter 15. Once again, in the examples of FIGS. 38-49, this is accomplished by pouring the tablets from container 175 into feeder device 19 through funnel 41'. Blocks 259, 261, 263, 265 and 267 described in connection with scan override counting mode are repeated for the UPC counting mode providing the opportunity for the user to verify and check the prescription for accuracy. The order status is set to Done at block 267 if verification is enabled. A record such as record 70*a* (FIG. 37A) of the completed order is stored in prescription record database in non-volatile data storage 61.

Figure 75:
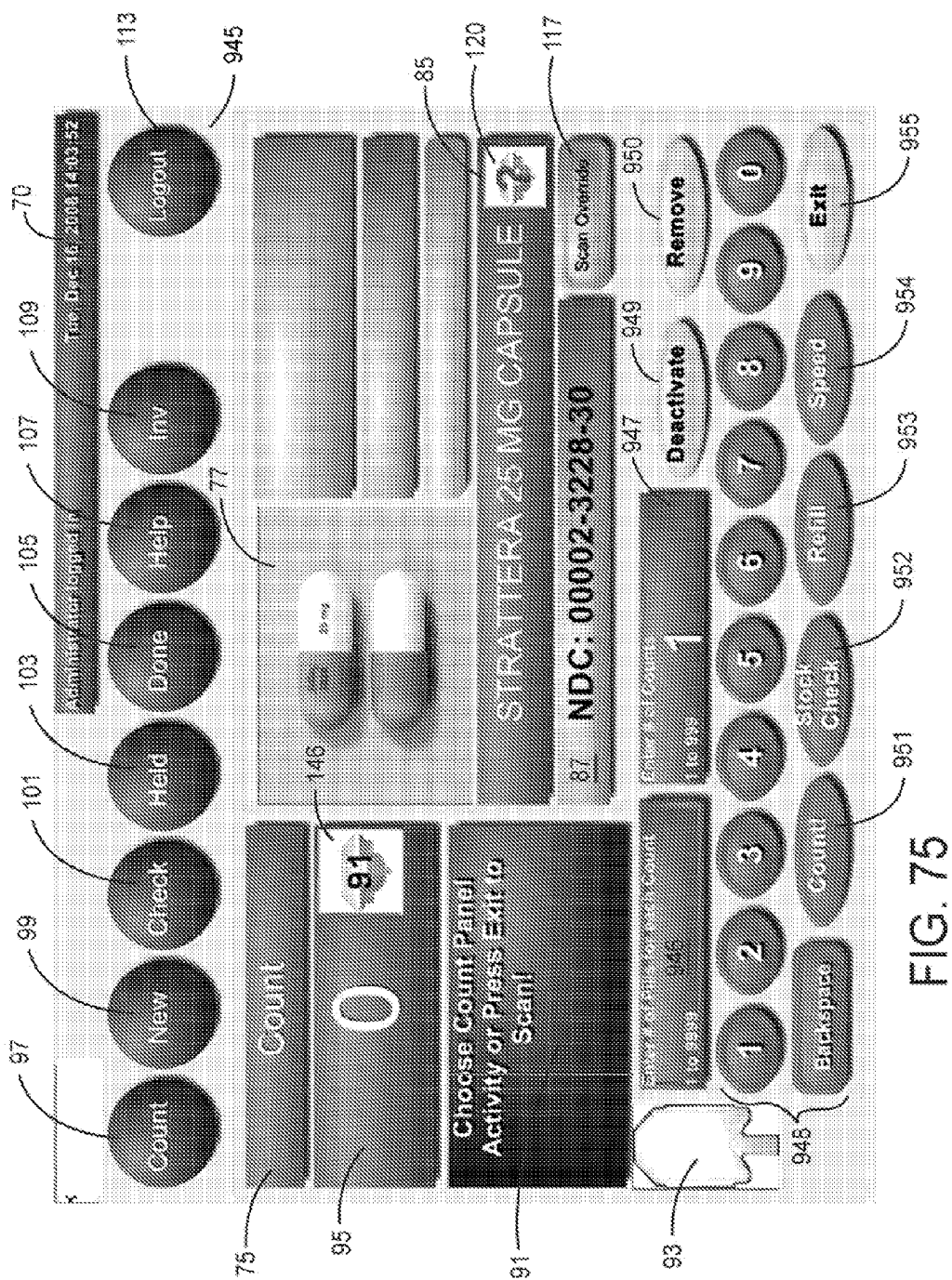

Referring now to FIG. 54C and to FIG. 75, the optional cassette count mode of tablet counting may be entered at entry block 298. The cassette count mode of tablet counting is provided for feeding tablets from a cassette 603 to fill a prescription or for another purpose such as unit-of-use container filling, inventory counting, or verification of a hand count. In the example, the cassette count mode of tablet counting is identical for both interfaced and non-interfaced systems 11'.

In block 298, selection and mounting of a cassette 603 on cassette mount 621 of cassette dispenser 601 without first scanning a label barcode (e.g., barcodes 143, 150) or making a prescription selection via software (FIG. 54A point 209) brings up Cassette Count screen 945. Cassette Count screen 945 appears when switch 639 is closed by action of cam 765 against switch arm 641 and optical reading of the cassette identification barcode 760 by reader 645 in block 299. Also in block 299, the software of data processing platform 17 will look up this unique cassette identification number in the cassette record database residing in non-volatile storage 61. Cassette Count screen 945 appears on display 37 if the cassette identification number is found in the cassette record database.

Referring to FIG. 75, Cassette Count screen 945 of interfaced and non-interfaced systems 11' shows exemplary fields and controls. All of the fields and controls described in connection with Start screen 73 (FIG. 55) are provided, and the description of such fields and controls is incorporated by reference herein.

Fields illustrated on Cassette Count screen 945 (FIG. 75) include: an Activity field 75 and a Medication Image field 77. Since no patient or prescription information is known for a Cassette Count mode count, no information is shown in the Prescription Status Indicator field 79 Customer/Patient field 81 and Prescription Number field 83. Other fields are a Medication Description field 85, a Medication NDC field 87 for medication contained in the cassette 603, a Main Instructions field 91, a Tray Status field 93 and a Count Status field 95. Fields for the User Name 94 and Date and Time of Day 96 are provided. A Count Data Entry field 946 and a Count Number Data Entry field 947. No Collated Prescription field is required because the cassette count mode is based on a count of a single medication and is not tied to a specific prescription.

Control push buttons on Cassette Count screen 945 (FIG. 75) include: a Count push button 97, a New push button 99, a Check push button 101, a Held push button 103, a Done push button 105, a Help push button 107, an Inv push button 109 and a Logout push button 113. Additional control push buttons can include a Cassette Query push button 120 and a Scan Override push button 117. These controls function as described previously.

An Errors push button identical to Errors push button 111 in FIG. 55 and located in the same position as button 111 can appear. An Errors push button could include information about a previous prescription which could not be completed as previously described. Selection of Errors push button displays prescriptions flagged with the error so that the user can determine the source of the error and make appropriate corrections so that the prescription can be fulfilled using system 11'.

Other controls include: a numeric keypad 948 (including backspace button), a Deactivate push button 949, a Remove push button 950, a Count push button 951, a Stock Check push button 952, a Refill push button 953, a Speed push button 954 and an Exit push button 955. As illustrated in FIG. 75, fields 77, 85 and 87 show information to assist the user with correctly identifying the Strattera 25 mg capsules to be counted from cassette 603 number "91" in the exemplary cassette count mode.

Keypad 948 (numbers and backspace keys) allow user entry of the number of tablets required and the number of count cycles required. The user first touches the Count Data Entry field 946 and then touches the numbers of keypad 948 to achieve the desired quantity. This process is repeated for Count Number Data Entry field 947.

Deactivate push button 949 is provided for use by authorized personnel responsible for operation of system 11'. Selection of deactivate push button 949 activates or deactivates the mounted cassette 603 allowing or disallowing use of the cassette 603. Remove push button 950 enables a user to associate or disassociate a medication with a cassette 603.

Selection of Count push button 951 initiates counting by cassette dispenser 615. Selection of Stock Check push button 952 begins emptying the cassette 603 counting the tablets to report how many were in the cassette 603. Selection of Refill push button 953 initiates a cassette refill process and brings up Refill Cassette window 616 (FIG. 68). Selection of Speed push button 954 enables the user to adjust the RPMs of motor 635 to improve movement of tablets (i.e., tablets 604, 606) from cassette 603. In the example, from one to six motor 635 speed settings are available. Selection of Exit push button 955 exits the Cassette Count screen 945 so that the user can enter a different count mode at step 207 (FIG. 54A).

At block 300, the user touches field 946 and uses keypad 948 to enter the quantity of tablets to count from cassette 603 and the quantity appears in Count Data Entry field 946. Also in block 300, the user touches field 948 and uses keypad 948 to enter the number of counts of this quantity which are desired and this information appears in Count Number Data Entry field 947. These settings are desirable when repetitively filling unit-of-use containers which include, for example, a 30, 60 or 90-day allotment of tablets. Such unit-of-use containers are routinely required for frequently-used medications. Any number of unit-of-use containers are loaded and then the containers are stocked at an accessible location, such as a "speed shelf," enabling rapid access to the containers by pharmacy personnel to fill patient prescriptions.

If cassette 603 has not yet been associated with a medication and is not registered as active to system 11', the operator is notified by a message in Main Instructions field 91. A cassette 603 may not be recognized, for example, if the cassette 603 has not been used previously with system 11'. If the cassette is not registered, push button 949 changes to "Activate" and push button 950 changes to "Add." If the user is authorized, the user can register the cassette 603 with the medication by pushing button 949 and following the refill process described previously. The cassette 603 code 760 is identified by data processing platform and the user will be required to confirm that this code is to be associated with a particular medication. Button 950, which states "Add" is pushed to confirm that the now-registered cassette 603 should be added to inventory of available cassettes and the cassette record database in non-volatile storage 61 is updated accordingly. If the user is not authorized to register the cassette 603, the user is denied the ability to count using the cassette 603.

Tablet counting begins immediately once the user selects the Count push button 951. Controller 607 automatically activates motor 635 resulting in rotation of rotor 767 and feeding of tablets one after the other through opening 781. Tablets 604, 606, 608, 610 fall along path 681 and past detector 605 whereupon a signal is sent via receiver 689 to controller 607 indicative of tablet detection. Controller 607 increments an actual count 830 for each detected tablet as previously described. Controller 607 stops motor 635 operation when the actual tablet count matches the required count entered by the user in field 946. Controller 607 may slow motor 635 as the tablet count approaches the required count as previously described.

Tablets (e.g., tablet 604) fed from cassette 603 fall past detector 605 and into funnel 41' and chute 43. First tablet counter 15 automatically counts each tablet as it falls through funnel 41' and chute 43 past collimated IR sources 308a, 308b and sensors 307a, 307b and into tray 45. The system software previously described performs the count, and Count Status fields 95, 1095 of Cassette Count screen 945 of FIG. 75 is instantaneously updated as each tablet is counted.

The tablet count from first tablet counter 15 is compared to the tablet count from the second tablet counter 615 during counting as previously described in connection with FIGS. 50-53B to ensure that the counts are within a predetermined number of the other, thereby ensuring that the required tablets are being fed out from the cassette 603.

Tray 45 is removed and the tablets in tray are poured into a unit-of-use container or other suitable container.

If multiple cassette count cycles are selected as indicated by Count Number Data Entry field 947, then insertion of tray 45 back into tray bay 47 is detected by system 11' and such detection triggers system 11' to immediately commence counting of the requested tablets. This process of counting, emptying tray 45 and replacing tray 45 in tray bay 47 is repeated until the requested number of cassette count cycles have been completed.

Blocks 259, 261, 263, 265 and 267 described in connection with scan override counting mode are repeated for the cassette counting mode providing the opportunity for the user to verify and check the counted tablets for accuracy. The count status is set to Done at block 267 if verification is enabled. A record such as record 70a (FIG. 37A) of the completed cassette count is stored in prescription record database in non-volatile data storage 61.

System 11' can also be configured to fulfill prescription orders for medication and other health-care-related products not requiring counting by first or second tablet counters 15, 615, thereby providing a more comprehensive tool with which to manage pharmacy workflow. For example, a patient prescription order may require an ointment or other product not requiring tablet counting as represented by box 174 illustrated in FIG. 12B. Box 174 includes a UPC barcode 176.

For interfaced systems 11', the medication or product contained in box 174 can appear as a separate prescription on New Order screen 119 (FIG. 57) or can appear in the Collated Order field 89. The patient name 121, prescription number 135, medication name, strength and form 137, count 139, image 138 and status 140 information can be provided for the medication or product in box 174. Barcode 176 can be scanned with scanner 51 and the UPC verified to confirm that the box contains the medication or other product required by the prescription. The medication in box 174 can then be verified as described in connection with blocks 247 and 249.

Exemplary system 11' provides a number of useful advantages. For example, dispensing of tablets (e.g., tablets 604, 606) by means of a cassette 603 enables pharmacy personnel to multitask, that is perform different tasks simultaneously. A technician can set the system 11' to dispense from a cassette 603 and simultaneously perform another task while the tablets 1 are being counted by system 11'.

System 11' can also save valuable pharmacy personnel time because the most frequently-used medications can be loaded in cassettes 603 and the cassettes for these medications can be stored in close proximity to system 11'. Such an arrangement permits pharmacy personnel to avoid having to walk to a static storage shelf location to retrieve a manufacturer's medication container 175.

System 11' can also save valuable pharmacy personnel time because cassette dispenser 601 can feed large quantities of tablets from a cassette 603 and count with second tablet counter 615 faster than pharmacy personnel can pour tablets into funnel 41. System 11' can be set to feed tablets faster than a vibratory dispenser while maintaining count accuracy. And, cassette-based dispensing is accurate because singulation made possible by cassette dispenser 601 avoids "overspeed" conditions (i.e., a pour-too-fast condition), thereby avoiding the necessity for a recount.

System 11' provides accurate counts because two tablet counters 15, 615 are used and the counts of each tablet counter 15, 615 are compared by data processing platform 17.

Finally, system 11' provides user-flexibility because tablets can be dispensed from a manufacturer's bulk storage container 175 (FIG. 12A), a cassette 603, or both.

Like system 11, patient prescription order workflow for a wide-range of medications can be easily managed by system 11'. Accuracy in prescription order fulfillment is improved by providing a greater level of certainty that the patient is receiving all of the medication required by the patient's prescription order and that the selected medication is correct. Because system 11' reduces the time required to fulfill patient prescription orders, the pharmacist is free to perform other valuable tasks such as counseling patients. The result of system 11' implementation is an improvement in pharmacy management and in the general level of patient care.

While the principles of this invention have been described in connection with specific embodiments, it should be understood clearly that these descriptions are made only by way of example and are not intended to limit the scope of the invention.

What is claimed is:

1. A prescription fulfillment system which counts manually-poured tablets and tablets fed from a cassette, comprising:
   a housing;
   an upright chute mounted with respect to the housing through which objects fall into the housing;
   a first automatic tablet counter within the housing which receives tablets from the chute and counts plural tablets simultaneously moving past a sensor;
   a cassette dispenser integrated with the system having a cassette mount which positions a cassette mounted thereon to feed tablets to the chute and first automatic tablet counter;
   a cassette dispenser drive system which powers a mounted cassette to feed tablets therefrom;
   a second automatic object tablet counter which counts single tablets moving past a sensor fed from a mounted cassette; and
   a data processing platform within the housing operatively connected to the first and second automatic tablet counters and the cassette dispenser drive system, the data processing platform being operative to:
   receive and store data for a plurality of prescriptions;
   retrieve data for fulfillment of a user-selected stored prescription, the data including a required tablet type and a required quantity:
   verify that a user-selected container or cassette contains the required type of tablet,
   if the required tablets are in the cassette, activate the cassette dispenser drive system to feed the required tablets from the mounted cassette to the first and second automatic tablet counters, deactivate the cassette dispenser drive system once the count of the second automatic tablet counter equals the required quantity;
   maintain the count of the first automatic tablet counter for the tablets poured from the user-selected container or fed from the cassette past said first automatic tablet counter; and
   indicate the count of the first automatic tablet counter.

2. The system of claim 1 wherein the data processing platform is further operative to compare the counts of the first and second tablet counters during counting to determine whether the counts differ by more than a predetermined amount.

3. The system of claim 2 wherein the data processing platform is further operative to generate a signal if the counts differ by more than the predetermined amount.

4. The system of claim 3 wherein the data processing platform is further operative to stop the drive system responsive to the signal.

5. The system of claim 3 further including a display and the data processing platform is further operative to display a visual message to a user responsive to the signal.

6. The system of claim 1 wherein the data processing platform is further operative to compare the counts of the first and second tablet counters to determine whether the counts match the required quantity.

7. The system of claim 1 further including a display and the data processing platform is operative to display the first automatic tablet counter count thereon.

8. The system of claim 1 wherein the first automatic tablet counter counts tablets both fed from a mounted cassette and poured manually while the cassette is mounted.

9. The system of claim 8 further including a funnel connected to the chute which directs tablets to the first automatic tablet counter, said funnel having an inlet sized to receive tablets fed from the mounted cassette or poured manually.

10. The system of claim 1 wherein the second automatic tablet counter comprises:
 a cassette dispenser detector which detects a tablet fed from a mounted cassette and generates a signal responsive to the detection; and
 a cassette dispenser controller which increments a count responsive to the detector signal for use by the data processing platform.

11. A pharmacy workflow management system including automatic tablet counters, comprising:
 a housing;
 a first automatic tablet counter within the housing;
 a cassette dispenser having a cassette mount which positions a cassette mounted thereon to feed tablets to the first automatic tablet counter;
 a cassette dispenser drive system which powers a mounted cassette to feed tablets therefrom;
 a second automatic tablet counter which counts tablets fed from a mounted cassette; and
 a data processing platform within the housing programmed with instructions that, when executed, perform a method of pharmacy workflow management, the method comprising:
  receiving data for a plurality of prescriptions;
  storing the received data for the prescriptions;
  retrieving the data for one of the stored prescriptions for fulfillment, the data including a type of tablet and a tablet quantity;
  verifying that a user-selected container or cassette contains the required type of tablet,
  if the required tablets are in the cassette, activating the cassette dispenser drive system to feed the tablets from the mounted cassette to the first and second automatic tablet counters, and deactivating the cassette dispenser drive system once the count of the second automatic tablet counter equals the quantity;
  maintaining the count of the first automatic tablet counter for the tablets poured from the user-selected container or fed from the cassette past the first automatic tablet counter;
  indicating the count of the first automatic tablet counter; and
  creating a record that the quantity of tablets required by the retrieved data for the prescription has been counted.

12. The system of claim 11 further comprising a display associated with the housing.

13. The system of claim 12 wherein the method performed by the instructions further comprises displaying at least one of the stored prescriptions on the display.

14. The system of claim 13 wherein the method performed by the instructions further comprises:
 displaying data for the retrieved prescription on the display; and
 comparing counts of the first and second automatic tablet counters for the displayed prescription data.

15. The system of claim 14 wherein the method performed by the instructions further comprises comparing the counts to determine whether the counts differ by more than a predetermined amount.

16. The system of claim 15 wherein the method performed by the instructions further comprises displaying a visual message on the display if the counts differ by more than the predetermined amount.

17. The system of claim 15 wherein the method performed by the instructions further comprises stopping the drive system if the counts differ by more than the predetermined amount.

18. The system of claim 11 wherein the method performed by the instructions further comprises comparing the counts to determine whether the counts match the quantity of tablets required by the retrieved prescription data.

19. A pharmacy workflow management system including an integrated automatic tablet counter, comprising:
 a housing;
 a code reader;
 a display;
 an upright chute mounted with respect to the housing through which tablets are manually poured into the housing;
 an automatic tablet counter within the housing which counts the tablets; and
 a data processing platform within the housing, the tablet counter and data processing platform being interfaced together and contained within the housing such that the housing, tablet counter and data processing platform comprise an integrated unit, the data processing platform being programmed with instructions that, when executed, perform a method of pharmacy workflow management, the method comprising the steps of:
  (a) receiving a plurality of prescriptions;
  (b) storing the received prescriptions;
  (c) retrieving one of the stored prescriptions for fulfillment;
  (d) displaying the retrieved prescription on the display together with information identifying an item required for fulfillment of the prescription;
  (e) if the prescription-required item is a quantity of manually-pourable tablets which require counting, then
   (i) reading with the code reader a code associated with a user-selected container of the prescription-required item;
   (ii) verifying that the user-selected container contains the prescription-required item;
   (iii) counting with the tablet counter the quantity of tablets manually poured from the verified container;
   (iv) creating a record with the data processing platform that the retrieved prescription was fulfilled; and
   (v) repeating step (c) and the subsequent steps for the next prescription; and
  (f) if the prescription-required item does not require counting, then
   (i) reading with the code reader a code associated with a user-selected container of the prescription-required item; and (ii) verifying that the user-selected container contains the prescription-required item;
(iv) creating a record with the data processing platform that the retrieved prescription was fulfilled;
(v) repeating step (c) and the subsequent steps for the next prescription.

20. The system of claim 19 wherein the automatic tablet counter is a first automatic tablet counter and the system further comprises:
   a cassette dispenser having a cassette mount which positions a cassette mounted thereon to feed tablets to the chute and first automatic tablet counter, thereby enabling the system to count manually-poured tablets and tablets fed from a mounted cassette;
   a cassette mounted to the cassette mount, said cassette containing the tablets required by the retrieved prescription;
   a cassette dispenser drive system which powers the mounted cassette to feed the tablets therefrom;
   a second automatic tablet counter which counts the tablets fed from the mounted cassette; and
   the method performed by the instructions further comprises, after step (d), the steps of:
      (g) if the prescription-required item is a quantity of tablets in the cassette which require counting, then
         (i) verifying that the cassette containing the prescription-required tablets is mounted to the cassette dispenser;
         (ii) operating the cassette dispenser drive system to feed tablets from the cassette;
         (iii) counting with the first and second tablet counters the tablets fed from the cassette;
         (iv) comparing counts of the first and second tablet counters;
         (v) creating a record with the data processing platform that the retrieved prescription was fulfilled; and
         (vi) repeating step (c) and the subsequent steps for the next prescription.

21. The system of claim 20 wherein the comparing step further comprises comparing counts of the first and second tablet counters to determine whether the counts differ by more than a predetermined amount.

22. The system of claim 21 wherein the method performed by the instructions further comprises generating a signal if the counts differ by more than the predetermined amount.

23. The system of claim 21 wherein the method performed by the instructions further comprises stopping the drive system if the counts differ by more than the predetermined amount.

24. The system of claim 20 wherein the comparing step (iv) further comprises comparing the counts to determine whether the counts match the quantity of tablets required by the retrieved prescription.

25. A system for feeding and counting discrete objects, comprising:
   a first automatic object counter which counts plural objects simultaneously moving past a sensor;
   a cassette dispenser having a cassette mount which positions a cassette mounted thereon to feed discrete objects to the first automatic object counter;
   a cassette dispenser drive system which powers a mounted cassette to feed objects therefrom;
   a second automatic object counter which counts single objects moving past a sensor fed from a mounted cassette; and
   a data processing platform which compares counts of the first and second object counters,
   wherein the first automatic object counter counts objects both fed from the mounted cassette and poured manually while the cassette is mounted.

* * * * *

UNITED STATES PATENT AND TRADEMARK OFFICE
CERTIFICATE OF CORRECTION

| | | |
|---|---|---|
| PATENT NO. | : 8,271,128 B1 | Page 1 of 2 |
| APPLICATION NO. | : 12/350684 | |
| DATED | : September 18, 2012 | |
| INVENTOR(S) | : David A. Schultz | |

It is certified that error appears in the above-identified patent and that said Letters Patent is hereby corrected as shown below:

In the Specification

In column 10, line 4, beginning with the word "Tablet", start a new paragraph.

In column 12, lines 54-63, delete

"　0000000000001111111100000000000001111111110000000
　0000000000001111111100000000000001111111110000000
　0000000000001111111100000000000001111111110000000
　0000000000001111111100000000000001111111110000000
　0000000000001111111100000000000001111111110000000
　0000000000001111111100000000000001111111110000000
　0000000000001111111100000000000001111111110000000
　0000000000001111111100000000000001111111110000000
　0000000000001111111100000000000001111000000000
　0000000000001111000000000000000000000000000 "

and insert

-- 　0000000000000000000000000000000001111000000000
　0000000000001110000000000000001111111110000000
　0000000000001111111100000000000001111111110000000
　0000000000001111111100000000000001111111110000000
　0000000000001111111100000000000001111111110000000
　0000000000001111111100000000000001111111110000000
　0000000000001111111100000000000001111111110000000
　0000000000001111111100000000000001111111110000000
　0000000000001111111100000000000001111111110000000
　0000000000001111111100000000000001111111110000000
　0000000000001111111100000000000001111000000000
　0000000000001111000000000000000000000000000 --.

Column 19, line 3, delete "1413" and insert --14B--.

Column 23, line 51, delete "11a" and insert --11 a--.

Column 28, line 7, delete "1413" and insert --14B--.

Signed and Sealed this
Twenty-first Day of October, 2014

Michelle K. Lee
*Deputy Director of the United States Patent and Trademark Office*

CERTIFICATE OF CORRECTION (continued)
U.S. Pat. No. 8,271,128 B1

Column 38, line 21, delete "exits" and insert --exists--.

Column 50, line 51, after the word "can", insert --be--.

Column 56, line 9, after the word "select", delete "the".

Column 63, line 31, after the word "is" insert --a--.

In the Claims

Column 72, claim 1, line 30, after the word "automatic", delete "object".

Column 73, claim 7, line 6, after the word "is", insert --further--.

Column 74, claim 19, line 62, align the subparagraph symbol "(f)" beneath the subparagraph symbol "(e)".

Column 75, claim 19, line 3, delete "(iv)" and insert --(iii)--.

Column 75, claim 19, line 5, delete "(v)" and insert --(iv)--.